(12) United States Patent
Burk et al.

(10) Patent No.: US 9,885,064 B2
(45) Date of Patent: Feb. 6, 2018

(54) METHODS AND ORGANISMS FOR UTILIZING SYNTHESIS GAS OR OTHER GASEOUS CARBON SOURCES AND METHANOL

(71) Applicant: Genomatica, Inc., San Diego, CA (US)

(72) Inventors: Mark J. Burk, San Diego, CA (US); Christophe H. Schilling, San Diego, CA (US); Anthony P. Burgard, Bellefonte, PA (US); John D. Trawick, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

(21) Appl. No.: 14/185,709

(22) Filed: Feb. 20, 2014

(65) Prior Publication Data

US 2015/0024468 A1    Jan. 22, 2015

Related U.S. Application Data

(60) Division of application No. 13/615,168, filed on Sep. 13, 2012, now Pat. No. 8,697,421, which is a continuation of application No. 13/106,764, filed on May 12, 2011, now Pat. No. 8,323,950, which is a continuation of application No. 12/863,978, filed as application No. PCT/US2009/031737 on Jan. 22, 2009, now Pat. No. 8,691,553.

(60) Provisional application No. 61/022,804, filed on Jan. 22, 2008, provisional application No. 61/059,256, filed on Jun. 5, 2008.

(51) Int. Cl.

| | |
|---|---|
| C12N 1/20 | (2006.01) |
| C12N 1/12 | (2006.01) |
| C12P 7/62 | (2006.01) |
| C12P 7/04 | (2006.01) |
| C07H 21/04 | (2006.01) |
| C12P 7/18 | (2006.01) |
| C12N 9/02 | (2006.01) |
| C12N 9/10 | (2006.01) |
| C12N 9/00 | (2006.01) |
| C12P 19/32 | (2006.01) |
| C12N 15/70 | (2006.01) |

(52) U.S. Cl.
CPC ............. *C12P 7/18* (2013.01); *C12N 9/0008* (2013.01); *C12N 9/0036* (2013.01); *C12N 9/1007* (2013.01); *C12N 9/93* (2013.01); *C12N 15/70* (2013.01); *C12P 19/32* (2013.01); Y02E 50/343 (2013.01)

(58) Field of Classification Search
None
See application file for complete search history.

(56) References Cited

U.S. PATENT DOCUMENTS

| | | |
|---|---|---|
| 3,912,586 A | 10/1975 | Kaneyuki et al. |
| 4,048,196 A | 9/1977 | Broecker et al. |
| 4,301,077 A | 11/1981 | Pesa et al. |
| 4,624,920 A | 11/1986 | Inoue et al. |
| 5,143,833 A | 9/1992 | Datta |
| 5,143,834 A | 9/1992 | Glassner et al. |
| 5,168,055 A | 12/1992 | Datta et al. |
| 5,173,429 A | 12/1992 | Gaddy et al. |
| 5,182,199 A | 1/1993 | Hartley |
| 5,192,673 A | 3/1993 | Jain et al. |
| 5,413,922 A | 5/1995 | Matsuyama et al. |
| 5,416,020 A | 5/1995 | Severson et al. |
| 5,478,952 A | 12/1995 | Schwartz |
| 5,504,004 A | 4/1996 | Guettler et al. |
| 5,512,465 A | 4/1996 | Matsuyama et al. |
| 5,521,075 A | 5/1996 | Guettler et al. |
| 5,573,931 A | 11/1996 | Guettler et al. |
| 5,686,276 A | 11/1997 | Lafend et al. |
| 5,770,435 A | 6/1998 | Donnelly et al. |
| 5,807,722 A | 9/1998 | Gaddy et al. |
| 5,869,301 A | 2/1999 | Nghiem et al. |

(Continued)

FOREIGN PATENT DOCUMENTS

| | | |
|---|---|---|
| EP | 1 473 368 | 11/2004 |
| EP | 1 647 594 A1 | 4/2006 |

(Continued)

OTHER PUBLICATIONS

Seravalli et al. Pulse-chase studies of the synthesis of acetyl-CoA by carbon monoxide dehydrogenase/ acetyl-CoA synthase, JBC, 283(13): 8384-8394, 2008.*

(Continued)

*Primary Examiner* — Iqbal H Chowdhury
(74) *Attorney, Agent, or Firm* — Kagan Binder, PLLC

(57) ABSTRACT

The invention provides a non-naturally occurring microbial organism having an acetyl-CoA pathway and the capability of utilizing syngas or syngas and methanol. In one embodiment, the invention provides a non-naturally occurring microorganism, comprising one or more exogenous proteins conferring to the microorganism a pathway to convert CO, $CO_2$ and/or $H_2$ to acetyl-coenzyme A (acetyl-CoA), methyl tetrahydrofolate (methyl-THF) or other desired products, wherein the microorganism lacks the ability to convert CO or $CO_2$ and $H_2$ to acetyl-CoA or methyl-THF in the absence of the one or more exogenous proteins. For example, the microbial organism can contain at least one exogenous nucleic acid encoding an enzyme or protein in an acetyl-CoA pathway. The microbial organism is capable of utilizing synthesis gases comprising CO, $CO_2$ and/or $H_2$, alone or in combination with methanol, to produce acetyl-CoA. The invention additionally provides a method for producing acetyl-CoA, for example, by culturing an acetyl-CoA producing microbial organism, where the microbial organism expresses at least one exogenous nucleic acid encoding an acetyl-CoA pathway enzyme or protein in a sufficient amount to produce acetyl-CoA, under conditions and for a sufficient period of time to produce acetyl-CoA.

10 Claims, 15 Drawing Sheets

(56) References Cited

U.S. PATENT DOCUMENTS

| | | |
|---|---|---|
| 5,908,924 A | 6/1999 | Burdette et al. |
| 5,958,745 A | 9/1999 | Gruys et al. |
| 6,117,658 A | 9/2000 | Dennis et al. |
| 6,136,577 A | 10/2000 | Gaddy et al. |
| 6,159,738 A | 12/2000 | Donnelly et al. |
| 6,280,986 B1 | 8/2001 | Hespell et al. |
| RE37,393 E | 9/2001 | Donnelly et al. |
| 6,340,581 B1 | 1/2002 | Gaddy et al. |
| 6,432,686 B1 | 8/2002 | Bulthuis et al. |
| 6,448,061 B1 | 9/2002 | Pan et al. |
| 6,455,284 B1 | 9/2002 | Gokarn et al. |
| 6,485,947 B1 | 11/2002 | Rajgarhia et al. |
| 6,686,194 B1 | 2/2004 | Mutzel et al. |
| 6,686,310 B1 | 2/2004 | Kourtakis et al. |
| 6,743,610 B2 | 6/2004 | Donnelly et al. |
| 6,838,276 B2 | 1/2005 | Falco et al. |
| 6,852,517 B1 | 2/2005 | Suthers et al. |
| 7,127,379 B2 | 10/2006 | Palsson et al. |
| 7,186,541 B2 | 3/2007 | Gokarn et al. |
| 7,223,567 B2 | 5/2007 | San et al. |
| 7,241,594 B2 | 7/2007 | Lee et al. |
| 7,244,610 B2 | 7/2007 | San et al. |
| 7,256,016 B2 | 8/2007 | San et al. |
| 7,262,046 B2 | 8/2007 | San et al. |
| 7,285,402 B2 | 10/2007 | Gaddy et al. |
| 7,309,597 B2 | 12/2007 | Liao et al. |
| 7,371,558 B2 | 5/2008 | Cervin et al. |
| 7,393,676 B2 | 7/2008 | Gorkarn et al. |
| 7,432,091 B2 | 10/2008 | Yukawa et al. |
| 7,569,380 B2 | 8/2009 | San et al. |
| 7,803,589 B2 | 9/2010 | Burk et al. |
| 7,858,350 B2 | 12/2010 | Burk et al. |
| 7,947,483 B2 | 5/2011 | Burgard et al. |
| 7,977,084 B2 | 7/2011 | Sun et al. |
| 8,026,386 B2 | 9/2011 | Burk et al. |
| 8,323,950 B2 * | 12/2012 | Burk et al. ................ 435/252.3 |
| 8,691,553 B2 * | 4/2014 | Burk et al. ................ 435/252.3 |
| 8,697,421 B2 * | 4/2014 | Burk et al. ................ 435/252.3 |
| 9,051,552 B2 * | 6/2015 | Burk et al. |
| 2002/0012939 A1 | 1/2002 | Palsson |
| 2002/0168654 A1 | 11/2002 | Maranas et al. |
| 2003/0028915 A1 | 2/2003 | Tilton et al. |
| 2003/0032153 A1 | 2/2003 | Yamamoto et al. |
| 2003/0059792 A1 | 3/2003 | Palsson et al. |
| 2003/0087381 A1 | 5/2003 | Gokarn |
| 2003/0182678 A1 | 9/2003 | Mitsky et al. |
| 2003/0224363 A1 | 12/2003 | Park et al. |
| 2003/0233218 A1 | 12/2003 | Schilling |
| 2004/0009466 A1 | 1/2004 | Maranas et al. |
| 2004/0029149 A1 | 2/2004 | Palsson et al. |
| 2004/0072723 A1 | 4/2004 | Palsson et al. |
| 2004/0096946 A1 | 5/2004 | Kealey et al. |
| 2004/0152159 A1 | 8/2004 | Causey et al. |
| 2005/0042736 A1 | 2/2005 | San et al. |
| 2005/0079482 A1 | 4/2005 | Maranas et al. |
| 2005/0287655 A1 | 12/2005 | Tabata et al. |
| 2006/0073577 A1 | 4/2006 | San et al. |
| 2006/0110810 A1 | 5/2006 | Rajgarhia et al. |
| 2006/0172399 A1 | 8/2006 | Nomoto et al. |
| 2006/0281156 A1 | 12/2006 | Aoyama et al. |
| 2007/0042476 A1 | 2/2007 | Lee et al. |
| 2007/0072279 A1 | 3/2007 | Meynial-Salles et al. |
| 2007/0087425 A1 | 4/2007 | Ohto et al. |
| 2007/0092957 A1 | 4/2007 | Donaldson et al. |
| 2007/0111294 A1 | 5/2007 | Burgard et al. |
| 2007/0117191 A1 | 5/2007 | Kamachi et al. |
| 2007/0184539 A1 | 8/2007 | San et al. |
| 2007/0190605 A1 | 8/2007 | Bessler et al. |
| 2007/0259410 A1 | 11/2007 | Donaldson et al. |
| 2007/0275447 A1 | 11/2007 | Lewis et al. |
| 2008/0138870 A1 | 6/2008 | Bramucci et al. |
| 2008/0171371 A1 | 7/2008 | Yukawa et al. |
| 2008/0182308 A1 | 7/2008 | Donaldson et al. |
| 2008/0199926 A1 | 8/2008 | Burgard et al. |
| 2008/0293125 A1 | 11/2008 | Subbian et al. |
| 2009/0047718 A1 | 2/2009 | Blaschek et al. |
| 2009/0075351 A1 | 3/2009 | Burk et al. |
| 2009/0305364 A1 | 12/2009 | Burgard et al. |
| 2010/0009419 A1 | 1/2010 | Burk et al. |
| 2010/0021978 A1 | 1/2010 | Burk et al. |
| 2010/0099925 A1 | 4/2010 | Kharas |
| 2010/0168481 A1 | 7/2010 | Fanner et al. |
| 2010/0184173 A1 | 7/2010 | Burk et al. |
| 2010/0304453 A1 | 12/2010 | Trawick et al. |
| 2011/0045575 A1 | 2/2011 | Van Dien et al. |
| 2011/0129904 A1 | 6/2011 | Burgard et al. |

FOREIGN PATENT DOCUMENTS

| | | |
|---|---|---|
| EP | 2 017 344 | 1/2009 |
| EP | 2 182 051 | 5/2010 |
| GB | 1230276 | 4/1971 |
| GB | 1314126 | 4/1973 |
| GB | 1344557 | 1/1974 |
| GB | 1512751 | 6/1978 |
| JP | 50 006776 | 1/1975 |
| JP | 60-070088 | 4/1985 |
| WO | WO 99/058686 | 11/1999 |
| WO | WO 00/68407 | 11/2000 |
| WO | WO 2002/055995 | 7/2002 |
| WO | WO 2002/090312 | 11/2002 |
| WO | WO 2003/106998 | 12/2003 |
| WO | WO 2004/062763 A2 | 7/2004 |
| WO | WO 2005/026338 | 3/2005 |
| WO | WO 2005/047498 | 5/2005 |
| WO | WO 2006/028063 | 3/2006 |
| WO | WO 2006/031424 | 3/2006 |
| WO | WO 2006/034156 | 3/2006 |
| WO | WO 2007/030830 | 3/2007 |
| WO | WO 2007/050671 A2 | 5/2007 |
| WO | WO 2008/018930 | 2/2008 |
| WO | WO 2008/080124 | 7/2008 |
| WO | WO 2008/089102 A2 | 7/2008 |
| WO | WO 2008/115840 | 9/2008 |
| WO | WO 2008/131286 | 10/2008 |
| WO | WO 2008/137403 | 11/2008 |
| WO | WO 2008/152016 | 12/2008 |
| WO | WO 2009/013160 A2 | 1/2009 |
| WO | WO 2009/023493 | 2/2009 |
| WO | WO 2009/031766 | 3/2009 |
| WO | WO 2009/049274 | 4/2009 |
| WO | WO 2009/094485 | 7/2009 |
| WO | WO 2009/103026 | 8/2009 |
| WO | WO 2009/111513 A1 | 9/2009 |
| WO | WO 2009/131040 | 10/2009 |

OTHER PUBLICATIONS

Doukov et al. Structural and Kinetic Evidence for an Extended Hydrogen bonding Network in Catalysis of Methyl Group Transfer, JBC (2007), 282(9): 6609-6618.*

Takahashi et al. Functional Assignment of the OKF2-iscS-iscU-iscA-hscB-hscA-fdx-0RF3 Gene Cluster Involved in the Assembly of Fe—S Clusters in *Escherichia coli*, J. Biochem. 126, 917-926, 1999).*

Clark, David P., "Regulation of Alcohol Fermentation in *Escherichia coli*," Progress report for Grant DE-FG02-88ER13941, pp. 1-7 (1994).

Dürre and Bahl, "Microbial Production of Acetone/Butanol/Isopropanol," In Biotechnology vol. 6: "Products of Primary Metabolism", Second edition pp. 230-268, M. Roehr, ed. Published jointly by: VCH Verlagsgesellschaft mbH, Weinheim, Federal Republic of Germany and VCH Publishers Inc., New York, NY (1996).

Vemuri et al. "Succinate production in dual-phase *Escherichia coli* fermentations depends on the time of transition from aerobic to anaerobic conditions," J. Ind. Microbiol. Biotechnol. 28:325-332 (2002).

Yang, "Location of the fadBA operon on the physical map of *Escherichia coil*," J. Bacteriol. 173(23):7405-7406 (1991).

Abadjieva et al., "The Yeast ARG7 Gene Product is Autoproteolyzed to Two Subunit Peptides, Yielding Active

(56) References Cited

OTHER PUBLICATIONS

Ornithine Acetyltransferase," J. Biol. Chem. 275(15):11361-11367 (2000).
Abe et al., "Discovery of amide (peptide) bond synthetic activity in Acyl-CoA synthetase," J. Biol. Chem. 283(17):11312-11321 (2008).
Aberhart and Hsu, "Stereospecific hydrogen loss in the conversion of [2H7] isobutyrate to β-hydroxyisobutyrate in Pseudomonas putida. The stereochemistry of β-hydroxyisobutyrate dehydrogenase," J. Chem. Soc. [Perkin1] 6:1404-1406 (1979).
Abo-Dalo et al., "A novel member of the GCN5-related N-acetyltransferase superfamily from Caenorhabditis elegans preferentially catalyses the N-acetylation of thialysine [S-(2-aminoethyl)-L-cysteine]," Biochem. J. 384:129-137 (2004).
Agnihotri and Liu, "Enoyl-CoA Hydratase: Reaction, Mechanism, and Inhibition," Bioorg. Med. Chem. 11(1):9-20 (2003).
Ahmed and Lewis, "Fermentation of Biomass-Generated Synthesis Gas: Effects of Nitric Oxide," *Biotechol Bioeng.* 97:1080-1086 (2007).
Ahmed et al., "Effects of biomass-generated producer gas constituents on cell growth, product distribution and hydrogenase activity of Clostridium carboxidivorans P7T," *Biomass Bioenergy* 30(7):665-672 (2006).
Akashi et al., "Molecular and biochemical Characterization of 2-Hydroxyisoflavanone Dehydratase. Involvement of Carboxylesterase-Like Proteins in Leguminous Isoflavone Biosynthesis," Plant. Physiol. 137:882-891 (2005).
Akhtar and Jones, "Construction of a synthetic YdbK-dependent pyruvate:H2 pathway in *Escherichia coli* BL21(DE3)," Metab. Eng. 11(3):139-147 (2009).
Alber et al., "Propionyl-Coenzyme A synthase from Chloroflexus aurantiacus, a key enzyme of the 3-hydroxypropionate cycle for autotrophic CO2 fixation," J. Biol. Chem. 277:12137-12143 (2002).
Alber et al., "Study of an alternate glyoxylate cycle for acetate assimilation by Rhodobacter sphaeroides," Mol. Microbiol. 61(2):297-309 (2006).
Alber et al., "Malonyl-Coenzyme A reductase in the modified 3-hydroxypropionate cycle for autotrophic carbon fixation in archaeal *Metallosphaera* and *Sulfolobus* spp.," *J. Bacteriol.* 188(24):8551-8559 (2006).
Alber et al., "3-Hydroxypropionyl-Coenzyme A synthetase from Metallosphaera sedula, an enzyme involved in autotrophic CO2 fixation," J. Bacteriol. 190:1383-1389 (2008).
Alexson et al., "NADH-sensitive propionyl-CoA hydrolase in brown-adipose-tissue mitochondria of the rat," Biochim. Biophys. Acta 1005(1):13-19 (1989).
Alper et al., "Construction of lycopene-overproducing *E. coli* strains by combining systematic and combinatorial gene knockout targets," *Nat. Biotechnol.* 23(5):612-616 (2005).
Alper et al., "Identifying gene targets for the metabolic engineering of lycopene biosynthesis in *Escherichi coli,*" *Metab. Eng.* 7(3):155-164 (2005).
Alper et al., "Engineering yeast transcription machinery for improved ethanol tolerance and production," *Science* 314(5805):1565-1568 (2006).
Altmiller and Wanger, "Purification and properties of dihydroxy acid dehydratase from soluble and mitochondrial fractions of Neurospora crassa," Arch. Biochem. Biophys. 138:160-170 (1970).
Anderson and Dawes, "Occurrence, metabolism, metabolic role, and industrial uses of bacterial polyhydroxyalkanoates," *Microbiol. Rev.* 54(4):450-472 (1990).
Andreesen and Ljungdahl, "Formate Dehydrogenase of Clostridium thermoaceticum: Incorporation of Selenium-75, and the Effects of Selenite, Molybate, and Tungstate on the Enzyme," *J. Bacteriol.* 116(2):867-873 (1973).
Aoshima et al., "A novel enzyme, citryl-CoA synthetase, catalysing the first step of the citrate cleavage reaction in Hydrogenobacter thermophilus TK-6," Mol. Microbiol. 52(3):751-761 (2004).

Aoshima et al., "A novel enzyme, citryl-CoA lyase, catalysing the second step of the citrate cleavage reaction in Hydrogenobacter thermophilus TK-6," Mol. Microbiol. 52(3):763-770 (2004).
Aoshima and Igarashi, "A novel biotin protein required for reductive carboxylation of 2-oxoglutarate by isocitrate dehydrogenase in Hydrogenobacter thermophilus TK-6," Mol. Microbiol. 51(3):791-798 (2004).
Aragon and Lowenstein, "A survey of Enzymes Which Generate or Use Acetoacetyl Thioesters in Rat Liver," J. Biol. Chem. 258(8):4725-4733 (1983).
Arendsen et al., "Nitrate-Dependent Regulation of Acetate Biosynthesis and Nitrate Respiration by clostridium thermoaceticum," *J. Bacteriol.* 181:1489-1495 (1999).
Arikawa et al., "Soluble fumarate reductase isoenzymes from *Saccharomyces cerevisiae* are required for anaerobic growth," FEMS Microbiol. Lett. 165:111-116 (1998).
Aristidou et al., "Metabolic flux analysis of *Escherichia coli* expressing the Bacillus subtilis Acetolactate Synthase in Batch and Continuous Cultures," Biotechnol. Bioeng. 63(6):737-749 (1999).
Armstrong et al., "Steroselectivity and sterospecificity of the α,β-dihydroxyacid dehydratase from *Salmonella typhimurium,*" Biochim. Biophys. Acta 498:282-293 (1977).
Arps et al., "Genetics of serine pathway enzymes in Methylobacterium extorquens AM1: phosphoenolpyruvate carboxylase and malyl Coenzyme A lyase," J. Bacteriol. 175:3776-3783 (1993).
Atsumi et al., "Metabolic engineering of *Escherichia coli* for 1-butanol production," *Metab. Eng.* 10(6):305-311 (2007).
Atsumi et al., "Non-fermentative pathways for synthesis of branched-chain higher alcohols as biofuels," *Nature* 451(7174):86-89 (2008).
Atteia et al., "Pyruvate formate-lyase and a novel route of eukaryotic ATP synthesis in Chlamydomonas mitochondria," J. Biol. Chem. 281:9909-9918 (2006).
Auerbach et al., "Lactate dehydrogenase from the hyperthermophilic bacterium thermotoga maritima: the crystal structure at 2.1 Å resolution reveals strategies for intrinsic protein stabilization," Structure 6:769-781 (1998).
Bakker et al., "Stoichiometry and compartmentation of NADH metabolism in *Saccharomyces cerevisiae,*" FEMS Microbiol. Rev. 25:15-37 (2001).
Barker et al., "Butyryl-CoA:Acetoacetate CoA-transferase from Lysine-fermenting clostridium," J. Biol. Chem. 253(4):1219-1225 (1978).
Barrick, et al., "Quantitative analysis of ribosome binding sites in *E. coli,*" *Nucleic Acids Res.* 22(7):1287-1295 (1994).
Bartsch et al., "Molecular analysis of two genes of the *Escherichia coli* gab cluster: nucleotide sequence of the glutamate:succinic semialdehyde transaminase gene (gabT) and characterization of the succinic semialdehyde dehydrogenase gene (gabD)," J. Bacteriol. 172(12):7035-7042 (1990).
Bartsch et al., "Only plant-type (GLYK) glycerate kinases produce d-glycerate 3-phosphate," *FEBS Lett.* 582(20):3025-3028 (2008).
Basset et al., "Folate synthesis in plants: the p-aminobenzoate branch is initiated by a bifunctional PabA-PabB protein that is targeted to plastids," Proc. Natl. Acad. Sci U. S. A 101:1496-1501 (2004).
Battaile et al., "Structures of isobutyryl-CoA dehydrogenase and enzyme-product complex: Comparison with isovaleryl- and short-chain acyl-CoA dehydrogenases," J. Biol. Chem. 279:16526-16534 (2004).
Bauer et al., "Improved Expression of Human Interleukin-2 in High-Cell-Density Fermentor Cultures of *Escherichia coli* K-12 by a Phosphotransacetylase Mutant," Appl. Environ. Microbiol. 56:1296-1302 (1990).
Benning et al., "New reactions in the crotonase superfamily: Structure of methylmalonyl CoA decarboxylase from *Escherichia coli,*" Biochemistry 39:4630-4639 (2000).
Berg et al., "A 3-Hydroxypropionate/4-Hydroxybutyrate Autotrophic Carbon Dioxide Assimilation Pathway in Archaea," *Science* 318(5857) 1782-1786 (2007).

(56) References Cited

OTHER PUBLICATIONS

Bermejo et al., "Expression of Clostidium acetobutylicum ATCC 824 Genes in *Escherichia coli* for Acetone Production and Acetate Detoxication," 64(3):1079-1085 (1998).
Berrios-Rivera et al., "Metabolic Engineering of *Escherichia coli*: Increase of NADH Availability by Overexpressing an NAD+-Dependent Formate Dehydrogenase," Metab Eng. 4(3):217-229 (2002).
Biellmann et al., "Aspartate-β-semialdehyde dehydrogenase from *Escherichia coli*. Purification and general properties," Eur. J. Biochem. 104(1):53-58 (1980).
Binieda et al., "Purification, characterization, DNA sequence and cloning of a pimeloyl-CoA synthetase from Pseudomonas mendocina 35," Biochem. J. 340:793-801 (1999).
Binstock and Schulz, "Fatty acid oxidation complex from *Escherichia coli*," Methods Enzymol. 71(Pt C):403-411 (1981).
Birch et al., "Cloning, sequencing, and expression of the gene encoding methylmalonyl-Coenzyme A mutase from Streptomyces cinnamonensis," J. Bacteriol. 175(11):3511-3519 (1993).
Birrer et al., "Electro-transformation of Clostridium beijerinckii NRRL B-592 with shuttle plasmid pHR106 and recombinant derivitives," Appl. Microbiol. Biotechnol., 41:32-38 (1994).
Bisswanger, "Substrate specificity of the Pyruvate Dehydrogenase Complex from *Escherichia coli*," J. Biol. Chem. 256(2):815-822 (1981).
Blaschkowski et al., "Routes of flavodoxin and ferredoxin reduction in *Escherichia coli*. CoA-acylating pyruvate: flavodoxin and NADPH: flavodoxin oxidoreductases participating in the activation of pyruvate formate-lyase," Eur. J. Biochem. 123(3):563-569 (1982).
Blazquez et al., "Identification and analysis of a glutaryl-CoA dehydrogenase-encoding gene and its cognate transcriptional regulator from *Azoarcus* sp. CIB," Environ. Microbiol. 10(2):474-482 (2008).
Blomqvist et al., "Characterization of the genes of the 2,3-butanediol operons from Klebsiella terrigena and Enterobacter aerogenes," J. Bacteriol. 175:1392-1404 (1993).
Bobik et al., "Propanediol Utilization Genes (pdu) of *Salmonella typhimurium*: Three Genes for the Propanediol Dehydratase," J. Bacteriol. 179(21):6633-6639 (1997).
Bock et al., "Purification and characterization of two extremely thermostable enzymes, phosphate acetyltransferase and acetate kinase, from the hyperthermophilic eubacterium Thermotoga maritima," J. Bacteriol. 181:1861-1867 (1999).
Bonner and Bloch, "Purification and properties of fatty acyl thioesterase I from *Escherichia coli*," J. Biol. Chem. 247(10):3123-3133 (1972).
Bose et al., "Genetic analysis of the methanol- and methylamine-specific methyltransferase 2 genes of Methanosarcina acetivorans C2A " J. Bacteriol. 190(11):4017-4026 (2008).
Bottomley et al., "Cloning, sequencing, expression, purification and preliminary characterization of type II dehydroquinase from Helicobacter pylori," Biochem. J. 319:559-565 (1996).
Bower et al., "Cloning, sequencing, and characterization of the Bacillus subtilis biotin biosynthetic operon," J. Bacteriol. 178(14):4122-4130 (1996).
Boynton et al., "Cloning, sequencing, and expression of clustered genes encoding β-hydroxybutyryl-Coenzyme A (CoA) dehydrogenase, crotonase, and butyryl-CoA dehydrogenase from Clostridium acetobutylicum ATCC 824," J. Bacteriol. 178(11):3015-3024 (1996).
Bräsen and Schönheit, "Unusual ADP-forming acetyl-Coenzyme A synthetases from the mesophilic halophilic euryarchaeon Haloarcula marismortui and from the hyperthermophilic crenarchaeon Pyrobaculum aerophilum," Arch. Microbiol. 182(4):277-287 (2004).
Bravo et al., "Reliable, sensitive, rapid and quantitative enzyme-based assay for gamma-hydroxybutyric acid (GHB)," *J. Forensic Sci.* 49:379-387 (2004).

Bredwell et al., "Reactor Design Issues for Synthesis-Gas Fermentations," *Biotechnol. Prog.* 15(5):834-844 (1999).
Breese et al., "Genes coding for the benzoyl-CoA pathway of anaerobic aromatic metabolism in the bacterium Thauera aromatics," Eur. J. Biochem. 256(1):148-154 (1998).
Breitkreuz et al., "A novel γ-hydroxybutyrate dehydrogenase: Identification and expression of an *Arabidopsis* cDNA and potential role under oxygen deficiency," *J. Biol. Chem.* 278:41552-41556 (2003).
Bremer, "Pyruvate Dehydrogenase, Substrate Specificity and Product Inhibition," Eur. J. Biochem. 8:535-540 (1969).
Brey et al., "Cloning of multiple genes involved with cobalamin (Vitamin B12) biosynthesis in Bacillus megaterium," J. Bacteriol. 167:623-630 (1986).
Bro et al., "In silico aided metabloic engineering of *Saccharomyces cerevisiae* for improved bioethanol production," *Metab. Eng.* 8(2):102-111 (2006).
Brown et al., "Comparative structural analysis and kinetic properties of lactate dehydrogenases from the four species of human malarial parasites," Biochemistry 43:6219-6229 (2004).
Buck et al., "Primary structure of the succinyl-CoA synthetase of *Escherichia coli*," Biochem. 24(22):6245-6252 (1985).
Buckel et al., "Glutaconate CoA-Transferase from Acidaminococcus fermentans," Eur. J. Biochem. 118:315-321 (1981).
Buckel and Golding, "Radical species in the catalytic pathways of enzymes from anaerobes," FEMS Microbiol. Rev. 22(5):523-541 (1999).
Buckel et al., "ATP-Driven electron transfer in enzymatic radical reactions," Curr. Opin. Chem. Biol. 8:462-467 (2004).
Buckel et al., "Radical-mediated dehydration reactions in anaerobic bacteria," Biol. Chem. 386:951-959 (2005).
Bueding and Yale, "Production of -methylbutyric acid by bacteria-free Ascaris lumbricoides," J. Biol. Chem. 193:411-423 (1951).
Bühler and Simon, "On the kinetics and mechanism of enoate reductase," *Hoppe Seylers Z. Physiol. Chem.* 363(6):609-625 (1982).
Bunch et al., "The 1dhA gene encoding the fermentative lactate dehydrogenase of *Escherichia coli*," Microbiol. 143:187-195 (1997).
Burgard et al., "Minimal Reaction Sets for *Escherichia coli* Metabolism under Different Growth Requirements and Uptake Environments," *Biotechnol. Prog.* 17:791-797 (2001).
Burgard et al., "Optknock: a bilevel programming framework for identifying gene knockout strategies for microbial strain optimization," *Biotechnol. Bioeng,* 84(6):647-657 (2003).
Burks et al., "Stereochemical and Isotopic Labeling Studies of 2-Oxo-hept-4-ene-1,7-dioate Hydratase: Evidence for an Enzyme-Catalyzed Ketonization Step in the Hydration Reaction," J. Am. Chem. Soc. 120(31):7665-7675 (1998).
Buu et al., "Functional characterization and localization of acetyl-CoA hydrolase, Ach1p, in *Saccharomyces cerevisiae*," J. Biol. Chem. 278:17203-17209 (2003).
Cahyanto et al., "Regulation of aspartokinase, asparate semialdehyde dehydrogenase, dihydrodipicolinate synthease and dihydropdipicolinate reductase in Lactobacillus plantarum," Microbiology. 152 (Pt 1): 105-112 (2006).
Campbell and Cronan, Jr., "The enigmatic *Escherichia coli* fadE gene is yafH," J. Bacteriol. 184(13):3759-3764 (2002).
Campbell et al., "A new *Escherichia coli* metabolic competency: growth on fatty acids by a novel anaerobic β-oxidation pathway," *Mol. Microbiol.* 47(3):793-805 (2003).
Cao et al., "Simultaneous Production and recovery of Fumaric Acid from Immobilized Rhizopus oryzae with a Rotary biofilm Contactor and an Adsorption Column," Appl. Environ. Microbiol. 62(8):2926-2931 (1996).
Carlini et al., "Guerbet condensation of methanol with n-propanol to isobutyl alcohol over heterogeneous copper chromite/Mg—Al mixed oxides catalysts," *J. Mol. Catal. A. Chem.* 220:215-220 (2004).
Carlini et al., "Selective synthesis of isobutanol by means of the Guerbet reaction Part 3: Methanol/n-propanol condensation by using bifunctional catalytic systems based on nickel, rhodium and ruthenium species with basic components," *J. Mol. Catal. A. Chem.* 206:409-418 (2003).

(56) References Cited

OTHER PUBLICATIONS

Carlini et al., "Selective synthesis of isobutanol by means of the Guebet reaction Part 1. Methanol/n-propanol condensation by using copper based catalytic systems," *J. Mol. Catal. A. Chem.* 184:273-280 (2002).
Carlini et al., "Selective synthesis of isobutanol by means of the Guerbet reaction Part 2. Reaction of methanol/ethanol and methanol/ethanol/n-propanol mixtures over copper based MeONa catalytic systems," *J. Mol. Catal. A. Chem.* 200:137-146 (2003).
Carpenter et al., "Structure of dehydroquinate synthase reveals an active site capable of multistep catalysis," *Nature* 394:299-302 (1998).
Carta et al., "Production of fumaric acid by fermentation of enzymatic hydrolysates derived from *Cassava bagasse,*" *Biores. Tech.* 68:23-28 (1999).
Cary et al., "Cloning and Expression of Clostridium acetobutylicum ATCC 824 Acetoacetyl-Coenzyme A:Acetate/Butyrate:Coenzyme A-Transferase in *Escherichia coli,*" *App. Environ. Microbiol.* 56(6):1576-1583 (1990).
Cary et al., "Cloning and expression of Clostridium acetobutylictun phosphotransbutyrylase and butyrate kinase genes in *Escherichia coli,*" *J. Bacteriol.* 170(10):4613-4618 (1988).
Caspi et al., "MetaCyc: a multiorganism database of metabolic pathways and enzymes," Nucleic Acids Res. 34(Database issue):D511-D516 (2006).
Chandra et al. "Pyruvate decarboxylase: a key enzyme for the oxidative metabolism of lactic acid by Acetobacter pasteurianus," Arch. Microbiol. 176:443-451 (2001).
Chang et al., "Glutarate semialdehyde dehydrogenase of *Pseudomonas.* Purification, properties, and relation to 1-lysine catabolism," J. Biol. Chem. 252(22):7979-7986 (1977).
Chang et al., "Molecular cloning, DNA sequencing, and biochemical analyses of *Escherichia coli* glyoxylate carboligase. An enzyme of the acetohydroxy acid synthase-pyruvate oxidase family," *J. Biol. Chem.* 268(6):3911-3919 (1993).
Chao and Ramsdell, "The effects of wall populations on coexistence of bacteria in the liquid phase of chemostat cultures," *J. Gen. Microbiol.* 131(5):1229-1236 (1985).
Chaparro-Riggers et al., "Comparison of Three Enoate Reductases and their Potential Use for Biotransformations," Adv. Synth. Catal. 349:1521-1531 (2007).
Charrier et al., "A novel class of CoA-transferase involved in short-chain fatty acid metabolism in butyrate-producing human colonic bacteria," Microbiology 152:179-185 (2006).
Chaudhuri et al., "Identification of the active-site lysine residues of two biosynthetic 3-dehydroquinases," Biochem. J. 275:1-6 (1991).
Chen et al., "Acetone-Butanol-Isopropanol Production by Clostridium Beijerinckii," Biotechnology Letters, 8(5):371-376 (1986).
Cheng et al., "Mammalian Wax Biosynthesis. I. Identification of two fatty acyl-Coenzyme A reductases with different substrate specificities and tissue distributions," *J. Biol. Chem.* 279(36):37789-37797 (2004).
Cheng et al., "Mammalian Wax Biosynthesis. II. Expression cloning of wax synthase cDNAs encoding a member of the acyltransferase enzyme family," *J. Biol. Chem.* 279(36):37798-37807 (2004).
Chistoserdova et al., "Purification and characterization of hydroxypyruvate reductase from the facultative methylotroph Methylobacterium extorquens AM1," *J. Bacteriol.* 173(22):7228-7232 (1991).
Chistoserdova et al., "Methylotrophy in Methylobacterium extorquens AM1 from a genomic point of view," *J. Bacteriol.* 185(10):2980-2987 (2003).
Cho et al., "Critical residues for the Coenzyme specificity of NAD+-dependent 15-hydroxyprostaglandin dehydrogenase," Arch. Biochem. Biophys. 419:139-146 (2003).
Chou et al., "Effect of Modulated Glucose Uptake on High-Level Recombinant Protein Production in a Dense *Escherichia coli* Culture," Biotechnol. Prog. 10:644-647 (1994).

Chowdhury et al., "Cloning and overexpression of the 3-hydroxyisobutyrate dehydrogenase gene from pseudomonas putida E23," Biosci. Biotechnol. Biochem. 67(2):438-441 (2003).
Chowdhury et al., "3-Hydroxyisobutyrate dehydrogenase from Pseudomonas putida E23: purification and characterization," Biosci. Biotechnol. Biochem. 60(12):2043-2047 (1996).
Chuakrut et al., "Characterization of a bifunctional archael acyl Coenzyme A carboxylase," J. Bacteriol. 185:938-947 (2003).
Clark and Ljungdahl, "Purification and Properties of 5,10-Methylenetetrahydrofolate Reductase, an Iron-sulfur Flavoprotein from Clostridium formicoaceticum," *J. Biol. Chem.* 259(17)10845-10849 (1984).
Clark and Ljungdahl, "Purification and properties of 5,10-methylenetetrahydrofolate reductase from Clostridium formicoaceticum," Methods Enzymol. 122:392-399 (1986).
Clark et al., "Mutants of *Escherichia coli* defective in acid fermentation," Appl. Biochem. Biotechnol. 17:163-173 (1988).
Clark, David P., "Regulation of Alcohol Fermentation in *Escherichia coli*," Progress report for Grant DE-FG02-88ER13941 (1994).
Clarke et al., "Rational construction of a 2-Hydroxyacid Dehydrogenase With New Substrate Specificity," Biochem. Biophys. Res. Commun. 148:15-23 (1987).
Colby and Chen, "Purification and properties of 3-hydroxybutyryl-Coenzyme A dehydrogenase from Clostridium beijerinckii ("Clostridium butylicum") NRRL B593," *Appl. Environ. Microbiol.* 58:3297-3302 (1992).
Cooper, "Glutamate-γ-aminobutyrate transaminase," Methods Enzymol. 113:80-82 (1985).
Corthesy-Theulaz et al., "Cloning and Characterization of Helicobacter pylori Succinyl CoA:Acetoacetate CoA-transferase, a Novel Prokaryotic Member of the CoA-transferase Family," J. Biol. Chem. 272(41):25659-25667 (1997).
Cox et al., "Development of a metabolic network design and optimization framework incorporating implementation constraints: A succinate production case study," Metab. Eng. 8(1):46-57 (2006).
Craney et al., "A synthetic luxCDABE gene cluster optimized for expression in high-GC bacteria," *Nucleic Acids Res.* 35(6):e46 (2007).
Cukalovic et al., "Feasibility of production method for succinic acid derivatives: a marriage of renewable resources and chemical technology," Biofuels Bioprod. Bioref. 2:505-529 (2008).
D'Ari and Rabinowitz, "Purification Characterization, cloning, and Amino Acid Sequence of the Bifunctional Enzyme 5,10-Methylenetetrahydrofolate Dehydrogenase/5,10-Methenyltetrahydrofolate Cyclohydrolase from *Escherichia coli,*" *J. Biol. Chem.* 266(35):23953-23958 (1991).
Dakoji et al., "Studies on the inactivation of bovine liver enoyl-CoA hydratase by (methylenecyclopropyl)formyl-CoA: elucidation of the inactivation mechanism and identification of cysteine-114 as the entrapped nucleophile," J. Am. Chem. Soc. 123(4):9749-9759 (2001).
Dal et al., "Transcriptional Organization of Genes for Protocatechuate and quinate Degradation from *Acinetobacter* sp. Strain ADP1," Appl. Environ. Microbiol. 71(2):1025-1034 (2005).
Das et al., "Characterization of a corrinoid protein involved in the C1 metabolism of strict anaerobic bacteritun Moorella thermoacetica," *Proteins* 67(1):167-176 (2007).
Datar et al., "Fermentation of biomass-generated producer gas to ethanol," *Biotechnol. Bioeng.* 86(5):587-594 (2004).
Datta et al., "Covalent structure of biodegradative threonine dehydratase of *Escherichi coli*: homology with other dehydratases," Proc. Natl. Acad. Sci. U.S.A. 84(2):393-397 (1987).
Davids et al, "Characterization of the N-acetyltransferases respectively responsible for arylalkylainine and diamine acetylation in Ascaris suum," Mol. Biochem. Parasitol. 64(2):341-344 (1994).
Davie et al., "Expression and assembly of a functional E1 component (2 2) of mammalian branched-chain-ketoacid dehydrogenase complex in *Escherichia coli,*" J. Biol. Chem. 267:16601-16606 (1992).

(56) References Cited

OTHER PUBLICATIONS

De Bok et al., "Two W-containing fonnate dehydrogenases (CO2-reductases) involving syntrophic propionate oxidation by Syntrophobacter fumaroxidans," *Eur. J. Biochem.* 270:2476-2485 (2003).
De Crecy et al., "Development of a novel continuous culture device for experimental evolution of bacterial populations," Appl. Microbiol. Biotechnol. 77(2): 489-496 (2007).
De Mata and Rabinowitz, "Formyl-methenyl-methylenetetrahydrofolate synthetase (combined) from yeast. Biochemical characterization of the protein from an ADE3 mutant lacking the formyltetrahydrofolate synthetase function," J. Biol Chem. 255:2569-2577 (1980).
De Mendonca et al., "Functional characterization by genetic complementation of aroB-encoded dehydroquinate synthase from *Mycobacterium tuberculosis* H37Rv and its heterologous expression and purification," J. Bacteriol. 189:6246-6252 (2007).
De Smidt et al., "The alcohol dehydrogenases of *Saccharomyces cerevisiae*: a comprehensive review," FEMS Yeast Rev. 7:967-978 (2008).
Deana, "Substrate specificity of a dicarboxyl-CoA: dicarboxylic acid Coenzyme A transferase from rat liver mitochondria," Biochem. Int. 26(4):767-773 (1992).
Department of Energy, "Top value added chemicals from biomass. vol. I—Results of Screening for Potential Candidates from Sugars and Synthesis Gas," Biomass, Aug. 2004.
Desvaux, "*Clostridium cellulolytictum*: model organism of mesophilic cellulolytic clostridia," *FEMS Microbiol. Rev.* 29(4):741-764 (2005).
Diao et al., "Crystallization of the butyrate kinase 2 from Thermotoga maritima mediated by vapor diffusion of acetic acid," *Acta. Crystallogr D. Biol. Crystallogr.* 59(Pt 6):1100-1102 (2003).
Diao et al., "Crystal structure of butyrate kinase 2 from Thermotoga maritima, a member of the ASKHA superfamily of phosphotransferases," J. Bacteriol. 191:2521-2529 (2009).
Dittrich et al., "Redistribution of Metabolic Fluxes in the Central Aerobic Metabolic Pathway of *E. coli* Mutant Strains with Deletion of the ackA-pta and poxB Pathways for the Synthesis of Isoamyl Acetate," Biotechnol Prog. 21(2):627-631 (2005).
Do et al., "Engineering *Escherichia coli* for fermentative dihydrogen production: potential role of NADH-ferredoxin oxidoreductase from the hydrogenosome of anaerobic protozoa," Appl. Biochem. Biotechnol. 153(1-3):21-33 (2009).
Do et al., "Growth of rhodospirillum rubrum on synthesis gas: conversion of CO to H2 and Poly-β-hydroxyalkanoate," *Biotechnol. Bioeng.* 97(2):279-286 (2007).
Dobbek et al., "Crystal structure of a carbon monoxide dehydrogenase reveals a [Ni—4Fe—5S] cluster," *Science* 293(5533):1281-1285 (2001).
Dombek and Ingram, "Ethanol production during batch fermentation with *Saccharomyces cerevisiae*: Changes in glycolytic enzymes and internal pH," Appl. Environ. Microbiol. 53:1286-1291 (1987).
Donnelly and Cooper, "Succinic semialdehyde dehydrogenases of *Escherichia coli*: Their role in the degradation of p-hydroxyphenylacetate and -aminobutyrate," Eur. J. Biochem. 113:555-561 (1981).
Donnelly and Cooper, "Two succinic semialdehyde dehydrogenases are induced when *Escherichia coli* K-12 Is grown on γ-aminobutyrate," J. Bacteriol. 145:1425-1427 (1981).
Donnelly et al., "A novel fermentation pathway in an *Escherichia coli* mutant producing succinic acid, acetic acid, and ethanol," App. Biochem. Biotech. 70-72:187-198 (1998).
Doughty et al., "Purification and properties of d-glycerate 3-kinase from *Escherichia coli*," *J. Biol. Chem.* 241(3):568-572 (1966).
Doyle et al., "Structural Basis for a Change in substrate Specificity: Crystal Structure of S113E Isocitrate Dehydrogenase in a Complex with Isopropylmalate, Mg2+ and NAPD," Biochemistry 40:4234-4241 (2001).
Drake and Daniel, "Physiology of the thermophilic acetogen Moorella thermoacetica," Res. Microbiol. 155(10):869-883 (2004).
Drake, "Acetogenesis, acetogenic bacteria, and the acetyl-CoA "Wood/Ljungdahl" pathway: past and current perspectives," in Acetogenesis, H. L. Drake, (ed.), Chapman & Hall, New York, p. 3-60 (1994).
Drake, "Demonstration of hydrogenase in extracts of the homoacetate-fermenting bacterium Clostridium thermoaceticum," *J. Bacteriol.* 150(2):702-709 (1982).
Drewke et al., "Ethanol formation in adh) mutants reveals the existence of a novel acetaldehyde-reducing activity in *Saccharomyces cerevisiae*," J. Bacteriol. 172:3909-3917 (1990).
Drummond and Stern, "Enzymes of ketone body metabolism. II. Properties of an acetoacetate-synthesizing enzyme prepared from ox liver," J. Biol. Chem. 235:318-325 (1960).
Du et al., "Succinic acid production from wheat using a biorefining strategy," Appl. Microbiol. Biotechnol. 76:1263-1270 (2007).
Duncan et al., "Acetate utilization and butyryl Coenzyme A (CoA):acetate-CoA transferase in butyrate-producing bacteria from the human large intestine," Appl. Environ, Microbiol. 68(10):5186-5190 (2002).
Duncombe and Frerman, "Molecular and catalytic properties of the acetoacetyl-Coenzyme A thiolase of *Escherichia coli*," Arch. Biochem. Biophys. 176(1):159-170 (1976).
Duran et al., "Characterization of cDNA clones for the 2-methyl branched-chain enoyl-CoA reductase. An enzyme involved in branched-chain fatty acid synthesis in anerobic mitochondria of the parasitic nematode *Ascaris suum*," J. Biol. Chem. 268(30):22391-22396 (1993).
Durner et al., "Accumulation of Poly[(R)-3-Hydroxyalkanoates] Pseudomonas oleovorans during Growth with Octanoate in continuous culture at Different Dilution Rates," Appl. Environ. Microbiol. 66(8):3408-3414 (2000).
Dürre et al., "6 Microbial Production of Acetone/Butanol/Isopropanol,": Biotechnology, 6:230-268 (1996).
Dürre et al., "Solventogenic enzymes of Clostridhun acetobutylicum: catalytic properties, genetic organization, and transcriptional regulation," FEMS Microbiol. Rev. 17:251-262 (1995).
Dürre, "New insights and novel developments in clostridial acetone/butanol/isopropanol fermentation," Appl. Microbiol. Biotechnol., 49:639-648 (1998).
Dürre, "Biobutanol: an attractive biofuel," *Biotechnol. J.* 2(12):1525-1534 (2007).
Dutscho et al., "Cloning and sequencing of the genes of 2-hydroxyglutaryl-CoA dehydratase from Acidaminococcus fermentans," Eur. J. Biochem. 181(3):741-746 (1989).
Dwyer et al., "Proton Abstraction reaction, Steady-State kinetics, and Oxidation-Reduction Potential of Human Glutaryl-CoA Dehydrogenase," Biochemistry 39:11488-11499 (2000).
Dykhuizen, "Chemostats used for studying natural selection and adaptive evolution," *Methods. Enzymol.* 224:613-631 (1993).
Eberhard and Gerlt, "Evolution of Function in the Crotonase Superfamily: The Stereochemical course of the Reaction catalyzed by 2-Ketocyclohexanecarboxyl-CoA Hydrolase," J. Am. Chem. Soc. 126:7188-7189 (2004).
Edegger et al., "Biocatalytic deuterium- and hydrogen-transfer using over-expressed ADH-'A': enhanced steroselectivity and 2H-labeled chiral alcohols," Chem. Commun. 22:2402-2404 (2006).
Edwards and Palsson, "Metabolic flux balance analysis and the in silico analysis of *Escherichia coli* K-12 gene deletions," *BMC Bioinform.* 1:1 (2000).
Edwards and Palsson, "The *Escherichia coil* MGI655 in silico Metabolic Genotype: Its Definition, Characteristics, and Capabilities," *Proc. Natl. Acad. Sci. U.S.A.* 97(10):5528-5533 (2000).
Edwards and Palsson, "Systems properties of the Haemophilus influenzae Rd metabolic genotype," J. Biol. Chem. 274(25):17410-17416 (1999).
Edwards et al., "Metabolic modelling of microbes: the flux-balance approach," *Environ. Microbiol.* 4(3):133-140 (2002).
Edwards et al., "In Silico Predictions of *Escherichia coli* metabolic capabilities are Consistent with Experimental Data," *Nat. Biotechnol.* 19(2):125-130 (2001).

(56) References Cited

OTHER PUBLICATIONS

Efe et al., "Options for biochemical production of 4-hydroxybutyrate and its lactone as a substitute for petrochemical production," Biotechnol. Bioeng. 99:1392-1406 (2008).
Elshahed et al., "Metabolism of Benzoate, Cyclohex-1-ene Carboxylate, and Cyclohexane Carboxylate by "Syntrophus aciditrophicus" Strain SB in Syntrophic Association with H2-Using Microorganisms," Appl. Environ. Microbiol. 67(4):1728-1738 (2001).
Engel, "Butyryl-CoA Dehydrogenase from Megasphaera elsdenii," Methods Enzymol. 71:359-366 (1981).
Enomoto et al., "Cloning and sequencing of the gene encoding the soluble fumarate reductase from Saccharomyces cerevisiae," DNA Res. 3:263-267 (1996).
Ensign and Ludden, "Characterization of the CO Oxidation/H2 Evolution System of Rhodospirillum rubrum. Role of a 22-kDa iron-sulfur protein in mediating electron transfer between carbon monoxide dehydrogenase and hydrogenase," J. Biol. Chem. 266(27)18395-18403 (1991).
Estévez et al., "X-ray crystallographic and kinetic correlation of a clinically observed human fumarase mutation," Protein Sci. 11(6):1552-1557 (2002).
Ezeji et al., "Butanol fermentation research: upstream and downstream manipulations," Chem. Rec. 4(5):305-314 (2004).
Faehnle et al., "A New Branch in the Family: Structure of Aspartate-β-semialdehyde Dehydrogenase from Methanococcus jannaschii," J. Mol. Biol. 353:1055-1068 (2005).
Feist et al., "Modeling methanogenesis with a genome-scale metabolic reconstruction of Methanosarcina barkeri," Mol. Syst. Biol. 2:2006.0004 (2006).
Fernandez-Valverde et al., "Purification of Pseudomonas putida Acyl Coenzyme A Ligase Active with a Range of aliphatic and Aromatic substrates," Appl. Environ. Microbiol. 59(4):1149-1154 (1993).
Flint et al., "The role and properties of the iron-sulfur cluster in Escherichia coli dihydroxy-acid dehydratase," J. Biol. Chem. 268:14732-14742 (1993).
Flint, "Initial kinetic and mechanistic characterization of Escherichia coli fumarase A," Arch. Biochem. Biophys. 311(2):509-516 (1994).
Fong and Palsson, "Metabolic gene-deletion strains of Escherichia coli evolve to computationally predicted growth phenotypes," Nat. Genet. 36(10):1056-1058 (2004).
Fong et al., "In Silico design and adaptive evolution of escherichia coli for production of lactic acid," Biotechnol. Bioeng. 91(5):643-648 (2005).
Fontaine et al., "Molecular charcterization and transcriptional analysis of adhE2, the gene encoding the NADH-dependent aldehyde/alcohol dehydrogenase responsible for butanol production in alcohologenic cultures of Clostridium acetobutylicum ATCC 824," J. Bacteriol. 184:821-830 (2002).
Ford et al., "Molecular properties of the lyst1+ gene and the regulation of α-aminoadipate reductase in Schizosaccharomyces pombe," Curr. Genet. 28:131-137 (1995).
Forster et al., "Genome-scale reconstruction of the Saccharomyces cerevisiae metabolic network," Genome Res. 13(2):244-253 (2003).
Fox et al., "Characterization of the region encoding the CO-induced hydrogenase of Rhodospirillum rubrum," J. Bacteriol. 178(21):6200-6208 (1996).
Freidrich et al., "The complete stereochemistry of the enzymatic dehydration of 4-hydroxybutyryl Coenzyme A to crotonyl Coenzyme A," Angew. Chem. Int. Ed. 47:3254-3257 (2008).
Frerman and Duncombe, "Studies on the subunits of Escherichia coli Coenzyme A transferase. Reconstitution of an active enzyme," Biochim. Biophys. Acta 580(2):289-297 (1979).
Fries et al., "Reaction Mechanism of the heterotetrameric (α2β2) E1 Component of 2-Oxo Acid Dehydrogenase Multienzyme Complexes," Biochemistry 42:6996-7002 (2003).
Frost et al., "Dehydroquinate synthase from Escherichia coli: purification, cloning, and construction of overproducers of the enzyme," Biochemistry 23:4470-4475 (1984).
Frost, "Redefining chemical manufacture. Replacing petroleum with plant-derived feedstocks," Ind. Biotechnol. 1(1):23-24 (2005).
Fu et al., "Crystal structures of human glutaryl-CoA dehydrogenase with and without an alternate substrate: structural bases of dehydrogenation and decarboxylation reactions," Biochemistry 43(30):9674-9684 (2004).
Fujishiro et al., "Crystallization and Some Properties of Acetylpolyamine Amidohydrolase From Mycoplana Bullata," Biochem. Biophys. Res. Commun. 157(3):1169-1174 (1988).
Fujita et al., "Novel Substrate Specificity of Designer 3-Isopropylmalate Dehydrogenase Derived from Thermus thermophilus HB8," Biosci. Biotechnol. Biochem. 65(12):2695-2700 (2001).
Fukao et al., "Succinyl-CoA:3-ketoacid CoA transferase (SCOT): cloning of the human SCOT gene, tertiary structural modeling of the human SCOT monomer, and characterization of three pathogenic mutations," Genomics 68:144-151 (2000).
Fukuda and Wakagi, "Substrate recognition by 2-oxoacid:ferredoxin oxidoreductase from Sulfolobus sp. Strain 7," Biochim. Biophys. Acta 1597:74-80 (2002).
Fukuda et al., "Role of a highly conserved YPITP motif in 2-oxoacid:ferredoxin oxidoreductase Heterologous expression of the gene from Sulfolobus sp. Strain 7, and characterization of the recombinant and variant enzymes," Eur. J. Biochem. 268:5639-5646 (2001).
Fukui et al., "Engineering of Ralstonia eutropha for production of poly(3-hydroxybutyrate-co-3-hydroxyhexanoate) from fructose and solid-state properties of the copolymer," Biomacromolecules 3(3):618-624 (2002).
Furdui and Ragsdale, "The role of pyruvate ferredoxin oxidoreductase in pyruvate synthesis during autotrophic growth by the Wood-Ljungdahl pathway," J. Biol. Chem. 275(37):28494-28499 (2000).
Furukawa et al., "Increased alcohol acetyltransferase activity by inositol limitation in Saccharomyces cerevisiae in sake mash," J. Biosci. Bioeng. 96(4):380-386 (2003).
Galagan et al., "The genome of M. acetivorans reveals extensive metabolic and physiological diversity," Genome Res. 12(4):532-542 (2002).
Gallagher et al., "The crystal structure of chorismate lyase shows a new fold and a tightly retained product," Proteins 44:304-311 (2001).
Garras et al., "Subcellular localisation and induction of NADH-sensitive acetyl-CoA hydrolase and propionyl-CoA hydrolase activities in rat liver under lipogenic conditions after treatment with sulfur-substituted fatty acids," Biochim. Biophys Acta 1255(2):154-160 (1995).
Garvie, "Bacterial lactate dehydrogenases," Microbiol. Rev. 44:106-139 (1980).
Genda et al., "Purification and characterization of fumarase from Corynebacterium glutamicum," Biosci. Biotechnol. Biochem. 70:1102-1109 (2006).
Gerhardt et al. "Fermentation of 4-aminobutyrate by Clostridium aminobutyricum: cloning of two genes involved in the formation dehydration of 4-hydroxybutyrl-CoA," Arch. Microbiol. 174:189-199 (2000).
Gerischer et al., "mRNA Analysis of the adc Gene Region of Clostridium acetobutylicum during the Shift to Solventogenesis," Journal of Bacteriology, 174 (2):426-433 (1992).
Giesel and Simon, "On the occurrence of enoate reductase and 2-oxo-carboxylate reductase in clostridia and some observations on the amino acid fermentation by Peptostreptococcus anaerobius," Arch. Microbiol. 135(1):51-57 (1983).
Glasemacher et al., "Purification and properties of acetyl-CoA synthetase (ADP-forming), an archael enzyme of acetate formation and ATP synthesis, from the hyperthermophile Pyrococcus furiosus," Eur. J. Biochem. 244:561-567 (1997).
Göbel et al., "Degradation of Aromatics and Chloroaromatics by Pseudomonas sp. Strain B13: Cloning, Characterization, and analy-

(56) References Cited

OTHER PUBLICATIONS sis of Sequences Encoding 3-Oxoadipate:Succinyl-Coenzyme A (CoA) Transferase and 3-oxoaipyl-CoA Thiolase," *J. Bacteriol.* 184(1):216-223 (2002).
Goldberg et al., "Improved Conversion of Fumarate to Succinate by *Escherichia coli* Strains Amplified for Fumarate Reductase," *Appl. Environ. Microbiol.* 45:1838-1847 (1983).
Gong et al., "Specificity Determinants for the Pyruvate Dehydrogenase Component Reaction Mapped with Mutated and Prosthetic Group Modified Lipoyl Domains," *J. Biol. Chem.* 275(18):13645-13653 (2000).
González and Robb, "Genetic analysis of Carboxydothermus hydrogenoformans carbon monoxide dehydrogenase genes cooF and cooS," *FEMS Microbiol. Lett.* 191(2):243-247 (2000).
Gonzalez et al., "Characterization of a (2R,3R)-2,3-Butanediol Dehydrogenase as the *Saccharomyces cerevisiae* YAL060W Gene Product," *J. Biol. Chem.* 275(46):35876-35885 (2000).
Gonzalez-Pajuelo et al., "Metabolic engineering of *Clostridium acetobutylicum* for the industrial production of 1,3-propanediol from glycerol," *Met. Eng.* 7:329-336 (2005).
Gordon and Doelle, "Purification, properties and immunological relationship of L(+)-lactate dehydrogenase from Lactobacillus casei," *Eur. J. Biochem.* 67:543-555 (1976).
Goupil et al., "Imbalance of Leucine Flux in Lactococcus lactis and Its Use for the Isolation of Diacetyl-Overproducing Strains," *Appl. Environ. Microbiol.* 62(7):2636-2640 (1996).
Gourley et al., "The two types of 3-dehydroquinase have distinct structures but catalyze the same overall reaction," *Nat. Struct. Biol.* 6:521-525 (1999).
Green and Bennett, "Genetic manipulation of acid and solvent formation in clostridium acetobutylicum ATCC 824," *Biotechnol. Bioeng.* 58(2-3):215-221 (1998).
Green and Nichols, "p-Aminobenzoate biosynthesis in *Escherichia coli*. Purification of aminodeoxychorismate lyase and cloning of pabC," *J. Biol. Chem.* 266:12971-12975 (1991).
Green et al., "Characterization and sequence of *Escherichia coli pabC*, the gene encoding aminodeoxychorismate lyase, a pyridoxal phosphate-containing enzyme," *J. Bacteriol.* 174:5317-5323 (1992).
Grethlein and Jain, "Bioprocessing of coal-derived synthesis gases by anaerobic bacteria," *Trends Biotech.* 10:418-423 (1992).
Grochowski et al., "Identification of lactaldehyde dehydrogenase in *Methanocaldococcus jannaschii* and its involvement in production of lactate for $F_{420}$ biosynthesis," *J. Bacteriol.* 188(8):2836-2844 (2006).
Gruez et al., "Crystal structure and kinetics identify *Escherichia coli* YdcW gene product as a medium-chain aldehyde dehydrogenase," *J. Mol. Biol.* 343(1):29-41 (2004).
Guest et al., "The fumarase genes of *Escherichia coli*: location of the fumB gene and discovery of a new gene (fumC)," *J. Gen. Microbiol.* 131(11):2971-2984 (1985).
Guettler et al., "*Actinobacillus succinogenes* sp. nov., a novel succinic-acid-producing strain from the bovine rumen," *Int. J. Syst. Bacteriol.* 49:207-216 (1999).
Guo and Bhattacharjee, "Posttranslational activation, site-directed mutation and phylogenetic analyses of the lysine biosynthesis enzymes α-aminoadipate reductase Lys1p (AAR) and the phosphopantetheinyl transferase Lys7p (PPTase) from Schizosaccharomyces pombe," *Yeast* 21:1279-1288 (2004).
Guo and Bhattacharjee, "Site-directed mutational analysis of the novel catalytic domains of α-aminoadipate reductase (Lys2p) from candida albicans," *Mol. Gen. Gemonics* 269:271-279 (2003).
Guterman et al., "Generation of phenylpropanoid pathway-derived volatiles in transgenic plants: rose alcohol acetyltransferase produces phenylethyl acetate and benzyl acetate in petunia flowers," *Plant Mol. Biol.* 60(4):555-563 (2006).
Hadfield et al., "Active Site Analysis of the Potential Antimicrobial Target Aspartate Semialdehyde Dehydrogenase," *Biochemistry* 40:14475-14483 (2001).

Hadfield et al., "Structure of Aspartate-β-semialdehyde Dehydrogenase from *Escherichia coli*, A Key Enzyme in the Aspartate Family of Amino Acid Biosynthesis," *J. Mol. Biol.* 289:991-1002 (1999).
Hahm et al., "Characterization and evaluation of a pta (phosphotransacetylase) negative mutant of *Escherichia coli* HB101 as a production host of foreign lipase," *Appl. Microbiol. Biotechnol.* 42:100-107 (1994).
Hagemeier et al., "Insight into the mechanism of biological methanol activation based on the crystal structure of the methanol-cobalamin methyltransferase complex," *Proc. Natl. Acad. Sci. U.S.A.* 103(50):18917-18922 (2006).
Hagishita et al., "Cloning and expression of the gene for serine-glyoxylate aminotransferase from an obligate methylotroph Hyphomicrobium methylovorum GM2," *Eur. J. Biochem.* 241(1):1-5 (1996).
Haller et al., "Discovering new enzymes and metabolic pathways: conversion of succinate to propionate by *Escherichia coli*," *Biochem.* 39(16):4622-4629 (2000).
Han et al., "Biochemical characterization and inhibitor discovery of shikimate dehydrogenase from Helicobacter pylori," *FEBS J.* 273:4682-4692 (2006).
Han et al., "Comparative characterization of Aedes 3-hydroxykynurenine transaminase/alanine glyoxylate transaminase and *Drosophila* serine pyruvate aminotransferase," FEBS Lett. 527(1-3):199-204 (2002).
Hanai et al., "Engineered synthetic pathway for isopropanol production in *Escherichia coli*," *Appl. Environ. Microbiol.* 73(24):7814-7818 (2007).
Hansen et al., "De novo biosynthesis of vanillin in fission yeast (*Schizosaccharomyces pombe*) and baker's yeast (*Saccharomyces cerevisiae*)," *Appl. Environ. Microbiol.* 75(9):2765-2774 (2009).
Hansford, "Control of mitochondrial substrate oxidation," *Curr. Top Bioenergy* 10:217-278 (1980).
Harder, "Anaerobic degradation of cyclohexane-1,2-diol by a new *Azoarcus* species," *Arch. Microbiol.* 168:199-204 (1997).
Harker and Bramley, "Expression of prokaryotic 1-deoxy-D-xylulose-5-phosphatases in *Escherichia coli* increases carotenoid and ubiquinone biosynthesis," *FEBS Lett.* 448:115-119 (1999).
Harms and Thauer, "Methylcobalamin: Coenzyme M methyltransferase isoenzymes MtaA and MtbA from Methanosarcina barkeri. Cloning, sequencing and differential transcription of the encoding genes, and functional overexpression of the mtaA gene in *Escherichia coli*," *Eur. J. Biochem.* 235(3):653-659 (1996).
Harrison and Harwood, "The pimFABCDE operon from Rhodopseudomonas palustris mediates dicarboxylic acid degradation and participates in anaerobic benzoate degradation," *Microbiology* 151:727-736 (2005).
Hartel et al., "Purification of glutaryl-CoA dehydrogenase from *Pseudomonas* sp., an enzyme involved in the anaerobic degradation of benzoate," *Arch. Mirobiol.* 159:174-181 (1993).
Harwood et al., "Anaerobic metabolism of aromatic compounds via the benzoyl-CoA pathway," *FEMS Microbiol. Rev.* 22:439-458 (1999).
Hasan and Nester, "Dehydroquinate synthase in Bacillus subtilis. An enzyme associated with chorismate synthase and flavin reductase," *J. Biol. Chem.* 253:4999-5004 (1978).
Hasegawa et al., "Transcriptional regulation of ketone body-utilizing enzyme, acetoacetyl-CoA synthetase, by C/EBPα during adipocyte differentiation," *Biochim. Biophys. Acta.* 1779(6-7):414-419 (2008).
Haselbeck and McAlister-Henn, "Isolation, nucleotide sequence, and disruption of the *Saccharomyces cerevisiae* gene encoding mitochondrial NADP(H)-specific isocitrate dehydrogenase," *J. Biol. Chem.* 266(4):2339-2345 (1991).
Hashimoto et al., "Activation of L-Lysine ε-Dehydrogenase from Agrobacterium tumefaciens by Several Amino Acids and Monocarboxylates," *J. Biochem.* 106:76-80 (1989).
Hawes et al., "Primary structure and tissue-specific expression of human β-hydroxyisobutyryl-Coenzyme A hydrolase," *J. Biol. Chem.* 271:26430-26434 (1996).

(56) References Cited

OTHER PUBLICATIONS

Hawes et al., "Mammalian 3-hydroxyisobutyrate dehydrogenase," *Methods Enzymol.* 324:218-228 (2000).
Hayashi et al., "Properties of 2-hydroxyglutarate dehydrogenase from Fusobacterium," *J. Nihon. Univ. Sch. Dent.* 28(1):12-21 (1986).
Hayden et al., "Glutamate dehydrogenase of Halobacterium salinartun: evidence that the gene sequence currently assigned to the NADP$^+$-dependent enzyme is in fact that of the NAD$^+$-dependent glutamate dehydrogenase," *FEMS Microbiol. Lett.* 211:37-41 (2002).
Hayes et al., "The Biofine Process: Production of Levulinic Acid, Furfural and Formic Acid from Lignocellulosic Feedstocks," In *Biorefineries: Industrial Proceses and Products,* Wiley, Weinheim, Germany, 139-164. (2006).
Haywood et al., "Characterization of two 3-ketothiolases possessing differing substrate specificities in the polyhydroxyalkanoate synthesizing organism Alcaligenes eutrophus," *FEMS Microbiol. Lett.* 52:91-96 (1988).
Heidlas and Tressl, "Purification and Properties of two oxidoreductases catalyzing the enantioselective reduction of diacetyl and other diketones from baker's yeast," *Eur. J. Biochem.* 188:165-174 (1990).
Heipieper and Isken, "Ethanol tolerance and membrane fatty acid adaptation in adh multiple and null mutants of *Kluyveromyces lactis,*" *Res. Microbiol.* 151:(9):777-784 (2000).
Heller et al., "Cloning and expression of the gene for the vitamin B$_{12}$ receptor protein in the outer membrane of *Escherichia coli,*" *J. Bacteriol.* 161:896-903 (1985).
Hemschemeier et al., "Biochemical and physiological characterization of the pyruvate formate-lyase Pf11 of Chlamydomonas reinhardtii, a typically bacterial enzyme in eukaryotic alga," *Eukaryot. Cell* 7:518-526 (2008).
Hendrick et al., "The Nonoxidative Decarboxylation of Hydroxypyruvate in Mammalian Systems," *Arch. Biochem. Biophys.* 105:261-269 (1964).
Henne et al., "Construction of environmental DNA libraries in *Escherichia coli* and screening for the presence of genes conferring utilization of 4-hydroxybutyrate," *Appl. Environ. Microbiol.* 65(9):3901-3907 (1999).
Hennessy et al., "The reactivity of gamma-hydroxybutyric acid (GHB) and gamma-butyrolactone (GBL) in alcoholic solutions," *J. Forensic. Sci.* 49(6):1220-1229 (2004). (provided electronically by publisher as pp. 1-10).
Henstra et al., "Microbiology of synthesis gas fermentation for biofuel production," *Curr. Opin. Biotechnol.* 18:200-206 (2007).
Herrmann et al., "Energy Conservation via Electron-Transferring Flavoprotein in Anaerobic Bacteria," *J. Bacteriol.* 190(3):784-791 (2008).
Herrmann et al., "Two β-alanyl-CoA:ammonia lyases in Clostridium propionicum," *FEBS J.* 272:813-821 (2005).
Hespell et al., "Stabilization of pet Operon Plasmids and Ethanol Production in *Escherichia coli* Strains Lacking Lactate Dehydrogenase and Pyruvate Formate-Lyase Activities," *Appl. Environ. Microbiol.* 62:4594-4597 (Dec. 1996).
Hesslinger et al., "Novel keto acid formate-lyase and propionate kinase enzymes are components of an anaerobic pathway in *Escherichia coli* that degrades L-threonine to propionate," *Mol. Microbiol.* 27(2):477-492 (1998).
Hester et al., "Purification of active E1α$_2$β$_2$ of Pseudomonas putida branched-chain-oxoacid dehydrogenase," *Eur. J. Biochem.* 233:828-836 (1995).
Hetzel et al., "Acryloyl-CoA reductase from clostridium propionicum. An enzyme complex of pripionyl-CoA dehydrogenase and electron-transferring flavoprotein," *Eur. J. Biochem.* 270:902-910 (2003).
Heydari et al., "Highly Stable L-Lysine 6-Dehydrogenase from the thermophile Geobacillus stearothermophilus Isolated from a Japanese Hot Spring: characterization, Gene Cloning and sequencing, and Expression," *Appl. Environ. Microbiol.* 70(2):937-942 (2004).
Hijarrubia et al., "Domain Structure Characterization of the Multifunctional α-Aminoadipate Reductase from Penicillium chrysogenum by Limited Proteolysis," *J. Biol. Chem.* 278(10):8250-8256 (2003).
Hill et al., "PCR based gene engineering of the Vibrio harveyi lux operon and the *Escherichia coli* trp operon provides for biochemically functional native and fused gene products," *Mol. Gen. Genet.* 226:41-48 (1991).
Hillmer and Gottschalk, "Particulate Nature of Enzymes Involved in the Fermentation of Ethanol and Acetate by Clostridium Kluyveri," *FEBS Lett.* 21(3):351-354 (1974).
Hillmer and Gottschalk, "Solubilization and partial characterization of particulate dehydrogenases from Clostridium kluyveri," *Biochim. Biophys. Acta* 334:12-23 (1974).
Hirano et al., "Purification and characerization of the Alcohol Dehydrogenase with a Broad Substrate Specificy Originated from 2-Phenylethanol-Assimilating *Brevibacterium* sp. KU 1309," *J. Biosci. Bioenn.* 100(3): 318-322 (2005).
Hiser et al., "ERG10 from *Saccharomyces cerevisiae* encodes acetoacetyl-CoA thiolase," *J. Biol. Chem.* 269:31383-31389 (1994).
Ho et al., "Regulation of serine biosynthesis in *Arabidopsis.* Crucial role of plastidic 3-phosphoglycerate dehydrogenase in non-photosynthetic tissues," *J. Biol. Chem.* 274:397-402 (1999).
Hoang et al., "A broad-host-range Flp-FRT recombination system for site-specific excision of chromosomally-located DNA sequences: application for isolation of unmarked Pseudomonas aeruginosa mutants," *Gene* 212(1):77-86 (1998).
Hoffmeister et al., "Mitochondrial trans-2-enoyl-CoA reductase of wax ester fermentation from Euglena gracilis defines a new family of enzymes involved in lipid synthesis," *J. Biol. Chem.* 280(6):4329-4338 (2005).
Hofmeister and Buckel, "(R)-lactyl-CoA dehydratase from Clostridium propionicum. Stereochemistry of the dehydration of (R)-2-hydroxybutyryl-CoA to crotonly-CoA," *Eur J. Biochem.* 206(2):547-552 (1992).
Hofmeister et al., "Cloning and expression of the two genes coding for $_L$-serine dehydratase from Peptostreptococcus asaccharolyticus: relationship of the iron-sulfur protein to both $_L$-serine dehydratases from *Escherichia coli,*" *J. Bacteriol.* 179(15):4937-4941 (1997).
Hogan et al., "Improved Specificity toward Substrates with Positively Charged Side chains by Site-Directed Mutagenesis of the $_L$-Lactate Dehydrogenase of Bacillus stearothermophilus," *Biochemistry* 34:4225-4230 (1995).
Holloway and Marsh, "Adenosylcobalamin-dependent glutamate mutase from Clostridium tetanomorphum. Overexpression in *Escherichia coli,* purification, and characterization of the recombinant enzyme," *J. Biol. Chem.* 269(32):20425-20430 (1994).
Holms, "The central metabolic pathways in *Escherichia coli:* relationship between flux and control at a branch point, efficiency of conversion to biomass, and excretion of acetate," *Curr. Top Cell. Regul.* 28:69-105 (1986).
Hong and Lee, "Metabolic flux analysis for succinic acid production by recombinant *Escherichia coli* with amplified malic enzyme activity," *Biotechnol. Bioeng.* 74(2):89-95 (2001).
Hong and Lee, "Enhanced Production of Succinic Acid by Metabolically Engineered *Escherichia coli* with Amplified Activities of Malic Enzyme and Fumarase," *Biotechnol. Bioprocess. Eng.* 9:4:252-255 (2004).
Hong et al., "Importance of redox balance on the production of succinic acid by metabolically engineered *Escherichia coli,*" *Appl. Microbiol. Biotechnol.* 58:286-290 (2002).
Horswill and Escalante-Semerena, "In vitro conversion of propionate to pyruvate by *Salmonella enterica* enzymes: 2-methylcitrate dehydratase (PrpD) and aconitas Enzymes catalyze the conversion of 2-methylcitrate to 2-methylisocitrate," *Biochemistry* 40(15):4703-4713 (2001).
Horton et al., "Heterologous expression of the *Saccharomyces cerevisiae* alcohol acetyltransferase genes in Clostridium acetobutylicum and *Escherichia coli* for the production of isoamyl acetate," *J. Ind. Microbiol. Biotechnol.* 30(7):427-432 (2003).

(56) References Cited

OTHER PUBLICATIONS

Hsu et al., "Expression of an aromatic-dependent decarboxylase which provides growth-essential $CO_2$ equivalents for the acetogenic (Wood) pathway of *Clostridium thermoaceticum*," J. Bacteriol. 172:5901-5907 (1990).

Huang et al., "Identification and characterization of a second butyrate kinase from Clostridium acetobutylicum ATCC 824," J. Mol. Microbiol. Biotechnol. 2(1):33-38 (2000).

Hughes et al.,"Evidence for isofinictional enzymes in the degradation of phenol, m- and p-toluate, and p-cresol via catechol meta-cleavage pathways in Alcaligenes eutrophus," J. Bacteriol. 158(1):79-83 (1984).

Hugler et al., "Malonyl-Coenzyme A Reductase from Chloroflexus aurantiacus, a Key Enzyme of the 3-Hydroxypropionate Cycle for Autotrophic CO2 Fixation," J. Bacteriol. 184(9):2404-2410 (2002).

Husain and Steenkamp, "Partial purification and characterization of glutaryl-Coenzyme A dehydrogenase, electron transfer flavoprotein, and electron transfer flavoprotein-Q oxidoreductase from Paracoccus denitrificans," J. Bacteriol. 163:709-715 (1985).

Hustede et al., "Cloning of poly(3-hydroxybutyric acid) synthase genes of Rhodobacter sphaeroides and Rhodospirillum rubum and heterologous expression in Alcaligenes eutrophys," FEMS Microbiol. Lett. 93:285-290 (1992).

Ibarra et al., "*Escherichia coli* K-12 undergoes adaptive evolution to achieve in silico predicted optimal growth," Nature 420(6912):186-189 (2002).

Ichikawa et al., "Catalytic reaction of 1,3-butanediol over solid acids," J. Mol. Catalysis A Chem. 256:106-112 (2006).

Ichikawa et al., "PIO study on 1,3-butanediol dehydration over $CeO_2$ (1 1 1) surface," J. Mol. Catalysis A Chem. 231:181-189 (2005).

Ingoldsby et al., "The discovery of four distinct glutamate dehydrogenase genes in a strain of Halobacterium salinarum," Gene 349:237-244 (2005).

Ingram and Vreeland, "Differential-Effects of Ethanol and Hexanol on the *Escherichia-coli* Cell-Envelope," J. Bacteriol. 144:481-488 (1980).

International Search Report for PCT/JP2009/057547 dated May 19, 2009.

Inui et al., "Occurrence of Oxygen-Sensitive, $NADP^+$-Dependent Pyruvate-Dehydrogenase in Mitochondria of Euglena-Gracilis," J. Biochem. 96:931-934 (1984).

Inui et al., "Pyruvate-$NADP^+$ Oxidoreductase from Euglena-Gracilis—the Kinetic-Properties of the Enzyme," Arch. Biochem Bipophys. 274:434-442 (1989).

Inui et al., "Purification and characterization of pyruvate:$NADP^+$ oxidoreductase in Euglena gracilis," J. Biol. Chem. 262(19):9130-9135 (1987).

Inui et al., "Pyruvate:$NADP^+$ oxidoreductase from Euglena gracilis: mechanism of $O_2$-inactivation of the enzyme and its stability in the aerobe," Arch. Biochem. Biophys. 280:292-298 (1990).

Inui et al., "The physiological role of oxygen-sensitive pyruvate dehydrogenase in mitochondrial fatty acid synthesis in Euglena gracilis," Arch. Biochem. Biophys. 237(2):423-429 (1985).

Ishida et al., "Efficient production of $_L$-Lactic acid by metabolically engineered *Saccharomyces cerevisiae* with a genome-integrated $_L$-lactate dehydrogenase gene," Appl. Envirom. Microbiol. 71:1964-1970 (2005).

Ishige et al., "Wax ester production from n-alkanes by *Acinetobacter* sp. strain M-1: ultrastructure of cellular inclusions and role of acyl Coenzyme A reductase," Appl. Environ. Microbiol. 68(3):1192-1195 (2002).

Ismaiel et al., "Purification and Characterization of a Primary-Secondary Alcohol Dehydrogenase from Two Strains of Clostridium beijerinckii," Journal of Bacteriology, 175(16):5097-5105 (1993).

Ismail et al., "Functional genomics by NMR spectroscopy. Phenylacetate catabolism in *Escherichia coli*," Eur. J. Biochem. 270(14):3047-3054 (2003).

Ito et al., "$_D$-3-hydroxybutyrate dehydrogenase from Pseudomonas fragi: molecular cloning of the enzyme gene and crystal structure of the enzyme," J. Mol. Biol. 355(4):722-733 (2006).

Iverson et al., "Structure of the *Escherichia coli* fumarate reductase respiratory complex," Science 284(5422):1961-1966 (1999).

Iwakura et al., "Studies on regulatory functions of malic enzymes. VI. Purification and molecular properties of NADP-linked malic enzyme from *Escherichia coli* W," J. Biochem. 85:1355-1365 (1979).

Izumi et al., "Structure and Mechanism of HpcG, a Hydratase in the Homoprotocatechuate Degradation Pathway of *Escherichia coli*," J. Mol. Biol. 370:899-911 (2007).

Jacobi et al., "The hyp operon gene products are required for the maturation of catalytically active hydrogenase isoenzymes in *Escherichia coli*," Arch. Microbiol. 158(6):444-451 (1992).

Jäger and Färber, "Die Alanatreduktion von β-Carbonyl-oxalylsäure-estern," Chem. Ber. 92:2492-2499 (1959).

James and Viola, "Production and characterization of bifunctional enzymes. Domain swapping to produce new bifunctional enzymes in the aspartate pathway," Biochemistry 41(11) 3720-3725 (2002).

Jansen and Wanders, "$_L$-2-hydroxyglutarate dehydrogenase: identification of a novel enzyme activity in rat and human liver. Implications for $_L$-2-hydroxyglutaric academia," Biochim. Biophys. Acta 1225(1):53-56 (1993).

Janssen, "Propanol as an end product of theonine fermentation," Arch. Microbiol. 182:482-486 (2004).

Jantama et al., "Combining metabolic engineering and metabolic evolution to develop nonrecombinant strains of *Escherichia coli* C that produce succinate and malate," Biotechnol. Bioeng. 99(5):1140-1153 (2008).

Jantama et al., "Eliminating Side Products and Increasing succinate Yields in Engineered Strains of *Escherichia coli* C," Biotechnol. Bioeng. 101(5) 881-893 (2008).

Jeng et al., "Ornithine degradation in Clostridium sticklandii; pyridoxial phosphate and Coenzyme A dependent thiolytic cleavage of 2-amino-4-ketopentanoate to alanine and acetyl Coenzyme A," Biochemistry 13(14):2898-2903 (1974).

Jenkins and Nunn, "Genetic and molecular characterization of the genes involved in short-chain fatty acid degradation in *Escherichia coli*: the ato system," J. Bacteriol. 169(1):42-52 (1987).

Jennert et al., "Gene transfer to Clostridium cellulolyticum ATCC 35319," Microbiol. 146:3071-3080 (2000).

Jeon et al., "Heterologous expression of the alcohol dehydrogenase (adhI) gene from Geobacillius thermoglucosidasius strain M10EXG," J. Biotechnol. 135:127-133 (2008).

Jewell et al., "Bioconversion of propionic, valeric and 4-hydroxybutyric acids into the corresponding alcohols by Clostridium acetobutylicum NRRL 527," Curr. Microbiol. 13(4):215-219 (1986).

Johanson et al., "Strain engineering for steroselective bioreduction of dicarbonyl compounds by yeast reductases," FEMS Yeast Res. 5:513-525 (2005).

Jojima et al., "Production of isopropanol by metabolically engineered *Esherichia coli*," Appl. Microbiol. Biotechnol., 77:1219-1224 (2008).

Jones et al., "Acetone-Butanol Fermentation Revisited," 50(4):484-524 (1986).

Kaclikova et al., "Fumaric acid overproduction in yeast mutants deficient in fumarase," FEMS Microbiol. Lett. 91(2):101-106 (1992).

Kakimoto et al., "β-aminoisobutyrate-α-ketoglutarate transaminase in relation to β-aminoisobutyric aciduria," Biochim. Biophys. Acta 156(2):374-380 (1968).

Kalpos, "On the mammalian acetone metabolism: from chemistry to clinical implications," Biochim. Biophys. Acta 1621(2):122-139 (2003).

Kalscheuer and Steinbuchel, "A novel bifunctional wax ester synthase/acyl-CoA:diacylglycerol acyltransferase mediates wax ester and triacylglycerol biosynthesis in Acinetobacter calcoaceticus ADP1," J. Biol. Chem. 278(10):8075-8082 (2003).

(56) References Cited

OTHER PUBLICATIONS

Kalscheuer et al., "Analysis of storage lipid accumulation in Alcanivorax borkumensis: Evidence for alternative triacylglycerol biosynthesis routes in bacteria," *J. Bacteriol.* 189(3):918-928 (2007).
Kanagawa et al., "Characterization of the 6-aminohexanoate-dimer hydrolase from *Pseudomonas* sp. NK87," *J. Gen. Microbiol.* 139(4):787-795 (1993).
Kanao et al., "Characterization of isocitrate dehydrogenase from the green sulfur bacterium Chlorbium limicola. A carbon dioxide-fixing enzyme in the reductive tricarboxylic acid cycle," *Eur. J. Biochem.* 269(7):1926-1931 (2002).
Kanehisa and Goto, "KEGG: Kyoto Encyclopedia of Genes and Genomes database," *Nucleic Acids Res.* 28(1):27-30 (2000).
Kapatral et al., "Genome Sequence and Analysis of the Oral Bacterium Fusobacterium nucleatum Strain ATCC 25586," *J. Bacteriol.* 184(7):2005-2018 (2002).
Kasberg et al., "Cloning, characterization, and sequence analysis of the clcE gene encoding the maleylacetate reductase of *Pseufomonas* sp. Strain B13," *J. Bacteriol.* 179:3801-3803 (1997).
Kaschabek and Reineke, "Degradation of chloroaromatics: purification and characterization of maleylacetate reductase from *Pseudomonas* sp. Strain B13," *J. Bacteriol.* 175:6075-6081 (1993).
Kaschabek and Reineke, "Maleylacetate reductase of *Pseufomonas* sp. Strain B13: specificity of substrate conversion and halide elimination," *J. Bacteriol.* 177:320-325 (1995).
Kaschabek et al., "Degradation of aromatics and chloroaromatics by *Pseudomonas* sp. strain B13: purification and characterization of 3-oxoadipate:succinyl-Coenzyme A (CoA) transferase and 3-oxoadipyl-CoA thiolase," *J. Bacteriol.* 184(1):207-215 (2002).
Kashket and Cao, "Isolation of a Degeneration-Resistant Mutant of clostridium acetobutylicum NCIMB 8052," *Appl. Environ. Microbiol.* 59:4198-4202 (1993).
Katz et al., "Screening of two complementary collections of *Saccharomyces cerevisiae* to identify enzymes involved in stereoselective reductions of specific carbonyl compounds: an alternative to protein purification," *Enzyme Microb. Technol.* 33:163-172 (2003).
Kazahaya et al, "Aerobic Dissimilation of Glucose by Heterolactic Bacteria III. Aldehyde dehydrogenase and alcohol dehydrogenase of luconostoc mesenteroids" *J. Gen. Appl. Microbiol.* 18(1):43-55 (1972).
Kehrer et al., "Glycerate kinase of the hyperthermophilic archaeon Thermoproteus tenax: new insights into the phylogenetic distribution and physiological role of members of the three different glycerate kinase classes," *BMC Genomics* 8:301 (2007).
Kellum and Drake, "Effects of cultivation gas phase on hydrogenase of the acetogen Clostridium thermoaceticum," *J. Bacteriol.* 160(1):466-469 (1984).
Kenealy et al., "Biochemical Aspects of Fumaric Acid Accumulation by *Rhizopus arrhizus*," *Appl. Environ. Microbiol.* 52:128-133 (1986).
Kerby et al., "Carbon Monoxide-Dependent Growth of Rhodospirillum rubrum," *J. Bacteriol.* 177:2241-2244 (1995).
Kerby, et al., "Genetic and physiological characterization of the Rhodospirillum rubrum carbon monoxide dehydrogenase system," *J. Bacteriol.* 174(16):5284-5294 (1992).
Kern et al., "Isoamyl alcohol-induced morphological change in *Saccharomyces cerevisiae* involves increases in mitochondria and cell wall chitin content," *FEMS Yeast Res.* 5:43-49 (2004).
Kessler et al., "Pyruvate-formate-lyase-deactivase and acetyl-CoA reductase activities of *Escherichia coli* reside on a polymeric protein particle encoded by adhE," *FEBS Lett.* 281(1-2):59-63 (1991).
Kim et al., "2-Hydroxyisocaproyl-CoA dehydratase and its activator from Clostridium difficile," *FEBS J.* 272:550-561 (2005).
Kim et al., "Construction of an *Escherichia coil* K-12 Mutant for Homoethanologic Fermentation of Glucose or Xylose without Foreign Genes," *Appl. Environ. Microbiol.* 73(6):1766-1771 (2007).

Kim et al., "Dehydration of (R)-2-hydroxyacyl-CoA to enoyl-CoA in the fermentation of a-amino acids by anaerobic bacteria," *FEMS Microbiol. Rev.* 28:455-468 (2004).
Kim et al., "Dihydrolipoamide dehydrogenase mutation alters the NADH sensitivity of pyruvate dehydrogenase complex of *Escherichia coli* K-12," *J. Bacteriol.* 190:3851-3858 (2008).
Kinoshita, "Purification of two alcohol dehydrogenases from Zymomonas mobilis and their properties," *Appl. Microbiol. Biotechnol.* 22:249-254 (1985).
Klasson, et al., "Biological conversion of coal and coal-derived synthesis gas," *Fuel* 72(12):1673-1678 (1993).
Klatt et al., "Comparative genomics provides evidence for the 3-hydroxypropionate autotrophic pathway in filamentous anoxygenic phototrophic bacteria and in hot spring microbial mats," *Environ. Microbiol.* 9:2067-2078 (2007).
Kleanthous et al., "A comparison of the enzymological and biophysical properties of two distinct classes of dehydroquinase enzymes," *Biochem. J.* 282(Pt3):687-695 (1992).
Klyosov, "Kinetics and specificity of human liver aldehyde dehydrogenases toward aliphatic, aromatic, and fused polycyclic aldehydes," *Biochemistry* 35(14):4457-4467 (1996).
Knapp et al., "Crystal Structure of the Truncated Cubic Core component of the *Escherichia coli* 2-Oxoglutarate Dehydrogenase Multienzyme Complex," *J. Mol. Biol.* 280:655-668 (1998).
Knappe and Sawers, "A radical-chemical route to acetyl-CoA: the anaerobically induced pyruvate formate-lyase system of *Escherichia coli*," FEMS. Microbiol. Rev. 75:383-398 (1990).
Knappe et al., "Post-translational activation introduces a free radical into pyruvate formate-lyase," Proc. Natl. Acad. Sci. U.S.A. 81:1332-1335 (1984).
Kobayashi et al., "Physicochemical, catalytic, and immunochemical properties of fumarases crystallized separately from mitochondrial and cytosolic fractions of rat liver," J. Biochem. 89(6):1923-1931 (1981).
Koch and Fuchs, "Enzymatic reduction of benzoyl-CoA to alicyclic compounds, a key reaction in anaerobic aromatic metabolism," *Eur. J. Biochem.* 205:195-202 (1992).
Koch et al., "Products of enzymatic reduction of benzoyl-CoA, a key reaction in anaerobic aromatic metabolism," *Eur. J. Biochem.* 211:649-661 (1993).
Koland and Gennis, "Proximity of Reactive Cysteine Residue and Flavin in *Escherichia coli* Pyruvate Oxidase As Estimated by Flourescence Energy Transfer," *Biochemistry* 21:4438-4442 (1982).
Kollmann-Koch et al.,"Nicotinic acid metabolism. Dimethylmaleate hydratase," *Hoppe Seylers Z Physiol Chem.* 365:s. 847-857 (1984).
Koo et al., "Cloning and characterization of the bifunctional alcohol/acetaldehyde dehydrogenase gene (adhE) in Leuconostoc mesenteroides isolated from kimchi," *Biotechnol. Lett.* 27(7):505-510 (2005).
Korbert et al., "Crystallization of the NADP+-dependent Glutamate Dehydrogenase from *Escherichia coli*," J. Mol. Biol. 234:1270-1273 (1993).
Korolev et al., "Autotracing of *Escherichia coil* acetate CoA-transferase α-subunit structure using 3.4 Å MAD and 1.9 l native data," *Acta. Crystallogr. D. Biol. Crystallogr.* 58(Pt 12):2116-2121 (2002).
Korotkova and Lidstrom, "Connection between poly-β-hydroxybutyrate biosynthesis and growth on $C_1$ and $C_2$ compounds in the methylotroph Methylobacterium extorquens AM1," *J. Bacteriol.* 183(3):1038-1046 (2001).
Kort et al., "Glutamate dehydrogenase from the hyperthermophilic bacterium Thermotoga maritima: molecular characterization and phylogenetic implications," *Extremophiles* 1:52-60 (1997).
Kosaka et al., "Characterization of the sol operon in butanol-hyperproducing Clostridium saccharoperbutylacetonicum strain N1-4 and its degeneration mechanism," *Biosci. Biotechnol. Biochem.* 71:58-68 (2007).
Koshiba et al., "Purification and Properties of Flavin- and Molybdenum-Containing Aldehyde Oxidase from Coleoptiles of Maize," *Plant Physiol.* 110(3):781-789 (1996).

(56) References Cited

OTHER PUBLICATIONS

Kosjek et al., "Purification and characterization of a chemotolerant alcohol dehydrogenase applicable to coupled redox reactions," *Biotechnol. Bioeng.* 86(1):55-62 (2004).

Kouzarides, "Acetylation: a regulatory modification to rival phosphorylation?" *EMBO J.* 19(6):1176-1179 (2000).

Kovachy et al., "Recognition, Isolation, and Characterization of Rat Liver D-Methylmalonyl Coenzyme A Hydrolase," *J. Biol. Chem.* 258(18):11415-11421 (1983).

Kreimeyer et al., "Identification of the Last Unknown Genes in the Fermentation Pathway of Lysine," *J. Biol. Chem.* 282(10):7191-7197 (2007).

Kuchta and Abeles, "Lactate Reduction in Clostridium propionicum Purification and properties of lactyl-CoA dehydratase," *J. Biol. Chem.* 260(24):13181-13189 (1985).

Kumari et al., "Cloning, Characterization, and Functional Expression of acs, the Gene Which Encodes Acetyl Coenzyme A Synthetase in *Escherichia coli*," *J. Bacteriol.* 177(10): 2878-2886 (1995).

Kuntze et al., "6-Oxocyclohex-1-ene-1-carbonyl-Coenzyme A hydrolases from obligately anaerobic bacteria: characterization and indentification of its gene as a functional marker for aromatic compounds degrading anaerobes," *Environ. Microbiol.* 10(6):1547-1556 (2008).

Kuznetsova et al., "Enzyme genomics: Application of general enzymatic screens to discover new enzymes," *FEMS Microbiol. Rev.* 29(2):263-279 (2005).

Laempe et al., "6-Hydroxycyclohex-1-ene-1-carbonyl-CoA dehydrogenase and 6-oxocyclohex-1-ene-1-carbonyl-CoA hydrolase, enzymes of the benzoyl-CoA pathway of anaerobic aromatic metabolism in the denitrifying bacterium Thauera aromatica," *Eur. J. Biochem.* 263(2):420-429 (1999).

Lamas-Maceiras et al., "Amplification and disruption of the phenylacetyl-CoA ligase gene of Penicillium chrysogenum encoding an aryl-capping enzyme that supplies phenylacetic acid to the isopenicillin N-acyltransferase," *Biochem. J.* 395(1):147-155 (2006).

Lamed and Zeikus, "Novel NADP-linked alcohol-aldehyde/ketone oxidoreductase in thermophilic ethanologenic bacteria," *Biochem. J.* 195:183-190 (1981).

Lawrence and Roth, "Evolution of Coenzyme $B_{12}$ synthesis among enteric bacteria: evidence for loss and reacquisition of a multigene complex," *Genetics* 142(1):11-24 (1996).

Lawrence and Roth, "Thee cobalamin (Coenzyme $B_{12}$) biosynthetic genes of *Escherichia coli*," *J. Bacteriol.* 177(22):6371-6380 (1995).

Lebbink et al., "Engineering activity and stability of Thermotoga maritima glutamate dehydrogenase I. Introduction of a six-residue ion-pair network in the hinge region," *J. Mol. Biol.* 280:287-296 (1998).

Lebbink et al., "Engineering Activity and Stability of Thermotoga maritima glutamate Dehydrogenase. II: construction of a 16-Residue Ion-pair Network at the Subunit Interface," *J. Mol. Biol.* 289:357-369 (1999).

Leduc et al., "The hotdog thioesterase EntH (YbdB) plays a role in vivo in optimal enterobactin biosynthesis by interacting with the ArCP domain of EntB," *J. Bacteriol.* 189(19):7112-7126 (2007).

Lee et al., "Batch and continuous cultivation of Anaerobiospirillum succiniciproducens for the production of succinic acid from whey," *Appl. Microbiol. Biotechnol.* 54(1):23-27 (2000).

Lee et al., "Biological conversion of wood hydrolysate to succinic acid by Anaerobiospirillum succiniciproducens," *Biotechnol. Lett.* 25(2):111-114 (2003).

Lee et al., "Biosynthesis of enantiopure (S)-3-hydroxybutyric acid in metabolically engineered *Escherichia coli*," *App. Microbiol. Biotechnol.* 79:633-641 (2008).

Lee et al., "Fermentative production of chemicals that can be used for polymer synthesis," *Macromol. Biosci.* 4:157-164 (2004).

Lee et al., "Genome-based metabolic engineering of Mannheimia succiniciproducens for succinic acid productiion," *Appl. Environ. Microbiol.* 72(3):1939-1948 (2006).

Lee et al., "Isolation and characterization of a new succinic acid-producing bacterium, Mannheimia succiniciproducens MBEL55E, from bovine rumen," *Appl. Microbiol. Biotechnol.* 58(5):663-668 (2002).

Lee et al., "Metabolic engineering of *Escherichia coli* for enhanced production of succinic acid, based on genome comparison and in silico gene knockout simulation," *Appl Environ Microbiol.* 71(12):7880-7887 (2005).

Lehtio and Goldman, "The pyruvate format lyase family: sequences, structures and activation," *Protein Eng. Des.Sel.* 17:545-552 (2004).

Lei et al., "A shared binding site for NAD+ and Coenzyme A in an acetaldehyde dehydrogenase involved in bacterial degradation of aromatic compounds," *Biochemistry* 47:6870-6882 (2008).

Leonardo et al., "Anaerobic Regulation of the adhE gene, Encoding the Fermentative Alcohol Dehydrogenase of *Escherichia coli*," *J. Bacteriol.* 175(3):870-878 (1993).

Leppänen et al., "Pyruvate formate lyase is structurally homologous to type I ribonucleotide reductase," *Structure* 7:733-744 (1999).

Lessner et al., "An unconventional pathway for reduction of CO2 to methane in CO-grown Methanosarcina acetivorans revealed by proteomics," *Proc. Natl. Acad. Sci. U.S.A.* 103(47):17921-17926 (2006).

Leutwein and Heider, "Succinyl-CoA(R)-benzylsuccinate CoA-Transferase: an enzyme of the anaerobic toluene catabolic pathway in denitrifying bacteria," *J. Bacteriol.* 183(14):4288-4295 (2001).

Li et al., "Properties of Nicotinamide Adenine Dinucleotide Phosphate-Dependent Formate Dehydrogenase from Clostridium thermoaceticum," *J. Bacteriol.* 92(2):405-412 (1966).

Li, Guang-Shan, "Development of a reporter system for the study of gene expression for solvent production in Clostridium beijerinckii NRRL B592 and Clostridium acetobutylicum ATCC 824," Dissertation, Department of Biochemistry, Virginia Polytechnic Institute and State University (Sep. 1998).

Lin et al., "Genetic Reconstruction of the Aerobic Central Metabolism in *Escherichia coli* for the Absolute Aerobic Production of Succinate," *Biotechnol. Bioeng.* 89(2):148-156 (2005).

Lin et al., "Increasing the Acetyl-CoA pool in the Presence of Overexpressed Phosphoenolpynivate Carboxylase or Pyruvate Carboxylase Enhances Succinate Production in *Escherichia coli*," *Biotechnol. Prog.* 20(5):1599-1604 (2004).

Lin et al., "Metabolic engineering of aerobic succinate production systems in *Escherichia coli* to improve process productivity and achieve the maximum theoretical succinate yield," *Metab. Eng.* 7(2):116-127 (2005).

Lin, "Metabolic Network Design and Engineering in *Escherichia coli*" Ph.D. Thesis, Rice University, Dept. of Bioengineering (2005).

Lin et al., "Effect of carbon sources differing in oxidation state and transport route on succinate production in metabolically engineered *Escherichia coil*," J. Ind. Microbiol. Biotechnol. 32:87-93 (2005).

Lin et al., "Chemostat culture characterization of *Escherichia coli* mutant strains metabolically engineered for aerobic succinate production: A study of the modified metabolic network based on metabolite profile, enzyme activity, and gene expression profile," Metab. Eng. 7(5-6):337-352 (2005).

Lin et al., "Fed-batch culture of a metabolically engineered *Escherichia coli* strain designed for high-level succinate production and yield under aerobic conditions," *Biotechnol. Bioeng.* 90:775-779 (2005).

Link et al., "Methods for generating precise deletions and insertions in the genome of wild-type *Eshcerichia coli:* application to open reading frame characterization," *J. Bacteriol.* 179:6228-6237 (1997).

Lion et al., "*Clostridium carboxidivorans* sp. nov., a solvent-producing clostridium isolated from an agricultural settling lagoon, and reclassification of the acetogen *Clostridium scatologenes* strain SL1 as *Clostridium drakei* sp. nov," *Int. J. Syst. Evol. Microbiol.* 55(Pt 5):2085-2091 (2005).

Liu et al., "Microbial production of R-3-hydroxybutyric acid by recombinant *E. coli* harboring genes of phbA, phbB, and tesB," *Appl. Microbiol. Biotechnol.* 76:811-818 (2007).

(56) References Cited

OTHER PUBLICATIONS

Liu et al., "Purification and characterization of ornithine acetyltransferase from *Saccharomyces cerevisiae*," *Eur. J. Biochem.* 228:291-296 (1995).

Liu et al., "Economical succinic acid production from cane molasses by *Actinobacillus succinogenes*," *Bioresour Technol* 99(6):1736-1742 (2008).

Liu et al., "A MOFRL family glycerate kinase from the thermophilic crenarchaeon, Sulfolobus tokodaii, with unique enzymatic properties," *Biotechnol. Lett.* 31(12):1937-1941 (2009).

Ljungdahl and Andreesen, "Tungsten, a component of active formate dehydrogenase from Clostridium thermoacetium," FEBS Lett. 54:279-282 (1975).

Ljungdahl and Andreesen, "Formate dehydrogenase, a selenium-tungsten enzyme from Clostridium thermoaceticum," *Methods Enzymol.* 53:360-372 (1978).

Ljungdahl, "The Autotrophic Pathway of Acetate Synthesis in Acetogenic Bacteria," *Ann. Rev. Microbiol.* 40:415-450 (1986).

Locher et al., "Crystal structure of the Acidaminococcus fermentans 2-hydroxyglutaryl-CoA dehydratase component A," J. Mol. Biol. 307(1):297-308 (2001).

Lokanath et al., "Crystal structure of novel NADP-dependent 3-hydroxyisobutyrate dehydrogenase from Thermus thermophilus HB8," J. Mol. Biol. 352(4):905-917 (2005).

Loke et al., "Active acetyl-CoA synthase from Clostridium thermoaceticum obtained by cloning and heterologous expression of acsAB in *Escherichia coli*," *Proc. Natl. Acad. Sci. U.S.A.* 97:12530-12535 (2000).

Lopez-Barragan et al., "The bzd gene cluster, coding for anaerobic benzoate catabolism, in *Azoarcus* sp. Strain CIB," J. Bacteriol. 186(17):5762-5774 (2004).

Louis et al., "Restricted distribution of the butyrate kinase pathway among butyrate-producing bacteria from the human colon," J. Bacteriol. 186:2099-2106 (2004).

Lovell et al., "Cloning and expression in *Escherichia coli* of the Clostridium thermoaceticum gene encoding thermostable formyltetrahydrofolate synthetase," Arch. Microbiol. 149(4):280-285 (1988).

Lovell, et al., "Primary structure of the thermostable formyltetrahydrofolate synthetase from Clostridium thermoaceticum," *Biochemistry* 20(29):5687-5694 (1990).

Lu et al., "Controlled Poetntial Enzymology of Methyl Transfer Reactions Involved in Acetyl-CoA Synthesis by CO Dehydrogenase and the Corrinoid/Iron-Sulfur Protein from Clostridium thermoaceticum," *J. Biol. Chem.* 265(6):3124-3133 (1990).

Lu et al., "Sequence and expression of the gene encoding the corrinoid/iron-sulfur protein from Clostridium thermoaceticum and reconstitution of the recombinant protein to full activity," *J. Biol. Chem.* 268(8):5605-5614 (1993).

Luli and Strohl, "Comparison of Growth, Acetate Production, and Acetate Inhibition of *Escherichia coli* Strains in Batch and Fed-Batch Fermentations," Appl. Environ. Microbiol. 56:1004-1011 (1990).

Lütke-Eversloh and Steinbüchel, "Biochemical and molecular characterization of a succinate semialdehyde dehydrogenase involved in the catabolism of 4-hydroxybutyric acid in Ralstonia eutropha," FEMS Microbiol. Lett. 181(1):63-71 (1999).

Lutz and Bujard, "Independent and tight regulation of transcriptional units in *Escherichia coli* via the LacR/O, the TetR/O and AraC/I1-I2 regulatory elements," Nucleic Acids Res. 25(6):1203-1210 (1997).

Lynch et al., "SCALEs: multiscale analysis of library enrichment," *Nat. Methods* 4(1):87-93 (2007).

Lynd et al., "Microbial Cellulose Utilization: Fundamentals and Biotechnology," *Microbiol. Mol. Biol. Rev.* 66:506-577 (2002).

Macis et al., "Properties and sequence of the Coenzyme $B_{12}$-dependent glycerol dehydratase of Clostridium pasteruianum," FEMS Microbiol. Lett. 164:21-28 (1998).

Mack and Buckel, "Conversion of glutaconate CoA-transferase from Acidaminococcus fermentans into an acyl-CoA hydrolase by site-directed mutagenesis," *FEBS Lett.* 405(2):209-212 (1997).

Mack et al., "Location of the two genes encoding glutaconate Coenzyme A-transferase at the beginning of the hydroxyglutarate operon in Acidaminococcus fermentans," *Eur. J. Biochem.* 226:41-51 (1994).

Maeda et al., "Enhanced hydrogen production from glucose by metabolically engineered *Escherichia coli*," *Appl. Microbiol. Biotechnol.* 77:879-890 (2007).

Maeder et al., "The Methanosarcina barkeri genome: comparative analysis with Methanosarcina acetivorans and Methanosarcina mazei reveals extensive rearrangement within methanosarcinal genomes," *J. Bacteriol.* 188(22):7922-7931 (2006).

Maes et al., "Crystallization of ornithine acetyltransferase from yeast by counter-diffusion and preliminary x-ray study," *Acta. Crystallogr. Sect. F. Struct. Biol. Cryst. Commun.* 62(Pt 12):1294-1297 (2006).

Mahadevan and Schilling, "The effects of alternate optimal solutions in constraint-based genome-scale metabolic models," *Metab. Eng.* 5(4):264-276 (2003).

Mai and Adams, "Purification and characterization of two reversible and ADP-dependent acetyl Coenzyme A synthetases from the hyperthermophilic archaeon Pyrococcus furiosus," J. Bacteriol. 178:5897-5903 (1996.).

Maicas, S. et al., "NAD(P)H regeneration is the key for heterolactic fermentation of hexoses in Oenococcus oeni," Microbiology 148: 325-332 (2002).

Maitra and Sprinson, "5-Dehydro-3-deoxy-D-arabino-heptulosonic acid 7-phosphate. An intermediate in the 3-dehydroquinate synthase reaction," J Biol. Chem. 253:5426-5430 (1978).

Majewski and Domach, "Simple Constrained-Optimization View of Acete Overflow in *E. coli*," *Biotechnol. Bioeng.* 35(7):732-738 (1990).

Maklashina et al., "Anaerobic expression of *Escherichia coli* succinate dehydrogenase: functional replacement of fumarate reductase in the respiratory chain during anaerobic growth," *J. Bacteriol.* 180(22):5989-5996 (1998).

Manjasetty et al., "Crystallization and preliminary X-ray analysis of dmpFG-encoded 4-hydroxy-2-ketovalerate aldolase-aldehyde dehydrogenase (acylating) from *Pseudomonas* sp strain CF600," *Acta. Crystallogr. D. Biol. Crystallogr.* 57(Pt 4):582-585 (2001).

Marks et al., "Molecular cloning and characterization of (R)-3-hydroxybutyrate dehydrogenase from human heart," J. Biol. Chem. 267(22):15459-15463 (1992).

Martin et al., "Engineering a mevalonate pathway in *Escherichia coli* for production of terpenoids," *Nat. Biotechnol.* 21:796-802 (2003).

Martínez-Blanco et al., "Purification and biochemical characterization of phenylacetyl-CoA ligase from Pseudomonas putida. A specific enzyme for the catabolism of phenylacetic acid," J. Biol. Chem. 265(12):7084-7090 (1990).

Martins et al., "Crystal structure of 4-hydroxybutyryl-CoA dehydratase: radical catalysis involving a [4Fe—4S] cluster and flavin," Proc. Natl. Acad. Sci. U.S.A. 101(44):15645-15649 (2004).

Mason and Dufour, "Alcohol acetyltransferases and the significance of ester synthesis in yeast," Yeast 16(14):1287-1298 (2000).

Mat-Jan et al., "Mutants of *Escherichia coli* Deficient in the Fermentative Lactate Dehydrogenase," J. Bacteriol. 171(1):342-348 (1989).

Matsuyama et al., "Industrial production of (R)-1,3-butanediol by new biocatalysts," *J. Mol. Catal. B: Enzym.* 11:513-521 (2001).

Matta et al., "Interactions of the antizyme AtoC with regulatory elements of the *Escherichia coli* atoDAEB operon," *J. Bacteriol.* 189(17):6324-6332 (2007).

Mattevi et al., "Atomic structure of the cubic core of the pyruvate dehydrogenase multienzyme complex," *Science* 255(5051):1544-1550 (1992).

Matthies and Schink, "Reciprocal Isomerization of Butyrate and Isobutyrate by the Strictly Anaerobic Bacterium Strain WoG13 and Methanogenic Isobutyrate Degradation by a Defined Triculture," *Appl. Environ. Microbiol.* 58(5):1435-1439 (1992).

(56) References Cited

OTHER PUBLICATIONS

Maurus et al., "Insights into the Evolution of Allosteric Properties. The NADH Binding Site of Hexameric Type II Citrate Synthases," *Biochemistry* 42:5555-5565 (2003).
Maynard et al., "Autocatalytic activation of acetyl-CoA synthase," *J. Biol. Inorg. Chem.* 9:316-322 (2004).
McAlister-Henn and Thompson, "Isolation and expression of the gene encoding yeast mitochondrial malate dehydrogenase," J. Bacteriol. 169:5157-5166 (1987).
McGregor et al., "argE-Encoded N-Acetyl-L-Ornithine Deacetylase from *Escherchia coli* Contains a Dinuclear Metalloactive Site," *J. Am. Chem. Soc.* 127:14100-14107 (2005).
McInerney et al., "The genome of Syntrophus aciditrophicus: Life at the thermodynamic limit of microbial growth," *Proc. Natl. Acad. Sci U.S.A.* 104:7600-7605 (2007).
McKinlay et al., "Prospects for a bio-based succinate industry," *Appl. Microbiol. Biotechnol.* 76(4):727-740 (2007).
McPherson et al., "Multiple interactions of lysine-128 of *Escherichia coli* glutamate dehydrogenase revealed by site-directed mutagenesis studies," Protein Eng. 2(2):147-152 (1988).
Mechichi et al., "*Alicycliphilus denitrificans* gen. nov., sp. nov., a cyclohexanol-degrading, nitrate-reducing β-proteobacterium," *Int. J. Syst. Evol. Microbiol.* 53:147-152 (2003).
Megraw et al., "Formation of lactyl-Coenzyme A and pyruvyl-Coenzyme A from lactic acid by *Escherichia coli*," *J. Bacteriol.* 90(4):984-988 (1965).
Melchiorsen et al., "The level of pyruvate-formate lyase controls the shift from homolactic to mixed-acid product formation in Lactococcus lactis," Appl. Microbiol. Biotechnol. 58:338-344 (2002).
Meng and Chuang, "Site-directed Mutagenesis and Functional Analysis of the Active-Site Residues of the E2 Component of Bovine Branched-Chain α-Keto Acid Dehydrogenase Complex," *Biochemistry* 33:12879-12885 (1994).
Meng and Li, "Cloning, expression and characterization of a thiolase gene from Clostridium pasteurianum," *Biotechnol. Lett.* 28(16):1227-1232 (2006).
Menon and Ragsdale, "Mechanism of the Clostridium thermoaceticum pyruvate:ferredoxin oxidoreductase: evidence for the common catalytic intermediacy of the hydroxyethylthiamine pyropyrosphate radical," *Biochemistry* 36(28):8484-8494 (1997).
Menzel et al., "Enzymatic evidence for an involvement of pyruvate dehydrogenase in the anaerobic glycerol metabolism of Klebsiella pneumoniae," *J. Biotech.* 56:135-142 (1997).
Menzel et al., "Kinetic, dynamic, and pathway studies of glycerol metabolism by Klebsiella pneumoniae in anaerobic continuous culsutre: IV. Enzymes and fluxes of pyruvate metabolism," *Botechnol. Bioeng.* 60(5):617-626 (1998).
Mermelstein et al., "Metabolic Engineering of Clostridium acetobutylicum ATCC 824 for Increased Solvent Production by Enhancement of Acetone Formation Enzyme Activities Using a Synthetic Acetone Operon," Biotechnology and Bioengineering, 42:1053-1060 (1993).
Metz et al., "Purification of a jojoba embryo fatty acyl-Coenzyme A reductase and expression of its cDNA in high erucic acid rapeseed," *Plant Phys.* 122:635-644 (2000).
Meynial-Salles, I., et al., "A new process for the continuous production of succinic acid from glucose at high yield, titer and productivity," *Biotechnol. Bioeng.* 99(1):129-135 (2008).
Millard et al., "Enhanced production of succinic acid by overexpression of phosphoenolpyruvate carboxylase in *Escherichia coli*," *Appl. Environ. Microbiol.* 62(5):1808-1810 (1996).
Miller and Jenesel, "Enzymology of butyrate Formation by Butyrivibrio-Fibrisolvens," *J. Bacteriol.* 138:99-104 (1979).
Miller et al., "The catalytic cycle of β-lactam synthetase observed by x-ray crystallographic snapshots," *Proc. Natl. Acad. Sci. U.S.A.* 99(23):14752-14757 (2002).
Minard and McAlister-Henn, "Isolation, nucleotide sequence analysis, and disruption of the MDH2 gene from *Saccharomyces cerevisiae:* evidence for three isozymes of yeast malate dehydrogenase," *Mol. Cell. Biol.* 11:370-380 (1991).

Misono and Nagasaki, "Occurrence of $_L$-Lysine ε-Dehydrogenase in Agrobacterium tumefaciens," *J. Bacteriol.* 150(1):398-401 (1982).
Misono et al., "Properties of L-lysine epsilon-dehydrogenase from Agrobacterium tumefaciens," *J. Biochem.* 105(6):1002-1008 (1989).
Mizobata et al., "Purification and characterization of a thermostable class II fumarase from Thermus thermophilus," *Arch. Biochem. Biophys.* 355(1):49-55 (1998).
Mizugaki et al. "Studies on the metabolism of unsaturated fatty acids. IX. Stereochemical studies of the reaction catalyzed by trans-2-enoyl-Coenzyme A reductase of *Escherichia coli*," *J. Biochem.* 92(5):1649-1654 (1982).
Mizugaki et al., "Studies on the Metabolism of Unsaturated Fatty Acids. V. Isomerization of Thiol Esters of cis-2-Alkenoic Acids during Their Preparation and Alkaline Hydrolysis," *Chem. Pharm. Bull.* 30(1):206-213 (1982).
Mohammadi et al., "Preliminary report of NAD+-dependent amino acid dehydrogenase producing bacteria isolated from soil," Iran Biomed. J. 11(2):131-135 (2007).
Monastiri et al., "β-Ketothiolase (2-methylacetoacetyl-CoA thiolase) deficiency: A frequent disease in Tunisia?" J. Inher. Metab. Dis. 22:932-933 (1999).
Monterrubio et al., "A common regulator for the operons encoding the enzymes involved in d-galactarate, d-glucarate, and d-glycerate utilization in *Escherichia coli*," *J. Bacteriol.* 182(9):2672-2674 (2000).
Moon et al., "Metabolic engineering of *Escherichia coli* for the production of malic acid," *Biochem. Eng. J.* 40(2):312-320 (2008).
Moore et al., "Expression and Purification of Aspartate β-Semialdehyde Dehydrogenase from Infectious Microorganisms," *Protein Expr. Purif.* 25:189-194 (2002).
Moresi et al., "Fumaric acid production from hydrolysates of starch-based substrates," *J. Chem. Technol. Biotechnol.* 54(3):283-290 (1992).
Mori et al., "Characterization, Sequencing, and Expression of the Genes Encoding a Reactivating Factor for Glycerol-inactivated Adenosylcobalamin-dependent Diol Dehydratase," *J. Biol. Chem.* 272(51):32034-32041 (1997).
Morris and Jinks-Robertson, "Nucleotide sequence of the LYS2 gene of *Saccharomyces cerevisiae:* homology to Bacillus brevis tyrocidine synthetase 1," *Gene* 98:141-145 (1991).
Morton et al., "Cloning, sequencing, and expressions of genes encoding enzymes of the autotrophic acetyl-CoA pathway in the acetogen Clostridium thermoacetictun," In M. Sebald (ed.), *Genetics and molecular biology of anaerobic bacteria,* Springer Verlag, New York, 389-406 (1992).
Morton et al., "The primary structure of the subunits of carbon monoxide dehydrogenase/acetyl-CoA synthase from Clostridium thermoaceticum," *J. Biol. Chem.* 266(35):23824-23828 (1991).
Moskowitz et al., "Metabolism of poly-hydroxybutyrate. II. Enzymatic synthesis of D-(-)-hydroxybutyryl Coenzyme A by an enoyl hydrase from rhodospirillum rubrum," Biochemistry 8:2748-2755 (1969).
Mouttaki et al., "Cyclohexane Carboxylate and Benzoate Formation from Crotonate in Syntrophus aciditrophicus," *Appl. Environl. Microbiol.* 73(3):930-938 (2007).
Müh et al., "4-Hydroxybutyryl-CoA dehydratase from Clostridium aminobutyricum: characterization of FAD and iron-sulfur clusters involved in an overall non-redox reaction," *Biochemistry* 35:11710-11718 (1996).
Müh et al., "Mössbauer study of 4-hydroxybutyryl-CoA dehydratase probing the role of an iron-sulfur cluster in an overall non-redox reaction," Eur. J. Biochem. 248:380-384 (1997).
Müller, "Energy Conservation in Acetogenic Bacteria," *Appl. Environ. Microbiol.* 69:6345-6353 (2003).
Muller and Buckel, "Activation of (R)-2-hydroxyglutaryl-CoA dehydratase from Acidaminococcus fennentans," Eur. J. Biochem. 230(2):698-704 (1995).
Muratsubaki and Enomoto, "One of the fumarate reductase isoenzymes from *Saccharomyces cerevisiae* is encoded by the OSM1 gene," Arch. Biochem. Biophys. 352:175-181 (1998).
Musfeldt and Schönheit, "Novel type of ADP-forming acetyl Coenzyme A synthetase in hyperthermophilic archaea: heterologous

(56) References Cited

OTHER PUBLICATIONS expression and characterization of isoenzymes from the sulfate reducer Archaeoglobus fulgidus and the methanogen Methanococcus jannaschii," *J. Bacteriol.* 184(3):636-644 (2002).
Muyrers et al., "Rapid modification of bacterial artificial chromosomes by ET-recombination," *Nucleic Acids Res.* 27:1555-1557 (1999).
Nagasawa et al., "Cloning and Nucleotide Sequence of the Alcohol Acetyltransferase II gene (ATF2) from *Saccharomyces cerevisiae* Kyokai No. 7," *Biosci. Biotechnol. Biochem.* 62:1852-1857 (1998).
Nagata et al., "Gene cloning, purification, and characterization of thermostable and halophilic leucine dehydrogenase from a halophilic thermophile, Bacillus licheniformis TSN9," *Appl. Microbiol. Biotechnol.* 44:432-438 (1995).
Naggert et al., "Cloning, sequencing, and characterization of *Escherichia coli* thioesterase II," *J. Biol. Chem.* 266(17):11044-11050 (1991).
Nahvi et al., "Genetic Control by a Metabolite Binding mRNA," *Chem. Biol.* 9:1043-1049 (2002).
Naidu and Ragsdale, "Characterization of a three-component vanillate O-demethylase from Moorella thermoacetica," *J. Bacteriol.* 183(11):3276-3281 (2001).
Najafpour and Younesi, "Ethanol and acetate synthesis from waste gas using batch culture of Clostridium ljungdahlii," *Enzyme Microb. Technol.* 38:223-228 (2006).
Nakahigashi and Inokuchi, "Nucleotide sequence of the fadA and fadB genes from *Escherichia coli*," *Nucleic Acids Res.* 18(16):4937 (1990).
Nakano et al., "Characterization of Anaerobic Fermentative Growth of Bacillus subtilis: Identification of Fermentation End Products and Genes Required for Growth," *J. Bacteriol.* 179(21):6749-6755 (1997).
Namba et al., "Coenzyme A- and Nicotinamide Adenine Dinucleotide-dependent Branched Chain -Keto Acid Dehydrogenase," J. Biol. Chem. 244(16):4437-4447 (1969).
Nimmo, "Kinetic mechanism of *Escherichia coli* isocitrate dehydrogenase and its inhibition by glyoxylate and oxaloacetate," Biochem. J. 234(2):317-323 (1986).
Nishimaki et al., "Studies on the Metabolism of Unsaturated Fatty Acids. XIV. Purification and Properties of NADPH-Dependent trans-2-Enoyl-CoA Reductase of *Escherichia coli* K-12," *J. Biochem.* 95(5):1315-1321 (1984).
Nishizawa et al., "Gene expression and characterization of two 2-oxoacid:ferredoxin oxidoreductases from Aeropyrum pernix K1," *FEBS Lett.* 579:2319-2322 (2005).
Nissen et al., "Expression of a cytoplasmic transhydrogenase in *Saccharomyces cerevisiae* results in formation of 2-oxoglutarate due to depletion of the NADPH pool," *Yeast* 18:19-32 (2001).
Noichinda et al., "Subcellular Localization of Alcohol Acetyltransferase in Strawberry Fruit," *Food Sci. Technol. Res.* 5(3):239-242 (1999).
Njau et al., "Novel β-hydroxyacid dehydrogenases in *Escherichia coli* and Haemophilus influenza," *J. Biol. Chem.* 275(49):38780-38786 (2000).
Nölling et al., "Genome sequence and comparative analysis of the solvent-producing bacterium Clostridium acetobutylicum," *J. Bacteriol.* 183(16):4823-4838 (2001).
Nuñez et al., "Biochemical characterization of the 2-ketoacid reductases encoded by ycdW and yiaE genes in *Escherichia coli*," Biochem. J. 354(Pt 3):707-715 (2001).
O'Brien and Gennis, "Studies of the Thiamin Pyrophosphate Binding Site of *Escherichia coli* Pyruvate Oxidase," *J. Biol. Chem.* 255(8):3302-3307 (1980).
O'Brien et al, "Regulation by Lipids of Cofactor Binding to a Peripheral Membrane Enzyme: Binding of Thiamin Pyrophosphate to Pyruvate Oxidase," *Biochemistry* 16(14):3105-3109 (1977).
O'Brien et al., "Chemical, physical and enzymatic comparisons of formyltetrahydrofolate synthetases from thermo- and mesophilic clostridia," *Experientia. Suppl.* 26:249-262 (1976).

O'Brien et al., "Insight into the Mechanism of the $B_{12}$-Independent Glycerol Dehydratase from Clostridium butyricum: Preliminary Biochemical and Structural Characterization," *Biochemistry* 43:4635-4645 (2004).
Obradors et al., "Site-directed mutagenesis studies of the metal-binding center of the iron-dependent propanediol oxidoreductase from *Escherichia coli*," Eur. J. Biochem. 258(1):207-213 (1998).
Ofman et al., "2-Methyl-3-hydroxybutyryl-CoA dehydrogenase deficiency is caused by mutations in the HADH2 gene," *Am. J. Hum. Genet.* 72:1300-1307 (2003).
Ohgami et al., "Expression of acetoacetyl-CoA synthetase, a novel cytosolic ketone body-utilizing enzyme, in human brain," *Biochem. Pharmacol.* 65:989-994 (2003).
Ohsugi et al., "Metabolism of L-β-Lysine by Pseudomonas. Purification and Properties of a Deacetylase-Thiolestrerase Utilizing 4-Acetamidobutyryl CoA and Related Compounds," *J. Biol. Chem.* 256(14):7642-7651 (1981).
Okino et al., "An effeicient succinic acid production process in a metabolically engineered Corynebacterium glutamicum strain," *Appl. Microbiol. Biotechnol.* 81(3):459-464 (2008).
Olivera et al., "Molecular characterization of the phenylacetic acid catabolic pathway in Pseudomonas putida U: the phenylacetyl-CoA catabolon," *Proc. Natl. Acad. Sci. U.S.A.* 95(11):6419-6424 (1998).
Orencio-Trejo et al., "Metabolic regluation analysis of an ethanologenic *Escherichia coli* strain based on RT-PCR and enzymatic activities," Biotechnol. Biofuels 1:8 (2008). (provided electronically by publisher as pp. 1-13).
Osipiuk et al., "X-ray crystal structure of GarR-tartronate semialdehyde reductase from *Salmonella typhimurium*," *J. Struct. Funct. Genomics* 10(3):249-253 (2009).
Overkamp et al., "Functional analysis of structural genes for $NAD^+$-dependent formate dehydrogenase in *Saccharomyces cerevisiae*," *Yeast* 19:509-520 (2002).
Overkamp et al., "In vivo analysis of the mechanism for oxidation of cytosolic NADH by *Saccharomyces cerevisiae* mitochondria," *J. Bacteriol.* 182:2823-2830 (2000).
Palosaari and Rogers, "Purification and Properties of the Inducible Coenzyme A-Linked Butyraldehyde Dehydrogenase from Clostridium acetobutylicum," J. Bacteriol. 170(7):2971-2976 (1988).
Parales and Harwood, "Characterization of the Genes Encoding β-Ketoadipate: Succinyl-Coenzyme A Transferase in Pseudomonas putida," J. Bacteriol. 174(14):4657-4666 (1992).
Park and Lee, "Biosynthesis of poly(3-hydroxybutyrate-co-3-hydroxyalkanoates) by metabolically engineered *Escherichia coli* strains," *Appl. Biochem. Biotechnol.* 113-116:335-346 (2004).
Park and Lee, "Identification and characterization of a new enoyl Coenzyme A hydratase involved in biosynthesis of medium-chain-length polyhydroxyalkanoates in recombinant *Escherichia coli*," *J. Bacteriol.* 185(18):5391-5397 (2003).
Park and Lee, "New FadB homologous enzymes and their use in enhanced biosynthesis of medium-chain-length polyhydroxyalkanoates in FadB mutant *Escherichia coli*," *Biotechnol. Bioeng.* 86(6):681-686 (2004).
Park et al., "Regulation of succinate dehydrogenase (sdhCDAB) operon expression in *Escherichia coli* in response to carbon supply and anaerobiosis: role of ArcA and Fnr," *Mol. Microbiol.* 15(3):473-482 (1995).
Park et al., "Utilization of Electrically Reduced Neutral Red by Actinobacillus succinogenes: Physiological Function of Neutral Red in Membrane-Driven Fumarate Reduction and Energy Conservation," *J. Bacteriol.* 181(8):2403-2410 (1999).
Park et al., "Metabolic engineering of *Escherichia coli* for the production of L-valine based on transcriptome analysis and in silico gene knockout simulation," *Proc. Natl. Acad. Sci. U.S.A.* 104(19):7797-7802 (2007).
Parke et al., "Cloning and Genetic Characterization of dca Genes Required for β-Oxidation of Straight-Chain Dicarboxylic Acids in *Acinetobacter* sp. Strain ADP1," Appl. Environ. Microbiol. 67(10):4817-4827 (2001).

(56) References Cited

OTHER PUBLICATIONS

Parkin et al., "Rapid and efficient electrocatalytic CO2/CO interconversions by Carboxydothermus hydrogenoformans CO dehydrogenase I on an electrode," *J. Am. Chem. Soc.* 129(34):10328-10329 (2007).
Patel and Clark, "Acetoacetate metabolism in rat brain. Development of acetoacetyl-Coenzyme A deacylase and 3-hydroxy-3-methylglutaryl-Coenzyme A synthase," *Biochem. J.* 176(3):951-958 (1978).
Patel et al., "β-ketoadipate enol-lactone hydrolases I and II from Acinetobacter calcoaceticus," *J. Biol. Chem.* 250:6567-6577 (1975).
Patil et al., "Use of genome-scale microbial models for metabolic engineering," *Curr. Opin. Biotechnol.* 15(1)64-69 (2004).
Pauli and Overath, "ato Operon: a Highly Inducible System for Acetoacetate and Butyrate Degradation in *Escherichia coli*," Eur. J. Biochem. 29:553-562 (1972).
Paxton et al., "Role of branched-chain 2-oxo acid dehydrogenase and pyruvate dehydrogenase in 2-oxobutyrate metabolism," Biochem. J. 234:295-303 (1986).
Pelletier and Harwood, "2-Ketocyclohexanecarboxyl Coenzyme A Hydrolase, the Ring cleavage Enzyme Required for Anaerobic Benzoate Degradation of Rhodopseudomonas palustris," *J. Bacteriol.* 180(9):2330-2336 (1998).
Peoples and Sinskey, "Fine structural analysis of the Zoogloea ramigera phbA-phbB locus encoding β-ketothiolase and acetoacetyl-CoA reductase: nucleotide sequence of phbB," *Mol. Microbiol.* 3:349-357 (1989).
Pereira et al., "Active site mutants of *Escherichia coli* citrate synthase. Effects of mutations on catalytic and allosteric properties," *J. Biol. Chem.* 269:412-417 (1994).
Peretz et al., "Molecular Cloning, Nucleotide Sequencing, and Expression of Genes Encoding Alcohol Dehydrogenases From the Thermophile Thermoanaerobacter," Anaerobe, 3:259-270 (1997).
Peretz and Burstein, "Amino acid sequence of alcohol dehydrogenase from the thermophilic bacterium Thermoanaerobium brockii," Biochemistry 28(16):6549-6555 (1989).
Perez et al., "*Escherichia coli* YqhD exhibits aldehyde reductase activity and protects from the harmful effect of lipid peroxidation-derived aldehydes," J. Biol. Chem. 283(12):7346-7353 (2008).
Petersen and Bennett, "Purification of acetoacetate decarboxylase from clostridium acetobutylicum ATCC 824 and cloning of the acetoacetate decarboxylase gene in *Escherichia coli*," *Appl. Environ. Microbiol.* 56:3491-3498 (1990).
Petitdemange et al., "Regulation of the NADH and NADPH-ferredoxin oxidoreductases in clostridia of the butyric group," *Biochim. Biophys. Acta* 421(2):334-347 (1976).
Pfluger et al., "Lysine-2,3-Aminomutase and β-Lysine Acetyltransferase Genes of Methanogenic Archaea Are Salt Induced and Are Essential for the Biosynthesis of Nε-Acetyl-β-Lysine and Growth at High Salinity," Appl. Environ. Microbiol. 69(10):6047-6055 (2003).
Pharkya et al., "OptiStrain: A computational Framework for redesign of microbial production systems," *Genome Res.* 14(11):2367-2376 (2004).
Pharkya et al., "Exploring the overproduction of amino acids using the bilevel optimization framework OptKnock," *Biotechnol. Bioeng.* 84(7):887-899 (2003).
Pierce et al., "The Complete Genome Sequence of Moorella thermoacetia (f. Clostridum thermoaceticum)," *Environ. Microbiol.* 10(10):2550-2573 (2008).
Pieulle et al., "Isolation and analysis of the gene encoding the pyruvate-ferredoxin oxidoreductase of Desulfovibrio africanus, production of the recombinant enzyme in *Escherichia coli*, and effect of carboxy-terminal deletions on its stability," *J. Bacteriol.* 179(18):5684-5692 (1997).
Pine et al., "Titanium-Mediated Methylene-Transfer Reactions. Direct Conversion of Esters into Vinyl Ethers," *J. Am. Chem. Soc.* 102:3270-3272 (1980).
Ploux et al., "Investigation of the first step of biotin biosynthesis in Bacillus sphericus," *Biochem. J.* 287:685-690 (1992).
Ploux et al., "The NADPH-linked acetoacetyl-CoA reductase from Zoogloea ramigera, Characterization and mechanistic studies of the cloned enzyme over-produced in *Escherichia coli*," *Eur. J. Biochem.* 174:177-182 (1988).
Pohl et al., "Remarkably broad Sutstrate Tolerance of Malonyl-CoA Synthetase, an Enzyme Capable of Intracellular Synthesis of Polyketide Precursors," *J. Am. Chem. Soc.* 123:5822-5823 (2001).
Pohlmann et al., "Genome sequence of the bioplastic-producing "Knallgas" bacterium Ralstonia eutropha H16," *Nat. Biotechnol.* 24(10):1257-1262 (2006).
Pollard et al., "Purification, characterisation and reaction mechanisms of monofunctional 2-hydroxypentadienoic acid hydratase from *Escherichia coli*," *Eur. J. Biochem.* FEBS 251:98-106 (1998).
Ponce, E., et al., "Cloning of the two pyruvate kinase isoenzyme structural genes from *Escherichia coli*: the relative roles of these enzymes in pyruvate biosynthesis," *J. Bacteriol.* 177(19):5719-5722 (1995).
Postma et al., "Phosphoenolpyruvate Carbohydrate Phosphotransferase Systems of Bacteria," *Microbiol Rev.* 57(3):543-594 (1993).
Powlowski et al., "Purification and properties of the physically associated meta-cleavage pathway enzymes 4-hydroxy-2-ketovalerate aldolase and aldehyde dehydrogenase (acylating) from *Pseudomonas* sp. strain CF600," *J. Bacteriol.* 175(2):377-385 (1993).
Price et al., "Genome-scale microbial in silico models: the constraints-based approach," *Trends Biotechnol.* 21(4):162-169 (2003).
Price et al., "Genome-scale models of microbial cells: evaluating the consequences of constraints," *Nat. Rev. Microbiol.* 2(11):886-897 (2004).
Pritchett and Metcalf, "Genetic, physiological and biochemical characterization of multiple methanol methyltransferase isozymes in Methanosarcina acetivorans C2A," *Mol. Microbiol.* 56(5):1183-1194 (2005).
Pronk et al., "Pyruvate metabolism in *Saccharomyces cerevisiae*," Yeast 12:1607-1633 (1996).
Purnell et al., "Modulation of higher-plant NAD(H)-dependent glutamate dehydrogenase activity in transgenic tobacco via alteration of β subunit levels," Planta 222:167-180 (2005).
Qiu et al., "Metabolic engineering of Aeromonas hydrophila for the enhanced production of poly(3-hydroxybutyrate-co-3-hydroxyhexanoate)," Appl. Microbiol. Biotechnol. 69(5):537-542 (2006).
Rado and Hoch, "Phosphotransacetylase from Bacillus subtilis: purification and physiological studies," *Biochim. Biophys. Acta* 321:114-125 (1973).
Ragsdale et al., "Acetogenesis and the Wood-Ljungdahl pathway of $CO_2$ fixation," *Biochimica. Biophysica. Acta* 1784(12):1873-1898 (2008).
Ragsdale, "Enzymology of the wood-Ljungdahl pathway of acetogenesis," *Ann. NY Acad Sci.* 1125:129-136 (2008).
Ragsdale, "Life with carbon monoxide," *Crit. Rev. Biochem. Mol. Biol.* 39(3):165-195 (2004).
Ragsdale, "Pyruvate ferredoxin oxidoreductase and its radical intermediate," *Chem. Rev.* 103(6):2333-2346 (2003).
Ramon-Maiques et al., "Structure of Acetylglutamate Kinase, a Key Enzyme for Arginine Biosynthesis and Prototype for the Amino Acid Kinase Enzyme Family, during Catalysis," *Structure* 10:329-342 (2002).
Ramos et al., "Mutations affecting the enzymes involved in the utilization of 4-aminobutyric acid as nitrogen source by the yeast *Saccharomyces cerevisiae*," *Eur.J Biochem.* 149:401-404 (1985).
Rangarajan et al., "Structure of [NiFe] hydrogenase maturation protein HypE from *Escherichia coli* and its interaction with HypF," *J. Bacteriol.* 190(4):1447-1458 (2008).
Rasmussen, L.J., et al. "Carbon Metabolism Regulates Expression of the pfl (Pyruvate-Formate-Lyase) Gene in *Escherichia coli*," *J. Bacteriol.* 173(20):6390-6397 (1991).
Rathinasabapathi, "Propionate, a source of β-alanine, is an inhibitor of β-alanine methylation in Limonium latifoilium Plunbaginaces," *J. Plant Physiol.* 159:671-674 (2002).

(56) References Cited

OTHER PUBLICATIONS

Ratnatilleke et al., "Cloning and sequencing of the Coenzyme $B_{12}$-binding domain of isobutyryl-CoA mutase from Streptomyces cinnamonensis, reconstitution of mutase activity, and characterization of the recombinant enzyme produced in Escherichia coli," J. Biol. Chem. 274(44):31679-31685 (1999).
Raux et al., "The role of Saccharomyces cerevisiae Met1p and Met8p in sirohaem and cobalamin biosynthesis," Biochem. J. 338 (pt. 3):701-708 (1999).
Raux et al., "Salmonella typhimurium cobalamin (vitamin B12) biosynthetic genes: functional studies in S. typhimurium and Escherichia coli," J. Bacteriol. 178(3):753-767 (1996).
Ravagnani et al., "Spo0A directly controls the switch from acid to solvent production in solvent-forming clostridia," Mol. Microbiol. 37(5):1172-1185 (2000).
Raybuck et al., "Kinetic characterization of the carbon monoxide-acetyl-CoA (carbonyl goup) exchange activity of the acetyl-CoA synthesizing CO dehydrogenase from Clostridium thermoaceticum," Biochemistry 27(20):7698-7702 (1988).
Raynaud et al., "Molecular characterization of the 1,3-propanediol (1,3-PD) operon of clostridium butyricum," Proc. Natl. Acad. Sci. U.S.A. 100:5010-5015 (2003).
Reda et al., "Reversible interconversion of carbon dioxide and formate by an electroactive enzyme," Proc. Natl. Acad. Sci. U.S.A. 105:10654-10658 (2008).
Reher et al., "Characterization of glycerate kinase (2-phosphoglycerate forming), a key enzyme of the nonphosphorylative Entner-Doudoroff pathway, from the thermoacidophilic euryarchaeon Picrophilus torridus," FEMS Microbiol. Lett. 259(1):113-119 (2006).
Reiser and Somerville, "Isolation of mutants of Acinetobacter calcoaceticus deficient in wax ester synthesis and complementation of one mutation with a gene encoding a fatty acyl Coenzyme A reductase," J. Bacteriol. 179(9):2969-2975 (1997).
Reshetnikov, et al., "Characterization of the ectoine biosynthesis genes of haloalkalotolerant obligate methanotroph 'Methylomicrobium alcaliphilum 20Z'," Arch. Microbiol. 184:286-297 (2006).
Resnekov et al., "Organization and regulation of the Bacillus subtilis odhAB operon, which encodes two of the subenzymes of the 2-oxoglutarate dehydrogenase complex," Mol. Gen. Genet. 234:285-296 (1992).
Rhodes et al., "Production of fumaric acid by Rhizopus arrhuzus," Appl. Microbiol. 7:74-80 (1959).
Rhodes et al., "Production of Fumaric Acid in 20-Liter Fermentors," Appl. Microbiol. 10(1)9-15 (1962).
Ringquist et al., "Translation initiation in Escherichia coli: sequences within the ribosome-binding site," Mol. Microbiol. 6(9):1219-1229 (1992).
Rioux et al., "Two outer membrane transport systems for vitamin $B_{12}$ in Salmonella typhimurium," J. Bacteriol. 171:2986-2993 (1989).
Rioux et al., "Vitamin $B_{12}$ transport in Escherichia coli K12 does not require the btuE gene of the btuCED operon," Mol. Gen. Genet. 217:301-308 (1989).
Riviere et al., "Acetyl: succinate CoA-transferase in procyclic Trypanosoma brucei. Gene identification and role in carbohydrate metabolism." J. Biol. Chem. 279:45337-45346 (2004).
Roa Engel et al., "Fumaric acid production by fermentation," Appl. Microbiol. Biotechnol. 78(3):379-389 (2008).
Roberts et al, "The Role of Enoyl-CoA Hydratase in the Metabolism of Isoleucine by Pseudomonas putida," Arch. Microbiol. 117:99-108 (1978).
Roberts et al., "Acetyl-Coenzyme A synthesis from methyltetrahydrofolate, CO, and Coenzyme A by enzymes purified from Clostridium thermoaceticum: attainment of in vivo rates and identification of rate-limiting steps," J. Bacteriol. 174(14):4667-4676 (1992).
Roberts et al., "Cloning and expression of the gene cluster encoding key proteins involved in acetyl-CoA synthesis in Clostridium thermoaceticum: CO dehydrogenase, the corrinoid/Fe—S protein, and methyltransferase," Proc. Natl. Acad. Sci. U.S.A. 86(1):32-36 (1989).
Robinson et al., "Studies on Rat Brain Acyl-Coenzyme A Hydrolase (Short Chain)," Biochem. Biophys. Res. Commun. 71(4):959-965 (1976).
Rofe et al., "Hepatic oxalate production: the role of hydroxypyruvate," Biochem. Med. Metab. Biol. 36(2):141-150 (1986).
Rohdich et al., "Enoate reductases of Clostridia. Cloning, sequencing, and expression," J. Biol. Chem. 276(8):5779-5787 (2001).
Rohwerder et al., "The alkyl tert-butyl ether intermediate 2-hydroxyisobutyrate is degraded via a novel cobalamin-dependent mutase pathway," Appl. Environ. Microbiol. 72(6):4128-4135 (2006).
Rose and Weaver, "The role of the allosteric B site in the fumarase reaction," Proc. Natl. Acad. Sci. U.S.A. 101(10): 3393-3397 (2004).
Rose et al., "Enzymatic phosphorylation of acetate," J. Biol. Chem. 211(2):737-756 (1954).
Rosenberg, "A Comparison of Lipid Patterns in Photosynthesizing and Nonphotosynthesizing Cells of Euglena Gracilis," Biochem. 2:1148-1154 (1963).
Roszak et al., "The Structure and Mechanism of the Type II Dehydroquinase from Streptomyces coelicolor," Structure 10:493-503 (2002).
Roth et al., "Characterization of the cobalamin (vitamin $B_{12}$) biosynthetic genes of Salmonella typhimurium," J. Bacteriol. 175:3303-3316 (1993).
Rother and Metcalf, "Anaerobic growth of Methanosarcina acetivorans C2A on carbon monoxide: an unusual way of life for a methanogenic archaeon," Proc. Natl. Acad. Sci. U.S.A. 101(48):16929-16934 (2004).
Rother et al., "Genetic and proteomic analyses of CO utilization by Methanosarcina acetivorans," Arch. Microbiol. 188(5):463-472 (2007).
Rudman and Meister, "Transamination in Escherichia coli," J. Biol. Chem. 200(2):591-604 (1953).
Saegesser et al., "Stability of broad host range cloning vectors in the phototrophic bacterium Rhodospirillum rubrum," FEMS Microbiol. Lett. 95:7-11 (1992).
Saito and Doi, "Microbial synthesis and properties of poly(3-hydroxybutyrate-co-4-hydroxybutyrate) in Comamonas acidovorans," Int. J Biol Macromol. 16:99-104 (1994).
Sakai et al, "Acetate and Ethanol Production from H2 and CO2 by Morrella sp. Using a Repeated Batch Culture," J. Biosci. Bioeng. 99:252-258 (2005).
Samanta and Harwood, "Use of Rhodopseudomonas palustris genome sequence to identify a single amino acid that contributes to the activity of Coenzyme A ligase with chlorinated substrates," Mol. Microbiol. 55(4):1151-1159 (2005).
Samuelov et al., "Whey fermentation by anaerobiospirillum succiniciproducens for production of a succinate-based animal feed additive," Appl. Environ. Microbiol. 65(5):2260-2263 (1999).
San et al., "Metabolic Engineering through Cofactor Manipulation and its Effects on Metabolic Flux Redistribution in Escherichia coli," Metab Eng. 4(2):182-192 (2002).
Sanchez et al., "Efficient succinic acid production from glucose through overexpression of pyruvate carboxylase in an Escherichia coli alcohol dehydrogenase and lactate dehydrogenase mutant," Biotechnol. Prog. 21(21:358-365 (2005).
Sanchez et al., "Novel pathway engineering design of the anaerobic central metabolic pathway in Escherichia coli to increase succinate yield and productivity," Metab. Eng. 7(3): 229-239 (2005).
Sanchez et al., "Batch culture characterization and metabolic flux analysis of succinate-producing Escherichia coli strains," Metab Eng. 8(3):209-226 (2006).
Sanchez et al., "Effect of different levels of NADH availability on metabolic fluxes of Escherichia coli chemostat cultures in defined medium," J. Biotechnol. 117(4):395-405 (2005).
Sanyal et al., "Biosyntehsis of pimeloyl-CoA, a biotin precursor in Escherichia coli, follows a modified fatty acid synthesis pathway: $^{13}$C-labeling studies," J. Am. Chem. Soc. 116:2637-2638 (1994).

(56) References Cited

OTHER PUBLICATIONS

Sariaslani, "Development of a Combined biological and Chemical Process for Production of Industrial aromatics from Renewable Resources," *Annu. Rev. Microbiol.* 61:51-69 (2007).
Sass et al., "Folding of fumarase during mitochondrial import determines its dual targeting in yeast," *J. Biol. Chem.* 278(46):45109-45116 (2003).
Sato et al., "Poly[(R)-3-hydroxybutyrate] formation in *Escherichia coli* from glucose through an enoyl-CoA hydratase-mediated pathway," *J. Biosci. Bioeng.* 103(1):38-44 (2007).
Sauer and Thauer, "Methanol:Coenzyme M methyltransferase from Methanosarcina barkeri. Identification of the active-site histidine in the corrinoid-harboring subunit MtaC by site-directed mutagenesis," *Eur. J. Biochem.* 253(3):698-705 (1998).
Sauer and Thauer, "Methanol:coenzyme M methyltransferase from Methanosarcina barkeri. Zinc dependence and thermodynamics of the methanol:cob(I)alamin methyltransferase reaction," *Eur. J. Biochem.* 249(1):280-285 (1997).
Sauer et al., "Methanol:Coenzyme M methyltransferase from Methanosarcina barkeri. Purification, properties and encoding genes of the corrinoid protein MT1," *Eur. J. Biochem.* 243(3):670-677 (1997).
Sauvageot et al., "Characterisation of the diol dehydratase pdu operon of Lactobacillus collinoides," *FEMS Microbiol. Lett.* 209:69-74 (2002).
Sawers and Boxer, "Purification and properties of membrane-bound hydrogenase isoenzyme 1 from anaerobically grown *Escherichia coli* K12," *Eur. J. Biochem.* 156(2):265-275 (1986).
Sawers et al., "Characterization and physiological roles of membrane-bound hydrogenase isoenzymes from *Salmonella typhimurium*," *J. Bacteriol.* 168(1):398-404 (1986).
Sawers et al., "Differential expression of hydrogenase isoenzymes in *Escherichia coli* K-12: evidence for a third isoenzyme," *J. Bacteriol.* 164(3):1324-1331 (1985).
Sawers, "The hydrogenases and formate dehydrogenases of *Escherichia coli*," *Antonie Van Leeuwenhoek* 66(1-3):57-88 (1994).
Saz and Weil, "The mechanism of the formation of -methylbutyrate from carbohydrate by Ascaris lumbricoides muscle," *J. Biol. Chem.* 235:914-918 (1960).
Scherf and Buckel, "Purification and properties of 4-hydroxybutyrate Coenzyme A transferase from Clostridium aminobutyricum," *Appl. Environ. Microbiol.* 57(9):2699-2702 (1991).
Scherf and Buckel, "Purification and properties of an iron-sulfur and FAD-containing 4-hydroxybutyryl-CoA dehadratase/vinylacetyl-CoA Δ3-Δ2-isomerase from Clostridium aminobutricum," *Eur. J. Biochem.* 215:421-429 (1993).
Scherf et al, "Succinate-ethanol fermentation in clostridium kluyveri: purification and characterisation of 4-hydroxybutyryl-CoA dehydratase/vinylacetyl-CoA Δ3-Δ2-isomerase," *Arch. Microbiol.* 161(3):239-245 (1994).
Schilling et al., "Genome-Scale Metabolic Model of Helicobacter pylori 26695," *J. Bacteriol.* 184:4582-4593 (2002).
Schilling et al., "Toward Metabolic Phenomics: Analysis of Genomic Data Using Flux Balances," *Biotechnol. Prog.* 15(3):288-295 (1999).
Schilling et al., "Combining Pathway Analysis with Flux Balance Analysis for the Comprehensive Study of Metabolic Systems," *Biotechnol. Bioeng.* 71(4):286-306 (2000/2001).
Schilling et al., "Theory for the Systematic Definition of Metabolic Pathways and Their Use in Interpreting Metabolic Function from a Pathway-Oriented Perspective," *J. Theor. Biol.* 203(3):229-248 (2000).
Schmid et al., "Plasmid-mediated uptake and metabolism of sucrose by *Escherichia coli* K-12," *J. Bacteriol.* 151(1):68-76 (1982).
Schnell et al., "Anaerobic degradation of aniline and dihydroxybenzenes by newly isolated sulfate-reducing bacteria and description of Desulfobacterium anilini," *Arch. Microbiol.* 152:556-563 (1989).
Schulz et al., "Stereospecific production of the herbicide phosphinothricin (glufosinate) by transamination: isolation and characterization of a phosphinothricin-specific transaminase from *Escherichia coli*," *Appl. Environ. Microbiol.* 56(1):1-6 (1990).
Schweiger and Buckel, "On the dehydration of (R)-lactate in the fermentation of alanine to propionat by Clostridium propionicum," *FEBS Lett.* 171:79-84 (1984).
Schweiger et al., "Purification of 2-hydroxyglutaryl-CoA dehydratase from Acidaminococcus fennentans. An iron-sulfur protein," *Eur. J. Biochem.* 169(2):441-448 (1987).
Scott and Jakoby, "Soluble γ-Aminobutyric-Glutamic Transaminase from *Pseudomonas fluorescens*," *J. Biol. Chem.* 234:932-936 (1959).
Scott, A.I., "Discovering nature's diverse pathways to vitamin $B_{12}$: a 35-year odyssey," *J. Org. Chem.* 68:2529-2539 (2003).
Seedorf et al., "The genome of Clostridium kluyveri, a strict anaerobe with unique metabolic features," *Proc. Natl. Acad. Sci. U.S.A.* 105(6):2128-2133 (2008).
Segre et al., "Analysis of optimality in natural and perturbed metabolic networks," *Proc. Natl. Acad. Sci. U.S.A.* 99:15112-15117 (2002).
Seibert et al., "Characterization of the maleylacteate reductase MacA of Rhodococcus opacus 1CP and evidence for the presence of an isofunctional enzyme," *J. Bacteriol.* 180:3503-3508 (1998).
Seibert et al., "Purification and characterization of maleylacetate reductase from Alcaligenes eutrophys JMP134(pJP4)," *J. Bacteriol.* 175:6745-6754 (1993).
Sekimoto et al., "Cloning and molecular characterization of plant aldehyde oxidase," *J. Biol. Chem.* 272(24):15280-15285 (1997).
Selmer et al., "Propionate CoA-transferase from Clostridium propionicum. Cloning of gene identification of glutamate 324 at the active site," Eur. J. Biochem. 269:372-380 (2002).
Sennett et al., "Transmembrane transport of cobalamin in prokaryotic and eukaryotic cells," Ann. Rev. Biochem. 50:1053-1086 (1981).
Seravalli et al., "Evidence that NiNi acetyl-CoA synthase is active and that the CuNi enzyme is not," *Biochemistry* 43(13):3944-3955 (2004).
Seravalli et al., "Mechanism of transfer of the methyl goup from (6S)-methyltetrahydrofolate to the corrinoid/iron-sulfur protein catalyzed by the methyltransferase from clostridium thermoaceticum: a key step in the Wood-Ljungdahl pathway of acetyl-CoA synthesis," *Biochemistry* 38(18):5728-5735 (1999).
Seyfried et al., "Cloning, Sequencing, and Overexpression of the Genes Encoding Coenzyme $B_{12}$-Dependent Glycerol Dehydratase of Citrobacter freundii," *J. Bacteriol.* 178(19):5793-5796 (1996).
Shafiani et al., "Cloning and characterization of aspartate-β-semialdehyde dehydrogenase from *Mycobacterium tuberculosis* H37 Rv," *J. Appl. Microbiol.* 98:832-838 (2005).
Shanley et al., "Cloning and expression of Acinetobacter calcoaceticus catBCDE genes in Pseudomonas putida and *Escherichia coli*," J. Bacteriol. 165:557-563 (1986).
Sharma et al., "Menaquinone (Vitamin K2) Biosynthesis: Nucleotide Sequence and Expression of themenB Gene from *Escherichia coli*," J. Bacteriol. 174(15): 5057-5062 (1992).
Sheppard et al., "Purification and Properties of NADH-Dependent 5,10-Methylenetetrahydrofolate Reductase (MetF) from *Escherichia coli*," *J. Bacteriol.* 181(3):718-725 (1999).
Shiba et al., "Engineering of the pyruate dehydrogenase bypass in *Saccharomyces cerevisiae* for high-level production of isoprenoids," *Metab. Eng.* 9:160-168 (2007).
Shibata et al., "Purification, characterization, and immunological properties of fumarase from *Euglena gracilis* var. *bacillaris*," *J. Bacteriol.* 164(2):762-768 (1985).
Shigeoka and Nakano, "The effect of thiamin on the activation of thiamin pyrophosphate-dependent 2-oxoglutarate decarboxylase in Euglena gracilis," Biochem. J. 292 (Pt 2):463-467 (1993).
Shimomura et al., "3-hydroxyisobutyiyl-CoA hydrolase," *Methods Enzymol.* 324:229-240 (2000).
Shimomura et al., "Purification and partial characterization of 3-hydroxyisobutyryl-Coenzyme A hydrolase of rat liver," *J. Biol. Chem.* 269(19):14248-14253 (1994).

(56) References Cited

OTHER PUBLICATIONS

Shimoyama et al., "MmcBC in Pelotomaculum thermopropionicum represents a novel group of prokaryotic fumarases," *FEMS Microbiol Lett.* 270(2):207-213 (2007).
Shlomi et al., "Regulatory on/off minimization of metabolic flux changes after genetic perturbations," *Proc.Natl. Acad. Sci. U.S.A.* 102:7695-7700 (2005).
Shukla et al., "Production of D(−)-lactate from sucrose and molasses," *Biotechnol. Lett.* 26(9):689-693 (2004).
Shuler and Kargi, Operating Considerations for Bioreactors for Suspension and Immobilized Cultures, in Bioprocess Engineering: Basic Concepts, Prentice Hall, Inc., Upper Saddle River, NJ., p. 245-247 (2002).
Siew et al., "Localization and characteristics of rat liver mitochondrial aldehyde dehydrogenases," Arch. Biochem. Biophys. 176(2):638-649 (1976).
Simanshu et al., "Structure and function of enzymes involved in the anaerobic degradation of L-threonine to propionate," *J. Biosci.* 32(6):1195-1206 (2007).
Sinclair et al., "Purification and characterization of the branched chain α-ketoacid dehydrogenase complex from *Saccharomyces cerevisiae*," Biochem. Mol. Biol. Int. 31(5):911-922 (1993).
Sipma et al., "Microbial CO conversions with applications in synthesis gas purification and bio-desulfurization," *Crit. Rev. Biotechnol.* 26:41-65 (2006).
Skarstedt and Silverstein, "*Escherichia coli* acetate kinase mechanism studied by net initial rate, equilibrium, and independent isotopic exchange kinetics," *J. Biol. Chem.* 251:6775-6783 (1976).
Slater et al., "Multiple β-ketothiolases mediate poly(β-hydroxyalkanoate) copolymer synthesis in Ralstonia eutropha," J. Bacteriol. 180(8):1979-1987 (1998).
Smith et al., "Purification and characteristics of a γ-glutamyl kinase involved in *Escherichia coli* proline biosynthesis," *J. Bacteriol.* 157:545-551 (1984).
Smith and Kaplan, "Purification, properties and kinetic mechanism of Coenzyme A-linked aldehyde dehydrogenase from Clostridium kluyveri," Arch. Biochem. Biophys. 203:663-675 (1980).
Smith et al., "Fumarate metabolism and the microaerophily of *Campylobacter* species," *Int. J. Biochem. Cell. Biol.* 31(9):961-975 (1999).
Smith et al., "Structural and functional organization of the animal fatty acid synthase," *Prog. Lipid. Res.* 42(4):289-317 (2003).
Söhling and Gottschalk, "Molecular analysis of the anaerobic succinate degradation pathway in Clostridium kluyveri," *J. Bacteriol.* 178:871-880 (1996).
Söhling and Gottschalk, "Purification and characterization of a Coenzyme-A-dependent succinate-semialdehyde dehydrogenase from Clostridium kluyveri," *Eur. J. Biochem.* 212:121-127 (1993).
Soini et al., "High cell density media for *Escherichia coli* are generally designed for aerobic cultivations—consequences for large-scale bioprocesses and shake flask cultures," *Microb. Cell. Fact.* 7:26 (2008).
Sokatch et al., "Purification of a Branched-Chain Keto Acid Dehydrogenase from Pseudomonas putida," *J. Bacteriol.* 148(2):647-652 (1981).
Somerville, "The Billion-Ton Biofuels Vision," *Science* 312(5778):1277 (2006).
Song et al., "Ultrasound-mediated DNA transfer for bacteria," *Nucl. Acids Res.* 35:e129 (2007).
Song et al, "Effects of dissolved $CO_2$ levels on the growth of *Mannheimia succinicproducens* and succinic acid production," *Biotechnol. Bioeng.* 98(6):1296-1304 (2007).
Song et al., "Construction of recombinant *Escherichia coli* strains producing poly (4-hydroxybutyric acid) homopolyester from glucose," *Wei Sheng Wu Xue.Bao.* 45:382-386 (2005).
Song et al., "Recovery of succinic acid produced by fermentation of a metabolically engineered Mannheimia succiniciproducens strain," *J. Biotechnol.* 132:445-452 (2007).

Song et al., "Stricture, function, and mechanism of the phenylacetate pathway hot dog-fold thioesterase PaaI" *J. Biol. Chem.* 281(16):11028-11038 (2006).
Soucaille et al., "Butanol tolerance and autobacteriocin production by Clostridium acetobutylicum," *Curr. Microbiol.* 14:295-299 (1987).
Sovik, "Mitochondrial 2-methylacetoacetyl-CoA thiolase deficiency: an inborn error of isoleucine and ketone body metabolism," *J. Inherit. Metab. Dis.* 16:46-54 (1993).
Sramek and Frerman, "Purification and properties of *Escherichia coli* Coenzyme A-transferase " *Arch. Biochem. Bionhys.* 171(1):14-26 (1975).
St. Maurice et al., "Flavodoxin:quinone reductase (FqrB): a redox partner of pyruvate:ferredoxin oxidoreductase that reversibly couples pyruvate oxidation to NADPH production in Helicobacter pylori and Campylobacter jejuni," *J. Bacteriol.* 189:4764-4773 (2007).
Stadtman, "The enzyme synthesis of β-alanyl Coenzyme A," *J. Plant Chem. Soc.* 77:5765-5766 (1955).
Starai et al., "Acetate excretion during growth of salmonella enerica on ethanolamine requires phosphotransacetylase (EutD) activity, and acetate recapture requires acetyl-CoA synthetase (Acs) and phosphotransacetylase (Pta) activities," *Microbiology,* 151:3793-3801 (2005).
Starai et al., "Residue Leu-641 of Acetyl-CoA synthetase is critical for the acetylation of residue Lys-609 by the Protein acetyltransferase enzyme of *Salmonella enterica,*" *J. Biol. Chem.* 280(28):26200-26205 (2005).
Steen et al., "Metabolic engineering of *Saccharomyces cerevisiae* for the production of n-butanol," *Microb. Cell. Fact.* 7:36 (provided electronically by publisher as pp. 1-8) (2008).
Steffan and McAlister-Henn, "Isolation and characterization of the yeast gene encoding the MDH3 isozyme of malate dehydrogenase," *J. Biol. Chem.* 267:24708-24715 (1992).
Steinbacher et al., "Enoate reductase family," in Flavins and Flavoproteins, Proceedings of the Fourteenth International Symposium, St. John's College, University of Cambridge, UK, Jul. 14-18, 2002, Chapman et al., pp. 941-949, Rudolf Weber, Agency for Scientific Publications Berlin.
Steinbuchel and Schlegel, "NAD-linked L(+)-lactate dehydrogenase from the strict aerobe alcaligenes eutrophus. 2. Kinetic properties and inhibition by oxaloacetate," *Eur. J. Biochem.* 130(2):329-334 (1983).
Steinbuchel and Schlegel, "A multifunctional fermentative alcohol dehydrogenase from the strict aerobe Alcaligenes eutrophus: purification and properties," *Eur. J. Biochem.* 141:555-564 (1984).
Stim-Herndon et al., "Characterization of an acetyl-CoA C-acetyltransferase (thiolase) gene from Clostridium acetobutylicum ATCC 824," *Gene* 154(1):81-85 (1995).
Stirling and Perry, "Purification and Properties of a Nicotinamide Adenine Dinucleotide-Linked Cyclohexanol Dehydrogenase from a *Cocardia* Species," *Curr. Microbiol.* 4:37-40 (1980).
Stols and Donnelly, "Production of succinic acid through overexpression of $NAD^+$-dependent malic enzyme in an *Escherichia coli* mutant," *Appl. Environ. Microbiol.* 63(7):2695-2701 (1997).
Stols et al., "Expression of Ascaris sutura malic enzyme in a mutant *Escherichia coli* allows production of succinic acid from glucose," *Appl. Biochem. Biotechnol.* 63-65: 153-158 (1997).
Stoyan et al., "Cloning, sequencing and overexpression of the leucine dehydrogenase gene from Bacillus cereus," *J. Biotechnol.* 54:77-80 (1997).
Straathof et al., "Feasibility of acrylic acid production by fermentation," *Appl. Microbiol. Biotechnol.* 67:727-734 (2005).
Strauss and Fuchs, "Enzymes of a novel autotrophic CO2 fixation pathway in the phototrophic bacterium Chloroflexus aurantiacus, the 3-hydroxypropionate cycle," *Eur. J. Biochem.* 215:633-643 (1993).
Streit and Entcheva, "Biotin in microbes, the genes involved in its biosynthesis, its biochemical role and perspectives for biotechnological production," Appl. Microbiol. Biotechnol. 61:21-31 (2003).

(56) References Cited

OTHER PUBLICATIONS

Suarez de Mata et al., "Propionyl-CoA condensing enzyme from Ascaris muscle mitochondria. I. Isolation and characterization of multiple forms," *Arch. Biochem. Biophys.* 285(1):158-165 (1991).
Suarez de Mata et al., "Propionyl-CoA condensing enzyme from Ascaris muscle mitochondria. II. Coenzyme A modulation," *Arch. Biochem. Biophys.* 285:166-171 (1991).
Suematsu et al., "Molecular cloning and functional expression of rat liver cytosolic acetyl-CoA hydrolase," *Eur. J. Biochem.* 268(9):2700-2709 (2001).
Sulzenbacher et al., "Crystal structure of *E. coli* alcohol dehydrogenase YqhD: evidence of a covalently modified NADP Coenzyme," *J. Mol. Biol.* 342(2):489-502 (2004).
Suzuki et al., "GriC and GriD Constitute a carboxylic acid reductase involved in grixazone biosynthesis in streptomyces griseus," *J. Antibiot.* 60(6):380-387 (2007).
Suzuki, "Phospotransacetylase of *Escherichia coli* B., activation by pyruvate and inhibition by NADH and certain nucleotides," *Biochem. Biophys. Acta* 191:559-569 (1969).
Svensson et al., "Characterization and isolation of enzymes that hydrolyze short-chain acyl-CoA in rat-liver mitochondria," *Eur. J. Biochem.* 238(2):526-531 (1996).
Svetlitchnyi et al., "A functional Ni—Ni—[4Fe—4S] cluster in the monomeric acetyl-CoA synthase from Carboxydothermus hydrogenoformans," *Proc. Natl. Acad. Sci. U.S.A.* 101(2):446-451 (2004).
Svetlitchnyi et al., "Two membrane-associated NiFeS-carbon monoxide dehydrogenases from the anaerobic carbon-monoxide-utilizing eubacteritun Carboxydothernms hydrogenoformans," *J. Bacteriol.* 183(17):5134-5144 (2001).
Tae-Kang et al., "Purification and characterization of a cyclohexanol dehydrogenase from *Rhodococcus* sp. TK6," *J. Microbiol. Biotechnol.* 12:39-45 (2002).
Takacs et al., "Formate hydrogenlyase in the hyperthermophilic archaeon, Thermococcus litoralis," *BMC Microbiol.* 8:88 (2008).
Takahashi-Abbe et al., "Biochemical and functional properties of a pyruvate formate-lyase (PFL)-activating system in *Streptococcus mutans*," *Oral Microbiol. Immunol.* 18:293-297 (2003).
Takanashi et al., "Characterization of a novel 3-hydroxybutyrate dehydrogenase from Ralstonia pickettii T1," *Antonie van Leeuwnhoek* 95(3):249-262 (2009).
Takahashi and Yamada, "Metabolic pathways for cytoxic and end product formation from glutamate- and aspartate-containing peptides by Porphyromonas gingivalis," *J. Bacteriol.* 182:4704-4710 (2000).
Takeo, "Existence and Properties of Two Malic Enzymes in *Escherichia coli* Especially of NAD-linked Enzyme," *J. Biochem.* 66:379-387 (1969).
Tallant and Krzycki, "Coenzyme M methylase activity of the 480-kilodalton corrinoid protein from Methanosarcina barkeri" *J. Bacteriol.* 178(5):1295-1301 (1996).
Tallant and Krzycki, "Methylthiol:Coenzyme M Methyltransferase from Methanosarcina barkeri, an enzyme of methanogenesis from dimethylsulfide and methylmercaptopropionate," *J. Bacteriol.* 179(22):6902-6911 (1997).
Tallant et al., "The MtsA subunit of the methylthiol:Coenzyme M methyltransferase of Methanosarcina barkeri catalyses both half-reactions of corrinoid-dependent dimethylsulfide: Coenzyme M methyl transfer," *J. Biol. Chem.* 276(6):4485-4493 (2001).
Tamaki et al., "Purification and properties of aldehyde dehydrogenase from Saccharomyces cerevisiae," *J. Biochem.* 82(1):73-79 (1977).
Tanaka et al., "Cloning and characterization of a human orthologue of testis-specific succinyl CoA: 3-oxo acid CoA transferase (Scot-t) cDNA," Mol. Hum. Reprod. 8:16-23 (2002).
Tani et al., "Thermostable NADP+-dependent medium-chain alcohol dehydrogenase from *Acinetobacter* sp. strain M-1: purification and characterization and gene expression in *Escherichia coli*," *Appl. Environ. Microbiol.* 66(12):5231-5235 (2000).

Tanous et al., "Glutamate dehydrogenase activity can be transmitted naturally to *Lactococcus lactis* strains to stimulate amino acid conversion to aroma compounds," *Appl. Environ. Microbiol.* 72(2):1402-1409 (2006).
Tardif et al., "Electrotransformation studies in Clostridium cellulolyticum," *J. Ind. Microbiol. Biotechnol.* 27(5):271-274 (2001).
Teipel et al., "The substrate specificity of fumarase," J. Biol. Chem. 243:5684-5694 (1968).
Teufel et al., "3-hydroxypropionyl-Coenzyme A dehydratase and acryloyl-Coenzyme A reductase, enzymes of the autotrophic 3-hydroxypropionate/4-hydroxybutyrate cycle in the Sulfolbales," *J. Bacteriol.* 191:4572-4581 (2009).
Thanos and Simon, "Electro-enzymic viologen-mediated stereospecific reduction of 2-enoates with free and immobilized enoate reductase on cellulose filters or modified carbon electrodes," *J. Biotechnol.* 6:13-29 (1987).
Thauer, "Microbiology. A Fifth Pathway of Carbon Fixation," *Science* 318:1732-1733 (2007).
Tischer et al., "Purification and Some Properties of a Hitherto-Unknown Enzyme Reducing the Carbon-Carbon Double Bond of $\alpha,\beta$-Unsaturated Carboxylate Anions," *Eur. J. Biochem.* 97(1):103-112 (1979).
Tobimatsu et al., "Molecular cloning, Sequencing and Characterization of the Genes for Adenosylcobalamin-deptendent Diol Dehydratase of Klebsiella pneumoniae," *Biosci. Biotechnol. Biochem.* 62(9):1744-1777 (1998).
Tobimatsu et al., "Molecular cloning, Sequencing and Expression of the Genes Encoding Adenosylcobalamin-dependent Diol Dehydrase of Klebsiella oxytoca," *J. Biol. Chem.* 270(13):7142-7148 (1995).
Tomas et al., "Overexpression of groESL in Clostridium acetobutylicum Results in Increased Solvent Production and Tolerance, Prolonged Metabolism, and Changes in the Cell's Transcriptional Program," *Appl. Environ. Microbiol.* 69:4951-4965 (2003).
Toraya et al., "Substrate Specificity of Coenzyme $B_{12}$-Dependent Diol Dehydrase: Glycerol as Both a Good Substrate and a Potent Inactivator," *Biochem. Biophys. Res. Commun.* 69:475-480 (1976).
Toth et al., "The ald Gene, Encoding a Coenzyme A-Acylating Aldehyde Dehydrogenase, Distinguishes Clostridium beijerinckii and Two Other Solvent-Producing Clostridia from Clostridium acetobutylicum," *App. Environ. Microbiol.* 65(11):4973-4980 (1999).
Tretter and Adam-Vizi, "Alpha-ketoglutarate dehydrogenase: a target and generator of oxidative stress," *Philos. Trans. R. Soc. B* 360:2335-2345 (2006).
Tsao et al., "Production of multifunctional organic acids from renewable resources," *Adv. Biochem. Eng. Biotechnol.* 65:243-280 (1999).
Tseng et al., "Metabolic Engineering of *Escherichia coli* for Enhanced Production of (R)- and (S)-3-Hydroxybutyrate," *App. Environ. Microbiol.* 75(10):3137-3145 (2009).
Tseng et al., "Oxygen- and growth rate-dependent regulation of *Escherichia coli* fumarase (FumA, FumB, and BumC) activity," *J. Bacteriol.* 183(2):461-467 (2001).
Tsujimoto et al., "L-Lysine biosynthetic pathway of Methylophilus methylotrophus and construction of an L-Lysine producer," *J. Biotechnol.* 124:327-337 (2006).
Tucci and Martin, "A novel prokaryotic trans-2-enoyl-CoA reductase from the spirochete Treponema denticola," *FEBS Lett.* 581(8):1561-1566 (2007).
Twarog and Wolfe, "Role of butyryl phosphate in the energy metabolism of Clostridium tetanomorphum," J. Bacteriol. 86:112-117 (1963).
Tyurin, et al., "Electrotransformation of Clostridum acetobutylicum ATCC 824 using high-voltage radio frequency modulated square pulses," *J. Appl. Microbiol.* 88(2):220-227 (2000).
Tyurin, et al., "Electrotransformation of Clostridium thermocellum," *Appl. Environ. Microbiol.* 70(2):883-890 (2004).
Ulaganathan et al., "Structure of *Staphylococcus aureus*1,4-dihydroxy-2-naphthoyl-CoA synthase (MenB) in complex with acetoacetyl-CoA," *Acta. Crystallogr. Sect. F. Struct. Biol. Cryst. Commun.* 63(Pt 11):908-913 (2007).

(56) References Cited

OTHER PUBLICATIONS

Underwood et al., "Genetic Changes to Optimize Carbon Partitioning between Ethanol and Biosynthesis in Ethanologenic *Escherichia coli*," App. Environ. Microbiol. 68(12):6263-6272 (2002).

Urbance et al., "Evaluation of succinic acid continuous and repeat-batch biofilm fermentation by Actinobacillus succinogenes using plastic composite support bioreactors," *Appl. Microbiol. Biotechnol.* 65(6):664-670 (2004).

Uttaro and Opperdoes, "Purification and characterisation of a novel isopropanol dehydrogenase from *Phytomonas* sp.," *Mol. Biochem. Parasitol.* 85:213-219 (1997).

Vadali et al., "Enhanced Isoamyl Acetate Production upon Manipulation of the Acetyl-CoA node in *Escherichia coli*," *Biotech. Prog.* 20:692-697 (2004).

Vadali et al., "Production of isoamyl acetate in ackA-pta and/or ldh mutants of *E. coli* with overexpression of yeast ATF2," *Appl. Microbiol. Biotechnol.* 63:698-704 (2004).

Vadali et al., "Cofactor engineering of intercellular CoA/acetyl-CoA and its effect on metabolic flux redistribution in *Escherichia coli*," *Metab Eng.* 6(2): 133-139 (2004).

Valentin et al., "Metabolic pathway for biosynthesis of poly(3-hydroxybutyrate-co-4-hydroxybutyrate) from 4-hydroxybutyrate by Alcaligenes eutrophus," *Eur. J. Biochem.* 227(1-2):43-60 (1995).

Valentine and Wolfe, "Purification and role of phosphotransbutyrylase," *J. Biol. Chem.* 235:1948-1952 (1960).

Vamecq et al., "The microsomal dicarboxylyl-CoA synthetase," *Biochem. J.* 230(3):683-693 (1985).

Van der Voorhorst et al., "Genetic and biochemcial characterization of a short-chain alcohol dehydrogenase from the hyperthermophilic archaeon Pyrococcus furiosus," *Eur. J. Biochem.* 268:3062-3068 (2001).

Van Der Westhuizen, et al., "Autolytic Activity and Butanol tolerance of Clostridium acetobutylicum," *Appl. Environ. Microbiol.* 44:1277-1281 (1982).

Van Grinsven et al., "Acetate:succinate CoA-transferase in the hydrogenosomes of Trichomonas vaginalis: identification and characterization," *J. Biol. Chem.* 283:1411-1418 (2008).

Van Loon and Young, "Intracellular sorting of alcohol dehydregenase isoenzymes in yeast: a cytosolic location oreflects absence of an amino-terminal targeting sequence for the mitochondrion," *EMBO J.* 5:161-165 (1986).

Vandecasteele et al., "Aldehyde dehydrogenases from Pseudomonas aeruginosa," *Methods Enzymol.* 89 Pt D:484-490 (1982).

Vanderwinkel et al., "Growth of *Escherichia coli* on fatty acids: requirement for Coenzyme A transferase activity," *Biochem. Biophys. Res. Commun.* 33(6):902-908 (1968).

Varadarajan and Miller, "Catalytic Upgrading of Fermentation-Derived Organic Acids," *Biotechnol. Prog.* 15:845-854 (1999).

Vardar-Schara et al., "Metabolically engineered bacteria for producing hydrogen via fermentation," *Microbio. Biotechnol.* 1:107-125 (2008).

Vanua and Palsson, "Stoichiometric Flux Balance Models Quantitatively Predice Growth and Metabolic By-Product Secretion in Wild-Type *Escherichia coli* W3110," *Appl Env. Microbiol.* 60(10):3724-3731 (1994).

Varma and Palsson, "Metabolic Flux Balancing: Basic Concepts, Scientific and Practical Use," *Biotechnology* 12:994-998 (1994).

Varma et al., "Biochemical Production Capabilities of *Escherichia coil*," *Biotechnol. Bioeng.* 42:59-73 (1993).

Varma et al., "Stoichiometric Interpretation of Escherichia coli Glucose Catabolism under Various Oxygenation Rates," *Appl. Environ. Microbiol.* 59:2465-2473 (1993).

Vazquez et al., "Phosphtransbutyrylase expression in Bacillus megaterium," *Curr. Microbiol.* 42:345-349 (2001).

Vega et al., "The Biological Production of Ethanol from Synthesis Gas," *Appl. Biochem. Biotechnol.* 20/21:781-797 (1989).

Venturi et al. Succinate production in dual J Inc Microbiol Biotechnol, 2002, 28(6) :325-32.

Venkitasubramanian et al. *Biocatalysis in the Pharmaceutical and Biotechnology Industires,* ed. R.N. Patel, Chapter 15, pp. 425-440, CRC Press LLC, Boca Raton, FL. 2007.

Venkitasubramanian et al., "Reduction of Carboxylic Acids by Nocardia Aldehyde Oxidoreductase Requires a Phosphopantetheinylated Enzyme," *J. Biol. Chem.* 282(1):478-485 (2007).

Verhaert et al., "Enzyme kinetics in reversed micelles. 2. Behaviour of enoate reductase," *Eur. J. Biochem.* 187:73-79 (1990).

Vey et al., "Structural basis for glycyl radical formation by pyruvate formate-lyase activating enzyme," Proc. Natl. Acad. Sci. U.S.A. 105:16137-16141 (2008).

Volkert, et al., "The Δ(argF-lacZ)205(U169) Deletion Greatly Enhances Resistance to Hydrogen Peroxide in Stationary-Phase *Escherichia coli*," J. Bact. 176(3):1297-1302 (1994).

Wakil et al., "Studies on the fatty acid oxidizing system of animal tissues. VI. β-Hydroxyacyl Coenzyme A dehydrogenase," J. Biol. Chem. 207(2):631-638 (1954).

Walter et al., "Molecular characterization of two Clostridium acetobutylicum ATCC 824 butanol dehydrogenase isozyme genes," *J. Bacteriol.* 174(22):7149-7158 (1992).

Walter et al., "Sequence and arrangement of two genes of the butyrate-synthesis pathway of Clostridium acetobutylicum ATCC 824," *Gene* 134(1):107-111 (1993).

Wang and Seah, "Determination of the metal ion dependence and substrate specificty of a hydratase involve din the degradation pathway of biphenyl/chlorobiphenyl," *FEBS J,* 272: 966-974 (2005).

Wang et al, "Molecular cloning and functional identification of a novel phenylacetyl-CoA ligase gene from Penicillium chrysogenum," *Biochem. Biopyhs. Res. Commun.* 360(2):453-458 (2007).

Wang et al., "The primary structure of branched-chain α-oxo acid dehydrogenase from Bacillus subtilis and its similarity to other α-oxo acid dehydrogenases," *Eur. J. Biochem.* 213:1091-1099 (1993).

Wang et al., "Bioconversion of fumaric acid to succinic acid by recombinant *E. coli*," *App. Biochem. Biotechnol.* 70-72: 919-928 (1998).

Wang et al., "Genome-scale in silico aided metabolic analysis and flux comparisons of *Escherichia coli* to improve succinate production," Appl. Microbiol. Biotechnol. 73(4):887-894 (2006).

Wanner and Tressl, "Purification and characterization of two enone reductases from *Saccharomyces cerevisia*," Eur. J. Biochem. 255(1):271-278 (1998).

Watanabe et al., "A novel α-ketoglutaric semialdehyde dehydrogenase: evolutionary insight into an alternative pathway of bacterial 1-arabinose metabolism," *J. Biol. Chem.* 281(39):28876-28888 (2006).

Weaver, "Structure of free fumarase C from *Escherichia coli*," *Acta. Crystallogr. D. Biol. Crystallog.* 61(Pt 10):1395-1401 (2005).

Weidner and Sawers, "Molecular characterization of the Genes Encoding Pyruvate Formate-Lyase and Its Activating enzyme of clostridium pasteruianum," *J. Bacteriol.* 178(8):2440-2444 (1996).

Welch et al., "Purification and Characterization of the NADH-Dependent Butanol Dehydrogenase from Clostridium acetobutylicum (ATCC 824)," *Arch. Biochem. Biophys.* 273(2):309-318 (1989).

Westin et al., "The identification of a succinyl-CoA thioesterase suggests a novel pathway for succinate production in peroxisomes," *J. Biol. Chem.* 280(46):38125-38132 (2005).

Wexler et al., "A wide host-range metagenomic library from a waste water treatment plant yields a novel alcohol/aldehyde dehdrogenase," *Environ. Microbial.* 7:1917-1926 (2006).

Whalen and Berg, "Analysis of an avtA::Mu dl (Ap lac) Mutant: Metabolic Role of Transaminase C," *J. Bacteriol.* 150(2):739-746 (1982).

Whelan et al., "Nylon 6 (PA6)," *Kunststof en Rubber,* Wyt en Zonen Uitgevers. Rotterdam, NL. 39(3):38-39 (1986).

Whisstock et al., "Prediction of protein function from protein sequence and structure," *Q. Rev. Biophysics.* 36(3):307-340 (2003).

White et al., "The structural biology of type II fatty acid biosynthesis," Ann. Rev. Biochem. 74:791-831 (2005).

(56) References Cited

OTHER PUBLICATIONS

White, "Biosynthesis of methanopterin," *Biochemistry* 35(11):3447-3456 (1996).
Whitehead and Rabinowitz, "Cloning and expression in *Escherichia coli* of the gene for 10-formyltetrahydrofolate synthetase from Clostridium acidiurici ("Clostridium acidi-urici")," *J. Bacteriol.* 167:205-209 (1986).
Whitehead and Rabinowitz, "Nucleotide Sequence of the Clostriditun acidiurici ("Clostridium acidi-urici") Gene for 10-Formyltetrahydrofolate Synthetase Shows Extensive Amino Acid Homology with the Trifunctional Enzyme C1-Tetrahydrofolate Synthase from *Saccharomyces cerevisiae*," *J. Bacteriol.* 170(7):3255-3261 (1988).
Wiesenborn et al., "Coenzyme A Transferase from clostridium acetobutylicum ATCC 824 and Its Role in the Uptake of Acids," *Appl. Environ. Microbiol.* 55(2):323-329 (1989).
Wiesenborn et al., "Phosphotransbutyrylase from clostridium acetobutylicum ATCC 824 and its role in acidogenesis," *Appl. Environ. Microbiol.* 55:317-322 (1989).
Wilks et al., "A specific, Highly Active Malate Dehydrogenase by Redesign of a Lactate Dehydrogenase Framework," *Science* 242:1541-1544 (1988).
Wilks et al., "Design of a Specific Phenyllactate Dehydrogenase by Peptide Loop Exchange on the Bacillus stearothermophilus Lactate Dehydrogenase Framework," *Biochemistry* 31:7802-7806 (1992).
Wilks et al., "Designs for a Broad Substrate Specificity Keto Acid Dehydrogenase," *Biochemistry* 29:8587-8591 (1990).
Willke and Vorlop, "Industrial bioconversion of renewable resources as an alternative to conventional chemistry," *Appl. Microbiol. Biotechnol.* 66(2):131-142 (2004).
Winzer et al., "Differential regulation of two thiolase genes from Clostridium acetobutylicum DSM 792," *J. Mol. Microbiol. Biotechnol.* 2(4):531-541 (2000).
Witkowski et al., "Conversion of β-ketoacyl synthase to a Malonyl Decarboxylase by replacement of the active cysteine with glutamine," Biochemistry 38:11643-11650 (1999).
Wolff and Kenealy, "Purification and characterization of the oxygen-sensitive 4-hydroxybutanoate dehydrogenase from Clostridium kluyveri," *Protein Expr. Purif.* 6:206-212 (1995).
Wong et al., "Molecular Properties of Pyruvate Formate-Lyase Activating Enzyme," Biochemistry 32:14102-14110 (1993).
Wood, "Life with CO or CO2 and H2 as a source of carbon and energy," *Fed. Amer. Societies Experi. Biol. J.* 5:156-163 (1991).
Woods, "Two biochemically distinct classes of fumarase in *Escherichia coli*," Biochim. Biophys. Acta 954(1):14-26 (1988).
Wu et al., "Thermotoga maritima 3-deoxy-D-arabino-heptulosonate 7-phosphate (DAHP) synthase: the ancestral eubacterial DAHP synthase?" J. Biol. Chem. 278:27525-27531 (2003).
Wu et al., "Life in hot carbon monoxide: the complete genome sequence of Carboxydothermus hydrogenoformans Z-2901," *PLoS Genet.* 1(5):e65 (2005).
Wynn et al., "Cloning and expression in *Escherichia coli* of mature E1 β subunit of bovine mitochondrial branched-chain α-keto acid dehydrogenase complex. Mapping of the E1 β-binding region on E2," *J. Biol.Chem.* 267:1881-1887 (1992).
Yabutani et al., "Analysis of β-ketothiolase and acetoacetyl-CoA reductase genes of a methylotrophic bacterium, Paracoccus denitrificans, and their expression in *Escherichia coli*," *FEMS Microbiol. Lett.* 133:85-90 (1995).
Yagi et al., "Glutamate-aspartate transaminase from microorganisms," *Methods Enzymol.* 113:83-89 (1985).
Yamamoto et al., "Carboxylation reaction catalyzed by 2-oxoglutarate:ferredoxin oxidoreductases from Hydrogenobacter thermophilus," *Extremophiles* 14:79-85 (2010).
Yamamoto et al., "Purification and Properties of NADP-dependent Formate Dehydrogenase from Clostridium thermoaceticum, a tungsten-Selenium-Iron Protein " *J. Biol. Chem,* 258(3):1826-1832 (1983).

Yan and Chen, "Coenzyme A-acylating aldehyde dehydrogenase from Clostridium beijerinckii NRRL B592," *Appl. Environ. Microbiol.* 56:2591-2599 (1990).
Yang et al., "Aspartate Dehydrogenase, a Novel Enzyme Identified from Structural and Functional Studies of TM1643," *J. Biol. Chem.* 278(10):8804-8808 (2003).
Yang et al., "Effect of inactivation of nuo and ackA-pta on redistribution of metabolic fluxes in *Escherichia coli*," *Biotechnol Bioeng.* 65(3):291-297 (1999).
Yang et al., "Effect of Variation of Klebsiella pneumoniae Acetolactate Synthase Expression on Metabolic Flux Redistribution in *Escherichia coli*," *Biotechnol. Bioeng.* 69(2)150-159 (2000).
Yang et al., "Metabolic Flux Analysis of *Escherichia coli* Deficient in the Acetate Production Pathway and Expressing the Bacillus subtilis Acetolactate Synthase," *Metab. Eng.* 1(1):26-34 (1999).
Yang et al., "Nucleotide sequence of the fadA gene. Primary structure of 3-ketoacyl-Coenzyme A thiolase from *Escherichia coli* and the structural organization of the fadAB operon," *J. Biol. Chem.* 265(18):10424-10429 (1990).
Yang et al., "Nucleotide sequence of the fadA gene. Primary structure of 3-ketoacyl-Coenzyme A thiolase from *Escherichia coli* and the structural organization of the fadAB operon," *J. Biol. Chem.* 266(24):16255 (1991).
Yang et al., "Nucleotide sequence of the promoter and fadB gene of the fadBA operon and primary structure of the multifunctional fatty acid oxidation protein from *Escherichia coli*," *Biochem.* 30(27):6788-6795 (1991).
Yang et al., "The effects of feed and intracellular pyruvate levels on the redistribution of metabolic fluxes in *Escherichia coli*," *Metab Eng.* 3(2):115-123 (2001).
Yeh and Owston, Evolutionarily Homologous $α_2β_2$ Oligomeric Structures in β-Ketoadipate Succinyl-CoA Transferases from Acinetobacter calcoaceticus and Pseudomonas putida, *J. Biol. Chem.* 256(4):1565-1569 (1981).
Ylianttila et al., "Crystal Structure of Yeast Peroxisomal Multifunctional Enzyme: Structural Basis for Substrate Specificity of (3R)-hydroxyacyl-CoA Dehydrogenase Units," *J. Mol. Biol.* 258:1286-1295 (2006).
Ylianttila et al., "Site-directed mutagenesis to enable and improve crystallizability of candida tropicalis (3R)-hydroxyacyl-CoA dehydrogenase," *Biochem. Biophys. Res. Commun.* 324:25-30 (2004).
Yoshida et al., "Cloning and expression of the gene for hydroxypyruvate reductase (d-glycerate dehydrogenase from an obligate methylotroph Hyphomicrobium methylovorum GM2)," *Eur. J. Biochem.* 223(3):727-732 (1994).
Yoshimoto, et al., "Isolation and Characterization of the ATF2 Gene Encoding Alcohol Acetyltransferase II in the Bottom Fermenting Yeast *Saccharomyces pastorianus*," *Yeast* 15:409-417 (1999).
Yoshioka and Hashimoto, "Ester formation by Alcohol Acetyltransferase from Brewers' Yeast," *Agric. Biol. Chem.* 45:2183-2190 (1981).
Youngleson et al., "Homology between hydroxybutyryl and hydroxyacyl Coenzyme A dehydrogenase enzymes from Clostridium acetobutylicum fermentation and vertebrate fatty acid β-oxidation pathways," *J. Bacteriol.* 171(12):6800-6807 (1989).
Yun et al., "The genes for anabolic 2-oxoglutarate: ferredoxin oxidoreductse from hydrogenobacter thermophilus TK-6," *Biochem. Biophvs. Res. Commun.* 282(2):589-594 (2001).
Yun et al., "ω-Amino acid:pyruvate transaminase from Alcaligenes denitrificans Y2k-2: a new catalyst for kinetic resolution of β-amino acids and amines," *Appl. Environ. Microbiol.* 70(4):2529-2534 (2004).
Yun et al., "Enhancement of lactate and succinate formation in adhE or pta-ackA mutants of NADH dehydrogenase-deficient *Escherichia coli*," *J. Appl. Microbiol.* 99(6):1404-1412 (2005).
Zeiher and Randall, "Identification and characterization of Mitochondrial Acetyl-Coenzyme A Hydrolase from *Pisum sativum* L. Seedlings," *Plant. Physiol.* 94:20-27 (1990).
Zeikus et al., "Biotechnology of succinic acid production and markets for derived industrial products," *Appl. Microbiol. Biotechnol.* 51: 545-552 (1999).

(56) References Cited

OTHER PUBLICATIONS

Zelle et al., "Malic acid production by *Saccharomyces cerevisiae*: engineering of pyruvate carboxylation, oxaloacetate reduction, and malate export," *Appl. Environ. Microbiol.* 74(9):2766-2777 (2008).

Zerbe-Burkhardt et al., "Cloning, sequencing, expression, and insertional inactivation of the gene for the large subunit of the Coenzyme $B_{12}$-dependent isobutyryl-CoA mutase from Streptomyces cinnamonensis," *J. Biol. Chem.* 273(11):6508-6517 (1998).

Zhang et al., "2-Oxoacid:Ferredoxin Oxidoreductase from the thermoacidophilic Archaeon, *sulfolobus* sp. Strain 7," *J. Biochem.* 120:587-599 (1996).

Zhang et al., "A new logic for DNA engineering using recombination in *Escherichia coli*," *Nat. Genet.* 20:123-128 (1998).

Zhang et al., "Functional characterization of the first two actinomycete 4-amino-4-deoxychorismate lyase genes," *Microbiology* 155:2450-2459 (2009).

Zhang et al., "Genes encoding acyl-CoA dehydrogenase (AcdH) homologues from Streptomyces coelicolor and Streptomyces avermitilis provide insights into the metabolism of small branched-chain fayy acids and marcrolide antibiotic production," *Microbiol.* 145 (Pt 9):2323-2334 (1999).

Zhang et al., "Molecular basis for the inhibition of the carboxyltransferase domain of acetyl-Coenzyme-A carboxylase by haloxfop and dicofop," *Proc. Natl. Acad. Sci. U.S.A.* 101:5910-5915 (2004).

Zhao and Winkler, "A novel α-ketoglutarate reductase activity of the serA-encoded 3-phosphoglycerate dehydrogenase of *Escherichia coli* K-12 and its possible implications for human 2-hydroxyglutaric aciduria," *J. Bacteriol.* 178(1):232-239 (1996).

Zhou et al., "Comparison of fumaric acid production by Rhizopus oryzae using different neutralizing agents," *Bioproc. Biosyst. Eng.* 25(3):179-181 (2002).

Zhou et al., "Engineering a native homoethanol pathway in *Escherichia coli* B for ethanol production," *Biotechnol. Lett.* 30:335-342 (2008).

Zhou et al., "The remarkable structural and functional organization of the eukaryotic pyruvate dehydrogenase complexes," *Proc. Natl. Acad. Sci. U.S.A.* 98:14802-14807 (2001).

Zhou et al., "Isolation, crystallization and preliminary X-ray analysis of a methanol-induced corrinoid protein from Moorella thermoacetica," *Acta. Crystallog. Sect. F. Struct. Biol. Cryst. Commun.* 61(Pt 5):537-540 (2005).

Zhuang et al., "The YbgC protein encoded by the ybgC gene of the tol-pal gene cluster of Haemophilus influenzae catalyzes acyl-Coenzyme A thioester hydrolysis," *FEBS Lett.* 516(1-3):161-163 (2002).

Zou et al., "Metabolic engineering for microbial production and applications of copolyesters consisting of 3-hydroxybutyrate and medium-chain-length 3-hydroxyalkanoates," *Macromol. Biosci.* 7:174-182 (2007).

One page from URL: 1.eee.energy.gov/biomass/information_resources.html (printed Apr. 19, 2010).

One page from URL: expressys.de/ (Printed Dec. 21, 2009).

Two pages from URL: toxnet.nlm.nih.gov/cgi-bin/sis/search/f?./temp/~FwAsma:1:BASIC (printed Feb. 17, 2010).

Two pages from URL: web.archive.org/web/20080302001450/ http://www.verenium.com/Pages/Technology/EnzymeTech/TechEnzyTGR.html (printed Apr. 12, 2010).

Gene Bridges, "Quick & Easy BAC Modification Kit by Red®/ET® Recombination," Technical Protocol, Cat. No. K001, Version 2.6 (2007).

One page from URL: <www.dtu.dk/English/Service/Phonebook.aspx?lg=showcommon&id=193466> Containing 182 page document: Patil, Ph.D. Thesis, "Systems Biology of Metabolic Networks: Uncovering Regulatory and stoichiometric Principles," 2006. (Printed from the Internet Jun. 8, 2011).

Two pages from URL: scientificamerican.com/article.cfm?id=turning-bacteria-into-plastic-factories-replacing-fossil-fuels (Printed Feb. 17, 2011).

Doukov, T., et al., (2000) "Crystal Structure of a Methyltetrahydrofolate- and Corrinoid-Dependent Methyltransferase", Structure, 8:817-830.

"Information on EC 2.1.1.258—5-methyltetrahydrofolate:corrinoid/iron-sulfur protein Co-methyltransferase", downloaded from www.brenda-enzymes.org/enzyme.php?ecno=2.1.1.258, 4 pages, downloaded on Aug. 21, 2017.

\* cited by examiner

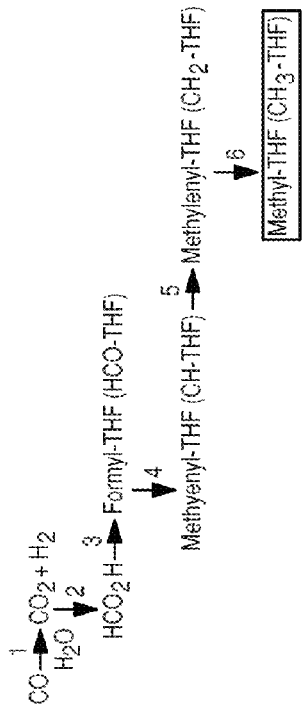

Syngas to Chemicals - Pathways 1

$CO + H_2 + CO_2$ (Syngas) → Chemicals, Fuels

2 Branches of Pathway

1.) Methyl Branch: Syngas → Methyl-tetrahydrofolate (Me-THF)

2.) Carbonyl Branch: Me-THF + Syngas → Acetyl-CoA

Methyl Branch- CO and $CO_2$ reduction

Methyl Branch Enzymes Implicated

1. Ferredoxin oxidoreductase
2. Formate dehydrogenase
3. Formyltetrahydrofolate synthetase
4. Methenyltetrahydrofolate cyclodehydratase
5. Methylenetetrahydrofolate dehydrogenase
6. Methylenetetrahydrofolate reductase

FIG. 1

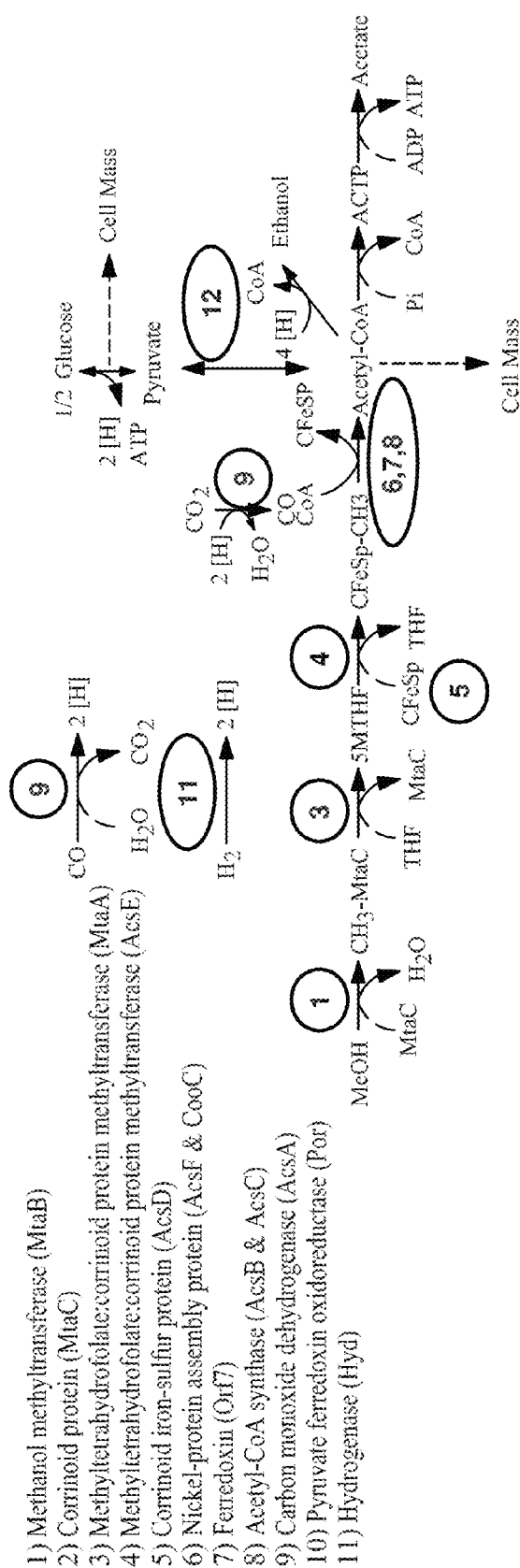

1) Methanol methyltransferase (MtaB)
2) Corrinoid protein (MtaC)
3) Methyltetrahydrofolate:corrinoid protein methyltransferase (MtaA)
4) Methyltetrahydrofolate:corrinoid protein methyltransferase (AcsE)
5) Corrinoid iron-sulfur protein (AcsD)
6) Nickel-protein assembly protein (AcsF & CooC)
7) Ferredoxin (Orf7)
8) Acetyl-CoA synthase (AcsB & AcsC)
9) Carbon monoxide dehydrogenase (AcsA)
10) Pyruvate ferredoxin oxidoreductase (Por)
11) Hydrogenase (Hyd)

FIG. 7

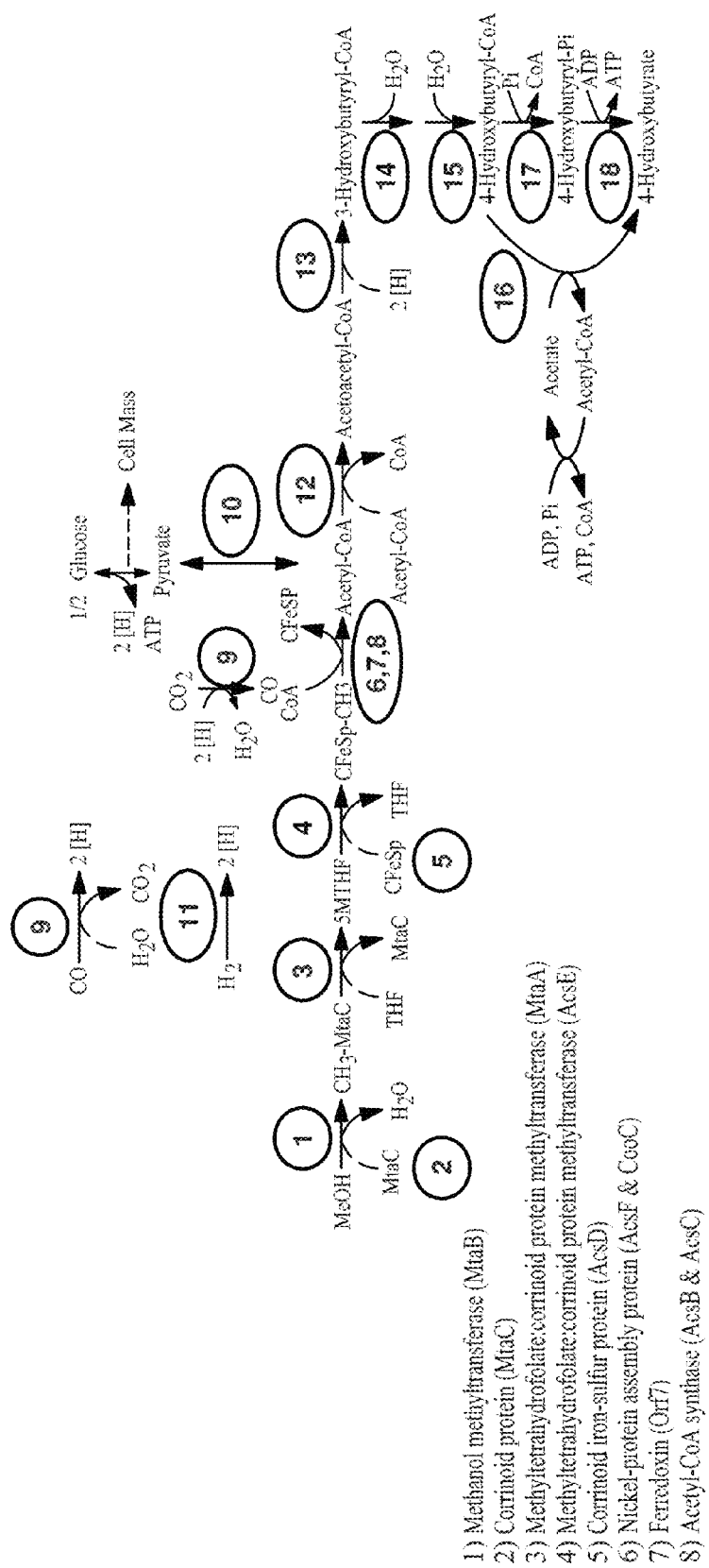

FIG. 11

1) Methanol methyltransferase (MtaB)
2) Corrinoid protein (MtaC)
3) Methyltetrahydrofolate:corrinoid protein methyltransferase (MtaA)
4) Methyltetrahydrofolate:corrinoid protein methyltransferase (AcsE)
5) Corrinoid iron-sulfur protein (AcsD)
6) Nickel-protein assembly protein (AcsF & CooC)
7) Ferredoxin (Orf7)
8) Acetyl-CoA synthase (AcsB & AcsC)
9) Carbon monoxide dehydrogenase (AcsA)
10) Pyruvate ferredoxin oxidoreductase (Por)
11) Hydrogenase (Hyd)
12) Acetoacetyl-CoA thiolase (AtoB)
13) 3-Hydroxybutyryl-CoA dehydrogenase (Hbd)
14) Crotonase (Crt)
15) Crotonyl-CoA hydratase (4-Budh)
16) 4-Hydroxybutyryl-CoA transferase
17) Phophotrans-4-hydroxybutyrylase
18) 4-Hydroxybutyrate kinase

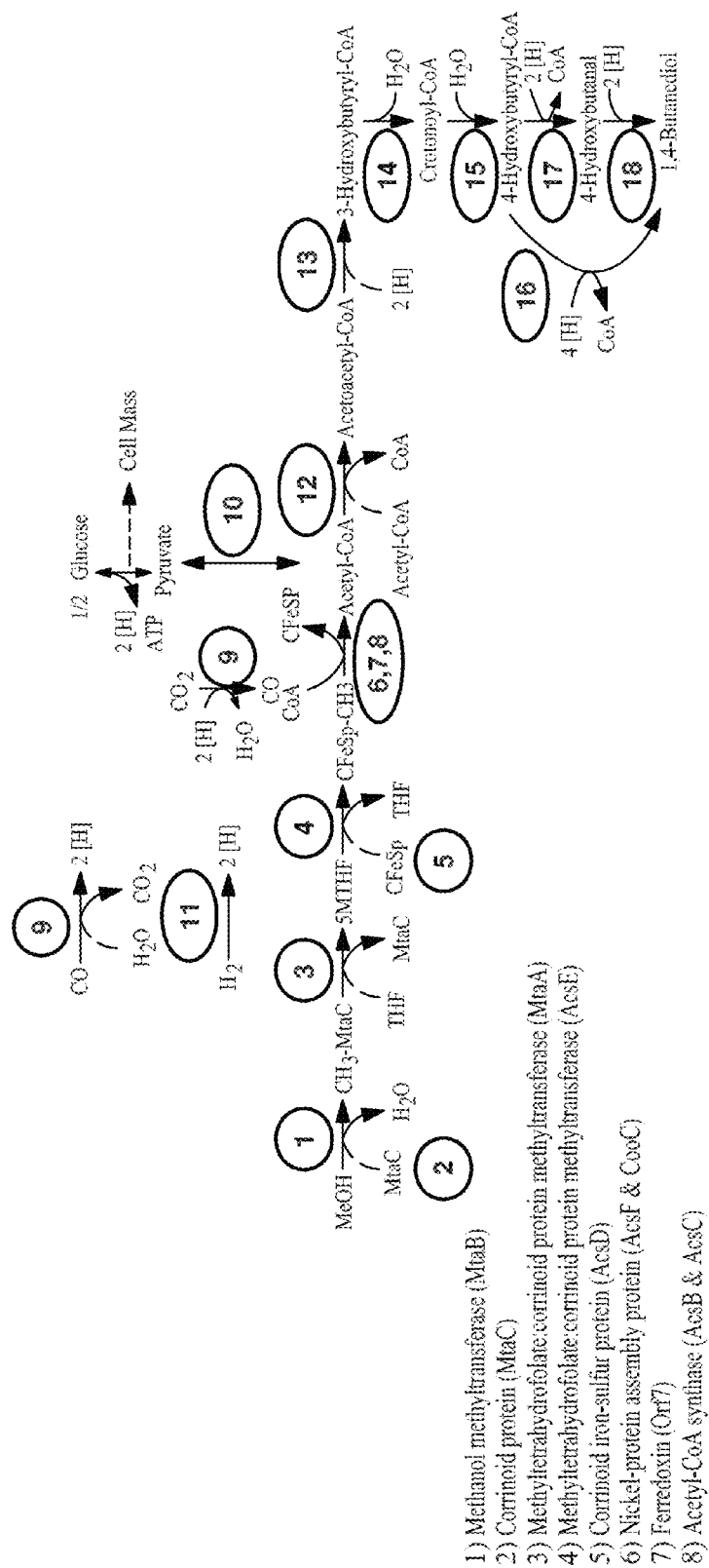

FIG. 12

1) Methanol methyltransferase (MtaB)
2) Corrinoid protein (MtaC)
3) Methyltetrahydrofolate:corrinoid protein methyltransferase (MtaA)
4) Methyltetrahydrofolate:corrinoid protein methyltransferase (AcsE)
5) Corrinoid iron-sulfur protein (AcsD)
6) Nickel-protein assembly protein (AcsF & CooC)
7) Ferredoxin (Orf7)
8) Acetyl-CoA synthase (AcsB & AcsC)
9) Carbon monoxide dehydrogenase (AcsA)
10) Pyruvate ferredoxin oxidoreductase (Por)
11) Hydrogenase (Hyd)
12) Acetoacetyl-CoA thiolase (AtoB)
13) 3-Hydroxybutyryl-CoA dehydrogenase (Hbd)
14) Crotonase (Crt)
15) Crotonyl-CoA hydratase (4-Budh)
16) 4-Hydroxybutyryl-CoA reductase (alcohol forming)
17) 4-Hydroxybutyryl-CoA reductase (aldehyde forming)
18) 1,4-Butanediol dehydrogenase

US 9,885,064 B2

METHODS AND ORGANISMS FOR UTILIZING SYNTHESIS GAS OR OTHER GASEOUS CARBON SOURCES AND METHANOL

This application is a divisional of application Ser. No. 13/615,168, filed Sep. 13, 2012, now U.S. Pat. No. 8,697,421, which is a continuation of application Ser. No. 13/106,764, filed May 12, 2011, now U.S. Pat. No. 8,323,950, which is a continuation of application Ser. No. 12/863,978, filed as a U.S. national stage application on Jul. 21, 2010, now U.S. Pat. No. 8,691,553, and which is a 371 of PCT US09/31737, having an international filing date of Jan. 22, 2009, which claims the benefit of priority of U.S. Provisional Ser. No. 61/022,804, filed Jan. 22, 2008, and U.S. Provisional Ser. No. 61/059,256, filed Jun. 5, 2008, each of which the entire contents are incorporated herein by reference.

BACKGROUND OF THE INVENTION

The present invention relates generally to biosynthetic processes and more specifically to organisms capable of using synthesis gas or other gaseous carbon sources and methanol.

Synthesis gas (syngas) is a mixture of primarily $H_2$ and CO that can be obtained via gasification of any organic feedstock, such as coal, coal oil, natural gas, biomass, or waste organic matter. Numerous gasification processes have been developed, and most designs are based on partial oxidation, where limiting oxygen avoids full combustion, of organic materials at high temperatures (500-1500° C.) to provide syngas as a 0.5:1-3:1 $H_2$/CO mixture. Steam is sometimes added to increase the hydrogen content, typically with increased $CO_2$ production through the water gas shift reaction.

Today, coal is the main substrate used for industrial production of syngas, which is traditionally used for heating and power and as a feedstock for Fischer-Tropsch synthesis of methanol and liquid hydrocarbons. Many large chemical and energy companies employ coal gasification processes on large scale and there is experience in the industry using this technology.

In addition to coal, many types of biomass have been used for syngas production. Gaseous substrates such as syngas and $CO_2$ represent the most inexpensive and most flexible feedstocks available for the biological production of renewable chemicals and fuels. During World War II, there were over 1 million small scale biomass gasification units in operation, mainly in Europe, for running cars, trucks, boats, and buses. Currently, there are at least three major biomass gasification technologies that have been or are in the process of being validated on a commercial scale (>20 million lb biomass/yr). Biomass gasification technologies are being practiced commercially, particularly for heat and energy generation. Integration with fuels or chemicals production is being developed and has not yet been demonstrated widely at a commercial scale.

Overall, technology now exists for cost-effective production of syngas from a plethora of materials, including coal, biomass, wastes, polymers, and the like, at virtually any location in the world. The benefits of using syngas include flexibility, since syngas can be produced from most organic substances, including biomass. Another benefit is that syngas is inexpensive, costing ≤$6 per million Btu, representing raw material costs of ≤$0.10/lb product. In addition, there are known pathways, as in organisms such as *Clostridium* spp., that utilize syngas effectively.

Despite the availability of organisms that utilize syngas, in general the known organisms are poorly characterized and are not well suited for commercial development. For example, *Clostridium* and related bacteria are strict anaerobes that are intolerant to high concentrations of certain products such as butanol, thus limiting titers and commercialization potential. The *Clostridia* also produce multiple products, which presents separations issues in obtaining a desired product. Finally development of facile genetic tools to manipulate *Clostridial* genes is in its infancy; therefore, they are not readily amenable to genetic engineering to improve yield or production characteristics of a desired product.

Thus, there exists a need to develop microorganisms and methods of their use to utilize syngas or other gaseous carbon sources for the production of desired chemicals and fuels. More specifically, there exists a need to develop microorganisms for synthesis gas utilization that also have existing and efficient genetic tools to enable their rapid engineering to produce valuable products at useful rates and quantities. The present invention satisfies this need and provides related advantages as well.

SUMMARY OF INVENTION

The invention provides anon-naturally occurring microbial organism having an acetyl-CoA pathway and the capability of utilizing syngas or syngas and methanol. In one embodiment, the invention provides a non-naturally occurring microorganism, comprising one or more exogenous proteins conferring to the microorganism a pathway to convert CO, $CO_2$ and/or $H_2$ to acetyl-coenzyme A (acetyl-CoA), methyl tetrahydrofolate (methyl-THF) or other desired products, wherein the microorganism lacks the ability to convert CO or $CO_2$ and $H_2$ to acetyl-CoA or methyl-THF in the absence of the one or more exogenous proteins. For example, the microbial organism can contain at least one exogenous nucleic acid encoding an enzyme or protein in an acetyl-CoA pathway. The microbial organism is capable of utilizing synthesis gases comprising CO, $CO_2$ and/or $H_2$, alone or in combination with methanol, to produce acetyl-CoA. The invention additionally provides a method for producing acetyl-CoA, for example, by culturing an acetyl-CoA producing microbial organism, where the microbial organism expresses at least one exogenous nucleic acid encoding an acetyl-CoA pathway enzyme or protein in a sufficient amount to produce acetyl-CoA, under conditions and for a sufficient period of time to produce acetyl-CoA.

BRIEF DESCRIPTION OF THE DRAWINGS

FIG. 1 shows an exemplary Wood-Ljungdahl pathway utilizing syngas as a carbon source. A methyl branch is depicted showing utilization of syngas to produce methyltetrahydrofolate (Me-THF).

FIG. 7 shows a synthetic metabolic pathway that allows the conversion of gases comprising CO, $CO_2$, and/or $H_2$ and methanol to acetyl-CoA. The specific enzymatic transformations that can be engineered into a production host are numbered. Additional abbreviation: MeOH: methanol.

FIG. 11 shows a synthetic metabolic pathway for the conversion of gases including CO, $CO_2$, and/or $H_2$, and methanol to acetyl-CoA and further to 4-hydroxybutyrate.

FIG. 12 shows a synthetic metabolic pathway for the conversion of gases including CO, $CO_2$, and/or $H_2$, and methanol to acetyl-CoA and further to 1,4-butanediol.

DETAILED DESCRIPTION OF THE INVENTION

Figure 2:
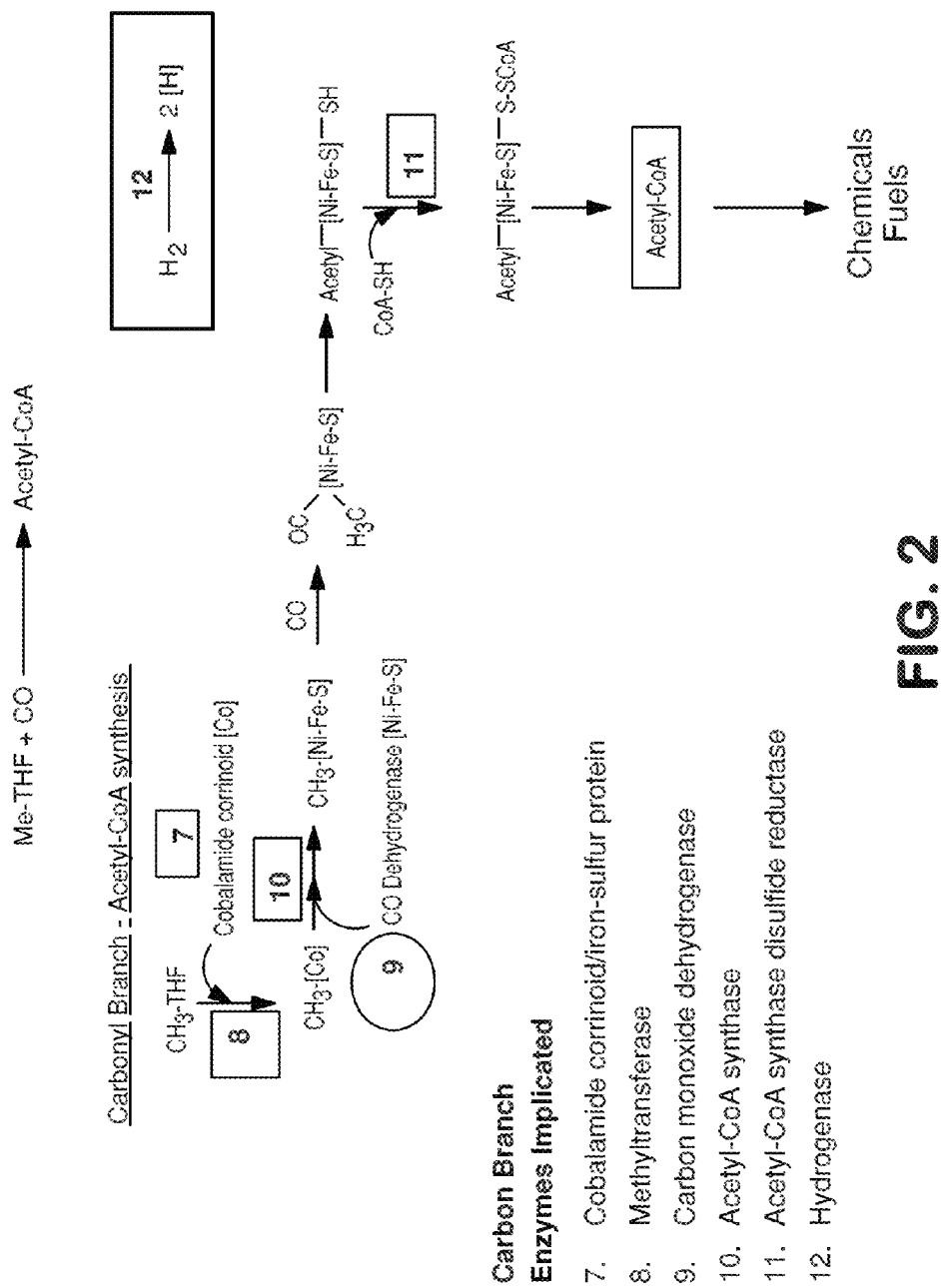
FIG. 2 shows an exemplary Wood-Ljungdahl pathway using syngas as a carbon source. A carbonyl branch is depicted showing utilization of syngas to produce acetyl-coenzyme A (acetyl-CoA). Hydrogenase (12) is required to convert hydrogen from syngas into reducing equivalents that are needed in many of the reactions depicted.

The present invention relates to developing and using microorganisms capable of utilizing syngas or other gaseous carbon sources to produce a desired product. The invention further relates to expanding the product range of syngas-utilizing microorganisms and generating recombinant organisms capable of utilizing syngas to produce a desired product and optimizing their yields, titers, and productivities. Development of a recombinant organism, for example, *Escherichia coli* or other organisms suitable for commercial scale up, that can efficiently utilize syngas as a substrate for growth and for chemical production provides cost-advantaged processes for renewable chemical and fuel manufacturing. The organisms can be optimized and tested rapidly and at reasonable costs.

The great potential of syngas as a feedstock resides in its ability to be efficiently and cost-effectively converted into chemicals and fuels of interest. Two main technologies for syngas conversion are Fischer-Tropsch processes and fermentative processes. The Fischer-Tropsch (F-T) technology has been developed since World War II and involves inorganic and metal-based catalysts that allow efficient production of methanol or mixed hydrocarbons as fuels. The drawbacks of F-T processes are: 1) a lack of product selectivity, which results in difficulties separating desired products; 2) catalyst sensitivity to poisoning; 3) high energy costs due to high temperatures and pressures required; and 4) the limited range of products available at commercially competitive costs.

For fermentative processes, syngas has been shown to serve as a carbon and energy source for many anaerobic microorganisms that can convert this material into products such as ethanol, acetate and hydrogen (see below and Table 1). The main benefits of fermentative conversion of syngas are the selectivity of organisms for production of single products, greater tolerance to syngas impurities, lower operating temperatures and pressures, and potential for a large portfolio of products from syngas. The main drawbacks of fermentative processes are that organisms known to convert syngas tend to generate only a limited range of chemicals, such as ethanol and acetate, and are not efficient producers of other chemicals, the organisms lack established tools for genetic manipulation, and the organisms are sensitive to end products at high concentrations.

The present invention relates to the generation of microorganisms that are effective at producing desired products, including chemicals and fuels, from syngas or other gaseous carbon sources. The organisms and methods of the present invention allow production of chemicals and fuels at costs that are significantly advantaged over both traditional petroleum-based products and products derived directly from glucose, sucrose or lignocellulosic sugars. In one embodiment, the invention provides a non-naturally occurring microorganism capable of utilizing syngas or other gaseous carbon sources to produce desired products in which the parent microorganism lacks the natural ability to utilize syngas (see Example VIII). In such microorganisms, one or more proteins or enzymes are expressed in the microorganism, thereby conferring a pathway to utilize syngas or other gaseous carbon source to produce a desired product. In other embodiments, the invention provides a non-naturally occurring microorganism that has been genetically modified, for example, by expressing one or more exogenous proteins or enzymes that confer an increased efficiency of production of a desired product, where the parent microorganism has the ability to utilize syngas or other gaseous carbon source to produce a desired product. Thus, the invention relates to generating a microorganism with a new metabolic pathway capable of utilizing syngas as well as generating a microorganism with improved efficiency of utilizing syngas or other gaseous carbon source to produce a desired product.

The present invention additionally provides a non-naturally occurring microorganism expressing genes encoding enzymes that catalyze and proteins associated with the carbonyl-branch of the Wood-Ljungdahl pathway in conjunction with a MtaABC-type methyltransferase system. Such an organism is capable of converting methanol, a relatively inexpensive organic feedstock that can be derived from synthesis gas, and gases comprising CO, $CO_2$, and/or $H_2$ into acetyl-CoA, cell mass, and products.

*Escherichia coli* is an industrial workhorse organism with an unrivaled suite of genetic tools. Engineering the capability to convert synthesis gas into acetyl-CoA, the central metabolite from which all cell mass components and many valuable products can be derived, into a foreign host such as *E. coli* can be accomplished following the expression of exogenous genes that encode various proteins of the Wood-Ljungdahl pathway. This pathway is highly active in acetogenic organisms such as *Moorella thermoacetica* (formerly, *Clostridium thermoaceticum*), which has been the model organism for elucidating the Wood-Ljungdahl pathway since its isolation in 1942 (Fontaine et al., *J Bacteriol.* 43:701-715 (1942)). The Wood-Ljungdahl pathway comprises two branches: the Eastern, or methyl, branch that allows the conversion of $CO_2$ to methyltetrahydrofolate (Me-THF) and the Western, or carbonyl, branch that allows the conversion of methyl-THF, CO, and Coenzyme-A into acetyl-CoA (see FIGS. 1 and 2). As disclosed herein, the invention provides a non-naturally occurring microorganism expressing genes that catalyze both branches of the Wood-Ljungdahl pathway. Such an organism is capable of converting gasses comprising CO, CO2, and/or H2 into acetyl-CoA, cell mass, and products. The invention additionally provides a non-naturally occurring microorganism expressing genes encoding enzymes that catalyze the carbonyl-branch of the Wood-Ljungdahl pathway in conjunction with a MtaABC-type methyltransferase system. Such an organism is capable of converting methanol, a relatively inexpensive organic feedstock that can be derived from synthesis gas, and gases comprising CO, $CO_2$, and/or $H_2$ into acetyl-CoA, cell mass, and products.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

As disclosed herein, gaseous carbon sources such as syngas comprising CO and/or $CO_2$ can be utilized by non-naturally occurring microorganisms of the invention to produce a desired product. Although generally exemplified herein as syngas, it is understood that any source of gaseous carbon comprising CO and/or $CO_2$ can be utilized by the non-naturally occurring microorganisms of the invention. Thus, the invention relates to non-naturally occurring microorganisms that are capable of utilizing CO and/or $CO_2$ as a carbon source.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $CO_2/H_2$ mixtures through the same basic set of enzymes and transformations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, *Acetogenesis*, pp. 3-60 Chapman and Hall, New York, (1994)). This can be summarized by the following equation:

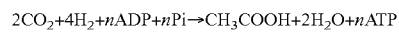

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-MY to acetyl-CoA. The reactions in the methyl branch are catalyzed in order by the following enzymes or proteins: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes or proteins: methyltetrahydrofolate:corrinoid protein methyltransferase (for example, AcsE), corrinoid iron-sulfur protein, nickel-protein assembly protein (for example, AcsF), ferredoxin, acetyl-CoA synthase, carbon monoxide dehydrogenase and nickel-protein assembly protein (for example, CooC). Following the teachings and guidance provided herein for introducing a sufficient number of encoding nucleic acids to generate a acetyl-CoA pathway, those skilled in the art will understand that the same engineering design also can be performed with respect to introducing at least the nucleic acids encoding the Wood-Ljungdahl enzymes or proteins absent in the host organism. Therefore, introduction of one or more encoding nucleic acids into the microbial organisms of the invention such that the modified organism contains one branch or the complete Wood-Ljungdahl pathway will confer syngas utilization ability.

Thus, the non-naturally occurring microorganisms of the invention can use syngas or other gaseous carbon sources providing CO and/or $CO_2$ to produce a desired product. In the case of $CO_2$, additional sources include, but are not limited to, production of $CO_2$ as a byproduct in ammonia and hydrogen plants, where methane is converted to $CO_2$; combustion of wood and fossil fuels; production of $CO_2$ as a byproduct of fermentation of sugar in the brewing of beer, whisky and other alcoholic beverages, or other fermentative processes; thermal decomposition of limestone, $CaCO_3$, in the manufacture of lime, CaO; production of $CO_2$ as byproduct of sodium phosphate manufacture; and directly from natural carbon dioxide springs, where it is produced by the action of acidified water on limestone or dolomite.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within an acetyl-CoA biosynthetic pathway.

A metabolic modification refers to a biochemical reaction that is altered from its naturally occurring state. Therefore, non-naturally occurring microorganisms can have genetic modifications to nucleic acids encoding metabolic polypeptides or, functional fragments thereof. Exemplary metabolic modifications are disclosed herein.

As used herein, the term "isolated" when used in reference to a microbial organism or microorganism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" is intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

The non-naturally occurring microbal organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as *E. coli* and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having acetyl-CoA biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

In one embodiment, the invention provides a non-naturally occurring microorganism comprising one or more exogenous proteins conferring to the microorganism a pathway to convert CO and/or $CO_2$ and $H_2$ to acetyl-coenzyme A (acetyl-CoA), wherein the microorganism lacks the ability to convert CO and/or $CO_2$ and $H_2$ to acetyl-CoA in the absence of the one or more exogenous proteins. For example, the one or more exogenous proteins or enzymes can be selected from cobalamide corrinoid/iron-sulfur protein, methyltransferase, carbon monoxide dehydrogenase, acetyl-CoA synthase, acetyl-CoA synthase disulfide reductase and hydrogenase (see FIG. 1 and Examples VII and VIII). The microorganism can also express two or more, three or more, and the like, including up to all the proteins and enzymes that confer a pathway to convert CO and/or $CO_2$ and $H_2$ to acetyl-CoA, for example, cobalamide corrinoid/iron-sulfur protein, methyltransferase, carbon monoxide dehydrogenase, acetyl-CoA synthase, acetyl-CoA synthase disulfide reductase and hydrogenase.

As disclosed herein, an embodiment of the invention relates to generating a non-naturally occurring microorganism that can utilize CO and/or $CO_2$ as a carbon source to produce a desired product. For example, the proteins and enzymes of the carbonyl and/or methyl branch of the Wood-Ljungdahl pathway (FIGS. 1 and 2) are introduced into a microorganism that does not naturally contain the Wood-Ljungdahl enzymes. A particularly useful organism for genetically engineering a Wood-Ljungdahl pathway is *E. coli*, which is well characterized in terms of available genetic manipulation tools as well as fermentation conditions (see Example VIII).

In another embodiment, the invention provides a non-naturally occurring microorganism comprising one or more exogenous proteins conferring to the microorganism a pathway to convert synthesis gas, also known as syngas, or other gaseous carbon source, comprising CO and $H_2$ to acetyl-coenzyme A (acetyl-CoA), wherein the microorganism lacks the ability to convert CO and $H_2$ to acetyl-CoA in the absence of the one or more exogenous proteins. Such a synthesis gas or other gas can further comprise $CO_2$. Thus, a non-naturally occurring microorganism of the invention can comprise a pathway that increases the efficiency of converting $CO_2$, CO and/or $H_2$ to acetyl-CoA. In addition, the invention provides a non-naturally occurring microorganism comprising one or more exogenous proteins conferring to the microorganism a pathway to convert a gaseous carbon source comprising $CO_2$ and $H_2$ to acetyl-CoA, wherein the microorganism lacks the ability to convert $CO_2$ and $H_2$ to acetyl-CoA in the absence of the one or more exogenous proteins. The gas can further comprise CO. As discussed herein, the exogenous proteins can be selected from cobalamide corrinoid/iron-sulfur protein, methyltransferase, carbon monoxide dehydrogenase, acetyl-CoA synthase, acetyl-CoA synthase disulfide reductase and hydrogenase.

In yet another embodiment, the invention provides a non-naturally occurring microorganism comprising one or more exogenous proteins conferring to the microorganism a pathway to convert CO and/or $CO_2$ and $H_2$ to methyl-tetrahydrofolate (methyl-THF), wherein the microorganism lacks the ability to convert CO and/or $CO_2$ and $H_2$ to methyl-THF in the absence of the one or more exogenous proteins. As disclosed herein, the one or more exogenous proteins can be selected from ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase (see FIG. 1 and Example VIII). The microorganism can also express two or more, three or more, and the like, including up to all the proteins and enzymes that confer a pathway to convert CO and/or $CO_2$ and $H_2$ to methyl-THF, including up to all of ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase.

The invention additionally provides a non-naturally occurring microorganism comprising one or more exogenous proteins conferring to the microorganism a pathway to convert synthesis gas or other gaseous carbon source comprising CO and $H_2$ to methyl-THF, wherein the microorganism lacks the ability to convert CO and $H_2$ to methyl-THF in the absence of the one or more exogenous proteins. The synthesis gas can further comprise $CO_2$. In addition, the invention provides a non-naturally occurring microorganism comprising one or more exogenous proteins conferring to the microorganism a pathway to convert a gaseous carbon source comprising $CO_2$ and $H_2$ to methyl-THF, wherein the microorganism lacks the ability to convert $CO_2$ and $H_2$ to methyl-THF in the absence of the one or more exogenous proteins. The gaseous carbon source can further comprise CO. As discussed above, the exogenous proteins can be selected from ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase.

Figure 6:
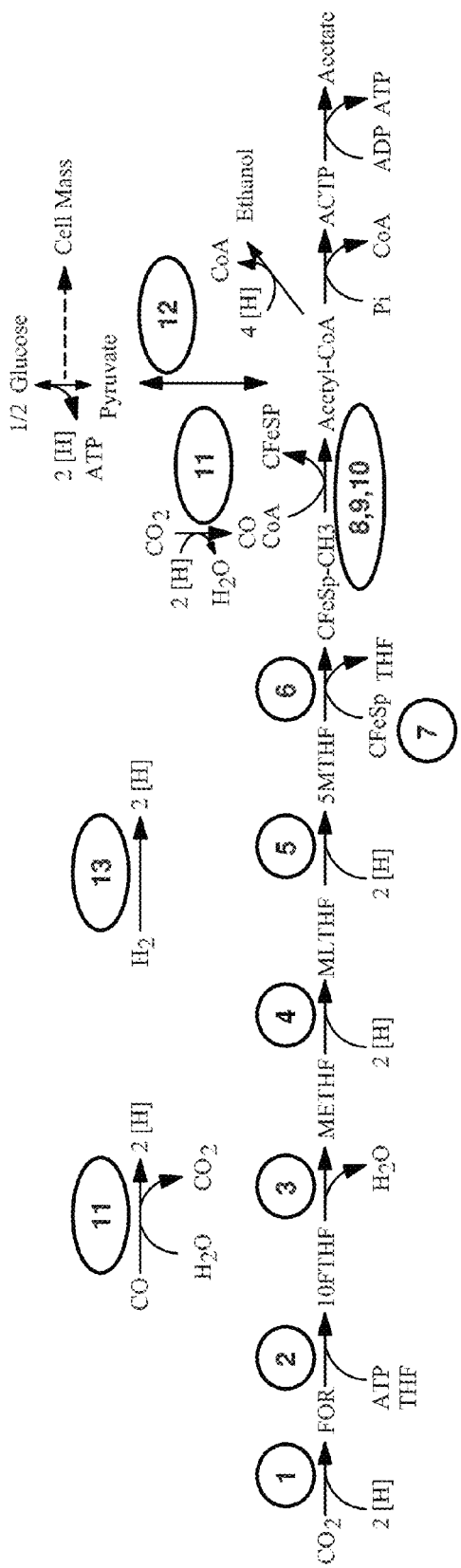
FIG. 6 shows a complete Wood-Ljungdahl pathway that allows the conversion of gases comprising CO, $CO_2$, and/or $H_2$ to acetyl-CoA, which can subsequently be converted to cell mass and products such as ethanol or acetate. Exemplary specific enzymatic transformations that can be engineered into a production host are numbered. Abbreviations: 10FTHF: 10-formyltetrahydrofolate, 5MTHF: 5-methyltetrahydrofolate, ACTP: acetyl phosphate, FOR: formate, METHF: methylene-tetrahydrofolate, MLTHF: methenyltetrahydrofolate, THF: tetrahydrofolate.

Thus, the invention relates to non-naturally occurring microorganisms and methods of utilizing such microorganisms to produce a desired product such as acetyl-CoA or methyl-THF from a synthesis gas or other gas comprising CO and/or $CO_2$ and particularly generating microorganisms capable of utilizing syngas or other gas comprising CO and/or $CO_2$ that were not previously capable of utilizing syngas or another gas comprising CO and/or $CO_2$ as a carbon source (see Example VIII). Further, a microorganism can be engineered to contain both the methyl and carbonyl branches of the Wood-Ljungdahl pathway (FIGS. 1, 2 and 6). In addition, other desired products can also be produced by engineering the microorganisms to produce a desired product by expressing proteins or enzymes capable of producing a desired product, for example, producing a product having acetyl-CoA or methyl-THF as a precursor (see FIG. 3). As disclosed herein, such microorganisms can be generated by expressing proteins or genes that confer a desired metabolic pathway or by determining deletions that can drive metabolism towards a desired product.

In addition, the invention provides a non-naturally occurring microorganism comprising a genetic modification conferring to the microorganism an increased efficiency of producing acetyl-CoA from CO and/or $CO_2$ and $H_2$ relative to the microorganism in the absence of the genetic modification, wherein the microorganism comprises a pathway to convert CO and/or $CO_2$ and $H_2$ to acetyl-CoA. In such a microorganism, the genetic modification can comprise expression of one or more nucleic acid molecules encoding one or more exogenous proteins, whereby expression of the one or more exogenous proteins increases the efficiency of producing acetyl-CoA from CO and/or $CO_2$ and $H_2$. The one or more exogenous proteins can be selected from cobalamide corrinoid/iron-sulfur protein, methyltransferase, carbon monoxide dehydrogenase, acetyl-CoA synthase, acetyl-CoA synthase disulfide reductase and hydrogenase, including up to all such proteins, as disclosed herein. Such a non-naturally occurring microorganism can alternatively or additionally have a genetic modification comprising one or more gene disruptions, whereby the one or more gene disruptions increases the efficiency of producing acetyl-CoA from CO and/or $CO_2$ and $H_2$. In addition, the invention provides a non-naturally occurring microorganism comprising a genetic modification conferring an increased efficiency of producing methyl-THF or other desired products using the methods disclosed herein. Thus, the invention additionally relates to improving the efficiency of production of a desired product in a microorganism already having the ability to produce the desired product from syngas or other gases comprising CO and/or $CO_2$.

The invention also relates to a non-naturally occurring microorganism comprising one or more proteins conferring utilization of syngas or other gas comprising CO and/or $CO_2$ as a carbon source to the microorganism, wherein the microorganism lacks the ability to utilize the carbon source in the absence of the one or more proteins conferring utilization of CO and/or $CO_2$. Further, the invention provides a non-naturally occurring microorganism comprising one or more proteins conferring utilization of carbon monoxide and/or carbon dioxide as a carbon source to the microorganism, wherein the microorganism lacks the ability to utilize the carbon source in the absence of the one or more proteins. In yet another embodiment, the invention provides a non-naturally occurring microorganism, comprising one or more proteins conferring utilization of CO and/or $CO_2$, in combination with $H_2$, as a carbon source to the microorganism, wherein the microorganism lacks the ability to utilize the carbon source in the absence of the one or more proteins. The invention additionally provides a non-naturally occurring microorganism comprising one or more proteins conferring utilization of CO, in combination with $H_2$ and $CO_2$, as a carbon source to the microorganism, wherein the microorganism lacks the ability to utilize the carbon source in the absence of the one or more proteins. Such a microorganism can be used to produce a desired product from the carbon source, for example, methyl-tetrahydrofolate or acetyl-coenzyme A (acetyl-CoA) or other desired products, as disclosed herein, including products synthesized from acetyl-CoA or methyl-THF. Such a non-naturally occurring microorganism can express one or more exogenous proteins that increase production of the product, as disclosed herein (see FIGS. 1 and 2).

The invention further provides a non-naturally occurring microorganism comprising one or more exogenous proteins conferring utilization of syngas or other gaseous carbon source to the microorganism, wherein the microorganism has the ability to utilize the carbon source in the absence of the one or more exogenous proteins, whereby expression of the one or more exogenous proteins increases the efficiency of utilization of the carbon source. Additionally the invention provides a non-naturally occurring microorganism comprising one or more exogenous proteins conferring utilization of carbon monoxide as a carbon source to the microorganism, wherein the microorganism has the ability to utilize the carbon source in the absence of the one or more exogenous proteins, whereby expression of the one or more exogenous proteins increases the efficiency of utilization of the carbon source.

In yet another embodiment, the invention provides a non-naturally occurring microorganism comprising one or more exogenous proteins conferring utilization of CO and/or $CO_2$, in combination with $H_2$, as a carbon source to the microorganism, wherein the microorganism has the ability to utilize the carbon source in the absence of the one or more exogenous proteins, whereby expression of the one or more exogenous proteins increases the efficiency of utilization of the carbon source. Additionally provided is a non-naturally occurring microorganism comprising one or more exogenous proteins conferring utilization of CO, in combination with $H_2$ and $CO_2$, as a carbon source to the microorganism, wherein the microorganism has the ability to utilize the carbon source in the absence of the one or more exogenous proteins, whereby expression of the one or more exogenous proteins increases the efficiency of utilization of the carbon source. Such a microorganism can be used to produce a desired product such as acetyl-CoA, methyl-THF or other desired products from the carbon source, as disclosed herein.

The invention also provides a non-naturally occurring microbial organism capable of producing acetyl-CoA utilizing methanol and syngas. Thus, the microbial organism is capable of utilizing methanol and CO, $CO_2$ and/or $H_2$, for example, $CO_2$, $CO_2$ and $H_2$, CO, CO and $H_2$, $CO_2$ and CO, or $CO_2$, CO and $H_2$, to produce acetyl-CoA. Since acetyl-CoA is produced in most microbial organisms, it is understood that a non-naturally occurring microbial organism of the invention that is capable of producing acetyl-CoA is one that has been engineered to include a desired pathway. Furthermore, the microbial organism is engineered to utilize methanol and syngas to produce acetyl-CoA (see Examples). In one embodiment, the invention provides a non-naturally occurring microbial organism having an acetyl-coenzyme A (acetyl-CoA) pathway comprising at least one exogenous nucleic acid encoding an acetyl-CoA pathway enzyme or protein expressed in a sufficient amount to produce acetyl-CoA, the acetyl-CoA pathway comprising methanol-methyltransferase and acetyl-CoA synthase/carbon monoxide dehydrogenase. In such a non-naturally occurring microbial organism, the acetyl-CoA pathway can confer the ability to convert $CO_2$, CO and/or $H_2$, that is, a combination thereof, to acetyl Co-A. The methanol-methyltransferase activity of such an acetyl-CoA pathway can comprise, for example, an enzyme or protein selected from methanol methyltransferase, corrinoid protein (such as MtaC) and methyltetrahydrofolate:corrinoid protein methyltransferase (such as MtaA)(see Examples II and III). The acetyl-CoA synthase/carbon monoxide dehydrogenase activity of such an acetyl-CoA pathway can comprise, for example, an enzyme or protein selected from methyltetrahydrofolate:corrinoid protein methyltransferase (such as AcsE), corrinoid iron-sulfur protein (such as AcsD), nickel-protein assembly protein (such as AcsF), ferredoxin, acetyl-CoA synthase, carbon monoxide dehydrogenase and nickel-protein assembly protein (such as CooC)(see Examples II and III). As disclosed herein, two or more, three or more, four or more, five or more, six or more, seven or more, eight or more, nine or more, and so forth, nucleic acids encoding an acetyl-CoA pathway can be expressed in a non-naturally occurring microbial organism of the invention. In a particular embodiment, the non-naturally occurring microbial organism can comprise ten exogenous nucleic acids that encode a methanol-methyltransferase comprising methanol methyltransferase, corrinoid protein (such as MtaC) and methyltetrahydrofolate:corrinoid protein methyltransferase (such as MtaA) and an acetyl-CoA synthase/carbon monoxide dehydrogenase comprising methyltetrahydrofolate:corrinoid protein methyltransferase (such as AcsE), corrinoid iron-sulfur protein (such as AcsD), nickel-protein assembly protein (such as CooC), ferredoxin, acetyl-CoA synthase, carbon monoxide dehydrogenase and nickel-protein assembly protein (such as AcsF).

In yet another embodiment, the non-naturally occurring microbial organism can further comprise pyruvate ferredoxin oxidoreductase. For example, the pyruvate ferredoxin oxidoreductase can be encoded by an exogenous nucleic acid. In still another embodiment, the non-naturally occurring microbial organism can further comprise hydrogenase, which can be encoded by an endogenous or exogenous nucleic acid, as disclosed herein (see Examples II and III).

As disclosed herein, a non-naturally occurring microbial organism can contain, for example, at least one exogenous nucleic acid that is a heterologous nucleic acid. As further disclosed herein, the non-naturally occurring microbial organism can be grown, for example, in a substantially anaerobic culture medium.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

The non-naturally occurring microbial organisms of the invention can be produced by introducing expressible nucleic acids encoding one or more of the enzymes or proteins participating in one or more acetyl-CoA biosynthetic pathways. Depending on the host microbial organism chosen for biosynthesis, nucleic acids for some or all of a particular acetyl-CoA biosynthetic pathway can be expressed. For example, if a chosen host is deficient in one or more enzymes or proteins for a desired biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve acetyl-CoA biosynthesis. Thus, a non-naturally occurring microbial organism of the invention can be produced by introducing exogenous enzyme or protein activities to obtain a desired biosynthetic pathway or a desired biosynthetic pathway can be obtained by introducing one or more exogenous enzyme or protein activities that, together with one or more endogenous enzymes or proteins, produces a desired product such as acetyl-CoA.

Depending on the acetyl-CoA biosynthetic pathway constituents of a selected host microbial organism, the non-naturally occurring microbial organisms of the invention will include at least one exogenously expressed acetyl-CoA pathway-encoding nucleic acid and up to all encoding nucleic acids for one or more acetyl-CoA biosynthetic pathways. For example, acetyl-CoA biosynthesis can be established in a host deficient in a pathway enzyme or protein through exogenous expression of the corresponding encoding nucleic acid. In a host deficient in all enzymes or proteins of a acetyl-CoA pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of acetyl-CoA can be included, such as the methanol-methyltransferase, which can include methanol methyltransferase, corrinoid protein (such as MtaC) and methyltetrahydrofolate:corrinoid protein methyltransferase (such as MtaA), and the acetyl-CoA synthase/carbon monoxide dehydrogenase, which can include methyltetrahydrofolate:corrinoid protein methyltransferase (such as AcsE), corrinoid iron-sulfur protein (such as AcsD), nickel-protein assembly protein (such as AcsF), ferredoxin, acetyl-CoA synthase, carbon monoxide dehydrogenase and nickel-protein assembly protein (such as CooC).

In another embodiment, in a pathway for producing acetyl-CoA from syngas or other gaseous carbon source, one or more proteins in the biosynthetic pathway can be selected from cobalamide corrinoid/iron-sulfur protein, methyltransferase, carbon monoxide dehydrogenase, acetyl-CoA synthase, acetyl-CoA synthase disulfide reductase and hydrogenase (see FIG. 2 and Examples VII and VIII). In a pathway for producing methyl-THF, one or more proteins in the biosynthetic pathway can be selected from ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase (see FIG. 1 and Example VIII). In addition, genes that encode the enzymes required to produce both acetyl-CoA and methyl-THF can be introduced into a microorganism (see FIG. 3 and Example VIII). Metabolic pathways for production of additional desired products, including succinate, 4-hydroxybutyrate and 1,4-butanediol are described, for example, in U.S. application Ser. No. 11/891,602, filed Aug. 10, 2007, and WO/2008/115840 (see Example VIII).

Given the teachings and guidance provided herein, those skilled in the art will understand that the number of encoding nucleic acids to introduce in an expressible form will, at least, parallel the acetyl-CoA pathway deficiencies of the selected host microbial organism. Therefore, a non-naturally occurring microbial organism of the invention can have one, two, three, four, five, six, seven, eight, nine or up to all nucleic acids encoding the enzymes or proteins constituting a acetyl-CoA biosynthetic pathway disclosed herein. In some embodiments, the non-naturally occurring microbial organisms also can include other genetic modifications that facilitate or optimize acetyl-CoA biosynthesis or that confer other useful functions onto the host microbial organism. One such other functionality can include, for example, augmentation of the synthesis of one or more of the acetyl-CoA pathway precursors such as methanol.

Generally, a host microbial organism is selected such that it produces the precursor of an acetyl-CoA pathway, either as a naturally produced molecule or as an engineered product that either provides de novo production of a desired precursor or increased production of a precursor naturally produced by the host microbial organism. A host organism can be engineered to increase production of a precursor, as disclosed herein. In addition, a microbial organism that has been engineered to produce a desired precursor can be used as a host organism and further engineered to express enzymes or proteins of an acetyl-CoA pathway.

In some embodiments, a non-naturally occurring microbial organism of the invention is generated from a host that contains the enzymatic capability to synthesize acetyl-CoA. In this specific embodiment it can be useful to increase the synthesis or accumulation of an acetyl-CoA pathway product to, for example, drive acetyl-CoA pathway reactions toward acetyl-CoA production. Increased synthesis or accumulation can be accomplished by, for example, overexpression of nucleic acids encoding one or more of the above-described acetyl-CoA pathway enzymes or proteins. Over expression the enzyme or enzymes and/or protein or proteins of the acetyl-CoA pathway can occur, for example, through exogenous expression of the endogenous gene or genes, or through exogenous expression of the heterologous gene or genes. Therefore, naturally occurring organisms can be readily generated to be non-naturally occurring microbial organisms of the invention, for example, producing acetyl-CoA, through overexpression of one, two, three, four, five, six, seven, eight, nine, or ten, that is, up to all nucleic acids encoding acetyl-CoA biosynthetic pathway enzymes or proteins. In addition, a non-naturally occurring organism can be generated by mutagenesis of an endogenous gene that results in an increase in activity of an enzyme in the acetyl-CoA biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

It is understood that, in methods of the invention, any of the one or more exogenous nucleic acids can be introduced into a microbial organism to produce a non-naturally occurring microbial organism of the invention. The nucleic acids can be introduced so as to confer, for example, an acetyl-CoA biosynthetic pathway onto the microbial organism. Alternatively, encoding nucleic acids can be introduced to produce an intermediate microbial organism having the biosynthetic capability to catalyze some of the required reactions to confer acetyl-CoA biosynthetic capability. For example, a non-naturally occurring microbial organism having a acetyl-CoA biosynthetic pathway can comprise at least two exogenous nucleic acids encoding desired enzymes or proteins, such as the combination of methanol methyltransferase and corrinoid protein; methanol methyltransferase and methyltetrahydrofolate:corrinoid protein methyltransferase; corrinoid protein and corrinoid iron-sulfur protein; nickel-protein assembly protein and ferredoxin, and the like. Thus, it is understood that any combination of two or more enzymes or proteins of a biosynthetic pathway can be included in a non-naturally occurring microbial organism of the invention. Similarly, it is understood that any combination of three or more enzymes or proteins of a biosynthetic pathway can be included in a non-naturally occurring microbial organism of the invention, for example, methanol methyltransferase, corrinoid iron-sulfur protein (such as AcsD) and acetyl-CoA synthase; corrinoid protein (such as MtaC), carbon monoxide dehydrogenase and nickel-protein assembly protein (such as CooC or AcsF); methyltetrahydrofolate:corrinoid protein methyltransferase (such as AcsE), ferredoxin and acetyl-CoA synthase, and so forth, as desired, so long as the combination of enzymes and/or proteins of the desired biosynthetic pathway results in production of the corresponding desired product. Similarly, any combination of four, five, six, seven, eight, nine or more enzymes or proteins of a biosynthetic pathway as disclosed herein can be included in a non-naturally occurring microbial organism of the invention, as desired, so long as the combination of enzymes and/or proteins of the desired biosynthetic pathway results in production of the corresponding desired product.

In addition to the biosynthesis of acetyl-CoA as described herein, the non-naturally occurring microbial organisms and methods of the invention also can be utilized in various combinations with each other and with other microbial organisms and methods well known in the art to achieve product biosynthesis by other routes. For example, one alternative to produce acetyl-CoA other than use of the acetyl-CoA producers is through addition of another microbial organism capable of converting an acetyl-CoA pathway intermediate to acetyl-CoA. One such procedure includes, for example, the fermentation of a microbial organism that produces an acetyl-CoA pathway intermediate. The acetyl-CoA pathway intermediate can then be used as a substrate for a second microbial organism that converts the acetyl-CoA pathway intermediate to acetyl-CoA. The acetyl-CoA pathway intermediate can be added directly to another culture of the second organism or the original culture of the acetyl-CoA pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods of the invention can be assembled in a wide variety of subpathways to achieve biosynthesis of, for example, acetyl-CoA. In these embodiments, biosynthetic pathways for a desired product of the invention can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of acetyl-CoA can be accomplished by constructing a microbial organism that contains biosynthetic pathways for conversion of one pathway intermediate to another pathway intermediate or the product. Alternatively, acetyl-CoA also can be biosynthetically produced from microbial organisms through co-culture or co-fermentation using two organisms in the same vessel, where the first microbial organism produces an acetyl-CoA intermediate and the second microbial organism converts the intermediate to acetyl-CoA.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce acetyl-CoA. In addition, since acetyl-CoA is a precursor of other desirable products, a non-naturally occurring microbial organism of the invention can be used as a host organism into which other desired pathways utilizing acetyl-CoA as a precursor or intermediate can be conferred, as desired.

Sources of encoding nucleic acids for an acetyl-CoA pathway enzyme or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli*, *Methanosarcina barkeri*, *Methanosarcina acetivorans*, *Moorella thermoacetica*, *Carboxydothermus hydrogenoformans*, *Rhodospirillum rubrum*, *Acetobacterium woodii*, *Butyribacterium methylotrophicum*, *Clostridium autoethanogenum*, *Clostridium carboxidivorans*, *Clostridium ljungdahlii*, *Eubacterium limosum*, *Oxobacter pfennigii*, *Peptostreptococcus productus*, *Rhodopseudomonas palustris* P4, *Rubrivivax gelatinosus*, *Citrobacter* sp Y19, *Methanosarcina acetivorans* C2A, *Methanosarcina barkeri*, *Desulfosporosinus orientis*, *Desulfovibrio desulfuricans*, *Desulfbvibrio vulgaris*, *Moorella thermoautotrophica*, *Carboxydibrachium pacificus*, *Carboxydocella thermoautotrophica*, *Thermincola carboxydiphila*, *Thermolithobacter carboxydivorans*, *Thermosinus carboxydivorans*, *Methanothermobacter thermoautotrophicus*, *Desulfotomaculum carboxydivorans*, *Desulfotomaculum kuznetsovii*, *Desulfotomaculum nigrificans*,

*Desulfotomaculum thermobenzoicum* subsp. *thermosyntrophicum, Syntrophobacter fumaroxidans, Clostridium acidurici, Desulfovibrio africanus,* and the like, as well as other exemplary species disclosed herein or available as source organisms for corresponding genes. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite acetyl-CoA biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations enabling biosynthesis of acetyl-CoA described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative acetyl-CoA biosynthetic pathway exists in an unrelated species, acetyl-CoA biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize acetyl-CoA.

Host microbial organisms can be selected from, and the non-naturally occurring microbial organisms generated in, for example, bacteria, yeast, fungus or any of a variety of other microorganisms applicable to fermentation processes. Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens,* and *Pseudomonas putida.* Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger* and *Pichia pastoris. E. coli* is a particularly useful host organisms since it is a well characterized microbial organism suitable for genetic engineering. Other particularly useful host organisms include yeast such as *Saccharomyces cerevisiae*. Exemplary acetogens suitable as host organisms include, but are not limited to, *Rhodospirillum rubrum, Moorella thermoacetica* and *Desulfitobacterium hafniense* (see Examples).

Methods for constructing and testing the expression levels of a non-naturally occurring acetyl-CoA-producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

Exogenous nucleic acid sequences involved in a pathway for production of acetyl-CoA can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more acetyl-CoA biosynthetic pathway encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

The invention additionally provides a method for producing acetyl-CoA by culturing a non-naturally occurring microbial organism of the invention having an acetyl-CoA pathway. The acetyl-CoA pathway can comprise, for example, at least one exogenous-nucleic acid encoding an acetyl-CoA pathway enzyme or protein expressed in a sufficient amount to produce acetyl-CoA, under conditions and for a sufficient period of time to produce acetyl-CoA, the acetyl-CoA pathway comprising methanol-methyltransferase and acetyl-CoA synthase/carbon monoxide dehydrogenase. In such an acetyl-CoA pathway, the methanol-methyltransferase can comprise an enzyme or protein selected from methanol methyltransferase, corrinoid protein (such as MtaC) and methyltetrahydrofolate:corrinoid protein methyltransferase (MtaA). Further, in such an acetyl-CoA pathway, the acetyl-CoA synthase/carbon monoxide dehydrogenase can comprise an enzyme or protein selected from methyltetrahydrofolate:corrinoid protein methyltransferase (such as AcsE), corrinoid iron-sulfur protein (such as AcsD), nickel-protein assembly protein (such as AcsF), ferredoxin, acetyl-CoA synthase, carbon monoxide dehydrogenase and nickel-protein assembly protein (such as CooC). A non-naturally occurring microbial organism can be in a substantially anaerobic culture medium. In a particular embodiment, the non-naturally occurring microbial organism can be cultured in the presence of CO2, CO and/or H2, that is, a combination thereof, and methanol. The non-naturally occurring microbial organism can further comprise pyruvate ferredoxin oxidoreductase, which can be expressed by an exogenous nucleic acid. The non-naturally occurring microbial organism can also further comprise hydrogenase, for example, encoded by an endogenous or exogenous nucleic acid.

In another embodiment, the non-naturally occurring microbial organism can be cultured in the presence of an electron acceptor, for example, nitrate, in particular under substantially anaerobic conditions (see Example III). It is understood that an appropriate amount of nitrate can be added to a microbial culture to achieve a desired increase in biomass, for example, 1 mM to 100 mM nitrate, or lower or higher concentrations, as desired, so long as the amount added provides a sufficient amount of electron acceptor for the desired increase in biomass. Such amounts include, but are not limited to, 5 mM, 10 mM, 15 mM, 20 mM, 25 mM, 30 mM, 40 mM, 50 mM, as appropriate to achieve a desired increase in biomass.

Suitable purification and/or assays to test for the production of acetyl-CoA can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art (see Example III).

The acetyl-CoA, or products derived from acetyl-CoA, can be separated from other components in the culture using a variety of methods well known in the art. Products derived from acetyl-CoA include, but are not limited to, ethanol, butanol, isobutanol, isopropanol, 1,4-butanediol, succinic acid, fumaric acid, malic acid, 4-hydroxybutyric acid, 3-hydroxypropionic acid, lactic acid, methacrylic acid, adipic acid, and acrylic acid. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products of the invention. For example, the acetyl-CoA producers can be cultured for the biosynthetic production of acetyl-CoA, or products derived from acetyl-CoA.

For the production of acetyl-CoA, the recombinant strains are cultured in a medium with a carbon and energy source of methanol and gases comprising CO, $CO_2$ and/or $H_2$ and other essential nutrients. It is highly desirable to maintain anaerobic conditions in the fermenter to reduce the cost of the overall process. Such conditions can be obtained, for example; by first sparging the medium with nitrogen and then sealing the flasks with a septum and crimp-cap. For strains where growth is not observed anaerobically, microaerobic conditions can be applied by perforating the septum with a small hole for limited aeration. Exemplary anaerobic conditions have been described previously and are well-known in the art Exemplary aerobic and anaerobic conditions are described, for example, in U.S. patent application Ser. No. 11/891,602, filed Aug. 10, 2007, and WO/2008/115840. Fermentations can be performed in a batch, fed-batch or continuous manner, as disclosed herein.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can include, for example, any carbohydrate source which can supply a source of carbon to the non-naturally occurring microorganism. Such sources include, for example, sugars such as glucose, xylose, arabinose, galactose, mannose, fructose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of acetyl-CoA.

Accordingly, given the teachings and guidance provided herein, those skilled in the art will understand that a non-naturally occurring microbial organism can be produced that expresses intracellular or secretes the biosynthesized compounds of the invention when grown on a carbon source such as a carbohydrate, methanol, and gases comprising CO, $CO_2$, and/or $H_2$. Such compounds include, for example, acetyl-CoA and any of the intermediate metabolites in the acetyl-CoA pathway, and products derived from acetyl-CoA including ethanol, butanol, isobutanol, isopropanol, 1,4-butanediol, succinic acid, fumaric acid, malic acid, 4-hydroxybutyric acid, 3-hydroxypropionic acid, lactic acid, methacrylic acid, adipic acid, and acrylic acid. All that is required is to engineer in one or more of the required enzyme or protein activities to achieve biosynthesis of the desired compound or intermediate including, for example, inclusion of some or all of the acetyl-CoA biosynthetic pathways. Accordingly, the invention provides a non-naturally occurring microbial organism that produces acetyl-CoA when grown on a carbohydrate or other carbon source and produces and/or secretes any of the intermediate metabolites shown in the acetyl-CoA pathway or produces and/or secretes a product derived from acetyl-CoA when grown on a carbohydrate or other carbon source. The acetyl-CoA producing microbial organisms of the invention can initiate synthesis from an intermediate, for example, 5-methyl-tetrahydrofolate (Me-THF).

The non-naturally occurring microbial organisms of the invention are constructed using methods well known in the art as exemplified herein to exogenously express at least one nucleic acid encoding an acetyl-CoA pathway enzyme or protein in sufficient amounts to produce acetyl-CoA. It is understood that the microbial organisms of the invention are cultured under conditions sufficient to produce acetyl-CoA. Following the teachings and guidance provided herein, the non-naturally occurring microbial organisms of the invention can achieve biosynthesis of acetyl-CoA resulting in intracellular concentrations between about 0.001-200 mM or more. Generally, the intracellular concentration of acetyl-CoA is between about 3-150 mM, particularly between about 5-125 mM and more particularly between about 8-100 mM, including about 10 mM, 20 mM, 50 mM, 80 mM, or more. Intracellular concentrations between and above each of these exemplary ranges also can be achieved from the non-naturally occurring microbial organisms of the invention.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. patent application Ser. No. 11/891,602, filed Aug. 10, 2007, and WO/2008/115840. Any of these conditions can be employed with the non-naturally occurring microbial organisms as well as other anaerobic conditions well known in the art. Under such anaerobic conditions, the acetyl-CoA producers can synthesize acetyl-CoA at intracellular concentrations of 5-10 mM or more as well as all other concentrations exemplified herein. It is understood that the above description refers to intracellular concentrations, and acetyl-CoA producing microbial organisms can produce acetyl-CoA intracellularly. In addition, a product derived from acetyl-CoA can be produced intracellularly and/or secreted. Such products include, but are not limited to, ethanol, butanol, isobutanol, isopropanol, 1,4-butanediol, succinic acid, fumaric acid, malic acid, 4-hydroxybutyric acid, 3-hydroxypropionic acid, lactic acid, methacrylic acid, adipic acid, and acrylic acid.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of acetyl-CoA includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of acetyl-CoA. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of acetyl-CoA. Generally, and as with non-continuous culture procedures, the continuous and/or near-continuous production of acetyl-CoA will include culturing a non-naturally occurring acetyl-CoA producing organism of the invention in sufficient nutrients and medium to sustain and/or nearly sustain growth in an exponential phase. Continuous culture under such conditions can be include, for example, 1 day, 2, 3, 4, 5, 6 or 7 days or more. Additionally, continuous culture can include 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of acetyl-CoA can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the acetyl-CoA producers of the invention for continuous production of substantial quantities of acetyl-CoA, the acetyl-CoA producers also can be, for example, simultaneously subjected to chemical synthesis procedures to convert the product to other compounds or the product can be separated from the fermentation culture and sequentially subjected to chemical conversion to convert the product to other compounds, if desired.

At least thirty different wild-type organisms have been isolated through the years and shown to grow on syngas or components of syngas, including microorganisms capable of converting syngas to ethanol (Vega et al., *Appl. Biochem. Biotechnol.* 20/21:781-797 (1989))(see Table 1). Candidate organisms for improved syngas fermentation include acetogens, phototrophs, sulfate reducing bacteria, and methanogens, which can utilize CO and/or $CO_2/H_2$ as the sole carbon and energy source (Sipma et al., *Crit. Rev. Biotechnol.* 26:41-65. (2006)). The mesophilic acetogen *Clostridium carboxidivorans* represents one of the most promising organisms for a syngas-to-chemicals platform as it has fast doubling times and have been shown to naturally produce ethanol and small quantities of butanol during growth on syngas (Henstra et al., *Curr. Opin. Biotechnol.* 18:200-206 (2007)). Genetic tools can be developed for this organism. The hydrogenic purple nonsulfur bacteria, *Rhodospirillum rubrum*, for which genetic tools exist for targeted gene deletions or insertions, is another good candidate organism for development of syngas utilization to produce desired products, although it naturally produces hydrogen from syngas and so metabolic changes can be engineered, as required.

Figure 3:
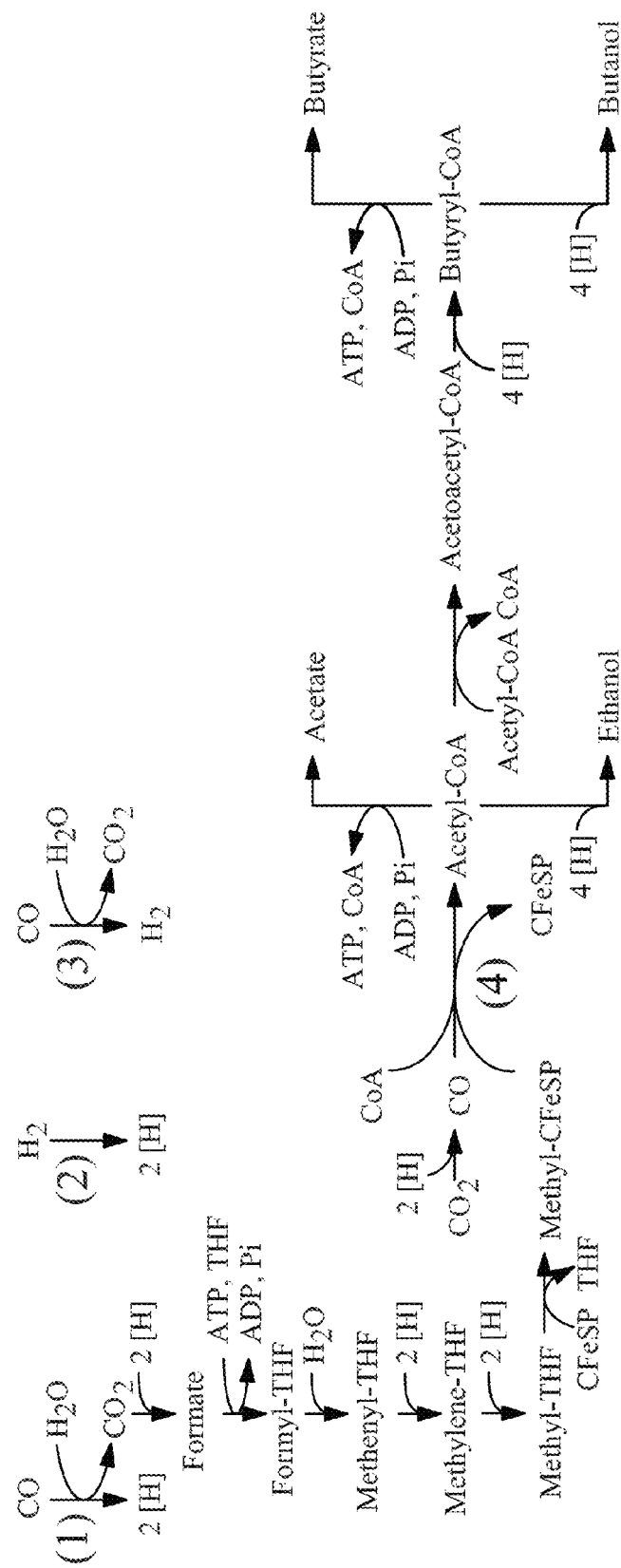
FIG. 3 shows a metabolic pathway diagram depicting the integration of the Wood-Ljungdahl and butanol production pathways. The transformations that are typically unique to organisms capable of growth on synthesis gas are: 1) CO dehydrogenase, 2) hydrogenase, 3) energy-conserving hydrogenase (ECH), and 4) bi-functional CO dehydrogenase/acetyl-CoA synthase.

The metabolism of some syngas utilizing organisms is known. For example, acetogens such as *C. carboxidivorans* can grow in the presence of CO or $CO_2$ by utilizing the Wood-Ljungdahl pathway, even in the absence of glucose, as long as hydrogen is present to supply the necessary reducing equivalents. The Wood-Ljungdahl pathway is illustrated in FIG. 3 (see also FIGS. 1 and 2) and shows the capacity of acetogens to utilize CO as the sole carbon and energy source through the production of the key metabolic intermediate acetyl-CoA. Specifically, CO can be oxidized to produce reducing equivalents and $CO_2$, or can be directly assimilated into acetyl-CoA, which is subsequently converted to either biomass or metabolites. Importantly, acetyl-CoA is a key metabolic intermediate that can serve as a precursor to a wide range of metabolites and other chemical entities. Hence, the ability of a microorganism to produce acetyl-CoA from syngas or other gaseous carbon source allows engineering of syngas-utilizing organisms, or organisms capable of utilizing other gaseous carbon sources, for production of a wide range of Chemicals and fuels as desired products.

In order to characterize the use of syngas or other gaseous carbon sources as a viable feedstock for the commercial production of chemicals and fuels through fermentation, feasibility studies are performed to address key questions and challenges associated with current systems. Preliminary metabolic modeling efforts have indicated that conversion of syngas to chemicals can be thermodynamically very favorable, and that specific chemicals can be made as the exclusive product. Not only does this reduce downstream processing needs, but also maximizes product yield. Furthermore, production of a desired product can be growth-associated, so that the fermentation can be done continuously, if desired. Because continuous processes are maintained at high cell concentration, and avoid batch turnaround time, they are more economically favorable.

As disclosed herein, the present invention relates to the development of microorganisms capable of utilizing syngas or other gaseous carbon sources, allowing the efficient conversion of CO and/or $CO_2$ to chemical products in high yield, titer, and productivity. One exemplary useful commercial embodiment relates to the development of an organism that can achieve production of a specific chemical with yields ≥80% of theoretical maximum, product tolerance≥50 g/L, titers≥50 g/L and productivity of at least 2 g/L/h. Although these criteria are particularly useful commercially, it is understood that an organism capable of achieving less than any or all of these criteria is also useful in the invention. For example, an organism can achieve production of a specific chemical with yields greater than or equal to any of 75%, 70%, 65%, 60%, 55%, 50%, 45%, 40%, 35%, 30%, 25%, 20%, and so forth so long as sufficient yields are achieved for a desired application. Similarly, an organism can achieve product tolerance greater than or equal to any of 45 g/L, 40 g/L, 35 g/L, 30 g/L, 25 g/L, 20 g/L, 15 g/L, 10 g/L, and so forth so long as sufficient yields are achieved for a desired application. Moreover, an organism can achieve titers greater than or equal to any of 200 g/L, 0.190 g/L, 180 g/L, 170 g/L, 160 g/L, 150 g/L, 140 g/L, 130 g/L, 120 g/L, 110 g/L, 100 g/L, 90 g/L, 80 g/L, 70 g/L, 60 g/L, 50 g/L, 45 g/L, 40 g/L, 35 g/L, 30 g/L, 25 g/L, 20 g/L, 15 g/L, 10 g/L, and so forth so long as sufficient yields are achieved for a desired application. In addition, an organism can achieve productivity of at least any of 1.5 g/L/h, 1 g/L/h, 0.5 g/L/h, and so forth so long as sufficient yields are achieved for a desired application.

As disclosed herein, the hypothetical analysis of butanol as a product from syngas utilization indicates that the ability to efficiently utilize cheap and readily available syngas as a feedstock and can lead to processes that potentially are ≥50% cost-advantaged over current petrochemical processes, especially in view of the low cost of syngas as a feedstock. In addition to low cost, syngas is an abundant and flexible substrate that can be produced from coal and many types of biomass, including energy crops such as switchgrass, as well as waste products such as wood waste, agricultural waste, dairy waste, and municipal solid waste. Thus, the ability to generate organisms capable of utilizing syngas or other gaseous carbon sources to produce a desired product allows production from almost any biomass source. This feature obviates the need to develop different processes specific for each type of biomass used for biofuel or chemical production. The use of waste products for the production of syngas can also be utilized to decrease environmental pollutants and alleviate serious disposal problems of bio-waste materials. In addition, syngas as a feedstock does not suffer from a feed versus fuel controversy associated with, for example, corn-based ethanol production. Given the broad range of substrates available for syngas production, the supply and cost structure of this feedstock is expected to remain relatively stable from year to year. Finally, syngas is used extensively for heating and energy and can therefore be used as a source of biomass-derived energy that can supplement or eliminate the need for petroleum-based energy for production, providing additional cost savings.

Although exemplified in various embodiments herein with butanol as a desired product, it is understood that any product capable of being produced by a microorganism of the invention can be generated and utilized to produce the product, as desired. Generally, desired products include but are not limited to hydrocarbons useful in chemical synthesis or as a fuel. Exemplary desired products include but are not limited to methanol, ethanol, butanol, acetate, butyrate, lactate, succinate, 4-hydroxybutyrate, 1,4-butanediol, and the like.

In other aspects, the present invention provides a non-naturally occurring microbial organism having a 4-hydroxybutryate pathway that can include at least one exogenous nucleic acid encoding an 4-hydroxybutryate pathway enzyme expressed in a sufficient amount to produce 4-hydroxybutryate. The 4-hydroxybutryate pathway enzyme can include an acetoacetyl-CoA thiolase, a 3-hydroxybutyryl-CoA dehydrogenase, a crotonase, a crotonyl-CoA hydratase, a 4-hydroxybutyryl-CoA transferase, a phosphotrans-4-hydroxybutyrylase, and a 4-hydroxybutyrate kinase.

In still other aspects, the present invention provides a non-naturally occurring microbial organism having a 1,4-butanediol pathway that can include at least one exogenous nucleic acid encoding a 1,4-butanediol pathway enzyme expressed in a sufficient amount to produce 1,4-butanediol. The 1,4-butanediol pathway enzyme can include an acetoacetyl-CoA thiolase, a 3-Hydroxybutyryl-CoA dehydrogenase, a crotonase, a crotonyl-CoA hydratase, a 4-hydroxybutyryl-CoA reductase (alcohol forming), a 4-hydroxybutyryl-CoA reductase (aldehyde forming), and a 1,4-butanediol dehydrogenase. Such an organism also can include an acetyl-CoA pathway having at least one exogenous nucleic acid encoding an acetyl-CoA pathway enzyme expressed in a sufficient amount to produce acetyl-CoA. The acetyl-CoA pathway enzyme can include a corrinoid protein, a methyltetrahydrofolate:corrinoid protein methyltransferase, a corrinoid iron-sulfur protein, a nickel-protein assembly protein, a ferredoxin, an acetyl-CoA synthase, a carbon monoxide dehydrogenase, a pyruvate ferredoxin oxidoreductase, and a hydrogenase.

In yet other aspects, the present invention provides a non-naturally occurring microbial organism having a 1,4-butanediol pathway that can include at least one exogenous nucleic acid encoding a 1,4-butanediol pathway enzyme expressed in a sufficient amount to produce 1,4-butanediol. The 1,4-butanediol pathway enzyme can include an acetoacetyl-CoA thiolase, a 3-Hydroxybutyryl-CoA dehydrogenase, a crotonase, a crotonyl-CoA hydratase, a 4-hydroxybutyryl-CoA reductase (alcohol forming), a 4-hydroxybutyryl-CoA reductase (aldehyde forming), and a 1,4-butanediol dehydrogenase. Such an organism also can include an acetyl-CoA pathway having at least one exogenous nucleic acid encoding an acetyl-CoA pathway enzyme expressed in a sufficient amount to produce acetyl-CoA. The acetyl-CoA pathway enzyme can include an acetyl-CoA synthase, a formate dehydrogenase, a formyltetrahydrofolate synthetase, a methenyltetrahydrofolate cyclohydrolase, a methylenetetrahydrofolate dehydrogenase, and a methylenetetrahydrofolate reductase.

In yet still further aspects, the present invention provides a method for producing 4-hydroxybutyrate that can include culturing a non-naturally occurring microbial organism having an 4-hydroxybutyrate pathway. The pathway can include at least one exogenous nucleic acid encoding an 4-hydroxybutyrate pathway enzyme expressed in a sufficient amount to produce 4-hydroxybutyrate under conditions and for a sufficient period of time to produce 4-hydroxybutyrate. The 4-hydroxybutyrate pathway can include an acetoacetyl-CoA thiolase, a 3-hydroxybutyryl-CoA dehydrogenase, a crotonase, a crotonyl-CoA hydratase, a 4-hydroxybutyryl-CoA transferase, a phosphotrans-4-hydroxybutyrylase, and a 4-hydroxybutyrate kinase.

In still other aspects, the present invention provides a method for producing 1,4-butanediol that can include culturing a non-naturally occurring microbial organism having an 1,4-butanediol pathway. The pathway can include at least one exogenous nucleic acid encoding an 1,4-butanediol pathway enzyme expressed in a sufficient amount to produce 1,4-butanediol under conditions and for a sufficient period of time to produce 1,4-butanediol. The 1,4-butanediol pathway can include an acetoacetyl-CoA thiolase, a 3-hydroxybutyryl-CoA dehydrogenase, a crotonase, a crotonyl-CoA hydratase, a 4-hydroxybutyryl-CoA reductase (alcohol forming), a 4-hydroxybutyryl-CoA reductase (aldehyde forming), a 1,4-butanediol dehydrogenase. Such an organism also can include an acetyl-CoA pathway comprising at least one exogenous nucleic acid encoding an acetyl-CoA pathway enzyme expressed in a sufficient amount to produce acetyl-CoA. The acetyl-CoA pathway enzyme can include a corrinoid protein, a methyltetrahydro-folate:corrinoid protein methyltransferase, a corrinoid iron-sulfur protein, a nickel-protein assembly protein, a ferredoxin, an acetyl-CoA synthase, a carbon monoxide dehydrogenase, a pyruvate ferredoxin oxidoreductase, and a hydrogenase.

Finally, in some aspects, the present invention provides a method for producing 1,4-butanediol that can include culturing a non-naturally occurring microbial organism having an 1,4-butanediol pathway. The pathway can include at least one exogenous nucleic acid encoding an 1,4-butanediol pathway enzyme expressed in a sufficient amount to produce 1,4-butanediol under conditions and for a sufficient period of time to produce 1,4-butanediol. The 1,4-butanediol pathway can include an acetoacetyl-CoA thiolase, a 3-hydroxybutyryl-CoA dehydrogenase, a crotonase, a crotonyl-CoA hydratase, a 4-hydroxybutyryl-CoA reductase (alcohol forming), a 4-hydroxybutyryl-CoA reductase (aldehyde forming), and a 1,4-butanediol dehydrogenase. Such an organism also can include an acetyl-CoA pathway having at least one exogenous nucleic acid encoding an acetyl-CoA pathway enzyme expressed in a sufficient amount to produce acetyl-CoA. The acetyl-CoA pathway enzyme can include an acetyl-CoA synthase, a formate dehydrogenase, a formyltetrahydrofolate synthetase, a methenyltetrahydrofolate cyclohydrolase, a methylenetetrahydrofolate dehydrogenase, and a methylenetetrahydrofolate reductase.

In other embodiments, organisms of the present invention have a functional methyltransferase system, the ability to synthesize acetyl-CoA, and the ability to synthesize 4-HB from acetyl-CoA as depicted in FIG. 11. Still other organisms described herein have a functional methyltransferase system, the ability to synthesize acetyl-CoA, and the ability to synthesize BDO from acetyl-CoA depicted in FIG. 12.

The invention also provides a non-naturally occurring microbial organism having a 4-hydroxybutryate pathway that can include at least one exogenous nucleic acid encoding an 4-hydroxybutryate pathway enzyme expressed in a sufficient amount to produce 4-hydroxybutryate. The 4-hydroxybutryate pathway enzyme can include an acetoacetyl-CoA thiolase, a 3-hydroxybutyryl-CoA dehydrogenase, a crotonase, a crotonyl-CoA hydratase, a 4-hydroxybutyryl-CoA transferase, a phosphotrans-4-hydroxybutyrylase, and a 4-hydroxybutyrate kinase.

Such organisms can also include at least one enzyme or polypeptide such as a corrinoid protein, a methyltetrahydrofolate:corrinoid protein methyltransferase, a corrinoid iron-sulfur protein, a nickel-protein assembly protein, a ferredoxin, an acetyl-CoA synthase, a carbon monoxide dehydrogenase, a pyruvate ferredoxin oxidoreductase, and a hydrogenase.

In some embodiments, organisms that have a 4-hydroxybutyrate pathway can include a methanol methyltransferase. Such organisms utilize a feedstock such as 1) methanol and CO, 2) methanol, $CO_2$, and $H_2$, 3) methanol, CO, $CO_2$, and $H_2$, 4) methanol and synthesis gas comprising CO and $H_2$, and 5) methanol and synthesis gas comprising CO, $CO_2$, and $H_2$.

Other organisms that have a 4-hydroxybutyrate pathway can have a formate dehydrogenase, a formyltetrahydrofolate synthetase, a methenyltetrahydrofolate cyclohydrolase, a methylenetetrahydrofolate dehydrogenase, and a methylenetetrahydrofolate reductase. Such organisms utilize a feedstock such as 1) CO, 2) $CO_2$ and $H_2$, 3) CO and $CO_2$, 4) synthesis gas comprising CO and $H_2$, and 5) synthesis gas comprising CO, $CO_2$, and $H_2$.

The present invention also provides a non-naturally occurring microbial organism having a 1,4-butanediol pathway that can include at least one exogenous nucleic acid encoding a 1,4-butanediol pathway enzyme expressed in a sufficient amount to produce 1,4-butanediol. The 1,4-butanediol pathway enzyme include, for example, an acetoacetyl-CoA thiolase, a 3-Hydroxybutyryl-CoA dehydrogenase, a crotonase, a crotonyl-CoA hydratase, a 4-hydroxybutyryl-CoA reductase (alcohol forming), a 4-hydroxybutyryl-CoA reductase (aldehyde forming), and a 1,4-butanediol dehydrogenase.

Such organisms can also include at least one enzyme or polypeptide such as a corrinoid protein, a methyltetrahydrofolate:corrinoid protein methyltransferase, a corrinoid iron-sulfur protein, a nickel-protein assembly protein, a ferredoxin, an acetyl-CoA synthase, a carbon monoxide dehydrogenase, a pyruvate ferredoxin oxidoreductase, and a hydrogenase.

In some embodiments, an organism having a 1,4-butanediol pathway can include a methanol methyltransferase. Such organisms utilize a feedstock such as 1) methanol and CO, 2) methanol, $CO_2$, and $H_2$, 3) methanol, CO, $CO_2$, and $H_2$, 4) methanol and synthesis gas comprising CO and $H_2$, and 5) methanol and synthesis gas comprising CO, $CO_2$, and $H_2$.

In other embodiments, an organism having a 1,4-butanediol pathway can include a formate dehydrogenase, a formyltetrahydrofolate synthetase, a methenyltetrahydrofolate cyclohydrolase, a methylenetetrahydrofolate dehydrogenase, and a methylenetetrahydrofolate reductase. Such organisms utilize a feedstock selected from the group consisting of 1) CO, 2) $CO_2$ and $H_2$, 3) CO and $CO_2$, 4) synthesis gas comprising CO and $H_2$, and 5) synthesis gas comprising CO, $CO_2$, and $H_2$.

Figure 13:
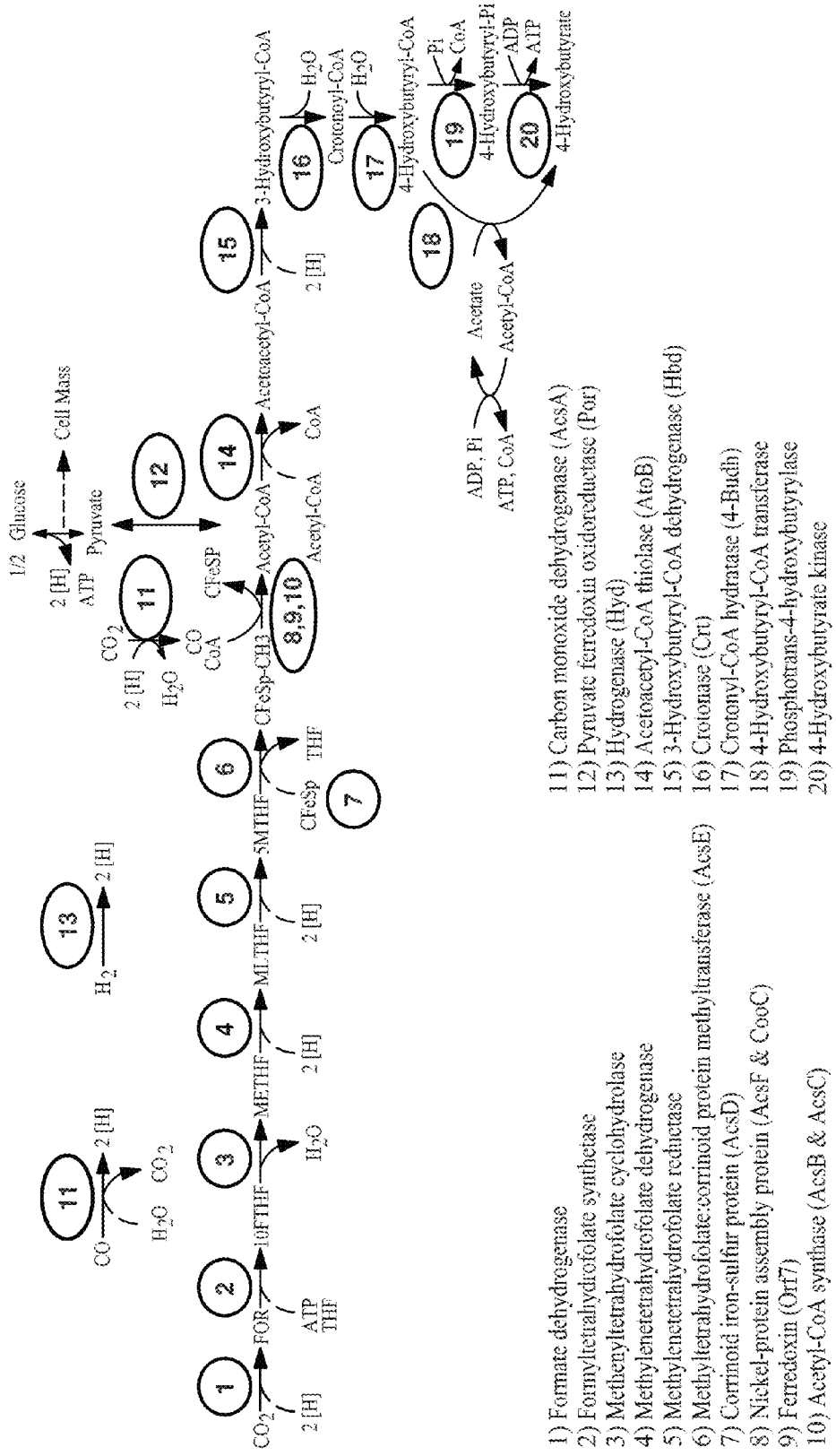
FIG. 13 shows a synthetic metabolic pathway for the conversion of gases including CO, $CO_2$, and/or $H_2$ to acetyl-CoA, and further to 4-hydroxybutyrate.
Figure 14:
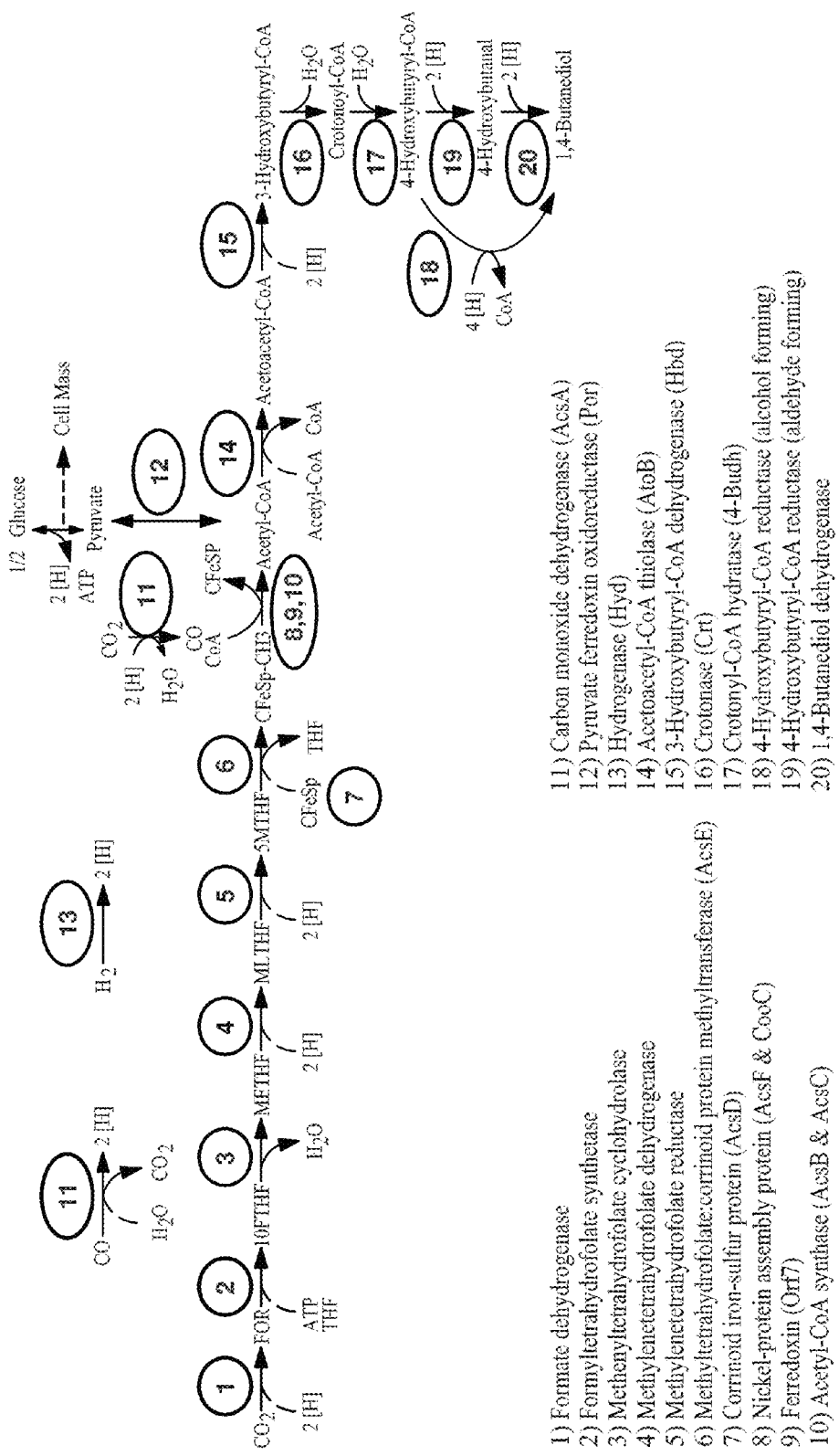
FIG. 14 shows a synthetic metabolic pathway for the conversion of gases including CO, $CO_2$, and/or $H_2$ to acetyl-CoA, and further to 1,4-butanediol.

An exemplary microbial organisms of the invention can contain a pathway as depicted in FIG. 13. Such an organism can contain a functional methyl branch of the Wood-Ljungdahl pathway, the ability to synthesize acetyl-CoA, and the ability to synthesize 4-hydroxybutyrate from acetyl-CoA. Another exemplary microbial organism of the invention can contain a pathway as depicted in FIG. 14. Such an microbial organism can contain a functional methyl branch of the Wood-Ljungdahl pathway, the ability to synthesize acetyl-CoA, and the ability to synthesize 1,4-butanediol from acetyl-CoA.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of acetyl-CoA or products derived from acetyl-CoA.

One computational method for identifying and designing metabolic alterations favoring biosynthesis of a desired product is the OptKnock computational framework (Burgard et al., *Biotechnol. Bioeng.* 84:647-657 (2003)). OptKnock is a metabolic modeling and simulation program that suggests gene deletion strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling, biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that enable an effective query of the performance limits of metabolic networks and provides methods for solving the resulting mixed-integer linear programming problems. The metabolic modeling and simulation methods referred to herein as OptKnock are described in, for example, U.S. publication 2002/0168654, filed Jan. 10, 2002, in International Patent No. PCT/US02/00660, filed Jan. 10, 2002, and U.S. patent application Ser. No. 11/891,602, filed Aug. 10, 2007, and WO/2008/115840.

Another computational method for identifying and designing metabolic alterations favoring biosynthetic production of a product is a metabolic modeling and simulation system termed SimPheny®. This computational method and system is described in, for example, U.S. publication 2003/0233218, filed Jun. 14, 2002, and in International Patent Application No. PCT/US03/18838, filed Jun. 13, 2003. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *E. coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

It is understood that modifications which do not substantially affect the activity of the various embodiments of this invention are also provided within the definition of the invention provided herein. Accordingly, the following examples are intended to illustrate but not limit the present invention.

Example I

Organisms and Pathways for Syngas Fermentation

This example describes organisms capable of utilizing syngas and exemplary pathways.

At least thirty different organisms have been isolated through the years and shown to grow on syngas or components of syngas such as CO, $CO_2$, and $H_2$ (Henstra et al., *Curr. Opin. Biotechnol.* 18:200-206 (2007); Sipma et al., *Crit. Rev. Biotechnol.* 26:41-65 (2006)). Table 1 provides examples of such organisms as well as a number of their properties such as their optimal temperature for growth, optimal pH for growth, doubling time, product profile, and physiological group.

TABLE 1

Examples of CO utilizing species and their physiological characteristics.

| | Species | Physiological Characterization | T (° C.) | pH | $t_d$ (h) | Products |
|---|---|---|---|---|---|---|
| Mesophillic Bacteria | *Acetobacterium woodii* | Acetogenic | 30 | 6.8 | 13 | Acetate |
| | *Butyribacterium metholytrophicum* | Acetogenic | 37 | 6 | 12-20 | Acetate, ethanol, butyrate, butanol |
| | *Clostridium autoethanogenum* | Acetogenic | 37 | 5.8-6.0 | nr | Acetate, ethanol |
| | *Clostridium carboxidivorans* | Aceteogenic | 38 | 6.2 | 6.25 | Acetate, ethanol, butyrate, butanol |
| | *Clostridium ljungdahlii* | Acetogenic | 37 | 6 | 3.8 | Acetate, ethanol |
| | *Eubacterium limosum* | Acetogenic | 38-39 | 7.0-7.2 | 7 | Acetate |
| | *Oxobacter pfennigii* | Acetogenic | 36-38 | 7.3 | 13.9 | Acetate, n-butyrate |
| | *Peptostrepococcus productus* | Acetogenic | 37 | 7 | 1.5 | Acetate |
| | *Rhodopseudomonas palustris* P4 | Hydrogenogenic, Phototroph | 30 | nr | 23 | $H_2$ |
| | *Rhodospirillum rubrum* | Hydrogenogenic, Phototroph | 30 | 6.8 | 8.4 | $H_2$ |
| | *Rubrivivax gelatinosus* | Hydrogenogenic, Phototroph | 34 | 6.7-6.9 | 6.7 | $H_2$ |
| | *Citrobacter* sp Y19 | Hydrogenogenic, Facultative Anaerobe | 30-40 | 5.5-7.5 | 8.3 | $H_2$ |
| | *Methanosarcina acetivorans* C2A | Methanogenic | 37 | 7 | 24 | Acetate, formate, $CH_4$ |
| | *Methanosarcina barkeri* | Methanogenic | 37 | 7.4 | 65 | $CH_4$, $CO_2$ |
| | *Desulfosporosinus orientis* | Sulfate reducing bacteria | 35 | 7 | nr | $H_2S$, $CO_2$ |
| | *Desulfovibrio desulfuricans* | Sulfate reducing bacteria | 37 | nr | nr | $H_2$, $CO_2$, $H_2S$ |
| | *Desulfovibrio vulgaris* | Sulfate reducing bacteria | 37 | nr | nr | $H_2$, $CO_2$, $H_2S$ |
| Thermophillic Bacteria | *Moorella thermoacetica* | Acetogenic | 55 | 6.5-6.8 | 10 | Acetate |
| | *Moorella thermoautotrophica* | Acetogenic | 58 | 6.1 | 7 | Acetate |
| | *Carboxydibrachium pacificus* | Hydrogenogenic, Obligate Anearobe | 70 | 6.8-7.1 | 7.1 | $H_2$ |
| | *Carboxydocella thermoautotrophica* | Hydrogenogenic, Obligate Anearobe | 58 | 7 | 1.1 | $H_2$ |
| | *Carboxydothermus hydrogenoformans* | Hydrogenogenic, Obligate Anearobe | 70-72 | 6.8-7.0 | 2 | $H_2$ |
| | *Thermincola carboxydiphila* | Hydrogenogenic, Obligate Anearobe | 55 | 8 | 1.3 | $H_2$ |
| | *Thermolithobacter carboxydivorans* | Hydrogenogenic, Obligate Anearobe | 70 | 7 | 8.3 | $H_2$ |
| | *Thermosinus carboxydivorans* | Hydrogenogenic, Obligate Anearobe | 60 | 6.8-7.0 | 1.2 | $H_2$ |
| | *Methanothermobacter thermoautotrophicus* | Methanogenic | 65 | 7.4 | 140 | $CH_4$, $CO_2$ |
| | *Desulfotomaculum carboxydivorans* | Sulfate reducing bacteria | 55 | 7 | 1.7 | $H_2$, $H_2S$ |
| | *Desulfotomaculum kuznetsovil* | Sulfate reducing bacteria | 60 | 7 | nr | Acetate, $H_2S$ |
| | *Desulfotomaculum nigrificans* | Sulfate reducing bacteria | 55 | 7 | nr | $H_2S$, $CO_2$ |
| | *Desulfotomaculum thermobenzoicum* subsp. *thermosyntrophicum* | Sulfate reducing bacteria | 55 | 7 | nr | Acetate, $H_2S$ |

Adapted from Henstra et al., *Curr. Opin. Biotechnol.* 18:200-206 (2007); Sipma et al., *Crit. Rev. Biotechnol.* 26:41-65 (2006)).

One type of organism for consideration of utilizing syngas is thermophilic acetogens due to their ability to tolerate temperatures as high as 72° C., which would reduce contamination issues and lower the heating cost associated with separating a product such as butanol via distillation. However, alcohol production from synthesis gas has yet to be demonstrated in thermophiles and their primary products are hydrogen, acetate, and/or $H_2S$. The doubling times of the acetogenic thermophiles were also longer than for mesophilic acetogens. Thus, initial studies are focused on mesophilic acetogenes for the production of a desired product such as butanol as these organisms have the fastest doubling times and have been shown to produce alcohols from syngas. Initial characterizations are performed on *Clostridium ljungdahlii* and *Clostridium carboxidivorans*. Of all syngas-utilizing organisms, *C. ljungdahlii* has a substantial body of knowledge relating to its metabolic capabilities and optimum fermentation conditions. *C. carboxidivorans* has been shown to naturally produce small quantities of butanol during growth on syngas (Henstra et al., *Curr. Opin. Biotechnol.* 18:200-206 (2007)).

The metabolic pathways of some exemplary syngas utilizing organisms are known. Two exemplary pathways utilizing syngas are shown in FIGS. 1 and 2.

Acetogens, such as *C. ljungdahlii* and *C. carboxidivorans*, can grow on a number of carbon sources ranging from hexose sugars to carbon monoxide. Hexoses, such as glucose, are metabolized first via Embden-Meyerhof-Parnas (EMP) glycolysis to pyruvate, which is then converted to acetyl-CoA via pyruvate:ferredoxin oxidoreductase. Acetyl-CoA can be used to build biomass precursors or can be converted to acetate, which produces energy via acetate kinase and phosphotransacetylase. The overall conversion of glucose to acetate, energy, and reducing equivalents is:

$$C_6H_{12}O_6 + 4ADP + 4Pi \rightarrow 2CH_3COOH + 2CO_2 + 4ATP + 8[H]$$

Acetogens extract even more energy out of the glucose to acetate conversion while also maintaining redox balance by further converting the $CO_2$ to acetate via the Wood-Ljungdahl pathway

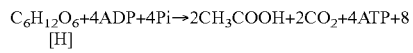

The coefficient n in the above equation signify that this conversion is an energy generating endeavor, as many acetogens can grow in the presence of $CO_2$ via the Wood-Ljungdahl pathway even in the absence of glucose as long as hydrogen is present to supply the necessary reducing equivalents.

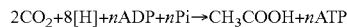

The Wood-Ljungdahl pathway, illustrated in FIG. 3, is coupled to the creation of $Na^+$ or $H^+$ ion gradients that can generate ATP via an $Na^+$- or $H^+$-dependant ATP synthase, respectively (Muller, *Appl. Environ Microbiol.* 69:6345-6353 (2003)). Based on these known transformations, acetogens also have the capacity to utilize CO as the sole carbon and energy source. Specifically, CO can be oxidized to produce reducing equivalents and $CO_2$, or directly assimilated into acetyl-CoA which is subsequently converted to either biomass or acetate.

Even higher acetate yields, however, can be attained when enough hydrogen is present to satisfy the requirement for reducing equivalents.

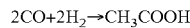

Following from FIG. 3, the production of acetate via acetyl-CoA generates one ATP molecule, whereas the production of ethanol from acetyl-CoA does not and requires two reducing equivalents. Thus ethanol production from syngas is not expected to generate sufficient energy for cell growth in the absence of acetate production. However, under certain conditions, *Clostridium ljungdahlii* produces mostly ethanol from synthesis gas (Klasson et al., *Fuel* 72:1673-1678 (1993)), indicating that some combination of the following pathways

does indeed generate enough energy to support cell growth. Hydrogenic bacteria such as *R. rubrum* can also generate energy from the conversion of CO and water to hydrogen (see FIG. 3) (Sipma et al., *Crit. Rev. Biotechnol.* 26:41-65 (2006)). The key mechanism is the coordinated action of an energy converting hydrogenase (ECH) and CO dehydrogenase. The CO dehydrogenase supplies electrons from CO which are then used to reduce protons to $H_2$ by ECH, whose activity is coupled to energy-generating proton translocation. The net result is the generation of energy via the water-gas shift reaction.

The product profile from syngas fermentations is determined by the choice of organism and experimental conditions. For example, *Clostridium ljungdahlii* produces a mixture of ethanol and acetate (Klasson et al., *Fuel* 72:1673-1678 (1993); Gaddy and Clausen, U.S. Pat. No. 5,173,429) while *Clostridium carboxidivorans* produces a mixture of ethanol, acetate, butanol, and butyrate (Liou et al., *Int. Syst. Evol. Microbiol.* 55(Pt 5):2085-2091 (2005)). Acetate and biomass concentrations as high as 26.8 g/L and 12.4 g/L, respectively, together with ethanol concentrations below 1 g/L have been reported with *C. ljungdahlii* (Gaddy, U.S. Pat. Nos. 5,807,722, 6,136,577 and 6,340,581). This product profile can be shifted, however, towards increased ethanol formation by traditional means of increasing solvent formation over acid production in *Clostridia*, for example, using nutrient limitation, media alteration, lower pH, reducing agent addition, and the like. Product profile sensitivity to a number of conditions, for example, calcium pantothenate limitation, cobalt limitation, 112 oversupply, CO oversupply, acetate conditioning, and the like, has been described (Gaddy et al., U.S. Pat. No. 7,285,402). Ethanol, acetate, and cell concentrations of 33.0 g/L, 4.0 g/L, and 2.7 g/L, respectively, were demonstrated with *C. ljungdahlii* strain C-01 without cell recycle under conditions optimized for ethanol production. Maximum ethanol productivities ranged from 21 g/L/day without cell recycle to 39 g/L/day with cell recycle.

Sensitivity of syngas fermentations to inhibitors can also be determined. Fewer efforts to optimize the fermentation conditions of *C. carboxidivorans* (Liou et al., *Int. J. Syst. Evol. Microbiol.* 55(Pt 5):2085-2091 (2005)) for the generation of a particular product have been reported. However, a number of recent studies have been aimed at the inhibition of *C. carboxidivorans* growth by syngas inhibitors. Specifically, inhibitors present in the biomass-generated producer gas stopped *C. carboxidivorans* growth and $H_2$ utilization, although growth could be recovered when "clean" bottled gasses consisting of only CO, $CO_2$, $N_2$, and $H_2$ were introduced (Datar et al., *Biotechnol. Bioeng.* 86:587-594 (2004)). Passing the gas through a 0.025 μm filter cleaned it well enough to allow cell growth, although $H_2$ utilization was still blocked (Ahmed et al., *Biomass Bioenergy* 30:665-672 (2006)). A scanning electron microscope analysis of the filter indicated that tar particulates, and not ash, was the likely culprit leading to cell dormancy. Potential tar species were identified as benzene, toluene, ethylbenzene, p-xylene, o-xylene, and napthalene. Cells were able to adapt to the tars present following the 0.2 μm filter within 10-15 days. The fact that $H_2$ utilization ceased regardless of filter size indicated that a non-filtered component was inhibiting the hydrogenase enzyme. This compound was later identified as nitric oxide. NO inhibits hydrogenase at ≥60 ppm levels (Ahmed and Lewis, *Biotechnol. Bioeng.* 97:1080-1086 (2007)). Similar studies can be performed to determine appropriate conditions for the utilization of syngas in a particular organism to produce a desired product.

In an exemplary experiment, it is assumed that synthesis gas exiting the gasifier is passed though a cyclone, a condensation tower, a scrubber, and a 0.2 μm filter, similar to the system described previously for switchgrass gasification (Datar et al., *Biotechnol. Bioeng.* 86:587-594 (2004); Ahmed et al., *Biomass Bioenergy* 30:665-672 (2006))). Oxygen blown gasification, as opposed to air blown, is used so that NO levels under 40 ppm can be achieved, as suggested previously (Ahmed and Lewis, *Biotechnol. Bioeng.* 97:1080-1086 (2007)). Furthermore, studies with *C. ljungdahlii* revealed that $H_2S$ levels under 2.7% are not inhibitory (Klasson et al., *Fuel* 72:1673-1678 (1993)), even when the cells are not acclimated beforehand, and levels are expected to be below that level with syngas obtained from biomass or even coal gasification. In addition, tolerance to tar particulates can be achieved through evolution or adaptation (Ahmed et al., *Biomass Bioenergy* 30:665-67. (2006)).

Example II

Design and Modeling of Microbial Strains for Utilization of Syngas

This example describes the design of exemplary microbial strains for the production of a desired product from syngas.

Initial studies utilize genome-scale models of *C. ljungdahlii*, *C. carboxidivorans*, and *R. rubrum* for the design of microbial strains capable of utilizing syngas as a carbon source. Metabolic models and simulation algorithms are used to develop strains that utilize syngas. Genomic sequences of desired microorganisms are utilized, along with sequences from closely related species, to construct genome-scale metabolic models of the target organisms. To facilitate this process, Genomatica has developed a comprehensive methodology to automatically build a first draft of a metabolic network based on an exhaustive sequence comparison with our existing high quality manually built metabolic models. Next, the automatically generated gene-protein-reaction (GPR) assignments, see FIG. 2, are checked manually and detailed notes are catalogued within Sim-Pheny™, Genomatica's proprietary model construction and simulation platform, to ensure that they are as transparent as possible. For the production of butanol as an exemplary product, enzymes in the butanol pathway are expressed in those organisms that do not produce butanol naturally, for example, *C. ljungdahlii* and *R. rubrum*.

The metabolic models are interrogated using a constraint-based modeling approach (Schilling et al., *Biotechnol. Prog.* 15:288-295 (1999); Edwards et al., *Environ. Microbiol.* 4:133-40 (2002); Varma and Palsson, *Biotechnol.* 12:994-998 (1994); Patil et al., *Curr. Opin. Biotechnol.* 15:64-69 (2004)). Briefly, rather than attempting to calculate and predict exactly what an organism does, the constraint-based approach narrows the range of possible phenotypes that an organism can display based on the successive imposition of governing physico-chemical constraints, for example, stoichiometric, thermodynamic, capacity, and regulatory (Price et al., *Trends Biotechnol.* 21:162-169 (2003); Price et al., *Nat. Rev. Microbiol.* 2:886-897 (2004)). Thus, instead of calculating an exact phenotypic "solution," that is exactly how an organism will behave under given genetic and environmental conditions, it can determine the feasible set of phenotypic solutions in which the organism can operate. In general, genome-scale constraint-based models have been shown to be useful in predicting several physiological properties such as growth and by-product secretion patterns (Edwards and Palsson, *Proc. Natl. Acad Sci. USA* 97:5528-5533 (2000); Varma et al., *Appl. Environ. Microbiol.* 59:2465-2473 (1993); Varma and Palsson, *Appl Environ Microbiol*, 60:3724-3731 (1994); Edwards et al., *Nat. Biotechnol.* 19:125-130 (2001)), determining the range of substrate utilization (Edwards and Palsson, supra, 2000), determining the minimal media for growth (Schilling et al., *J Bacteriol.* 184:4582-4593 (2002), predicting the outcome of adaptive evolution (Ibarra et al., *Nature* 420:186-189 (2002)), calculating theoretical product yields (Varma et al., *Biotechnol. Bioengineer.* 42:59-73 (1993)), predicting knockout phenotypes (Edwards and Palsson, *BMC Bioinformatics* 1:1 (2000); Segre et al., *Proc. Natl. Acad. Sci. USA* 99:15112-15117 (2002); Shlomi et al., *Proc. Natl. Acad. Sci. USA* 102:7695-7700 (2005)) and comparing metabolic capabilities of different organisms (Forster et al., *Genome Res.* 13:244-253 (2003)). Based on these predictive capabilities, the models are used to characterize the metabolic behavior of industrial microbes under laboratory and production scale fermentation conditions. Constraint-based approaches have matured to the point where they are commonly applied to pinpoint successful genetic manipulations aimed at improving strain performance (Bro et al., *Metab. Eng.* 8:102-111 (2006); Alper et al., *Nat. Biotechnol.* 23:612-616 (2005); Alper et al., *Metab. Eng.* 7:155464 (2005); Fong et al., *Biotechnol. Bioeng.* 91:643-648 (2005); Park et al., *Proc. Natl. Acad. Sci. USA* 104:7797-7802 (2007)). Characteristics are continued to be monitored in order to implement further optimization of conditions.

Additional optimization of organisms can be performed by determining gene knockouts to enhance for production of a desired product, including growth-coupled production of a desired product such as butanol (see Example V). *C. ljungdahlii* currently can convert mixtures of CO, $CO_2$, and $H_2$ to acetate and ethanol, while *C. carboxidivorans* produces a mixture of acetate, ethanol, butyrate, and butanol. *R. rubrum* does not produce alcohols naturally, but has been shown to accumulate high levels of poly-β-hydroxyalkanoates (PHAs). Modeling analysis allows predictions of the effects on cell growth of shifting the metabolism of a biocatalyst organism towards more efficient production of a desired product such as butanol. The modeling also points at metabolic manipulations aimed at driving the metabolic flux through a desired production pathway, for example, the production of butanol. One modeling method is the bilevel optimization approach, OptKnock (Burgard et al., *Biotechnol. Bioengineer.* 84:647-657 (2003)), which is applied to select gene knockouts that collectively result in the growth-coupled production of a desired product such as butanol. Strains designed with a gene knockout strategy are forced, due to network stoichiometry, to produce high levels of a desired product such as butanol for efficient growth, because all other growth options have been removed. Such strains are self-optimizing and stable. Accordingly, they typically maintain or improve upon production levels even in the face of strong growth selective pressures, making them amenable to batch or continuous bioprocessing and also evolutionary engineering.

Several candidate strain are designed and optimization of production conditions are performed. Fermentation conditions are tested in triplicate, alongside control fermentations using the original process parameters. Using data from test fermentations, simulations can be performed to assess changes in metabolism that result from process changes and compared to predictions. If productivity significantly falls short of that anticipated, further simulations are performed using this new knowledge for a second iteration of the design process in order to optimize strains.

Example III

Development of Genetic Tools for Target Organisms

This example describes the development of tools for genetic manipulation and engineering of target organisms.

Genetic systems are developed in candidate strains for utilization of syngas. In particular, genetic systems are developed for *C. ljungdahlii* and *C. carboxidivorans*. Genetic transformations are also tested in *Rhodospirillum rubrum*. Antibiotic resistance is tested to determine potential markers for selection of desired genetic elements. For example, many *Clostridia* are sensitive to erythromycin and chloramphenicol. DNA transfer methods are developed using well known methods, including but not limited to electroporation, conjugation or ultrasound transformation. Additional testing is performed on several expression vectors of gram positive bacteria, particularly the vectors used in *C. acetobutylicum*, to determine their effectiveness for expression of desired genetic elements in *C. ljungdahlii* and/or *C. carboxidivorans*. Additional vectors can be developed by replacing the promoter of the vectors with a native *C. ljungdahlii* or *C. carboxidivorans* promoter. In addition, several suicide plasmids, including those of *C. acetobutylicum* and *C. cellulolyticum*, are tested for genetic manipulation. The knockdown technique of antisense RNA inhibition developed for other *Clostridia* are also tested.

The transformation, expression and antisense RNA inhibition tools are available for mesophilic species *Clostridium cellulolyticum* and *Clostridium acetobutylicum*. *C. cellulolyticum* is a model system for cellulose degradation (Desvaux, *FEMS Microbiol Rev.* 741-764 (2005)), whereas *C. acetobutylicum* has been intensively characterized for its ability to produce solvents such as butanol (Durre, *Biotechnol. J.* 2:1525-1534 (2007)). Notably, both species are capable of producing ethanol and hydrogen as an end product. Therefore, knowledge from these two strains is instructive for other ethanol- and/or hydrogen-producing *Clostridia* species. Studies of targeted mutagenesis in *C. cellulolyticum* have been initiated and can be similarly used on other candidate organisms.

The results of these studies allow for phenotypic characterization of the mutants generated as well as allow genetic engineering of *C. ljungdahlii* and/or *C. carboxidivorans*. Additional optimization is performed, as needed, to develop genetic systems by varying methods, plasmids and conditions to achieve an optimized result (Lynd et al., *Microbiol. Mol. Biol. Rev.* 66:506-577 (2002)).

In more detail, profiling the antibiotic resistance capacities of *C. ljungdahlii* and *C. carboxidivorans* is performed. An important step in developing genetic systems is to determine the native antibiotic resistance characteristics of the target strains. Erythromycin and chloramphenicol are two antibiotics with resistance markers that have been shown to be functional on plasmids in *C. acetobutylicum* and *C. cellulolyticum* (Kashket and Cao, *Appl. Environ. Microbiol.* 59:4198-4202 (1993); Green and Bennett, *Biotechnol. Bioeng.* 58:215-221 (1998)). However, they are usually not available for common suicide plasmids, which instead often contain antibiotic markers of ampicillin, gentamycin, rifampicin, kanamycin and tetracycline. In order to determine antibiotic sensitivity, *C. ljungdahlii* and *C. carboxidivorans* are grown in defined medium in an anaerobic chamber (Ahmed and Lewis, *Biotechnol. Bioeng.* 97:1080-1086 (2007); Younesi et al., *Bioresour. Technol.* Jun. 18, 2007). Common antibiotics as indicated above are added at gradient concentrations from 1 µg/ml to 500 µg/ml. An instrument such as a Type FP-1100-C Bioscreen C machine (Thermo Labsystems; Waltham Mass.) is used to control the growth temperature at 37° C. and automatically measure the optical density of cell growth at different intervals. All of the physiological studies are performed in replicate, for example, triplicates, so that the average and standard deviation can be calculated. This growth data indicates the sensitivity of *C. ljungdahlii* and *C. carboxidivorans* to the antibiotics being tested. The antibiotics that inhibit growth of the strain are used in further studies.

In more detail, DNA transfer methods and gene expression systems are developed to provide simple and efficient DNA delivery methods for genetic engineering. Methods for bacterial DNA transfer include conjugation, electroporation, chemical transformation, transduction and ultrasound transformation. Among them, electroporation and conjugation have been previously established in several *Clostridial* species (Jennert et al., *Microbiol.* 146:3071-3080 (2000); Tardif et al., *J. Ind. Microbiol. Biotechnol.* 27:271-274 (2001); Tyurin et al., *Appl. Microbiol.* 88:220-227 (2000); Tyurin et al., *Appl. Environ. Microbiol.* 70:883-890 (2004)). Ultrasound transformation is a convenient and efficient method that provides high transformation efficiency (>$10^6$ CFU/µg DNA) for gram negative bacteria (Song et al., *Nucl. Acids Res.* 35:e129 (2007)) and can be tested in gram positive bacteria.

Electroporation, ultrasound transformation, and conjugation are tested for *C. ljungdahlii* and *C. carboxidivorans* transformation efficiencies. A variety of plasmids from gram positive bacteria with different replicons, for example, pIP404, pAMβ1 and pIM13, are tested. If needed, subcloning is employed to replace the antibiotic resistance cassettes of existing plasmids with the suitable ones based on antibiotic resistance testing. Standard molecular subcloning techniques, including restriction enzyme digestion, ligation by T4 ligase and *E. coli* transformation, are used for engineering of the plasmids (Sambrook et al., *Molecular Cloning: A Laboratory Manual* Cold Spring Harbor Laboratory Press (1989)). As required for many other *Clostridial* species, these plasmids are methylated prior to DNA delivery to protect them from degradation by the host bacteria. For electroporation and conjugation, existing protocols of *C. cellulolyticum* and *C. acetobutylicum* are tested first. Parameters such as electroporation setup, recovery time, and concentration of $Ca^{2+}$ and $Mg^{2+}$ in the electroporation buffer are varied to optimize, the transformation efficiency. For ultrasound transformation, experiments are conducted under conditions of low frequency ultrasound, for example, 40 kHz, and extended recovery time as previously described (Song et al., supra, 2007)).

Once an efficient DNA transfer protocol is established for certain plasmids, the plasmids are engineered to incorporate a native *C. ljungdahlii* or *C. carboxidivorans* promoter followed by a multiple cloning site to generate expression vectors. It is expected that the existing expression vectors of *C. acetobutylicum*, such as pSOS95 and pIMP1, can likely work in *C. ljungdahlii* or *C. carboxidivorans* without changes of the promoter, so these plasmids are used for initial testing.

To develop gene disruption methods, several suicide plasmids such as pKNOCK, pDS3.0, pSPUC and pBluescript SKII are screened for suitability as suicide plasmids for *C. ljungdahlii* and/or *C. carboxidivorans*. As discussed above, if the results either existing antibiotic resistance cassettes are used or are replaced with suitable antibiotic resistance cassettes. A DNA fragment of a selected target gene is subcloned into appropriate suicide plasmids. The genes selected as the initial targets are those encoding the alcohol dehydrogenases responsible for ethanol production. These genes were selected because they lead to byproduct formation, are likely to be identified as targets for disruption for butanol-producing strains, and provide for an easy screen by analyzing ethanol in the fermentation broth. If deletion of an alcohol dehydrogenase in *C. carboxidivorans* lowers butanol production in addition to lowering ethanol production due to the broad substrate specificity of these enzymes, an alcohol dehydrogenase which favors butanol formation over ethanol formation, such as the adhE2 from *C. acetobutylicum* (Atsumi et al., *Metab. Eng.* Sep. 14, 2007), can be cloned along with the other butanol pathway genes to construct a butanol pathway.

The engineered suicide plasmids are methylated and transferred into *C. ljungdahlii* and *C. carboxidivorans*. Colonies are selected on solid medium containing the appropriate antibiotics. PCR amplification and subsequent sequencing of the disrupted genomic region, southern blot, and physiological studies are employed to verify the correct disruption of the targeted gene(s) in the genome. The expression systems can also be used as an alternative to gene disruption to express the antisense RNA of the target gene, which will inhibit but not completely abolish its gene expression. Therefore, the antisense RNA system serves as a convenient approach of gene knock-down of a desired gene.

Example IV

Genetic Assessment of *Rhodospirillum rubrum*

This example describes development of genetic tools for *Rhodospirillum rubrum* as an organism for utilization of syngas.

Figure 5:
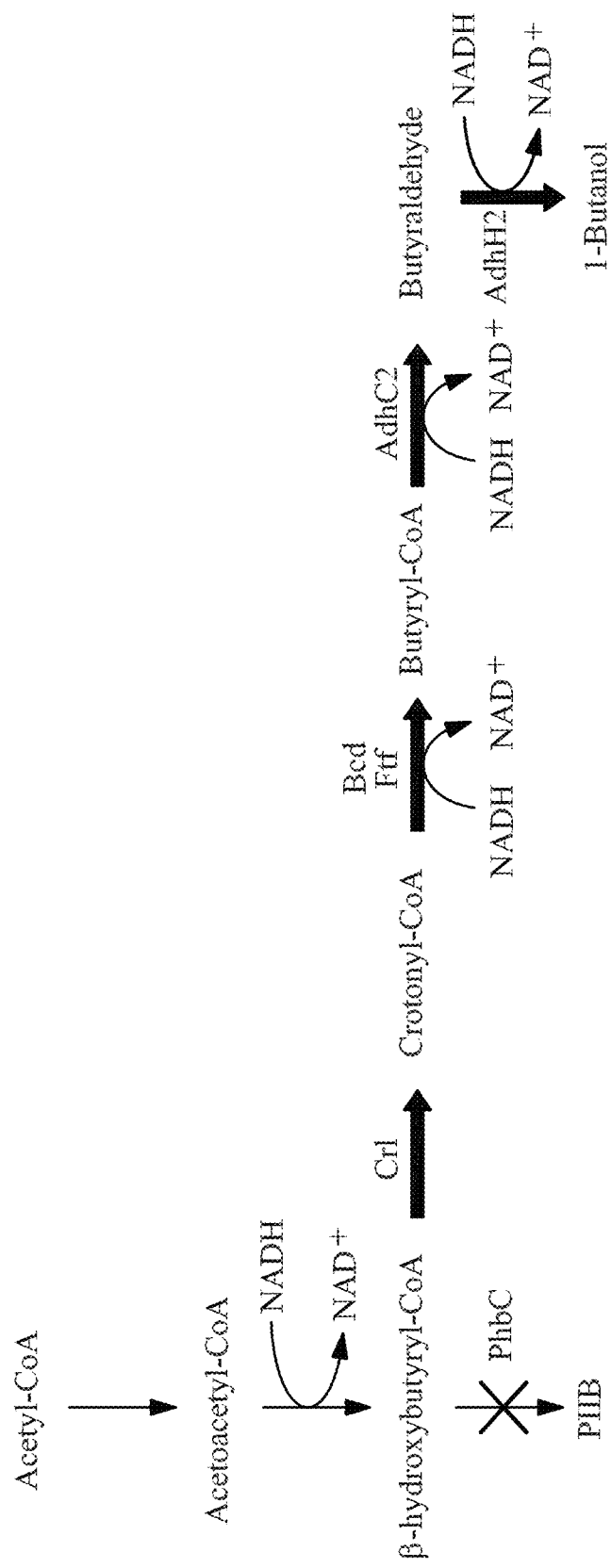
FIG. 5 shows a proposed polyhydroxybutyrate (PHB) pathway modification in *R. rubrum* to form 1-butanol. Bold arrows indicate reaction steps that are introduced via heterologous expression of a 4-gene operon forming the 1-butanol pathway from *C. acetobutylicum*. Abbreviations used are PHB, poly-β-hydroxybutyrate; PhbC, PHB synthase; Crt, crotonase; Bcd, butyryl-CoA dehydrogenase; Etf, electron transfer flavoprotein; AdhE2, aldehyde/alcohol dehydrogenase.

*Rhodospirillum rubrum* is a Gram negative, purple nonsulfur bacterium which oxidizes CO under anaerobic conditions (Kerby et al., *J. Bacteriol.* 177:2241-2244 (1995); Kerby et al., *J. Bacteriol.* 174:5284-5294 (1992)). *R. rubrum* possess a Ni—Fe—S CO dehydrogenase (CODH) that catalyzes the oxidation of CO, which is coupled to the formation of hydrogen (Ensign and Ludden, *J. Biol. Chem.* 1991. 266:18395-18403 (1991)). Given its CO oxidation capacity and ability to fix $CO_2$, *R. rubrum* is capable of efficient growth on syngas in the dark (Do et al., *Biotechnol. Bioeng.* 97:279-286 (2007)). In addition, it has been shown that during growth on syngas, up to 34% of the total cellular carbon is stored in the form of poly-p-hydroxyalkanoates (PHA) that consist primarily of β-hydroxybutyrate (PHB). The ability of *R. rubrum* to efficiently direct cellular carbon to form reduced 4-carbon compounds make it an attractive platform for engineering production of a desired product such as 1-butanol. In addition, a genetic system has been established for *R. rubrum*, and a wide range of cloning vectors including the broad-host range RK2 derivatives are available (Saegesser et al., *FEMS Microbiol. Lett.* 95:7-12 (1992)). Another attractive aspect of utilizing *R. rubrum* is that there is considerable overlap in the pathways leading to PHB and 1-butanol synthesis (FIG. 5). Since PHB synthesis has been studied for its use as a biodegradable plastic, considerable information is available regarding PHB pathway regulation and over expression (Anderson and Dawes, *Microbiol. Rev.* 54:450-472 (1990)). In parallel to establishing the genetic tools necessary for manipulating the Clostridial strains as discussed above, a synthetic operon consisting of several genes from *Clostridium acetobutylicum* that form the 1-butanol synthesis pathway is developed as well.

Since *R. rubrum* has been sequenced and has a tractable genetic system (Saegesser et al., *FEMS Microbiol. Lett.* 95:7-12 (1992)), it is expected that targeted deletions can be made in selected loci. Broad-host range, site-specific gene excision systems are available which allow markerless deletions to be generated (Hoang et al., *Gene* 212:77-86 (1998)). Therefore, it will be possible to generate multiple knockouts in a single strain without relying on multiple antibiotic selections. This method can be tested by deleting the PIM synthase gene, which is the terminal step in PHB synthesis (Hustede et al., *FEMS Microbiol. Lett.* 72:285-290 (1992)). This is chosen because PHB synthesis will likely compete with the proposed butanol pathway for 4-carbon precursors and reducing equivalents (FIG. 5). Successful deletion of the equivalent gene in *Methylobacterium extorquens*, a gram negative bacterium also known to accumulate over 30% by weight PHB, has been reported with no deleterious effect on growth (Korotkova and Lidstrom, *J. Bacteriol.* 183:1038-1046 (2001)).

Example V

Engineering Microorganisms for Production of Butanol from Syngas

This example describes engineering microorganisms for production of butanol formation from syngas.

In initial studies, Clostridial strains, in particular, *C. carboxidivorans*, are used to engineer utilization of syngas for production of and tolerance to butanol. *C. carboxidivorans* has been shown to produce butanol from synthesis gas (Liou et al., *Int. J Syst. Evol. Microbiol.* 55(Pt 5):2085-2091 (2005)). *C. carboxidivorans* is engineered to increase syngas utilization efficiency, increase the efficiency of butanol production from syngas as an exemplary desired product, and to increase product tolerance so that higher yields of a desired product can be obtained.

Preliminary metabolic network analysis has revealed that the theoretical conversion of lignocellulosic-derived syngas to butanol compares favorably to sugar fermentation.

Syngas to Butanol:

$$12CO + 5H_2O \rightarrow 8ATP + 8CO_2 + 1C_4H_{10}O$$

$$4CO + 8H_2 \rightarrow 4ATP + 3H_2O + 1C_4H_{10}O$$

$$4CO_2 + 12H_2 \rightarrow 2ATP + 7H_2O + 1C_4H_{10}O$$

Sugar to Butanol:

$$1C_6H_{12}O_6 \rightarrow 2ATP + 2CO_2 + 1H_2O + C_4H_{10}O$$

$$1.2C_5H_{10}O_5 \rightarrow 1.7ATP + 2CO_2 + 1H_2O + C_4H_{10}O$$

Given that biomass gasification can optimally provide a 1:1 ratio of CO to $H_2$, the production of one mole of butanol will require 12 moles of $CO+H_2$. Importantly, the fermentative conversion of syngas to butanol is an energy-generating endeavor, therefore supporting cell growth at high product yields. Furthermore, initial calculations reveal the substrate cost to be cheaper than the equivalent amount of sugar that would be required.

As discussed above, models and genetic tools are utilized to design strains that facilitate the production of butanol or other desired products as an obligatory product of cell growth. In other words, the cell is engineered so that butanol is a necessary electron sink during growth on CO. The strains are constructed, which may have a combination of gene knockouts and overexpression of appropriate enzymes, and can be evolved for improved production and tolerance of growth conditions.

For construction of *Clostridial* strains producing butanol, genome analysis as discussed above is used to identify biological pathways necessary for establishing, and/or improving butanol production in *C. ljungdahlii* and *C. carboxidivorans*. Additional improvement in butanol production can be achieved by increasing expression of syngas utilization pathway and/or butanol production pathway proteins and enzymes. To express the gene(s), in the targeted biological pathway, gene expression vectors developed as discussed above are used. If there is more than one gene, the genes are PCR amplified and cloned into an expression vector as a synthetic operon. The resulting expression plasmid is transferred into *C. ljungdahlii* and *C. carboxidivorans*. Northern blot and/or real time PCR, or other suitable techniques, are used to examine gene expression at the transcriptional level.

To improve butanol production, it is likely that endogenous gene(s) of *C. ljungdahlii* and *C. carboxidivorans* will be inactivated to reroute the redox potential toward butanol production. To this end, an internal DNA fragment of a targeted gene will be PCR amplified and cloned into a suicide plasmid. Then the plasmid is transferred into *C. ljungdahlii* and *C. carboxidivorans*, resulting in disruption of the target gene by single crossover recombination. The correct disruption is confirmed by sequencing of the PCR product amplified from the disrupted genomic locus and/or Southern blot, or using other suitable analytical techniques. If there is more than one targeted gene, the suicide plasmids are engineered to change antibiotic marker so that multiple gene knockouts can be generated in a single strain. It is expected that up to 3 to 6 gene deletions may be beneficial in optimizing butanol production.

For genetic engineering of *Rhodospirillum rubrum* for butanol production, a synthetic operon is developed consisting of several genes that form the butanol synthesis pathway in *Clostridium acetobutylicum*. A similar approach for allowing butanol production in *E. coli* was recently reported, proving that heterologous expression of the pathway in Gram negative organisms is possible (Atsumi et al., *Metab. Eng.* Sep. 14, 2007). The necessary genes for butanol production in *R. rubrum* can be expressed on a broad-host-range expression vector. Expression can be controlled using an inducible promoter such as the tac promoter. The) synthetic, 4-gene operon is constructed using a fusion PCR technique and will include genes for crotonase, butyryl-CoA dehydrogenase, electron transfer flavoprotein, and aldehyde/alcohol dehydrogenase activities. Fusion/assembly PCR techniques have been used to construct synthetic operons for expression in heterologous hosts (Craney et al., *Nucl. Acids Res.* 35:e46 (2007); Hill et al., *Mol. Gen. Genet.* 226:41-48 (1991)). The butanol operon is transformed into both the wild-type and PHB synthesis deficient *R. rubrum* strains, and tested as described below. It is also possible that more than one gene is desirable to be targeted for removal based on modeling studies. These deletions can be implemented using the markerless method, as discussed above.

As intermediate strains are being constructed, they are tested physiologically to evaluate progress towards butanol production, as well as the ability to sustain robust growth and reduced byproduct formation. Initial screening for growth and butanol production is performed initially in 1 mL microreactors (such as MicroReactor Technologies, Inc.; Mountain View, Calif.). Configurations such as 24-well plates can be controlled for pH, temperature, and gas composition. As a next step, serum bottles are vigorously shaken in temperature and gas composition controlled incubators. This allows sampling and analysis of the gas headspace as well as the liquid phase. Products such as butanol, ethanol, and organic acids can be analyzed by gas chromatography (GC/MS) or HPLC using routine procedures. $H_2$, CO, and $CO_2$ in the headspace will be analyzed by GC with Thermal Conductivity Detector (TCD) detection using 15% Ar as an internal standard, as described previously (Najafpour and Younesi, *Enzyme Microb. Technol.* 38:223-228 (2006)). In these experiments, synthetic syngas with 1/1 ratio of $H_2$ in CO is used. The effect of gas composition is explored during the fermentation optimization.

Initially, strains with one or more deletions is analyzed to compare growth and fermentation profiles relative to wild-type cells. It is possible that growth in multiple deletion strains will be poor without enhanced expression of the butanol pathway. Strains expressing one or more butanol pathway genes, or other targets identified by metabolic modeling, are tested in the wild-type host to assess the ability to enhance flux through the butanol pathway and provide a preliminary assessment of which steps are likely bottlenecks. Different gene orders, and if possible alternate promoters and ribosome binding sites, are tested to optimize the synthetic operon construct. The construct(s) yielding the most positive results are transformed into the host containing the prescribed gene deletions, and tested as described above. Results are compared to model predictions to assess where unforeseen limitations and metabolic bottlenecks may exist.

After genetic engineering manipulations are made, adaptive evolution can be utilized to optimize production in a desired strain. Based on strain design that couples the production of butanol to growth applies selection pressure that favors cells with improved growth rate and/or yield and will lead to higher butanol yield. Adaptive evolution is therefore performed to improve both growth and production characteristics (Fong and Nilsson, *Nat. Genet.* 36:1056-1058

(2004); Alper et al., *Science* 314:1565-1568 (2006)). Based on the results, subsequent rounds of modeling and genetic engineering can be utilized to further optimize production. The evolutionary engineering step can be carried out in a device that automatically maintains cells in prolonged exponential growth by the serial passage of batch cultures into fresh medium before the stationary phase is attained. Specifically, when a certain cell density is reached, a fraction of the media with exponentially growing cells is passed from one region to an adjacent region while fresh media is added for the dilution. By automating optical density measurement and liquid handling, serial transfer can be performed at high rates, thus approaching the efficiency of a chemostat for evolution of cell fitness (Dykhuizen, *Methods Enzymol.* 224:613-631 (1993)). However, in contrast to a chemostat, which maintains cells in a single vessel, this procedure eliminates the possibility of detrimental selection for cells adapted for wall-growth (Chao and Ramsdell, *J. Gen. Microbiol.* 131:1229-1236 (1985); Lynch et al., *Nat. Methods* 4:87-93 (2007)). In addition, this method allows the cells to be maintained in a closed system that ensures strict anaerobic conditions, a requirement for growing the *Clostridia*.

An additional role that adaptive evolution can play is to develop strains that are more tolerant to butanol and impurities such as NOx and tars. Butanol tolerance levels have not been published for *C. ljungdahlii* and *C. carboxidivorans*, and this is measured for wild-type cells to determine tolerated levels. Wild-type *C. acetobutylicum* has been reported to have a tolerance of approximately 180 mM (1.2% w/v) (Tomas et al., *Appl. Environ. Microbiol.* 69:4951-4965 (2003)) and have been engineered to achieve a tolerance levels as high as 2.1% (Ezeji et al., *Chem. Rec.* 4:305-314 (2004)). Two approaches are currently prevalent to improve the butanol tolerance capacity of *Clostridia*. One involves changing the lipid composition and the fluidity of the membrane via rational genetic modification of lipid content, or by evolution methods such as serial enrichment (Soucaille et al., *Curr. Microbiol.* 14:295-299 (1987)) or random mutagenesis (Jain et al., U.S. Pat. No. 5,192,673 1993). However, tolerance is a complex function of multiple factors and is difficult to achieve with directed modification alone. Further, the cells are reported to lyse at high concentrations of butanol (Van Der Westhuizen et al., *Appl. Environ. Microbiol.* 44:1277-1281 (1982)). Therefore, optimization of strains is based on a combination of genetics, evolution, and metabolic modeling. The wild type strains can be evolved adaptively in the presence of successively increasing concentrations of butanol to demonstrate that butanol tolerance in *Clostridium* can be improved through this process. One goal is to optimize cells by evolving the cells to obtain a tolerance of butanol, for example, a concentration as high as 25 g/L. A similar procedure can be performed a similar procedure can be used to evaluate the tolerance of strains to syngas impurities using, for example, NO and aromatic compounds prevalent in tars. Adaptive evolutions for optimization of production and/or tolerance of impurities can be performed sequentially or concurrently. This approach can also be integrated with directed mutation of genes associated with butanol tolerance and membrane fluidity, to optimize tolerance levels suitable for commercial scale production.

Figure 4A:
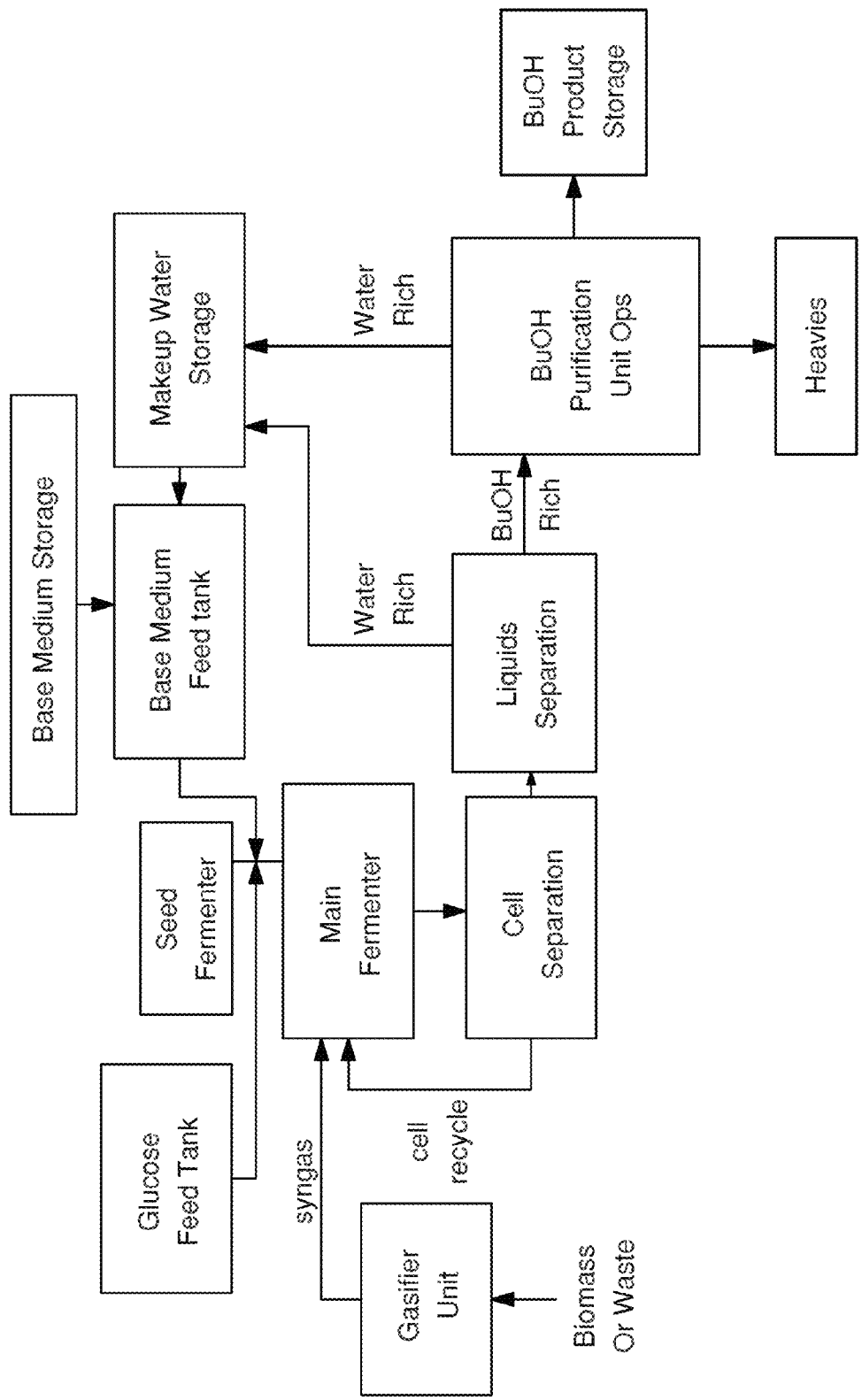
FIG. 4A shows a block flow diagram for a syngas to butanol process.
Figure 4B:
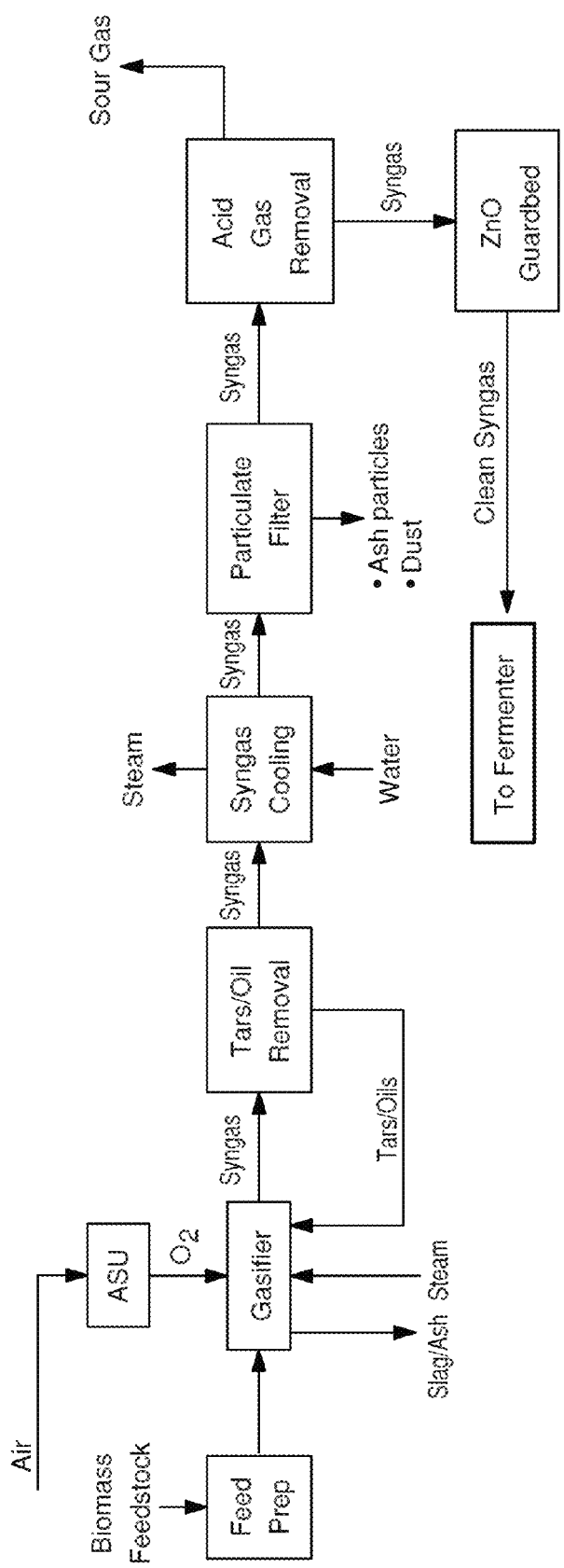
FIG. 4B shows details of the gasifier. ASU represents air separation unit.

An exemplary syngas to butanol process is illustrated in FIG. 4. FIG. 4 illustrates a block flow diagram for a process of utilizing syngas to produce butanol.

Example VI

Development and Optimization of Syngas Fermentation Processes

This example describes the development and optimization of syngas fermentation processes. A laboratory-scale syngas fermentation using authentic syngas is performed to demonstrate and optimize target yields for commercial scale production.

Important process considerations for a syngas fermentation are high biomass concentration and good gas-liquid mass transfer (Bredwell et al., *Biotechnol. Prog.* 15:834-844 (1999)). The solubility of CO in water is somewhat less than that of oxygen. Continuously gas-sparged fermentations can be performed in controlled fermenters with constant off-gas analysis by mass spectrometry and periodic liquid sampling and analysis by GC and HPLC. The liquid phase can function in batch mode. Butanol and byproduct formation is measured as a function of time. Although the final industrial process will likely have continuous liquid flow, batch operation can be utilized to study physiology in the early stages of characterization and optimization. All piping in these systems are glass or metal to maintain anaerobic conditions. The gas sparging is performed with glass frits to decrease bubble size and improve mass transfer. Various sparging rates are tested, ranging from about 0.1 to 1 vvm (vapor volumes per minute). To obtain accurate measurements of gas uptake rates, periodic challenges are performed in which the gas flow is temporarily stopped, and the gas phase composition is monitored as a function of time.

Fermentation systems specific for syngas utilization are also developed. Although designs are tested with engineered organisms, testing of fermentation systems can be done in parallel to strain development, using wild-type organisms at first. In order to achieve the overall target productivity, methods of cell retention or recycle are employed. A usual concern about such systems operated continuously is that cells could evolve to non-producing phenotypes. Because the organisms are designed for growth-coupled production of a desired product, the organisms are genetically stable. One method to increase the microbial concentration is to recycle cells via a tangential flow membrane from a sidestream. Repeated batch culture can also be used, as previously described for production of acetate by *Moorella* (Sakai S., Y. Nakashimada, K. Inokuma, M. Kita, H. Okada, and N. Nishio, Acetate and ethanol production from 112 and CO2 by *Moorella* sp. using a repeated batch culture. *J. Biosci. Bioeng.* 99:252-258 (2005)). Various other methods can also be used (Bredwell et al., *Biotechnol. Prog.* 15:834-844 (1999); Datar et al., *Biotechnol. Bioeng.* 86:587-594 (2004)). Additional optimization can be tested such as overpressure at 1.5 atm to improve mass transfer (Najafpour and Younesi, *Enzyme Microb. Technol.* 38:223-228 (2006)).

Once satisfactory performance is achieved using pure $H_2$/CO as the feed, synthetic gas mixtures are generated containing inhibitors likely to be present in commercial syngas. For example, a typical impurity profile is 4.5% $CH_4$, 0.1% $C_2H_2$, 0.35% $C_2H_6$, 1.4% $C_2H_4$, and 150 ppm nitric oxide (Datar et al., *Biotechnol. Bioeng.* 86:587-594 (2004)). Tars, represented by compounds such as benzene, toluene, ethylbenzene, p-xylene, o-xylene, and naphthalene, are added at ppm levels to test for any effect on production. For example, it has been shown that 40 ppm NO is inhibitory to *C. carboxidivorans* (Ahmed and Lewis, *Biotechnol. Bioeng.* 97:1080-1086 (2007)). Cultures are tested in shake-flask cultures before moving to a fermenter. Also, different levels of these potential inhibitory compounds are tested to quantify the effect they have on cell growth. This knowledge is used to develop specifications for syngas purity, which is utilized for scale up studies and production. If any particular component is found to be difficult to decrease or remove from syngas used for scale up, adaptive evolution procedure can be utilized, as discussed above, to adapt cells to tolerate one or more impurities.

Example VII

Minimal Gene Sets for Generating Syngas Utilizing Microorganisms

This example describes determination of a minimal gene/protein sets for generation of syngas utilizing microorganisms, particularly in an microorganism that does not naturally utilize syngas to produce a desired product.

In general, microorganisms have the ability to generate tetrahydrofolate, and methyl-tetrahydrofolate (Me-THF) is a common intermediate in biosynthesis, for example, in methionine production. Hence, the Methyl Branch outlined above and shown in FIG. 1 is not a unique feature of organisms that utilize syngas. However, the enzymes required for generating Me-THF have been found to be much more active in syngas-utilizing organisms relative to organisms that do not use syngas. In fact, tetrahydrofolate-dependent enzymes from acetogens have 50 to 100× higher specific activities than those from other sources such as *E. coli* and eukaryotes (Morton et al., *Genetics and Molecular Biology of Anaerobic Bacteria*, M. Sebald, ed., Chapter 28, pp 389-406, Springer-Verlage, New York, N.Y. (1993)). A more appropriate and unique way to define a set of genes/proteins for designing an organism that can utilize syngas is to use the Carbonyl Branch of the pathway (see FIG. 2). This branch includes genes for the following six (6) proteins: cobalamide corrinoid/iron-sulfur protein, methyltransferase, carbon monoxide dehydrogenase (CODH), acetyl-CoA synthase (ACS), acetyl-CoA synthase disulfide reductase, and a CO-tolerant hydrogenase. Therefore, these six genes/proteins represent a set of one or more proteins for conferring a syngas utilization pathway capable of producing acetyl-CoA.

Example VIII

Gene Sets for Generating Syngas Utilizing Microorganisms

This example describes exemplary gene sets for generating syngas utilizing microorganisms.

Formate Dehydrogenase.

Formate dehydrogenase is a two subunit selenocysteine-containing protein that catalyzes the incorporation of $CO_2$ into formate in *Moorella thermoacetica* (Andreesen and Ljungdahl, *J. Bacteriol.* 116:867-873 (1973); Li et al., *J. Bacteriol.* 92:405-412 (1966); Yamamoto et al., *J. Biol. Chem.* 258:1826-1832 (1983). The loci, Moth_2312 and Moth_2313, are actually one gene that is responsible for encoding the alpha subunit of formate dehydrogenase while the beta subunit is encoded by Moth_2314 (Pierce et al., *Environ. Microbiol.* (2008)). Another set of genes encoding formate dehydrogenase activity with a propensity for $CO_2$ reduction is encoded by Sfum_2703 through Sfum_2706 in *Syntrophobacter fumaroxidans* (de Bok et al., *Eur. J. Biochem.* 270:2476-2485 (2003)); Reda et al., *Proc. Natl. Acad. Sci. U.S.A.* 105:10654-10658 (2008)). Similar to their *M. thermoacetica* counterparts, Sfum_2705 and Sfum_2706 are actually one gene. A similar set of genes presumed to carry out the same function are encoded by CHY_0731, CHY_0732, and CHY_0733 in *C. hydrogenoformans* (Wu et al., *PLoS Genet.* 1:e65 (2005)).

| Protein | GenBank ID | Organism |
|---|---|---|
| Moth_2312 | YP_431142 | *Moorella thermoacetica* |
| Moth_2313 | YP_431143 | *Moorella thermoacetica* |
| Moth_2314 | YP_431144 | *Moorella thermoacetica* |
| Sfum_2703 | YP_846816.1 | *Syntrophobacter fumaroxidans* |
| Sfum_2704 | YP_846817.1 | *Syntrophobacter fumaroxidans* |
| Sfum_2705 | YP_846818.1 | *Syntrophobacter fumaroxidans* |
| Sfum_2706 | YP_846819.1 | *Syntrophobacter fumaroxidans* |
| CHY_0731 | YP_359585.1 | *Carboxydothermus hydrogenoformans* |
| CHY_0732 | YP_359586.1 | *Carboxydothermus hydrogenoformans* |
| CHY_0733 | YP_359587.1 | *Carboxydothermus hydrogenoformans* |

Formyltetrahydrofolate Synthetase.

Formyltetrahydrofolate synthetase ligates formate to tetrahydrofolate at the expense of one ATP. This reaction is catalyzed by the gene product of Moth_0109 in *M. thermoacetica* (Lovell et al., *Arch. Microbiol* 149:280-285 (1988); Lovell et al., *Biochemistry* 29:5687-5694 (1990); O'brien et al., *Experientia. Suppl.* 26:249-262 (1976), FHS in *Clostridium acidurici* (Whitehead and Rabinowitz, *J. Bacteriol.* 167:205-209(1986); Whitehead and Rabinowitz, *J. Bacteriol.* 170:3255-3261 (1988)), and CHY_2385 in *C. hydrogenoformans* (Wu et al., *PLoS Genet.* 1:e65 (2005)).

| Protein | GenBank ID | Organism |
|---|---|---|
| Moth_0109 | YP_428991.1 | *Moorella thermoacetica* |
| CHY_2385 | YP_361182.1 | *Carboxydothermus hydrogenoformans* |
| FHS | P13419.1 | *Clostridium acidurici* |

Methenyltetrahydrofolate Cyclohydrolase and Methylenetetrahydrofolate Dehydrogenase.

In *M. thermoacetica*, *E. coli*, and *C. hydrogenoformans*, methenyltetrahydrofolate cyclohydrolase and methylenetetrahydrofolate dehydrogenase are carried out by the bi-functional gene products of Moth_1516, folD, and CHY_1878, respectively (D'Ari and Rabinowitz, *J. Biol. Chem.* 266:23953-23958 (1991); Pierce et al., *Environ. Microbiol* (2008); Wu et al., *PLoS Genet,* 1:e65 (2005)).

| Protein | GenBank ID | Organism |
|---|---|---|
| Moth_1516 | YP_430368.1 | *Moorella thermoacetica* |
| folD | NP_415062.1 | *Escherichia coli* |
| CHY_1878 | YP_360698.1 | *Carboxydothermus hydrogenoformans* |

Methylenetetrahydrofolate Reductase.

The final step of the methyl branch of the Wood-Ljungdahl pathway is catalyzed by methylenetetrahydrofolate reductase. In *M. thermoacetica*, this enzyme is oxygen-sensitive and contains an iron-sulfur cluster (Clark and Ljungdahl, *J Biol Chem.* 259:10845-10849 (1984)). This enzyme is encoded by metF in *E. coli* (Sheppard et al., *J. Bacteriol.* 181:718-725 (1999)) and CHY_1233 in *C. hydrogenoformans* (Wu et al., *PLoS Genet.* 1:e65 (2005)). The *M. thermoacetica* genes, and its *C. hydrogenoformans* counterpart, are located near the CODH/ACS gene cluster, separated by putative hydrogenase and heterodisulfide reductase genes.

| Protein | GenBank ID | Organism |
| --- | --- | --- |
| metF | NP_418376.1 | *Escherichia coli* |
| CHY_1233 | YP_360071.1 | *Carboxydothermus hydrogenoformans* |

Acetyl-CoA Synthase/Carbon Monoxide Dehydrogenase (ACS/CODH) and Related Proteins.

ACS/CODH is the central enzyme of the carbonyl branch of the Wood-Ljungdahl pathway. It catalyzes the reversible reduction of carbon dioxide to carbon monoxide and also the synthesis of acetyl-CoA from carbon monoxide, Coenzyme A, and the methyl group from a methylated corrinoid-iron-sulfur protein. The corrinoide-iron-sulfur-protein is methylated by methyltetrahydrofolate via a methyltransferase. Expression of ACS/CODH in a foreign host involves introducing many, if not all, of the following proteins and their corresponding activities.

Methyltetrahydrofolate:corrinoid protein methyltransferase (AcsE)
Corrinoid iron-sulfur protein (AcsD)
Nickel-protein assembly protein (AcsF)
Ferredoxin (Orf7)
Acetyl-CoA synthase (AcsB and AcsC)
Carbon monoxide dehydrogenase (AcsA)
Nickel-protein assembly protein (CooC)

The genes required for carbon-monoxide dehydrogenase/acetyl-CoA synthase activity typically reside in a limited region of the native genome that may be an extended operon (Morton et al., *J. Biol. Chem.* 266:23824-23828 (1991); Ragsdale, *Crit. Rev. Biochem. Mol. Biol.* 39:165-195 (2004); Roberts et al., *Proc. Natl. Acad. Set. USA* 86:32-36 (1989)). Each of the genes in this operon from the acetogen, *M. thermoacetica*, has already been cloned and expressed actively in *E. coli* (Lu et al., *J. Biol. Chem.* 268:5605-5614 (1993); Morton et al., supra, 1991; Roberts et al., supra, 1989)). The protein sequences of these genes can be identified by the following GenBank accession numbers.

| Protein | GenBank ID | Organism |
| --- | --- | --- |
| AcsE | YP_430054 | *Moorella thermoacetica* |
| AcsD | YP_430055 | *Moorella thermoacetica* |
| AcsF | YP_430056 | *Moorella thermoacetica* |
| Orf7 | YP_430057 | *Moorella thermoacetica* |
| AcsC | YP_430058 | *Moorella thermoacetica* |
| AcsB | YP_430059 | *Moorella thermoacetica* |
| AcsA | YP_430060 | *Moorella thermoacetica* |
| CooC | YP_430061 | *Moorella thermoacetica* |

The hydrogenogenic bacterium, *Carboxydothermus hydrogenoformans*, can utilize carbon monoxide as a growth substrate by means of acetyl-CoA synthase (Wu et al., *PLoS Genet.* 1:e65. (2005)). In strain Z-2901, the acetyl-CoA synthase enzyme complex lacks carbon monoxide dehydrogenase due to a frameshift mutation (We et al., supra, 2005), whereas in strain DSM 6008, a functional unframeshifted full-length version of this protein has been purified (Svetlitchnyi et al., *Proc. Natl. Acad. Sci. USA* 101:446-451 (2004)). The protein sequences of the *C. hydrogenoformans* genes from strain Z-2901 can be identified by the following GenBank accession numbers. Sequences for *Carboxydothermus hydrogenoformans* DSM 6008 are not currently accessible in publicly available databases but can be readily determined as the sequences become available.

| Protein | GenBank ID | Organism |
| --- | --- | --- |
| AcsE | YP_360065 | *Carboxydothermus hydrogenoformans* |
| AcsD | YP_360064 | *Carboxydothermus hydrogenoformans* |
| AcsF | YP_360063 | *Carboxydothermus hydrogenoformans* |
| Orf7 | YP_360062 | *Carboxydothermus hydrogenoformans* |
| AcsC | YP_360061 | *Carboxydothermus hydrogenoformans* |
| AcsB | YP_360060 | *Carboxydothermus hydrogenoformans* |
| CooC | YP_360059 | *Carboxydothermus hydrogenoformans* |

The methanogenic archaeon, *Methanosarcina acetivorans*, can also grow on carbon monoxide, exhibits acetyl-CoA synthase/carbon monoxide dehydrogenase activity, and produces both acetate and formate (Lessner et al., *Proc. Natl. Acad. Sci. USA* 103:17921-17926 (2006)). This organism contains two sets of genes that encode ACS/CODH activity (Rother and Metcalf, *Proc. Natl. Acad. Sci. USA* 101:16929-16934 (2004)). The protein sequences of both sets of *M. acetivorans* genes can be identified by the following GenBank accession numbers.

| Protein | GenBank ID | Organism |
| --- | --- | --- |
| AcsC | NP_618736 | *Methanosarcina acetivorans* |
| AcsD | NP_618735 | *Methanosarcina acetivorans* |
| AcsF, CooC | NP_618734 | *Methanosarcina acetivorans* |
| AcsB | NP_618733 | *Methanosarcina acetivorans* |
| AcsEps | NP_618732 | *Methanosarcina acetivorans* |
| AcsA | NP_618731 | *Methanosarcina acetivorans* |
| AcsC | NP_615961 | *Methanosarcina acetivorans* |
| AcsD | NP_615962 | *Methanosarcina acetivorans* |
| AcsF, CooC | NP_615963 | *Methanosarcina acetivorans* |
| AcsB | NP_615964 | *Methanosarcina acetivorans* |
| AcsEps | NP_615965 | *Methanosarcina acetivorans* |
| AcsA | NP_615966 | *Methanosarcina acetivorans* |

The AcsC, AcsD, AcsB, AcsEps, and AcsA proteins are commonly referred to as the gamma, delta, beta, epsilon, and alpha subunits of the methanogenic CODH/ACS. Homologs to the epsilon encoding genes are not present in acetogens such as *M. thermoacetica* or hydrogenogenic bacteria such as *C. hydrogenoformans*. Hypotheses for the existence of two active CODH/ACS operons in *M. acetivorans* include catalytic properties (that is, $K_m$, $V_{max}$, $k_{cat}$) that favor carboxidotrophic or aceticlastic growth or differential gene regulation enabling various stimuli to induce CODH/ACS expression (Rother et al., *Arch. Microbiol.* 188:463-472 (2007)).

In both *M. thermoacetica* and *C. hydrogenoformans*, additional CODH encoding genes are located outside of the ACS/CODH operons. These enzymes provide the ability to extract electrons, or reducing equivalents, from the conversion of carbon monoxide to carbon dioxide. The reducing equivalents are then passed to accepters such as oxidized ferredoxin, NADP+, water, or hydrogen peroxide to form reduced ferredoxin, NADPH, $H_2$, or water, respectively. In some cases, hydrogenase encoding genes are located adjacent to a CODH. In *Rhodospirillum rubrum*, the encoded CODH/hydrogenase proteins form a membrane-bound enzyme complex that is proposed to be a site where energy, in the form of a proton gradient, is generated from the conversion of CO to $CO_2$ and $H_2$ (Fox et al., *J. Bacteriol.* 178:6200-6208 (1996)). The CODH-I of *C. hydrogenoformans* and its adjacent genes have been proposed to catalyze a similar functional role based on their similarity to the *R. rubrum* CODH/hydrogenase gene cluster (Wu et al., *PLoS Genet.* 1:e65 (2005)). The *C. hydrogenoformans* CODH-I was also shown to exhibit intense CO oxidation and $CO_2$ reduction activities when linked to an electrode (Parkin et al., *J. Am. Chem. Soc.* 129:10328-10329 (2007)). The genes encoding the *C. hydrogenoformans* CODH-II and CooF, a neighboring protein, were cloned and sequenced (Gonzalez and Robb, *FEMS Microbiol. Lett.* 191:243-247 (2000)). The resulting complex was membrane-bound, although cytoplasmic fractions of CODH-II were shown to catalyze the formation of NADPH suggesting an anabolic role (Svetlitchnyi et al., *J. Bacteriol.* 183:5134-5144 (2001)). The crystal structure of the CODH-II is also available (Dobbek et al., *Science* 293:1281-1285 (2001)). The protein sequences of exemplary CODH and hydrogenase genes can be identified by the following GenBank accession numbers.

| Protein | GenBank ID | Organism |
| --- | --- | --- |
| CODH (putative) | YP_430813 | *Moorella thermoacetica* |
| CODH-I (CooS-I) | YP_360644 | *Carboxydothermus hydrogenoformans* |
| CooF | YP_360645 | *Carboxydothermus hydrogenoformans* |
| HypA | YP_360646 | *Carboxydothermus hydrogenoformans* |
| CooH | YP_360647 | *Carboxydothermus hydrogenoformans* |
| CooU | YP_360648 | *Carboxydothermus hydrogenoformans* |
| CooX | YP_360649 | *Carboxydothermus hydrogenoformans* |
| CooL | YP_360650 | *Carboxydothermus hydrogenoformans* |
| CooK | YP_360651 | *Carboxydothermus hydrogenoformans* |
| CooM | YP_360652 | *Carboxydothermus hydrogenoformans* |
| CooM | AAC45116 | *Rhodospirillum rubrum* |
| CooK | AAC45117 | *Rhodospirillum rubrum* |
| CooL | AAC45118 | *Rhodospirillum rubrum* |

Acetyl-CoA Synthase Disulfide Reductase.

In *Moorella thermoacetica*, a set of genes encoding a heterodisulfide reductase (Moth_1194 to Moth_1196) is located directly downstream of the acs gene cluster discussed above. In addition, like *M. thermoacetica*, *C. hydrogenoformans* contains a set of genes encoding heterodisulfide reductase directly following acsE.

| Protein | GenBank ID | Organism |
| --- | --- | --- |
| HdrC | YP_430053 | *Moorella thermoacetica* |
| HdrB | YP_430052 | *Moorella thermoacetica* |
| HdrA | YP_430052 | *Moorella thermoacetica* |
| HdrC | YP_360066 | *Carboxydothermus hydrogenoformans* |
| HdrB | YP_360067 | *Carboxydothermus hydrogenoformans* |
| HdrA | YP_360068 | *Carboxydothermus hydrogenoformans* |

Hydrogenase (Hyd).

Unlike the redox neutral conversion of CO and methanol to acetyl-CoA or acetate, the production of more highly reduced products such as ethanol, butanol, isobutanol, isopropanol, 1,4-butanediol, succinic acid, fumaric acid, malic acid, 4-hydroxybutyric acid, 3-hydroxypropionic acid, lactic acid, methacrylic acid, adipic acid, and acrylic acid at the highest possible yield requires the extraction of additional reducing equivalents from both CO and $H_2$ (for example, see ethanol formation in FIG. 7). Specifically, reducing equivalents (for example, 2[H] in FIG. 6) are obtained by the conversion of CO and water to $CO_2$ via carbon monoxide dehydrogenase as described in Example II or directly from the activity of a hydrogen-utilizing hydrogenase which transfers electrons from $H_2$ to an acceptor such as ferredoxin, flavodoxin, FAD+, NAD+, or NADP+.

Native to *E. coli* and other enteric bacteria are multiple genes encoding up to four hydrogenases (Sawers, *Antonie Van Leeuwenhoek* 66:57-88 (1994); Sawers et al., *J. Bacteriol.* 164:1324-1331 (1985); Sawers and Boxer, *Eur. J. Biochem.* 156:265-275 (1986); Sawers et al., *J. Bacteriol.* 168:398-404 (1986)). Given the multiplicity of enzyme activities, it is possible that *E. coli* or another host organism can provide sufficient hydrogenase activity to split incoming molecular hydrogen and reduce the corresponding acceptor. Among the endogenous hydrogen-lyase enzymes of *E. coli* are hydrogenase 3, a membrane-bound enzyme complex using ferredoxin as an acceptor, and hydrogenase 4, which also uses a ferredoxin acceptor. Hydrogenase 3 and 4 are encoded by the hyc and hyf gene clusters, respectively. Hydrogenase activity in *E. coli* is also dependent upon the expression of the hyp genes whose corresponding proteins are involved in the assembly of the hydrogenase complexes (Jacobi et al., *Arch. Microbiol.* 158:444-451 (1992); Rangarajan et al., *J. Bacteriol.* 190:1447-1458 (2008)). The *M. thermoacetica* hydrogenases are suitable candidates should the production host lack sufficient endogenous hydrogenase activity. *M. thermoacetica* can grow with $CO_2$ as the exclusive carbon source, indicating that reducing equivalents are extracted from $H_2$ to allow acetyl-CoA synthesis via the Wood-Ljungdahl pathway (Drake, *J. Bacteriol.* 150:702-709 (1982); Drake and Daniel, *Res. Microbiol.* 155:869-883 (2004); Kellum and Drake, *J. Bacteriol.* 160:466-469 (1984)) (see FIG. 6). *M. thermoacetica* has homologs to several hyp, hyc, and hyf genes from *E. coli*. These protein sequences encoded for by these genes can be identified by the following GenBank accession numbers. In addition, several gene clusters encoding hydrogenase and/or heterodisulfide reductase functionality are present in *M. thermoacetica* and their corresponding protein sequences are also provided below.

Hyp Assembly Proteins.

| Protein | GenBank ID | Organism |
| --- | --- | --- |
| HypA | NP_417206 | *Escherichia coli* |
| HypB | NP_417207 | *Escherichia coli* |
| HypC | NP_417208 | *Escherichia coli* |
| HypD | NP_417209 | *Escherichia coli* |
| HypE | NP_417210 | *Escherichia coli* |
| HypF | NP_417192 | *Escherichia coli* |

Proteins in *M. thermoacetica* Whose Genes are Homologous to the *E. coli* Hyp Genes.

| Protein | GenBank ID | Organism |
| --- | --- | --- |
| Moth_2175 | YP_431007 | *Moorella thermoacetica* |
| Moth_2176 | YP_431008 | *Moorella thermoacetica* |
| Moth_2177 | YP_431009 | *Moorella thermoacetica* |
| Moth_2178 | YP_431010 | *Moorella thermoacetica* |
| Moth_2179 | YP_431011 | *Moorella thermoacetica* |
| Moth_2180 | YP_431012 | *Moorella thermoacetica* |
| Moth_2181 | YP_431013 | *Moorella thermoacetica* |

Hydrogenase 3.

| Protein | GenBank ID | Organism |
| --- | --- | --- |
| HycA | NP_417205 | *Escherichia coli* |
| HycB | NP_417204 | *Escherichia coli* |
| HycC | NP_417203 | *Escherichia coli* |
| HycD | NP_417202 | *Escherichia coli* |
| HycE | NP_417201 | *Escherichia coli* |
| HycF | NP_417200 | *Escherichia coli* |
| HycG | NP_417199 | *Escherichia coli* |
| HycH | NP_417198 | *Escherichia coli* |
| HycI | NP_417197 | *Escherichia coli* |

Hydrogenase 4.

| Protein | GenBank ID | Organism |
| --- | --- | --- |
| HyfA | NP_416976 | Escherichia coli |
| HyfB | NP_416977 | Escherichia coli |
| HyfC | NP_416978 | Escherichia coli |
| HyfD | NP_416979 | Escherichia coli |
| HyfE | NP_416980 | Escherichia coli |
| HyfF | NP_416981 | Escherichia coli |
| HyfG | NP_416982 | Escherichia coli |
| HyfH | NP_416983 | Escherichia coli |
| HyfI | NP_416984 | Escherichia coli |
| HyfJ | NP_416985 | Escherichia coli |
| HyfR | NP_416986 | Escherichia coli |

Proteins in *M. thermoacetica* Whose Genes are Homologous to the *E. coli* Hyc and/or Hyf Genes.

| Protein | GenBank ID | Organism |
| --- | --- | --- |
| Moth_2182 | YP_431014 | Moorella thermoacetica |
| Moth_2183 | YP_431015 | Moorella thermoacetica |
| Moth_2184 | YP_431016 | Moorella thermoacetica |
| Moth_2185 | YP_431017 | Moorella thermoacetica |
| Moth_2186 | YP_431018 | Moorella thermoacetica |
| Moth_2187 | YP_431019 | Moorella thermoacetica |
| Moth_2188 | YP_431020 | Moorella thermoacetica |
| Moth_2189 | YP_431021 | Moorella thermoacetica |
| Moth_2190 | YP_431022 | Moorella thermoacetica |
| Moth_2191 | YP_431023 | Moorella thermoacetica |
| Moth_2192 | YP_431024 | Moorella thermoacetica |

Additional Hydrogenase-Encoding Gene Clusters in *M. thermoacetica*.

| Protein | GenBank ID | Organism |
| --- | --- | --- |
| Moth_0439 | YP_429313 | Moorella thermoacetica |
| Moth_0440 | YP_429314 | Moorella thermoacetica |
| Moth_0441 | YP_429315 | Moorella thermoacetica |
| Moth_0442 | YP_429316 | Moorella thermoacetica |
| Moth_0809 | YP_429670 | Moorella thermoacetica |
| Moth_0810 | YP_429671 | Moorella thermoacetica |
| Moth_0811 | YP_429672 | Moorella thermoacetica |
| Moth_0812 | YP_429673 | Moorella thermoacetica |
| Moth_0813 | (possible psuedogene, GenBank ID unavailable) | Moorella thermoacetica |
| Moth_0814 | YP_429674 | Moorella thermoacetica |
| Moth_0815 | YP_429675 | Moorella thermoacetica |
| Moth_0816 | YP_429676 | Moorella thermoacetica |
| Moth_1193 | YP_430050 | Moorella thermoacetica |
| Moth_1194 | YP_430051 | Moorella thermoacetica |
| Moth_1195 | YP_430052 | Moorella thermoacetica |
| Moth_1196 | YP_430053 | Moorella thermoacetica |
| Moth_1717 | YP_430562 | Moorella thermoacetica |
| Moth_1718 | YP_430563 | Moorella thermoacetica |
| Moth_1719 | YP_430564 | Moorella thermoacetica |
| Moth_1883 | YP_430726 | Moorella thermoacetica |
| Moth_1884 | YP_430727 | Moorella thermoacetica |
| Moth_1885 | YP_430728 | Moorella thermoacetica |
| Moth_1886 | YP_430729 | Moorella thermoacetica |
| Moth_1887 | YP_430730 | Moorella thermoacetica |
| Moth_1888 | YP_430731 | Moorella thermoacetica |
| Moth_1452 | YP_430305 | Moorella thermoacetica |
| Moth_1453 | YP_430306 | Moorella thermoacetica |
| Moth_1454 | YP_430307 | Moorella thermoacetica |

A host organism engineered with these capabilities that also naturally possesses the capability for anapleurosis (for example, *E. coli*) can potentially grow more efficiently on the syngas-generated acetyl-CoA in the presence of a suitable external electron acceptor such as nitrate. This electron acceptor is required to accept electrons from the reduced quinone formed via succinate dehydrogenase. A further advantage of adding an external electron acceptor is that additional energy for cell growth, maintenance, and product formation can be generated from respiration of acetyl-CoA. An alternative strategy involves engineering a pyruvate ferredoxin oxidoreductase (PFOR) enzyme into the strain to allow synthesis of biomass precursors in the absence of an external electron acceptor.

Pyruvate Ferredoxin Oxidoreductase (PFOR).

Anaerobic growth on synthesis gas and methanol in the absence of an external electron acceptor is conferred upon the host organism with ACS/CODH activity by allowing pyruvate synthesis via pyruvate ferredoxin oxidoreductase (PFOR). The PFOR from *Desulfovibrio africanus* has been cloned and expressed in *E. coli*, resulting in an active recombinant enzyme that was stable for several days in the presence of oxygen (Pieulle et al., *J. Bacteriol.* 179:5684-5692 (1997)). Oxygen stability is relatively uncommon in PFORs and is believed to be conferred by a 60 residue extension in the polypeptide chain of the *D. africanus* enzyme. The *M. thermoacetica* PFOR is also well characterized (Menon and Ragsdale, *Biochemistry* 36:8484-8494 (1997)) and was shown to have high activity in the direction of pyruvate synthesis during autotrophic growth (Furdui and Ragsdale, *J. Biol. Chem.* 275:28494-28499 (2000)). Further, *E. coli* possesses an uncharacterized open reading frame, ydbK, that encodes a protein that is 51% identical to the *M. thermoacetica* PFOR. Evidence for pyruvate oxidoreductase activity in *E. coli* has been described (Blaschkowski et al., *Eur. J. Biochem.* 123:563-569 (1982)). The protein sequences of these exemplary PFOR enzymes can be identified by the following GenBank accession numbers. Several additional PFOR enzymes have been described (Ragsdale, *Chem. Rev.* 103:2333-2346 (2003)).

| Protein | GenBank ID | Organism |
| --- | --- | --- |
| Por | CAA70873.1 | Desulfovibrio africanus |
| Por | YP_428946.1 | Moorella thermoacetica |
| YdbK | NP_415896.1 | Escherichia coli |

This example describes exemplary gene sets for engineering an organism to produce acetyl-CoA from gasses comprising at least one of CO, $CO_2$, and $H_2$.

Example IX

Engineering a Syngas Utilization Pathway into a Microorganism

This example describes engineering a microorganism to contain a syngas utilization pathway.

In addition to improving the efficiency of microorganisms such as *Clostridial* species that have the natural ability to utilize CO and/or $CO_2$ as a carbon source (Examples II, III and V), microorganisms that do not have the natural ability to utilize CO and/or $CO_2$ are engineered to express one or more proteins or enzymes that confer a CO and/or $CO_2$ utilization pathway. One exemplary pathway is the Wood-Ljungdahl pathway, which allows the utilization of CO and/or $CO_2$ as a carbon source, thereby allowing the microorganism to utilize syngas or other gaseous carbon source (see Examples I and VII).

In initial studies, *Escherichia coli*, which does not utilize syngas naturally, is used as a target organism to introduce a CO and/or $CO_2$ utilization pathway such as the Wood- Ljungdahl pathway. The Wood-Ljungdahl pathway involves oxygen sensitive and membrane bound proteins as well as specific co-factors that are not native in *E. coli*. While several Wood-Ljungdahl pathway genes have been cloned into *E. coli*, only one enzyme, methyltransferase, was found be expressed in active form (Roberts et al., *Proc. Natl. Acad. Sci. USA* 86:32-36 (1989)). Purification of the carbonyl branch (see FIG. 2) pathway genes from *Clostridium thermoaceticum* revealed the minimum set of enzymes required for in vitro conversion of methyl-THF to acetyl-CoA studies (Roberts et al., *J. Bacteriol.* 174:4667-4676 (1992)).

Initial studies are directed to engineering a Wood-Ljungdahl pathway, in particular the carbonyl branch (FIG. 2), into *E. coli* and testing growth and acetate production from both methyl-THF and syngas. *E. coli* provides a good model for developing a non-naturally occurring microorganism capable of utilizing syngas or other gaseous carbon sources since it is amenable to genetic manipulation and is known to be capable of producing various products like ethanol, acetate, and succinate effectively under anaerobic conditions from glucose.

To generate an *E. coli* strain engineered to contain a Wood-Ljungdahl pathway, nucleic acids encoding proteins and enzymes required for the carbonyl branch of the pathway (see FIG. 2 and Example VII) are expressed in *E. coli* using well known molecular biology techniques (see, for example, Sambrook, supra, 2001; Ausubel supra, 1999; Roberts et al., supra, 1989). As described previously, the gene cluster encoding key proteins in acetyl-CoA synthesis in. *Clostridium thermoaceticum* has been cloned and expressed in *E. coli* (Roberts et al., supra, 1989). Specific variation of conditions, such as metal composition of the medium, is required to ensure production of active proteins. Genes encoding cobalamide corrinoid/iron-sulfur protein, methyltransferase, carbon monoxide dehydrogenase (CODH), acetyl-CoA synthase (ACS), acetyl-CoA synthase disulfide reductase, and a CO-tolerant hydrogenase are cloned and expressed in *E. coli* to introduce carbonyl branch enzymes of the Wood-Ljungdahl pathway (for Wood-Ljungdahl pathway genes, see also Ragsdale, *Critical Rev. Biochem. Mol. Biol.* 39:165-195 (2004)). Since *E. coli* does not normally synthesize cobalamin or cobalamin-like cofactors, which is required for the cobalamide-corrinoid/iron sulfur protein activity, the cofactors or genes encoding proteins and enzymes for synthesis of the required cofactors can also be introduced. The cobalamin or cobalamin-like cofactors can be provided to the medium, although cost would possibly prohibit this approach for scale up and commercial manufacture. A better alternative is to clone and express the requisite genes in the *E. coli* strain expressing the cobalamin-requiring proteins. This has been demonstrated by transfer and functional expression of a cobalamin operon containing 20 genes from *Salmonella typhimurium* into *E. coli* (Raux et al., *J. Bacteriol.* 178:753-767 (1996)).

The expression of Wood-Ljungdahl pathway genes is tested using routine assays for determining the expression of introduced genes, for example, Northern blots, PCR amplification of mRNA, immunoblotting, or other well known assays to confirm nucleic acid and protein expression of introduced genes. Enzymatic activity of the expressed enzymes can be tested individually or for production of a product such as acetyl-CoA (see, for example, Roberts et al., supra, 1989). The ability of the engineered *E. coli* strain to utilize CO and/or $CO_2$ as a carbon source to produce acetyl-CoA can be analyzed directly using gas chromatography-mass spectrometry (GCMS) or liquid chromatography-mass spectrometry (LCMS), or through the use of metabolic radioactive or isotopic labeling, for example, with radioactive CO or $CO_2$ and analysis of incorporation of radioactive label into the acetyl-CoA product or incorporation of an isotopically labeled CO or $CO_2$ precursor and analysis by techniques such as mass spectrometry (GCMS or LCMS) or nuclear magnetic resonance spectroscopy (NMR). Growth of *E. coli* using only CO and/or $CO_2$ as a sole carbon source, with or without the presence of $H_2$, is another useful test for a fully functional pathway.

Once a functional Wood-Ljungdahl pathway has been engineered into an *E. coli* strain, the strain is optimized for efficient utilization of the pathway. The engineered strain can be tested to determine if any of the introduced genes are expressed at a level that is rate limiting. As needed, increased expression of one or more proteins or enzymes that may limit the flux through the pathway can be used to optimize utilization of the pathway and production of acetyl-CoA.

Metabolic modeling can be utilized to optimize growth conditions (see Example II). Modeling can also be used to design gene knockouts that additionally optimize utilization of the pathway (see Examples II, IV and V and, for example, U.S. patent publications US 2002/0012939, US 2003/0224363, US 2004/0029149, US 2004/0072723, US 200310059792, US 2002/0168654 and US 200410009466, and in U.S. Pat. No. 7,127,379). Modeling analysis allows predictions of the effects on cell growth of shifting the metabolism towards more efficient production of acetyl-CoA or other desired product. One modeling method is the bilevel optimization approach, OptKnock (Burgard et al., *Biotechnol. Bioengineer.* 84:647-657 (2003)), which is applied to select gene knockouts that collectively result in the growth-coupled production of acetyl-CoA or other desired products, as discussed below. Strains designed with a gene knockout strategy are forced, due to network stoichiometry, to produce high levels of a desired product for efficient growth, because all other growth options have been removed. Such strains are self-optimizing and stable. Accordingly, they typically maintain or improve upon production levels even in the face of strong growth selective pressures, making them amenable to batch or continuous bioprocessing and also evolutionary engineering. Adaptive evolution can be used to further optimize the production of acetyl-CoA (see Example V). Adaptive evolution is therefore performed to improve both growth and production characteristics (Fong and Palsson, *Nat. Genet.* 36:1056-1058 (2004); Alper et al., *Science* 314:1565-1568 (2006)). Based on the results, subsequent rounds of modeling, genetic engineering and adaptive evolution can be utilized to further optimize production and tolerance of enzymes to syngas or impurities in syngas.

Once an engineered microbial strain has been optimized for utilization of the Wood-Ljungdahl pathway, optimization of the fermentation process can be performed to increase yields using well known methods and as described, for example, in Example VI). For example, a productivity level of 20 g/L acetate at 0.5 g/L/h from syngas would represent a desirable production range towards which further optimization of the strain for efficient utilization of the pathway as well as optimization of fermentation conditions can be employed to achieve a desired production level.

Although exemplified with introduction of the carbonyl branch to confer the ability to utilize CO and/or $CO_2$ to an engineered microbial strain, a similar approach is applied to introduce enzymes for production of methyl-THF to *E. coli*. As discussed above in Example VII, *E. coli* has the ability to produce methyl-THF, but THF-dependent enzymes from acetogens have higher specific activities (Morton et al., supra, 1993). Using methods as described above to introduce the carbonyl branch of the Wood-Ljungdahl pathway, methyl branch enzymes are introduced into *E. coli* using similar techniques. Genes encoding one or more of the enzymes ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase are introduced (see FIG. 1). In this case, the genes are introduced to increase an endogenous enzyme activity and/or to increase the efficiency of utilization of CO and/or $CO_2$ to produce methyl-THF. Optimization of the pathway and fermentation conditions is carried out as described above. In addition, both the carbonyl and methyl branches of the Wood-Ljungdahl pathway can be introduced into the same microorganism. In such an engineered organism, the increased production of methyl-THF from CO and/or $CO_2$ can be utilized to further increase the production of acetyl-CoA in an organism engineered to utilize CO and/or $CO_2$ using the carbonyl branch of the Wood-Ljungdahl pathway (see FIGS. 3 and 6).

Acetyl-CoA can function as a precursor for other desired products. Once the acetyl-CoA-producing microorganism has been generated, additional genes can be introduced into the microorganism to utilize acetyl-CoA as a precursor to produce other desired products from CO and/or $CO_2$ as carbon source. For example, enzymes for butanol production can be introduced (see FIG. 3 and Example V). Representative genes for butanol pathway from acetyl-CoA are: AtoB, acetyl-CoA acetyltransferase; Th1, acetyl-CoA thiolase; Hbd, 3-hydroxbutyrl-CoA dehydrogenase; Crt, crotonase; Bcd, butyryl-CoA dehydrogenase; Etf, electron transfer flavoprotein; AdhE2, aldehyde/alcohol dehydroenase (see Atsumi et al., *Metabolic Engineering* Sep. 14, 2007).

Metabolic pathways for production of additional desired products, including succinate, 4-hydroxybutyrate and 1,4-butanediol are described, for example, in U.S. application Ser. No. 11/891,602, filed Aug. 10, 2007, and WO/2008/115840, and enzymes for such pathways can similarly be introduced, for example, succinyl-CoA ligase, succinyl-CoA: CoA transferase, succinate semialdehyde dehydrogenase, 4-hydroxybutyric acid dehydrogenase, glutamate:succinic semialdehyde transaminase, 4-hydroxybutyryl-CoA transferase, a CoA-dependent aldehyde dehydrogenase, alcohol dehydrogenase, and the like. Acetyl-CoA feeds directly into the TCA cycle of all cells and succinate is a TCA cycle intermediate. Thus, additional enzymes conferring pathways capable of utilizing acetyl-CoA produced from CO and/or $CO_2$ can be engineered and optimized, as described above, to produce a desired product from the engineered microorganism.

Example X

Pathways for the Production of Acetyl-CoA from Synthesis Gas and Methanol

This example describes exemplary pathways for utilization of synthesis gas (syngas) and methanol to produce acetyl-CoA.

An organism capable of producing acetyl-CoA from syngas and methanol contains two key capabilities, which are depicted in FIG. 7. One capability is a functional methyltransferase system that allows the production of 5-methyltetrahydrofolate (Me-THF) from methanol and THF. A second capability is the ability to combine CO, Coenzyme A, and the methyl group of Me-THF to form acetyl-CoA. The organism is able to 'fix' carbon from exogenous CO and/or $CO_2$ and methanol to synthesize acetyl-CoA, cell mass, and products. This pathway to form acetyl-CoA from methanol and syngas is energetically advantageous compared to utilizing the full Wood-Ljungdahl pathway. For example, the direct conversion of synthesis gas to acetate is an energetically neutral process (see FIG. 6). Specifically, one ATP molecule is consumed during the formation of formyl-THF by formyl-THF synthase, and one ATP molecule is produced during the production of acetate via acetate kinase. This new strategy involving methanol circumvents the ATP consumption requirement by ensuring that the methyl group on the methyl branch product, methyl-THF, is obtained from methanol rather than $CO_2$. This thereby ensures that acetate formation has a positive ATP yield that can help support cell growth and maintenance. A host organism engineered with these capabilities that also naturally possesses the capability for anapleurosis (for example, *E. coli*) can grow on the methanol and syngas-generated acetyl-CoA in the presence of a suitable external electron acceptor such as nitrate. This electron acceptor is required to accept electrons from the reduced quinone formed via succinate dehydrogenase. A further advantage of adding an external electron acceptor is that additional energy for cell growth, maintenance, and product formation can be generated from respiration of acetyl-CoA.

An alternative strategy involves engineering a pyruvate ferredoxin oxidoreductase (PFOR) enzyme into the strain to allow synthesis of biomass precursors in the absence of an external electron acceptor. A further characteristic of the engineered organism is the capability for extracting reducing equivalents from molecular hydrogen. This allows a high yield of reduced products such as ethanol, butanol, isobutanol, isopropanol, 1,4-butanediol, succinic acid, fumaric acid, malic acid, 4-hydroxybutyric acid, 3-hydroxypropionic acid, lactic acid, methacrylic acid, adipic acid, and acrylic acid.

The organisms can produce acetyl-CoA, cell mass, and targeted chemicals from the following sources: 1) methanol and CO, 2) methanol, $CO_2$, and $H_2$, 3) methanol, CO, $CO_2$, and $H_2$, 4) methanol and synthesis gas comprising CO and $H_2$, and 5) methanol and synthesis gas comprising CO, $CO_2$, and $H_2$.

Successfully engineering this pathway into an organism involves identifying an appropriate set of enzymes, cloning their corresponding genes into a production host, optimizing the stability and expression of these genes, optimizing fermentation conditions, and assaying for product formation following fermentation (see Examples II-IV). Described below are a number of enzymes that catalyze each step of the pathway required for the conversion of synthesis gas and methanol to acetyl-CoA. To engineer a production host for the utilization of syngas and methanol, one or more exogenous DNA sequence(s) encoding the requisite enzymes are expressed in the microorganism.

This example describes exemplary pathways for acetyl-CoA production from syngas and methanol.

Example XI

Gene Sets for Generating Methanol and Syngas Utilizing Microorganisms

This example describes exemplary gene sets for generating methanol and syngas utilizing microorganisms.

Methanol-Methyltransferase (MTR).

Expression of the modified Wood-Ljungdahl pathway in a foreign host (see FIG. 7) requires introducing a set of methyltransferases to utilize the carbon and hydrogen provided by methanol and the carbon provided by CO and/or $CO_2$. A complex of 3 methyltransferase proteins, denoted MtaA, MtaB, and MtaC, perform the desired methanol methyltransferase activity (Naidu and Ragsdale, *J. Bacteriol.* 183:3276-3281 (2001); Ragsdale, *Crit. Rev. Biochem. Mol. Biol.* 39:165-195 (2004); Sauer et al., *Eur. J. Biochem.* 243:670-677 (1997); Tallant and Krzycki, *J. Bacteriol.* 178: 1295-1301 (1996); Tallant and Krzycki, *J. Bacteriol.* 179: 6902-6911(1997); Tallant et al., *J. Biol. Chem.* 276:4485-4493 (2001)).

Methanol Methyltransferase (MtaB) and Corrinoid Protein (MtaC).

MtaB is a zinc protein that catalyzes the transfer of a methyl group from methanol to MtaC, a corrinoid protein. Exemplary genes encoding MtaB and MtaC can be found in methanogenic archaea such as *Methanosarcina barkeri* (Maeder et al., *J. Bacteriol.* 188:7922-7931 (2006)) and *Methanosarcina acetivorans* (Galagan et al., *Genome Res.* 12:532-542 (2002)), as well as the acetogen, *Moorella thermoacetica* (Das et al., *Proteins* 67:167-176 (2007)). In general, the MtaB and MtaC genes are adjacent to one another on the chromosome as their activities are tightly interdependent. The protein sequences of various MtaB and MtaC encoding genes in *M. barkeri, M. acetivorans*, and *M. thermoaceticum* can be identified by their following GenBank accession numbers.

| Protein | GenBank ID | Organism |
| --- | --- | --- |
| MtaB1 | YP_304299 | *Methanosarcina barkeri* |
| MtaC1 | YP_304298 | *Methanosarcina barkeri* |
| MtaB2 | YP_307082 | *Methanosarcina barkeri* |
| MtaC2 | YP_307081 | *Methanosarcina barkeri* |
| MtaB3 | YP_304612 | *Methanosarcina barkeri* |
| MtaC3 | YP_304611 | *Methanosarcina barkeri* |
| MtaB1 | NP_615421 | *Methanosarcina acetivorans* |
| MtaB1 | NP_615422 | *Methanosarcina acetivorans* |
| MtaB2 | NP_619254 | *Methanosarcina acetivorans* |
| MtaC2 | NP_619253 | *Methanosarcina acetivorans* |
| MtaB3 | NP_616549 | *Methanosarcina acetivorans* |
| MtaC3 | NP_616550 | *Methanosarcina acetivorans* |
| MtaB | YP_430066 | *Moorella thermoacetica* |
| MtaC | YP_430065 | *Moorella thermoacetica* |

The MtaB1 and MtaC1 genes, YP_304299 and YP_304298, from *M. barkeri* were cloned into *E. coli* and sequenced (Sauer et al., *Eur. J. Biochem.* 243:670-677 (1997)). The crystal structure of this methanol-cobalamin methyltransferase complex is also available (Hagemeier et al., *Proc. Natl. Acad. Sci. USA* 103:18917-18922 (2006)). The MtaB genes, YP_307082 and YP_304612, in *M. barkeri* were identified by sequence homology to YP_304299. In general, homology searches are an effective means of identifying methanol methyltransferases because MtaB encoding genes show little or no similarity to methyltransferases that act on alternative substrates such as trimethylamine, dimethylamine, monomethylamine, or dimethylsulfide. The MtaC genes, YP_307081 and YP_304611, were identified based on their proximity to the MtaB genes and also their homology to YP_304298. The three sets of MtaB and MtaC genes from *M. acetivorans* have been genetically, physiologically, and biochemically characterized (Pritchett and Metcalf, *Mol. Microbiol.* 56:1183-1194 (2005)). Mutant strains lacking two of the sets were able to grow on methanol, whereas a strain lacking all three sets of MtaB and MtaC genes sets could not grow on methanol. This suggests that each set of genes plays a role in methanol utilization. The *M. thermoacetica* MtaB gene was identified based on homology to the methanogenic MtaB genes and also by its adjacent chromosomal proximity to the methanol-induced corrinoid protein, MtaC, which has been crystallized (Zhou et al., *Acta Crystallogr. Sect. F Struct. Biol. Cryst. Commun.* 61:537-540 (2005)) and further characterized by Northern hybridization and Western blotting (Das et al., *Proteins* 67:167-176 (2007)).

Methyltetrahydrofolate: Corrinoid Protein Methyltransferase (MtaA).

MtaA is zinc protein that catalyzes the transfer of the methyl group from MtaC either to Coenzyme M in methanogens or to tetrahydrofolate in acetogens. MtaA can also utilize methylcobalamin as the methyl donor. Exemplary genes encoding MtaA can be found in methanogenic archaea such as *Methanosarcina barkeri* (Maeder et al., *J. Bacteriol.* 188:7922-7931 (2006)) and *Methanosarcina acetivorans* (Galagan et al., *Genome Res.* 12:532-542 (2002)), as well as the acetogen, *Moorella thermoacetica* (Das et al., *Proteins* 67:167-176 (2007)). In general, MtaA proteins that catalyze the transfer of the methyl group from $CH_3$-MtaC are difficult to identify bioinformatically as they share similarity to other corrinoid protein methyltransferases and are not oriented adjacent to the MtaB and MtaC genes on the chromosomes. Nevertheless, a number of MtaA encoding genes have been characterized. The protein sequences of these genes in *M. barkeri* and *M. acetivorans* can be identified by the following GenBank accession numbers.

| Protein | GenBank ID | Organism |
| --- | --- | --- |
| MtaA | YP_304602 | *Methanosarcina barkeri* |
| MtaA1 | NP_619241 | *Methanosarcina acetivorans* |
| MtaA2 | NP_616548 | *Methanosarcina acetivorans* |

The MtaA gene, YP_304602, from *M. barkeri* was cloned, sequenced, and functionally overexpressed in *E. coli* (Harms and Thauer, *Eur. J. Biochem.* 235:653-659 (1996)). In *M. acetivorans*, MtaA1 is required for growth on methanol, whereas MtaA2 is dispensable even though methane production from methanol is reduced in MtaA2 mutants (Bose et al., *J. Bacteriol.* 190:4017-4026 (2008)). It is also important to note that there are multiple additional MtaA homologs in *M. barkeri* and *M. acetivorans* that are as yet uncharacterized, but may also catalyze corrinoid protein methyltransferase activity.

Putative MtaA encoding genes in *M. thermoacetica* were identified by their sequence similarity to the characterized methanogenic MtaA genes. Specifically, three *M. thermoacetica* genes show high homology (>30% sequence identity) to YP_304602 from *M. barkeri*. Unlike methanogenic MtaA proteins that naturally catalyze the transfer of the methyl group from $CH_3$-MtaC to Coenzyme M, an *M. thermoacetica* MtaA is likely to transfer the methyl group to tetrahydrofolate given the similar roles of tetrahydrofolate and Coenzyme M in methanogens and acetogens, respectively. The protein sequences of putative MtaA encoding genes from *M. thermoacetica* can be identified by the following GenBank accession numbers.

| Protein | GenBank ID | Organism |
| --- | --- | --- |
| MtaA | YP_430937 | *Moorella thermoacetica* |
| MtaA | YP_431175 | *Moorella thermoacetica* |
| MtaA | YP_430935 | *Moorella thermoacetica* |

Acetyl-CoA Synthase/Carbon Monoxide Dehydrogenase (ACS/CODH).

ACS/CODH is the central enzyme of the carbonyl branch of the Wood-Ljungdahl pathway. It catalyzes the reversible reduction of carbon dioxide to carbon monoxide, and also the synthesis of acetyl-CoA from carbon monoxide, Coenzyme A, and the methyl group from a methylated corrinoid-iron-sulfur protein. The corrinoide-iron-sulfur-protein is methylated by methyltetrahydrofolate via a methyltransferase. Expression of ACS/CODH in a foreign host involves introducing many, if not all, of the following proteins and their corresponding activities.

Methyltetrahydrofolate:corrinoid protein methyltransferase (AcsE)
Corrinoid iron-sulfur protein (AcsD)
Nickel-protein assembly protein (AcsF)
Ferredoxin (Orf7)
Acetyl-CoA synthase (AcsB and AcsC)
Carbon monoxide dehydrogenase (AcsA)
Nickel-protein assembly protein (CooC)

The genes required for carbon-monoxide dehydrogenase/acetyl-CoA synthase activity typically reside in a limited region of the native genome that may be an extended operon (Morton et al., *J. Biol. Chem.* 266:23824-23828 (1991); Ragsdale, *Crit. Rev. Biochem. Mol.* 39:165-195 (2004); Roberts et al., *Proc. Natl. Acad. Sci. USA* 86:32-36 (1989)). Each of the genes in this operon from the acetogen, *M. thermoacetica*, has already been cloned and expressed actively in *E. coli* (Lu et al., *J. Biol. Chem.* 268:5605-5614 (1993); Morton et al., supra, 1991; Roberts et al., supra, 1989)). The protein sequences of these genes can be identified by the following GenBank accession numbers.

| Protein | GenBank ID | Organism |
| --- | --- | --- |
| AcsE | YP_430054 | Moorella thermoacetica |
| AcsD | YP_430055 | Moorella thermoacetica |
| AcsF | YP_430056 | Moorella thermoacetica |
| Orf7 | YP_430057 | Moorella thermoacetica |
| AcsC | YP_430058 | Moorella thermoacetica |
| AcsB | YP_430059 | Moorella thermoacetica |
| AcsA | YP_430060 | Moorella thermoacetica |
| CooC | YP_430061 | Moorella thermoacetica |

The hydrogenogenic bacterium, *Carboxydothermus hydrogenoformans*, can utilize carbon monoxide as a growth substrate by means of acetyl-CoA synthase (Wu et al., *PLoS Genet.* 1:e65. (2005)). In strain Z-2901, the acetyl-CoA synthase enzyme complex lacks carbon monoxide dehydrogenase due to a frameshift mutation (We et al., supra, 2005), whereas in strain DSM 6008, a functional unframeshifted full-length version of this protein has been purified (Svetlitchnyi et al., *Proc. Natl. Acad. Sci. USA* 101:446-451 (2004)). The protein sequences of the *C. hydrogenoformans* genes from strain Z-2901 can be identified by the following GenBank accession numbers. Sequences for *Carboxydothermus hydrogenoformans* DSM 6008 are not currently accessible in publicly available databases but can be readily determined as the sequences become available.

| Protein | GenBank ID | Organism |
| --- | --- | --- |
| AcsE | YP_360065 | Carboxydothermus hydrogenoformans |
| AcsD | YP_360064 | Carboxydothermus hydrogenoformans |
| AcsF | YP_360063 | Carboxydothermus hydrogenoformans |
| Orf7 | YP_360062 | Carboxydothermus hydrogenoformans |
| AcsC | YP_360061 | Carboxydothermus hydrogenoformans |
| AcsB | YP_360060 | Carboxydothermus hydrogenoformans |
| CooC | YP_360059 | Carboxydothermus hydrogenoformans |

The methanogenic archaeon, *Methanosarcina acetivorans*, can also grow on carbon monoxide, exhibits acetyl-CoA synthase/carbon monoxide dehydrogenase activity, and produces both acetate and formate (Lessner et al., *Proc. Natl. Acad. Sci. USA* 103:17921-17926 (2006)). This organism contains two sets of genes that encode ACS/CODH activity (Rother and Metcalf, *Proc. Natl. Acad. Sci. USA* 101:16929-16934 (2004)). The protein sequences of both sets of *M. acetivorans* genes can be identified by the following GenBank accession numbers.

| Protein | GenBank ID | Organism |
| --- | --- | --- |
| AcsC | NP_618736 | Methanosarcina acetivorans |
| AcsD | NP_618735 | Methanosarcina acetivorans |
| AcsF, CooC | NP_618734 | Methanosarcina acetivorans |
| AcsB | NP_618733 | Methanosarcina acetivorans |
| AcsEps | NP_618732 | Methanosarcina acetivorans |
| AcsA | NP_618731 | Methanosarcina acetivorans |
| AcsC | NP_615961 | Methanosarcina acetivorans |
| AcsD | NP_615962 | Methanosarcina acetivorans |
| AcsF, CooC | NP_615963 | Methanosarcina acetivorans |
| AcsB | NP_615964 | Methanosarcina acetivorans |
| AcsEps | NP_615965 | Methanosarcina acetivorans |
| AcsA | NP_615966 | Methanosarcina acetivorans |

The AcsC, AcsD, AcsB, AcsEps, and AcsA proteins are commonly referred to as the gamma, delta, beta, epsilon, and alpha subunits of the methanogenic CODH/ACS. Homologs to the epsilon encoding genes are not present in acetogens such as *M. thermoacetica* or hydrogenogenic bacteria such as *C. hydrogenoformans*. Hypotheses for the existence of two active CODH/ACS operons in *M. acetivorans* include catalytic properties (that is, $K_m$, $V_{max}$, $k_{cat}$) that favor carboxidotrophic or aceticlastic growth or differential gene regulation enabling various stimuli to induce CODH/ACS expression (Rother et al., *Arch. Microbiol.* 188:463-472 (2007)).

In both *M. thermoacetica* and *C. hydrogenoformans*, additional CODH encoding genes are located outside of the ACS/CODH operons. These enzymes provide a means for extracting electrons (or reducing equivalents) from the conversion of carbon monoxide to carbon dioxide. The reducing equivalents are then passed to accepters such as oxidized ferredoxin, NADP+, water, or hydrogen peroxide to form reduced ferredoxin, NADPH, $H_2$, or water, respectively. In some cases, hydrogenase encoding genes are located adjacent to a CODH. In *Rhodospirillum rubrum*, the encoded CODH/hydrogenase proteins form a membrane-bound enzyme complex that is proposed to be a site where energy, in the form of a proton gradient, is generated from the conversion of CO to $CO_2$ and $H_2$ (Fox et al., *J. Bacteriol.* 178:6200-6208 (1996)). The CODH-I of *C. hydrogenoformans* and its adjacent genes have been proposed to catalyze a similar functional role based on their similarity to the *R. rubrum* CODH/hydrogenase gene cluster (Wu et al., *PLoS Genet.* 1:e65 (2005)). The *C. hydrogenoformans* CODH-I was also shown to exhibit intense CO oxidation and $CO_2$ reduction activities when linked to an electrode (Parkin et al., *J. Am. Chem. Soc.* 129:10328-10329 (2007)). The genes encoding the *C. hydrogenoformans* CODH-II and CooF, a neighboring protein, were cloned and sequenced (Gonzalez and Robb, *FEMS Microbiol. Lett.* 191:243-247 (2000)). The resulting complex was membrane-bound, although cytoplasmic fractions of CODH-II were shown to catalyze the formation of NADPH suggesting an anabolic role (Svetlitchnyi et al., *J. Bacteriol.* 183:5134-5144 (2001)). The crystal structure of the CODH-II is also available (Dobbek et al., *Science* 293:1281-1285 (2001)). The protein sequences of exemplary CODH and hydrogenase genes can be identified by the following GenBank accession numbers.

| Protein | GenBank ID | Organism |
| --- | --- | --- |
| CODH (putative) | YP_430813 | *Moorella thermoacetica* |
| CODH-I (CooS-I) | YP_360644 | *Carboxydothermus hydrogenoformans* |
| CooF | YP_360645 | *Carboxydothermus hydrogenoformans* |
| HypA | YP_360646 | *Carboxydothermus hydrogenoformans* |
| CooH | YP_360647 | *Carboxydothermus hydrogenoformans* |
| CooU | YP_360648 | *Carboxydothermus hydrogenoformans* |
| CooX | YP_360649 | *Carboxydothermus hydrogenoformans* |
| CooL | YP_360650 | *Carboxydothermus hydrogenoformans* |
| CooK | YP_360651 | *Carboxydothermus hydrogenoformans* |
| CooM | YP_360652 | *Carboxydothermus hydrogenoformans* |
| CooM | AAC45116 | *Rhodospirillum rubrum* |
| CooK | AAC45117 | *Rhodospirillum rubrum* |
| CooL | AAC45118 | *Rhodospirillum rubrum* |
| CooX | AAC45119 | *Rhodospirillum rubrum* |
| CooU | AAC45120 | *Rhodospirillum rubrum* |
| CooH | AAC45121 | *Rhodospirillum rubrum* |
| CooF | AAC45122 | *Rhodospirillum rubrum* |
| CODH (CooS) | AAC45123 | *Rhodospirillum rubrum* |
| CooC | AAC45124 | *Rhodospirillum rubrum* |
| CooT | AAC45125 | *Rhodospirillum rubrum* |
| CooJ | AAC45126 | *Rhodospirillum rubrum* |
| CODH-II (CooS-II) | YP_358957 | *Carboxydothermus hydrogenoformans* |
| CooF | YP_358958 | *Carboxydothermus hydrogenoformans* |

Pyruvate Ferredoxin Oxidoreductase (PFOR).

Anaerobic growth on synthesis gas and methanol in the absence of an external electron acceptor is conferred upon the host organism with MTR and ACS/CODH activity by allowing pyruvate synthesis via pyruvate ferredoxin oxidoreductase (PFOR). The PFOR from *Desulfovibrio africanus* has been cloned and expressed in *E. coli*, resulting in an active recombinant enzyme that was stable for several days in the presence of oxygen (Pieulle et al., *J. Bacteriol.* 179:5684-5692 (1997)). Oxygen stability is relatively uncommon in PFORs and is believed to be conferred by a 60 residue extension in the polypeptide chain of the *D. africanus* enzyme. The *M. thermoacetica* PFOR is also well characterized (Menon and Ragsdale, *Biochemistry* 36:8484-8494 (1997)) and was shown to have high activity in the direction of pyruvate synthesis during autotrophic growth (Furdui and Ragsdale, *J. Biol. Chem.* 275:28494-28499 (2000)). Further, *E. coli* possesses an uncharacterized open reading frame, ydbK, that encodes a protein that is 51% identical to the *M. thermoacetica* PFOR. Evidence for pyruvate oxidoreductase activity in *E. coli* has been described (Blaschkowski et al., *Eur. J. Biochem.* 123:563-569 (1982)). The protein sequences of these exemplary PFOR enzymes can be identified by the following GenBank accession numbers. Several additional PFOR enzymes have been described (Ragsdale, *Chem. Rev.* 103:2333-2346 (2003)).

| Protein | GenBank ID | Organism |
| --- | --- | --- |
| Por | CAA70873.1 | *Desulfovibrio africanus* |
| Por | YP_428946.1 | *Moorella thermoacetica* |
| YdbK | NP_415896.1 | *Escherichia coli* |

Hydrogenase (Hyd).

Unlike the redox neutral conversion of CO and methanol to acetyl-CoA or acetate, the production of more highly reduced products such as ethanol, butanol, isobutanol, isopropanol, 1,4-butanediol, succinic acid, fumaric acid, malic acid, 4-hydroxybutyric acid, 3-hydroxypropionic acid, lactic acid, methacrylic acid, adipic acid, and acrylic acid at the highest possible yield requires the extraction of additional reducing equivalents from both CO and $H_2$ (for example, see ethanol formation in FIG. 7). Specifically, reducing equivalents (for example, 2[H] in FIG. 6) are obtained by the conversion of CO and water to $CO_2$ via carbon monoxide dehydrogenase as described in Example II or directly from the activity of a hydrogen-utilizing hydrogenase which transfers electrons from $H_2$ to an acceptor such as ferredoxin, flavodoxin, FAD+, NAD+, or NADP+.

Native to *E coil* and other enteric bacteria are multiple genes encoding up to four hydrogenases (Sawers, *Antonie Van Leeuwenhoek* 66:57-88 (1994); Sawers et al., *J. Bacteriol.* 164:1324-1331 (1985); Sawers and Boxer, *Eur. J. Biochem.* 156:265-275 (1986); Sawers et al., *J. Bacteriol.* 168:398-404 (1986)). Given the multiplicity of enzyme activities, it is possible that *E. coli* or another host organism can provide sufficient hydrogenase activity to split incoming molecular hydrogen and reduce the corresponding acceptor. Among the endogenous hydrogen-lyase enzymes of *E. coli* are hydrogenase 3, a membrane-bound enzyme complex using ferredoxin as an acceptor, and hydrogenase 4, which also uses a ferredoxin acceptor. Hydrogenase 3 and 4 are encoded by the hyc and hyf gene clusters, respectively. Hydrogenase activity in *E. coli* is also dependent upon the expression of the hyp genes whose corresponding proteins are involved in the assembly of the hydrogenase complexes (Jacobi et al., *Arch. Microbiol.* 158:444-451 (1992); Rangarajan et al., *J. Bacteriol.* 190:1447-1458 (2008)). The *M. thermoacetica* hydrogenases are suitable candidates should the production host lack sufficient endogenous hydrogenase activity. *M. thermoacetica* can grow with $CO_2$ as the exclusive carbon source, indicating that reducing equivalents are extracted from $H_2$ to allow acetyl-CoA synthesis via the Wood-Ljungdahl pathway (Drake, *J. Bacteriol.* 150:702-709. (1982); Drake and Daniel, *Res. Microbiol.* 155:869-883 (2004); Kellum and Drake, *J. Bacteriol.* 160:466-469 (1984)) (see FIG. 6). *M. thermoacetica* has homologs to several hyp, hyc, and hyf genes from *E. coli*. These protein sequences encoded for by these genes can be identified by the following GenBank accession numbers. In addition, several gene clusters encoding hydrogenase and/or heterodisulfide reductase functionality are present in *M. thermoacetica* and their corresponding protein sequences are also provided below.

Hyp Assembly Proteins.

| Protein | GenBank ID | Organism |
| --- | --- | --- |
| HypA | NP_417206 | *Escherichia coli* |
| HypB | NP_417207 | *Escherichia coli* |
| HypC | NP_417208 | *Escherichia coli* |
| HypD | NP_417209 | *Escherichia coli* |

-continued

| Protein | GenBank ID | Organism |
| --- | --- | --- |
| HypE | NP_417210 | *Escherichia coli* |
| HypF | NP_417192 | *Escherichia coli* |

Proteins in *M. thermoacetica* Whose Genes are Homologous to the *E. coli* Hyp Genes.

| Protein | GenBank ID | Organism |
| --- | --- | --- |
| Moth_2175 | YP_431007 | *Moorella thermoacetica* |
| Moth_2176 | YP_431008 | *Moorella thermoacetica* |
| Moth_2177 | YP_431009 | *Moorella thermoacetica* |
| Moth_2178 | YP_431010 | *Moorella thermoacetica* |
| Moth_2179 | YP_431011 | *Moorella thermoacetica* |
| Moth_2180 | YP_431012 | *Moorella thermoacetica* |
| Moth_2181 | YP_431013 | *Moorella thermoacetica* |

Hydrogenase 3.

| Protein | GenBank ID | Organism |
| --- | --- | --- |
| HycA | NP_417205 | *Escherichia coli* |
| HycB | NP_417204 | *Escherichia coli* |
| HycC | NP_417203 | *Escherichia coli* |
| HycD | NP_417202 | *Escherichia coli* |
| HycE | NP_417201 | *Escherichia coli* |
| HycF | NP_417200 | *Escherichia coli* |
| HycG | NP_417199 | *Escherichia coli* |
| HycH | NP_417198 | *Escherichia coli* |
| HycI | NP_417197 | *Escherichia coli* |

Hydrogenase 4.

| Protein | GenBank ID | Organism |
| --- | --- | --- |
| HyfA | NP_416976 | *Escherichia coli* |
| HyfB | NP_416977 | *Escherichia coli* |
| HyfC | NP_416978 | *Escherichia coli* |
| HyfD | NP_416979 | *Escherichia coli* |
| HyfE | NP_416980 | *Escherichia coli* |
| HyfF | NP_416981 | *Escherichia coli* |
| HyfG | NP_416982 | *Escherichia coli* |
| HyfH | NP_416983 | *Escherichia coli* |
| HyfI | NP_416984 | *Escherichia coli* |
| HyfJ | NP_416985 | *Escherichia coli* |
| HyfR | NP_416986 | *Escherichia coli* |

Proteins in *M. thermoacetica* Whose Genes are Homologous to the *E. coli* Hyc and/or Hyf Genes.

| Protein | GenBank ID | Organism |
| --- | --- | --- |
| Moth_2182 | YP_431014 | *Moorella thermoacetica* |
| Moth_2183 | YP_431015 | *Moorella thermoacetica* |
| Moth_2184 | YP_431016 | *Moorella thermoacetica* |
| Moth_2185 | YP_431017 | *Moorella thermoacetica* |
| Moth_2186 | YP_431018 | *Moorella thermoacetica* |
| Moth_2187 | YP_431019 | *Moorella thermoacetica* |
| Moth_2188 | YP_431020 | *Moorella thermoacetica* |
| Moth_2189 | YP_431021 | *Moorella thermoacetica* |
| Moth_2190 | YP_431022 | *Moorella thermoacetica* |
| Moth_2191 | YP_431023 | *Moorella thermoacetica* |
| Moth_2192 | YP_431024 | *Moorella thermoacetica* |

Additional Hydrogenase-Encoding Gene Clusters in *M. thermoacetica*.

| Protein | GenBank ID | Organism |
| --- | --- | --- |
| Moth_0439 | YP_429313 | *Moorella thermoacetica* |
| Moth_0440 | YP_429314 | *Moorella thermoacetica* |
| Moth_0441 | YP_429315 | *Moorella thermoacetica* |
| Moth_0442 | YP_429316 | *Moorella thermoacetica* |
| Moth_0809 | YP_429670 | *Moorella thermoacetica* |
| Moth_0810 | YP_429671 | *Moorella thermoacetica* |
| Moth_0811 | YP_429672 | *Moorella thermoacetica* |
| Moth_0812 | YP_429673 | *Moorella thermoacetica* |
| Moth_0813 | (possible psuedogene, GenBank ID unavailable) | *Moorella thermoacetica* |
| Moth_0814 | YP_429674 | *Moorella thermoacetica* |
| Moth_0815 | YP_429675 | *Moorella thermoacetica* |
| Moth_0816 | YP_429676 | *Moorella thermoacetica* |
| Moth_1193 | YP_430050 | *Moorella thermoacetica* |
| Moth_1194 | YP_430051 | *Moorella thermoacetica* |
| Moth_1195 | YP_430052 | *Moorella thermoacetica* |
| Moth_1196 | YP_430053 | *Moorella thermoacetica* |
| Moth_1717 | YP_430562 | *Moorella thermoacetica* |
| Moth_1718 | YP_430563 | *Moorella thermoacetica* |
| Moth_1719 | YP_430564 | *Moorella thermoacetica* |
| Moth_1883 | YP_430726 | *Moorella thermoacetica* |
| Moth_1884 | YP_430727 | *Moorella thermoacetica* |
| Moth_1885 | YP_430728 | *Moorella thermoacetica* |
| Moth_1886 | YP_430729 | *Moorella thermoacetica* |
| Moth_1887 | YP_430730 | *Moorella thermoacetica* |
| Moth_1888 | YP_430731 | *Moorella thermoacetica* |
| Moth_1452 | YP_430305 | *Moorella thermoacetica* |
| Moth_1453 | YP_430306 | *Moorella thermoacetica* |
| Moth_1454 | YP_430307 | *Moorella thermoacetica* |

This example describes exemplary gene sets for engineering an organism to produce acetyl-CoA froth syngas and methanol.

Example XII

Cloning, Expression and Activity Assays for Genes and Encoded Enzymes for Engineering an Organism to Produce Acetyl-CoA from Synthesis Gas and Methanol This example describes the cloning and expression of genes encoding enzymes that provide a syngas and methanol utilizing organism.

Methanol-Methyltransferase (MTR).

At least the minimal set of genes, for example, MtaA, MtaB, and MtaC, for producing Me-THF from methanol are cloned and expressed in *E. coli*. These genes are cloned via proof-reading PCR and linked together for expression in a high-copy number vector such as pZE22-S under control of the repressible PA1-lacO1 promoter (Lutz and Bujard, *Nucleic Acids Res.* 25:1203-1210 (1997)). Coenzyme B12 is added to the growth medium as these methyltransferase activities require cobalamin as a cofactor. Cloned genes are verified by PCR and/or restriction enzyme mapping to demonstrate construction and insertion of the 3-gene set into the expression vector. DNA sequencing of the presumptive clones is carried out to confirm the expected sequences of each gene. Once confirmed, the final construct is expressed in *E. coli* K-12 (MG1655) cells by addition of isopropyl β-D-1-thiogalactopyranoside (IPTG) inducer between 0.05 and 1 mM final concentration. Expression of the cloned genes is monitored using SDS-PAGE of whole cell extracts. To determine if expression of the MtaABC proteins confers upon *E. coli* the ability to transfer methyl groups from methanol to tetrahydrofolate (THF), methanol is fed to the recombinant strain at varying concentrations and its uptake is monitored along with methyl-THF synthesis. Activity of the methyltransferase system is assayed anaerobically as described for vanillate as a methyl source in *M. thermoacetica* (Naidu and Ragsdale, *J. Bacteriol.* 183:3276-3281 (2001)) or for the *Methanosarcina barkeri* methanol methyltransferase (Sauer et al., *Eur. J. Biochem.* 243:670-677 (1997); Tallant and Krzycki. *J. Bacteriol.* 178:1295-1301 (1996); Tallant and Krzycki. *J Bacteriol.* 179:6902-6911 (1997); Tallant et al., *J. Biol. Chem.* 276:4485-4493 (2001)). For a positive control, *E. coli* cells are cultured in parallel, and endogenous methyltransferase activity is monitored. Demonstration that activity depends on exogenously added coenzyme B12 confirms expression of methanol:corrinoid methyltransferase activity in *E. coli*.

Acetyl-CoA Synthase/Carbon Monoxide Dehydrogenase (ACS/CODH).

Using standard PCR methods, the entire operons encoding the genes essential for ACS/CODH activity from *M. thermoacetica*, *C. hydrogenoformans*, and *M. acetivorans* are assembled into a low or medium copy number vector such as pZA33-S (P15A-based) or pZS13-S (pSC101-based). As described for the methyltransferase genes, the structure and sequence of the cloned genes are confirmed. Expression is monitored via protein gel electrophoresis of whole-cell lysates grown under strictly anaerobic conditions with the requisite metals (Ni, Zn, Fe) and coenzyme B12 provided. As necessary, the gene cluster is modified for *E. coli* expression by identification and removal of any apparent terminators and introduction of consensus ribosomal binding sites chosen from sites known to be effective in *E. coli* (Barrick et al., *Nucleic Acids Res.* 22:1287-1295 (1994); Ringquist et al., *Mol. Microbiol.* 6:1219-1229 (1992)). However, each gene cluster is cloned and expressed in a manner parallel to its native structure and expression. This helps ensure the desired stoichiometry between the various gene products, most of which interact with each other. Once satisfactory expression of the CODH/ACS gene cluster under anaerobic conditions is achieved, the ability of cells expressing these genes to fix CO and/or $CO_2$ into cellular carbon is assayed. Initial conditions employ strictly anaerobically grown cells provided with exogenous glucose as a carbon and energy source via substrate-level phosphorylation or anaerobic respiration with nitrate as an electron acceptor. Additionally, exogenously provided $CH_3$-THF is added to the medium.

Assaying Activity of the Combined MTR and ACS/CODH Pathway.

The ACS/CODH genes as described in Example II are cloned and expressed in cells also expressing the methanol-methyltransferase system also as described in Example II. This is achieved by introduction of compatible plasmids expressing ACS/CODH into MTR-expressing cells. For added long-term stability, the ACS/CODH and MTR genes can also be integrated into the chromosome. After strains of *E. coli* capable of utilizing methanol to produce Me-THF and of expressing active CODH/ACS gene are made, they are assayed for the ability to utilize both methanol and syngas for incorporation into cell mass and acetate. Initial conditions employ strictly anaerobically grown cells provided with exogenous glucose as a carbon and energy source. Alternatively, or in addition to glucose, nitrate can be added to the fermentation broth to serve as an electron acceptor and initiator of growth. Anaerobic growth of *E. coli* on fatty acids, which are ultimately metabolized to acetyl-CoA, has been demonstrated in the presence of nitrate (Campbell et at, *Mol. Microbiol.* 47:793-805 (2003)). Similar conditions can be employed by culturing the microbial organisms in the presence of an electron acceptor such as nitrate. Oxygen can also be provided as long as its intracellular levels are maintained below any inhibition threshold of the engineered enzymes. "Synthetic syngas" of a composition suitable for these experiments is employed along with methanol. $^{13}$C-labeled methanol or $^{13}$C-labeled CO are provided to the cells, and analytical mass spectrometry is employed to measure incorporation of the labeled carbon into acetate and cell mass, for example, proteinogenic amino acids.

Pyruvate Ferredoxin Oxidoreductase.

The pyruvate ferredoxin oxidoreductase genes from *M. thermoacetica*, *D. africanus*, and *E. coli* are cloned and expressed in strains exhibiting MTR and ACS/CODH activities. Conditions, promoters, and the like, are described above. Given the large size of the PFOR genes and oxygen sensitivity of the corresponding enzymes, tests are performed using low or single-copy plasmid vectors or single-copy chromosomal integrations. Activity assays (as described in Furdui and Ragsdale, *J. Biol. Chem.* 275: 28494-28499 (2000)) are applied to demonstrate activity. In addition, demonstration of growth on the gaseous carbon sources and methanol in the absence of an external electron acceptor provides further evidence for PFOR activity in viva.

Hydrogenase.

The endogenous hydrogen-utilizing hydrogenase activity of the host organism is tested by growing the cells as described above in the presence and absence of hydrogen. If a dramatic shift towards the formation of more reduced products during fermentation is observed (for example, increased ethanol as opposed to acetate), this indicates that endogenous hydrogenase activity is sufficiently active. In this case, no heterologous hydrogenases are cloned and expressed. If the native enzymes do not have sufficient activity or reduce the needed acceptor, the genes encoding an individual hydrogenase complex are cloned and expressed in strains exhibiting MTR, ACS/CODH, and PFOR activities. Conditions, promoters, and the like, are described above.

This example describes the cloning and expression of genes conferring a syngas and methanol utilization pathway and assay for appropriate activities.

Example XIII

Development and Optimization of Fermentation Process for Production of Acetyl-CoA from an Organism Engineered to Utilize Syngas and Methanol This example describes development and optimization of fermentation conditions for syngas and methanol utilizing organisms.

Important process considerations for a syngas fermentation are high biomass concentration and good gas-liquid mass transfer (Bredwell et al., *Biotechnol. Prog.* 15:834-844 (1999)). The solubility of CO in water is somewhat less than that of oxygen. Continuously gas-sparged fermentations can be performed in controlled fermenters with constant off-gas analysis by mass spectrometry and periodic liquid sampling and analysis by GC and HPLC. The liquid phase can function in batch mode. Fermentation products such as alcohols, organic acids, and residual glucose along with residual methanol are quantified by HPLC (Shimadzu, Columbia Md.), for example, using an Aminex® series of HPLC columns (for example, HPX-87 series) (BioRad, Hercules Calif.), using a refractive index detector for glucose and alcohols, and a UV detector for organic acids. The growth rate is determined by measuring optical density using a spectrophotometer (600 nm). All piping in these systems is glass or metal to maintain anaerobic conditions. The gas sparging is performed with glass frits to decrease bubble size and improve mass transfer. Various sparging rates are tested, ranging from about 0.1 to 1 vvm (vapor volumes per minute). To obtain accurate measurements of gas uptake rates, periodic challenges are performed in which the gas flow is temporarily stopped, and the gas phase composition is monitored as a function of time.

In order to achieve the overall target productivity, methods of cell retention or recycle are employed. One method to increase the microbial concentration is to recycle cells via a tangential flow membrane from a sidestream. Repeated batch culture can also be used, as previously described for production of acetate by *Moorella* (Sakai et al., *J. Biosci. Bioeng.* 99:252-258 (2005)). Various other methods can also be used (Bredwell et al., *Biotechnol. Prog.* 15:834-844 (1999); Datar et al., *Biotechnol. Bioeng.* 86:587-594 (2004)). Additional optimization can be tested such as overpressure at 1.5 atm to improve mass transfer (Najafpour and Younesi, *Enzyme and Microbial Technology* 38:223-228 (2006)).

Once satisfactory performance is achieved using Pure $H_2$/CO as the feed, synthetic gas mixtures are generated containing inhibitors likely to be present in commercial syngas. For example, a typical impurity profile is 4.5% $CH_4$, 0.1% $C_2H_2$, 0.35% $C_2H_6$, 1.4% $C_2H_4$, and 150 ppm nitric oxide (Datar et al., *Biotechnol. Bioeng.* 86:587-594 (2004)). Tars, represented by compounds such as benzene, toluene, ethylbenzene, p-xylene, o-xylene, and naphthalene, are added at ppm levels to test for any effect on production. For example, it has been shown that 40 ppm NO is inhibitory to *C. carboxidivorans* (Ahmed and Lewis, *Biotechnol. Bioeng.* 97:1080-1086 (2007)). Cultures are tested in shake-flask cultures before moving to a fermentor. Also, different levels of these potential inhibitory compounds are tested to quantify the effect they have on cell growth. This knowledge is used to develop specifications for syngas purity, which is utilized for scale up studies and production. If any particular component is found to be difficult to decrease or remove from syngas used for scale up, an adaptive evolution procedure is utilized to adapt cells to tolerate one or more impurities.

This example describes development and optimization of fermentation conditions for syngas and methanol utilizing organisms.

Example XIV

Methods for Handling CO and Anaerobic Cultures

This example describes methods for handling CO and anaerobic cultures.

Handling of CO in small quantities for assays and small cultures. CO is an odorless, colorless and tasteless gas that is a poison. Therefore, cultures and assays that utilize CO can require special handling. Several assays, including CO oxidation, acetyl-CoA synthesis, CO concentration using myoglobin, and CO tolerance/utilization in small batch cultures, call for small quantities of the CO gas that can be dispensed and handled within a fume hood. The biochemical assays called for saturating very small quantities (<2 ml) of the biochemical assay medium or buffer with CO and then performing the assay. All of the CO handling steps were performed in a fume hood with the sash set at the proper height and blower turned on; CO was dispensed from a compressed gas cylinder and the regulator connected to a Schlenk line. The latter ensures that equal concentrations of CO will be dispensed to each of several possible cuvettes or vials. The Schlenk line was set up containing an oxygen scrubber on the input side and an oil pressure release bubbler and vent on the other side. Alternatively, a cold trap can be used. Assay cuvettes were both anaerobic and CO-containing. Therefore, the assay cuvettes were tightly sealed with a rubber stopper and reagents added or removed using gas-tight needles and syringes. Secondly, small (~50 ml) cultures were grown with saturating CO in tightly stoppered serum bottles. As with the biochemical assays, the CO-saturated microbial cultures were equilibrated in the fume hood using the Schlenk line setup. Both the biochemical assays and microbial cultures were in portable, sealed containers and in small volumes making for safe handling outside of the fume hood. The compressed CO tank was adjacent to the fume hood.

Typically, a Schlenk line was used to dispense CO to cuvettes, each vented. Rubber stoppers on the cuvettes are pierced with 19 or 20 gage disposable syringe needles and are vented with the same. An oil bubbler is used with a CO tank and oxygen scrubber. The glass or quartz spectrophotometer cuvettes have a circular hole on top into which a Kontes stopper sleeve, Sz7 774250-0007 was fitted. The CO detector unit was positioned proximal to the fume hood.

Handling of CO in larger quantities fed to large-scale cultures. Fermentation cultures are fed either CO or a mixture of CO and $H_2$ to simulate syngas or syngas as a feedstock in fermentative production. Therefore, quantities of cells ranging from 1 liter to several liters can include the addition of CO gas to increase the dissolved concentration of CO in the medium. In these circumstances, fairly large and continuously administered quantities of CO gas will be added to the cultures. At different points, the cultures are harvested or samples removed. Alternatively, cells can be harvested with an integrated continuous flow centrifuge that is part of the fermenter.

The fermentative processes are generally carried out under anaerobic conditions. In some cases, it is uneconomical to pump oxygen or air into fermenters to ensure adequate oxygen saturation to provide a respiratory environment. In addition, the reducing power generated during anaerobic fermentation is likely to be needed in product formation rather than respiration. Furthermore, many of the enzymes being considered for various pathways are oxygen-sensitive to varying degrees. Classic acetogens such as *M. thermoacetica* are obligate anaerobes and the enzymes in the Wood-Ljungdahl pathway are highly sensitive to irreversible inactivation by molecular oxygen. While there are oxygen-tolerant acetogens, the repertoire of enzymes in the Wood-Ljungdahl pathway are likely to all have issues in the presence of oxygen because most are metallo-enzymes, key components are ferredoxins, and regulation may divert metabolism away from the Wood-Ljungdahl pathway to maximize energy acquisition. At the same time, cells in culture act as oxygen scavengers that moderate the need for extreme measures in the presence of large cell growth.

Anaerobic chamber and conditions. Exemplary anaerobic chambers are available commercially (see, for example, Vacuum Atmospheres Company, Hawthorne Calif.; MBraun, Newburyport Mass.). Exemplary conditions include an $O_2$ concentration of 1 ppm or less and 1 atm pure $N_2$. In one example, 3 oxygen scrubbers/catalyst regenerators can be used, and the chamber can include an $O_2$ electrode (such as Teledyne; City of Industry Calif.). Nearly all items and reagents are cycled 4× in the airlock of the chamber prior to opening the inner chamber door. Reagents with a volume>5 ml are sparged with pure $N_2$ prior to introduction into the chamber. Gloves are changed ~2×/yr and the catalyst containers are regenerated periodically when the chamber displays increasingly sluggish response to changes in oxygen levels. The chamber's pressure is controlled through one-way valves activated by solenoids. This feature is very convenient because it allows setting the chamber pressure at a level higher than the surroundings to allow transfer of very small tubes through the purge valve.

The anaerobic chambers can achieve levels of $O_2$ that can be reached that are consistently very low and are needed for highly oxygen sensitive anaerobic conditions. However, growth and handling of cells does not usually require such precautions. In an alternative anaerobic chamber configuration, platinum or palladium can be used as a catalyst that requires some hydrogen gas in the mix. Instead of using solenoid valves, pressure release is controlled by a bubbler. Instead of using instrument-based O2 monitoring, test strips can be used instead. To improve the anaerobic conditions a few relatively simple changes in our system can be made; some are already in progress.

Anaerobic microbiology. Small cultures are handled as described above for CO handling. In particular, serum or media bottles are fitted with thick rubber stoppers and aluminum crimps are employed to seal the bottle. Medium, such as Terrific Broth, is made in a conventional manner and dispensed to an appropriately sized serum bottle. The bottles are sparged with nitrogen for ~30 min of moderate bubbling. This removes most of the oxygen from the medium and, after this step; each bottle is capped with a rubber stopper (such as Bellco 20 mm septum stoppers; Bellco, Vineland, N.J.) and crimp-sealed (Bellco 20 mm). Then the bottles of medium are autoclaved using a slow (liquid) exhaust cycle. At least sometimes a needle can be poked through the stopper to provide exhaust during autoclaving; the needle needs to be removed immediately upon removal from the autoclave. The sterile medium has the remaining medium components, for example buffer or antibiotics, added via syringe and needle. Prior to addition of reducing agents, the bottles are equilibrated for 30-60 minutes with nitrogen (or CO depending upon use). A reducing agent such as a 100×150 mM sodium sulfide, 200 mM cysteine-HCl can be added. This was made by weighing the sodium sulfide into a dry beaker and the cysteine into a serum bottle, bringing both into the anaerobic chamber, dissolving the sodium sulfide into anaerobic water, then adding this to the cysteine in the serum bottle. The bottle should be stoppered immediately as the sodium sulfide solution will generate hydrogen sulfide gas upon contact with the cysteine. When injecting into the culture, a syringe filter is used to sterilize the solution. Other components can be added through syringe needles, such as B12 (10 μM cyanocobalamin), nickel chloride ($NiCl_2$, 20 microM final concentration from a 40 mM stock made in anaerobic water in the chamber and sterilized by autoclaving or by using a syringe filter upon injection into the culture), and ferrous ammonium sulfate (final concentration needed is 100 μM—made as 100-1000× stock solution in anaerobic water in the chamber and sterilized by autoclaving or by using a syringe filter upon injection into the culture). To facilitate faster growth under anaerobic conditions, the 11 bottles were inoculated with 50 ml of a preculture grown anaerobically. Induction of the pA1-lacO1 promoter in the vectors was performed by addition of isopropyl β-D-1-thiogalactopyranoside (IPTG) to a final concentration of 0.2 mM and was carried out for ~3 hrs.

Large cultures can be grown in larger bottles using continuous gas addition while bubbling. A rubber stopper with a metal bubbler is placed in the bottle after medium addition and sparged with nitrogen for 30 minutes or more prior to setting up the rest of the bottle. Each bottle is put together such that a sterile filter will sterilize the gas bubbled in and the hoses on the bottles are compressible with small C clamps. Medium and cells are stirred with magnetic stir bars. Once all medium components and cells are added, the bottles can be incubated in an incubator in room air but with continuous nitrogen sparging into the bottles.

This example describes the handling of CO and anaerobic cultures.

Example XV

CO Oxidation (CODH) Assay

This example describes assay methods for measuring CO oxidation (CO dehydrogenase; CODH).

The 7 gene CODH/ACS operon of *Moorella thermoacetica* was cloned into *E. coli* expression vectors. The intact ~10 kbp DNA fragment was cloned, and it is likely that some of the genes in this region are expressed from their own endogenous promoters and all contain endogenous ribosomal binding sites. *M. thermoacetica* is Gram positive, and ribosome binding site elements are expected to work well in *E. coli*. These clones were assayed for CO oxidation, using an assay that quantitatively measures CODH activity. Antisera to the *M. thermoacetica* gene products was used for Western blots to estimate specific activity. This activity, described below in more detail, was estimated to be ~1/50th of the *M. thermoacetica* specific activity.

It is possible that CODH activity of recombinant *E. coli* cells could be limited by the fact that *M. thermoacetica* enzymes have temperature optima around 55° C. Therefore, a mesophilic CODH/ACS pathway could be advantageous such as the close relative of *Moorella* that is mesophilic and does have an apparently intact CODH/ACS operon and a Wood-Ljungdahl pathway, *Desulfitobacterium hafniense*. Acetogens as potential host organisms include, but are not limited to, *Rhodospirillum rubrum, Moorella thermoacetica* and *Desulfitobacterium hafniense*.

CO oxidation is both the most sensitive and most robust of the CODH/ACS assays. It is likely that an *E. coli*-based syngas using system will ultimately need to be about as anaerobic as *Clostridial* (i.e., *Moorella*) systems, especially for maximal activity. Improvement in CODH should be possible but will ultimately be limited by the solubility of CO gas in water.

Initially, each of the genes was cloned individually into expression vectors. Combined expression units for multiple subunits/I complex were generated. Expression in *E. coli* at the protein level was determined. Both combined *M. thermoacetica* CODH/ACS operons and individual expression clones were made.

CO oxidation assay. This assay is one of the simpler, reliable, and more versatile assays of enzymatic activities within the Wood-Ljungdahl pathway and tests CODH (Seravalli et al., Biochemistry 43:3944-3955 (2004)). A typical activity of *M. thermoacetica* CODH specific activity is 500 U at 55° C. or ~60 U at 25° C. This assay employs reduction of methyl viologen in the presence of CO. This is measured at 578 nm in stoppered, anaerobic, glass cuvettes.

In more detail, glass rubber stoppered cuvettes were prepared after first washing the cuvette 4× in deionized water and 1× with acetone. A small amount of vacuum grease was smeared on the top of the rubber gasket. The cuvette was gassed with CO, dried 10 min with a 22 Ga. needle plus an exhaust needle. A volume of 0.98 ml of reaction buffer (50 mM Hepes, pH 8.5, 2 mM dithiothreitol (DTT) was added using a 22 Ga. needle, with exhaust needled, and 100% CO. Methyl viologen ($CH_3$ viologen) stock was 1 M in water. Each assay used 20 microliters for 20 mM final concentration. When methyl viologen was added, an 18 Ga needle (partial) was used as a jacket to facilitate use of a Hamilton syringe to withdraw the $CH_3$ viologen. 4-5 aliquots were drawn up and discarded to wash and gas equilibrate the syringe. A small amount of sodium dithionite (0.1 M stock) was added when making up the $CH_3$ viologen stock to slightly reduce the $CH_3$ viologen. The temperature was equilibrated to 55° C. in a heated Otis spectrophotometer (Bogart GA). A blank reaction ($CH_3$ viologen+buffer) was run first to measure the base rate of $CH_3$ viologen reduction. Crude *E. coli* cell extracts of ACS90 and ACS91 (CODH-ACS operon of *M. thermoacetica* with and without, respectively, the first cooC). 10 microliters of extract were added at a time, mixed and assayed. Reduced $CH_3$ viologen turns purple. The results of an assay are shown in Table X

TABLE 2

Crude extract CO Oxidation Activities.

| ACS90 | 7.7 mg/ml | ACS91 | 11.8 mg/ml |
|---|---|---|---|
| Mta98 | 9.8 mg/ml | Mta99 | 11.2 mg/ml |

| Extract | Vol | OD/ | U/ml | U/mg |
|---|---|---|---|---|
| ACS90 | 10 microliters | 0.073 | 0.376 | 0.049 |
| ACS91 | 10 microliters | 0.096 | 0.494 | 0.042 |
| Mta99 | 10 microliters | 0.0031 | 0.016 | 0.0014 |
| ACS90 | 10 microliters | 0.099 | 0.51 | 0.066 |
| Mta99 | 25 microliters | 0.012 | 0.025 | 0.0022 |
| ACS91 | 25 microliters | 0.215 | 0.443 | 0.037 |
| Mta98 | 25 microliters | 0.019 | 0.039 | 0.004 |
| ACS91 | 10 microliters | 0.129 | 0.66 | 0.056 |

| Averages | |
|---|---|
| ACS90 | 0.057 U/mg |
| ACS91 | 0.045 U/mg |
| Mta99 | 0.0018 U/mg |

Mta98/Mta99 are *E. coli* MG1655 strains that express methanol methyltransferase genes from *M. thermoacetia* and, therefore, are negative controls for the ACS90 ACS91 *E. coli* strains that contain *M. thermoacetica* CODH operons.

If 1% of the cellular protein is CODH, then these figures would be approximately 100× less than the 500 U/mg activity of pure *M. thermoacetica* CODH. Actual estimates based on Western blots are 0.5% of the cellular protein, so the activity is about 50× less than for *M. thermoacetica* CODH. Nevertheless, this experiment did clearly demonstrate CO oxidation activity in recombinant *E. coli* with a much smaller amount in the negative controls. The small amount of CO oxidation ($CH_3$ viologen reduction) seen in the negative controls indicates that *E. coli* may have a limited ability to reduce $CH_3$ viologen.

Figure 9:
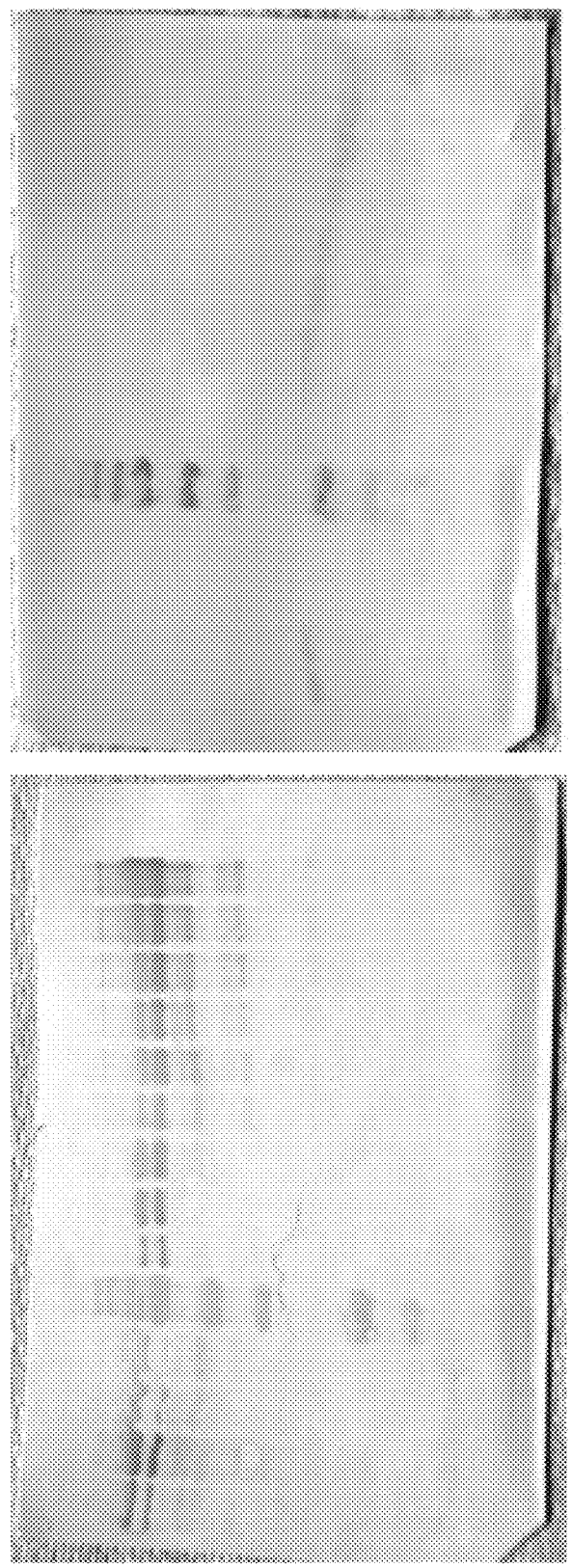
FIG. 9 shows Western blots of 10 micrograms ACS90 (lane 1), ACS91 (lane 2), Mta98/99 (lanes 3 and 4) cell extracts with size standards (lane 5) and controls of *M. thermoacetica* CODH (Moth_1202/1203) or Mtr (Moth_1197) proteins (50, 150, 250, 350, 450, 500, 750, 900, and 1000 ng).

To estimate the final concentrations of CODH and Mtr proteins, SDS-PAGE followed by Western blot analyses were performed on the same cell extracts used in the CO oxidation, ACS, methyltransferase, and corrinoid Fe—S assays. The antisera used were polyclonal to purified *M. thermoacetica* CODH-ACS and Mtr proteins and were visualized using an alkaline phosphatase-linked goat-anti-rabbit secondary antibody. The Westerns were performed and results are shown in FIGS. 9A and 9B. The amounts of CODH in ACS90 and ACS91 were estimated at 50 ng by comparison to the control lanes. Expression of CODH-ACS operon genes including 2 CODH subunits and the methyltransferase were confirmed via Western blot analysis. Therefore, the recombinant *E. coli* cells express multiple components of a 7 gene operon. In addition, both the methyltransferase and corrinoid iron sulfur protein were active in the same recombinant *E. coli* cells. These proteins are part of the same operon cloned into the same cells.

Figure 10:
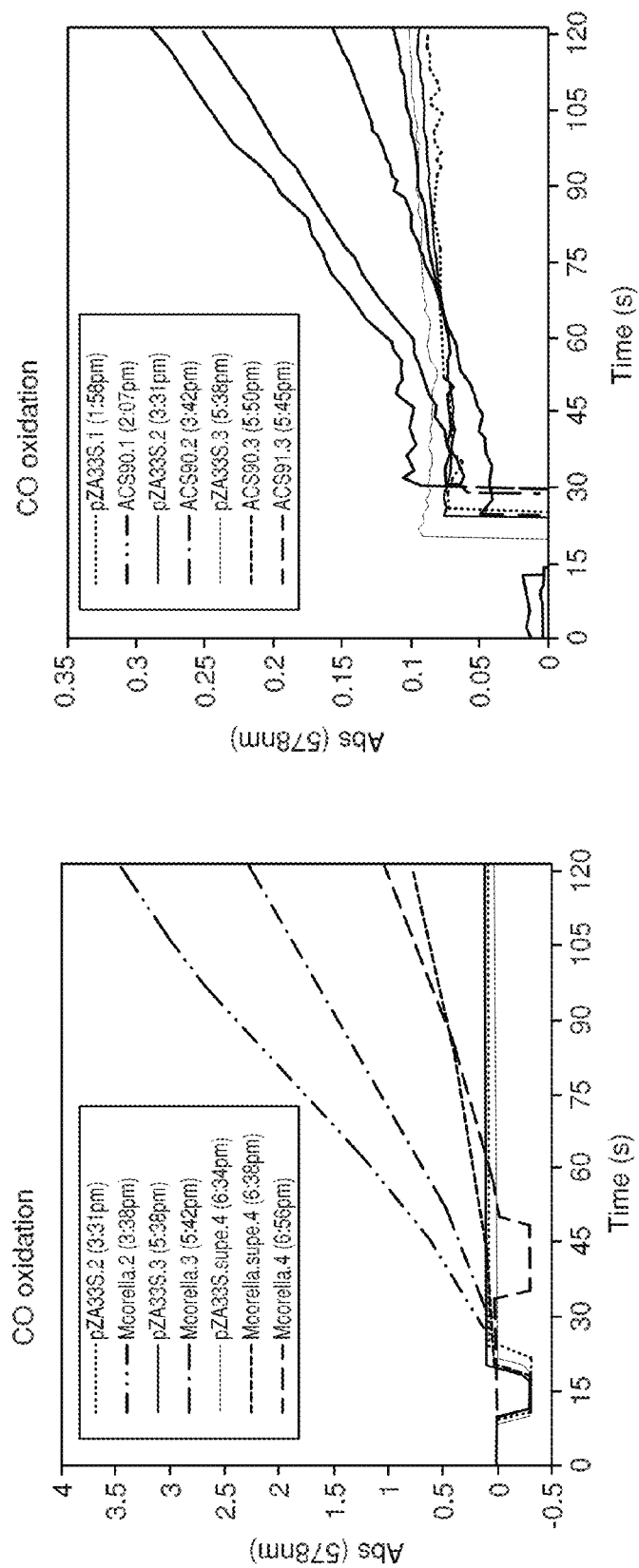
FIG. 10 shows CO oxidation assay results. Cells (*M. thermoacetica* or *E. coli* with the CODH/ACS operon; ACS90 or ACS91 or empty vector: pZA33S) were grown and extracts prepared. Assays were performed at 55° C. at various times on the day the extracts were prepared. Reduction of methylviologen was followed at 578 nm over a 120 sec time course.

The CO oxidation assays were repeated using extracts of *Moorella* thermoacetica cells for the positive controls. Though CODH activity in *E. coli* ACS90 and ACS91 was measurable, it was at about 130-150× lower than the *M. thermoacetica* control. The results of the assay are shown in FIG. 10. Briefly, cells (*M. thermoacetica* or *E. coli* with the CODH/ACS operon; ACS90 or ACS91 or empty vector: pZA33S) were grown and extracts prepared as described above. Assays were performed as described above at 55° C. at various times on the day the extracts were prepared. Reduction of methylviologen was followed at 578 nm over a 120 sec time course.

These results describe the CO oxidation (CODH) assay and results. Recombinant *E. coli* cells expressed CO oxidation activity as measured by the methyl viologen reduction assay.

Example XVI

Acetyl-CoA Synthase (ACS) Activity Assay (CO Exchange Assay)

This example describes an ACS assay method.

This assay measures the ACS-catalyzed exchange of the carbonyl group of acetyl-CoA with CO (Raybuck et al., *Biochemistry* 27:7698-7702 (1988)). ACS (as either a purified enzyme or part of a cell extract) is incubated with acetyl-CoA labeled with $^{14}C$ at the carbonyl carbon under a CO atmosphere. In the presence of active ACS, the radioactivity in the liquid phase of the reaction decreases exponentially until it reaches a minimum defined by the equilibrium between the levels of $^{14}C$-labeled acetyl-CoA and $^{14}C$-labeled CO. The same cell extracts of *E. coli* MG1655 expressing ACS90 and ACS91 employed in the other assays as well as control extracts were assayed by this method.

Briefly in more detail, in small assay vials under normal atmosphere, a solution of 0.2 mM acetyl-CoA, 0.1 mM methyl viologen, and 2 mM Ti(III)citrate in 0.3M MES buffer, pH 6.0, was made. The total reaction volume when all components are added was 500 μl. Vials were sealed with rubber stoppers (Bellco) and crimp aluminum seals (Bellco) to create a gas-tight reaction atmosphere. Each vial was sparged with 100% CO for several minutes, long enough to completely exchange the vials' atmosphere, and brought into an anaerobic chamber. The assay vials were placed in a 55° C. sand bath and allowed to equilibrate to that temperature. A total of 10 scintillation vials with 40 μl of 1M HCl were prepared for each assay vial. A gas-tight Hamilton syringe was used to add ACS to the assay vial and incubated for approximately 2-3 minutes for the reaction to come to equilibrium. A gas-tight Hamilton syringe was used to add 1 μl (0.36 nmoles) $^{14}C$-acetyl-CoA to start the assay (time=0 min). Time points were taken starting immediately. Samples (40 μl) were removed from the assay vials with a gas-tight Hamilton syringe. Each sample was added to the 40 μl of HCl in the prepared scintillation vials to quench the reaction. As the ACS enzyme transfers $^{14}C$ label to CO from acetyl-CoA, the concentration of the isotope decreases exponentially. Therefore, the assay was sampled frequently in the early time points. The precise time for each sample was recorded. The exact pace of the reaction depends on the ACS enzyme, but generally several samples are taken immediately and sampled over the initial 10-15 minutes. Samples are continued to be taken for 1-2 hours.

In a particular exemplary assay, four assay conditions were used: blank (no ACS), 12 µl of purified *E. coli* strains expressing *M. thermoacetica* ACS, 4 µl of purified *E. coli* ACS, and 3.7 µl of *M. thermoacetica* CODH/ACS. In another exemplary assay, four assay conditions were used: 108 µg CODH/ACS, 1 mg Mta99 cell extract, 1 mg ACS90 cell extract, and 1 mg ACS91 cell extract. The enzymes were added as 100 µl solutions (50 mM KPi, 0.1M NaCl, pH7.6). A more sensitive assay that can be used for most of the CODH-ACS activities is the synthesis assay described below.

This example describes the assay conditions for measuring ACS activity.

Example XVII

Acetyl-CoA Synthesis and Methyltransferase Assays

This example describes acetyl-CoA synthesis and methyltransferase assays.

Synthesis assay. This assay is an in vitro reaction that synthesizes acetyl-CoA from methyl-tetrahydrofolate, CO, and CoA using CODH/ACS, methyltransferase (MeTr), and corrinoid Fe—S protein (CFeSP) (Raybuck et al., *Biochemistry* 27:7698-7702 (1988)). By adding or leaving out each of the enzymes involved, this assay can be used for a wide range of experiments, from testing one or more purified enzymes or cell extracts for activity, to determining the kinetics of the reaction under various conditions or with limiting amounts of substrate or enzyme. Samples of the reaction taken at various time points are quenched with 1M HCl, which liberates acetate from the acetyl-CoA end product. After purification with Dowex columns, the acetate can be analyzed by chromatography, mass spectrometry, or by measuring radioactivity. The exact method will be determined by the specific substrates used in the reaction.

A $^{14}$C-labeled methyl-THF was utilized, and the radioactivity of the isolated acetate samples was measured. The primary purpose was to test CFeSP subunits. The assay also included +/− purified methyltransferase enzymes. The following 6 different conditions were assayed: (1) purified CODH/ACS, MeTr, and CFeSP as a positive control; (2) purified CODH/ACS with ACS90 cell extract; (3) purified CODH/ACS with ACS91 cell extract; (4) purified CODH/ACS, MeTr with ACS90 cell extract; (5) purified CODH/ACS, MeTr with ACS91 cell extract; (6) purified CODH/ACS, MeTr with as much ACS91 cell extract as possible (excluding the MES buffer).

The reaction is assembled in the anaerobic chamber in assay vials that are filled with CO. The total reaction volume is small compared to the vial volume, so the reagents can be added before or after the vial is filled with CO, so long as a gas-tight Hamilton syringe is used and the reagents are kept anaerobic. The reaction (~60 ul total) consisted of the cell extract (except assay #1), CoA, Ti(III)citrate, MES (except assay #6), purified CODH/ACS, $^{14}$C-methyl-tetrahydrofolate, methyl-viologen, and ferredoxin. Additionally, purified MeTr was added to assays #1 and #4-6, and purified CFeSP was added to assay #1.

The reaction was carried out in an anaerobic chamber in a sand bath at 55° C. The final reagent added was the $^{14}$C-methyl-tetrahydrofolate, which started the reaction (t=0 s). An initial sample was taken immediately, followed by samples at 30 minutes, 1 hour, and 2 hours. These time points are not exact, as the 6 conditions were run concurrently (since this experiment was primarily a qualitative one). The 15 µl samples were added to 15 µl of 1M HCl in scintillation vials. For the last sample, if less than 15 µl was left in the reactions, the assay vials were rinsed with the 15 ul of HCl to take the remainder of the reaction. A volume of 10 µl of cell extract was used for assay #2-5, and 26.4 µl of cell extract was used for assay #6.

Typical amounts of purified enzyme to be used in the assays is as follows: CODH/ACS=~0.2 nmoles; MeTr=0.2 nmoles; CFeSP=0.05 nmoles. Typical assay concentrations are used as follows: CODH/ACS=1 uM; Me-CFeSP=0.4 uM; MeTr=1 uM; Ferredoxin=3 uM; CoA=0.26 mM; $^{14}$C methyl-THF=0.4 mM; methyl viologen=0.1 mM; and Ti(III) citrate=3 mM.

After counting the reaction mixtures, it was determined that the corrinoid Fe—S protein in ACS90 extracts was active with total activity approaching approximately ⅕ of the positive control and significantly above the negative control (no extract).

A non-radioactive synthesis assay can also be used. Optional non-radioactive assay conditions are as follows: Assay condition #1: 100 mM MES, pH6.0; 1 mM CoA; 1 mM Me-THF; 0.33 mM Ti(III) citrate, volume to 950 ul, +50 ul of extract; incubated under a CO atmosphere (Ar for control), at 55° C. These reactions should be carried out in the dark, as the corrinoid methyl carrier is light sensitive. Assay condition #2: 100 mM MES, pH6.0; 1 mM CoA; 1 mM Me-THF; 1 mM methyl viologen; volume to 950 ul, +50 ul of extract; incubated under a CO atmosphere, at 55° C., in the dark. The reaction was quenched with 10 µl of 10% formic acid, with samples taken at 1 hr, 3 hrs, and 6.5 hrs, and stored at −20°. Assay condition #3: 100 mM Tris, pH 7.6; 5 mM CoA; 7.5 mM Me-THF; 1 mM Me-viologen; volume to 90 µl, +10 µl extract; incubated under CO or Ar, at 55° C. in the dark for 1 hr, quenched with 10 µl 10% formic acid, and stored at −20° C.

In Lu et al., (*J. Biol. Chem.* 265:3124-3133. (1990)), the pH optimum for the synthesis reaction was found to be between 7.2-7.5. Lu et al. also found that CoA concentrations above 10 mM were inhibitory. Lu et al. described using methyl iodide as the methyl donor instead of Me-THF, and used 5-7.5 mM concentrations. Lu et al. also determined that DTT or other reducing agents were not necessary, although they did use ferredoxin as an electron carrier. Methyl viologen was substituted in the above-described reactions. In addition, Maynard et al., *Biol. Inorg. Chem.* 9:316-322 (2004), has determined that the electron carrier was not strictly necessary, but that failure to include one resulted in a time lag of the synthesis. Maynard et al. used 1 mM methyl viologen as electron carrier when one was used.

Methyltransferase Assay. Within the CODH-ACS operon is encoded an essential methyltransferase activity that catalyzes the transfer of $CH_3$ from methyl-tetrahydrofolate to the ACS complex as part of the synthesis of acetyl-CoA. This is the step that the methyl and carbonyl pathways join together. Within the operon in *M. thermoacetica*, the Mtr-encoding gene is Moth_1197 and comes after the main CODH and ACS subunits. Therefore, Mtr activity would constitute indirect evidence that the more proximal genes can be expressed.

Mtr activity was assayed by spectroscopy. Specifically, methylated CFeSP, with Co(III), has a small absorption peak at ~450 nm, while non-methylated CFeSP, with Co(I), has a large peak at ~390 nm. This spectrum is due to both the cobalt and iron-sulfur cluster chromophores. Additionally, the CFeSP can spontaneously oxidize to Co(II), which creates a broad absorption peak at ~470 nm (Seravalli et al., *Biochemistry* 38:5728-5735 (1999)). Recombinant methyltransferase is tested using *E. coli* cell extracts, purified CFeSP from *M. thermoacetica*, and methyl-tetrahydrofolate. The methylation of the corrinoid protein is observed as a decrease in the absorption at 390 nm with a concurrent increase in the absorption at 450 nm, along with the absence of a dominant peak at 470 nm.

Non-radioactive assays are also being developed using $^{13}$C-methanol. This should transfer to tetrahydrofolate and create a MTHF of molecular mass +1. Alternatively, the methyltransferase is thought to also work by transfer of the methanol methyl group to homocysteine to form methionine. This assay is also useful because methionine +1 mass is more readily detectable than MTHF+1 or some other possibilities. In addition to using $^{13}$C, deuterium can also be used as a tracer, both of which can be measured using mass spectrometry. These tracers can also be used in in vivo labeling studies. Other assay methods can be used to determine various intermediates or products including, for example, electron paramagnetic resonance (EPR), Mossbauer spectroscopy, Electron-Nuclear DOuble Resonance (ENDOR), infrared, magnetic circular dichroism (MCD), crystallography, X-ray absorption, as well as kinetic methods, including stopped flow and freeze-quench EPR.

Figure 8:
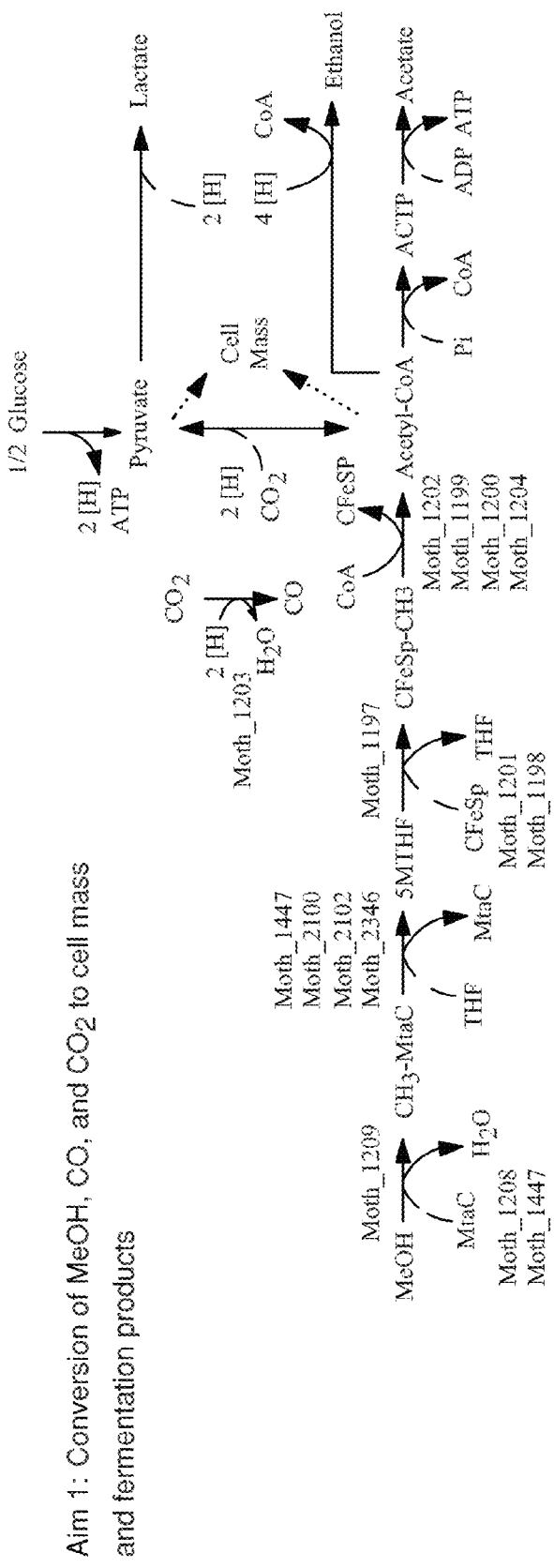
FIG. 8 shows a pathway for conversion of methanol, CO and $CO_2$ to cell mass and fermentation products.

FIG. 8 illustrates how methanol methyltransferase can be fitted into a CODH/ACS ('syngas') pathway. Essentially, the methyl group of methanol is transferred via a cobabalamin-dependent process to tetrahydrofolate and then to the corrinoid-FeS protein of CODH/ACS (also a cobalamin protein) and that, in turn, donates the methyl group to the ACS reaction that results in acetate synthesis. The methanol methyltransferase complex consists of three gene products; two of these, MtaB and MtaC, (Moth_1209 and Moth_1208) are adjacent and were readily cloned. The third, MtaA, may be encoded by three different genes (Moth_2100, Moth_2102, and Moth_2346), and it unclear whether all three genes are required or whether a subset of the three can function. All cloning in *E. coli* was performed using the Lutz-Bujard vectors (Lutz and Bujard, *Nucleic Acids Res.* 25:1203-1210 (1997)).

The following assay can be used to determine the activity of MtaB that encodes a methanol methyltransferase gene product. A positive control for the latter can be performed with vanillate o-demethylation.

Methanol Methyltransferase reaction. An examplary methanol methyl-transfer reaction has been described previously (Sauer and Thauer, *Eur. J. Biochem.* 249:280-285 (1997); Naidu and Ragsdale, *J. Bacteriol.* 183:3276-3281 (2001)). The reaction conditions are as follows: 50 mM MOPS/KOH, pH 7.0; 10 mM MgCl$_2$; 4 mM Ti(III) citrate; 0.2% dodecylmaltoside (replacing SDS, see Sauer and Tauer, *Eur. J. Biochem.* 253:698-705 (1998)); 25 µM hydroxycobalamin; 1% MeOH or 1 mM vanillate (depending on the methyl transferase version).

These reactions are measured by spectrograph readings in the dark at 37° C. or 55° C. This assay tests the ability of MtaB or MtvB to transfer the methyl group to cobalamin from methanol or vanillate, respectively.

Example XVIII

*E. coli* CO Tolerance Experiment and CO Concentration Assay (Myoglobin Assay)

This example describes the tolerance of *E. coli* for high concentrations of CO.

To test whether or not *E. coli* can grow anaerobically in the presence of saturating amounts of CO, cultures were set up in 120 ml serum bottles with 50 ml of Terrific Broth medium (plus reducing solution, NiCl$_2$, Fe(II)NH$_4$SO$_4$, cyanocobalamin, IPTG, and chloramphenicol) as described above for anaerobic microbiology in small volumes. One half of these bottles were equilibrated with nitrogen gas for 30 min. and one half was equilibrated with CO gas for 30 min. An empty vector (pZA33) was used as a control, and cultures containing the pZA33 empty vector as well as both ACS90 and ACS91 were tested with both N$_2$ and CO. All were inoculated and grown for 36 hrs with shaking (250 rpm) at 37° C. At the end of the 36 hour period, examination of the flasks showed high amounts of growth in all. The bulk of the observed growth occurred overnight with a long lag.

Given that all cultures appeared to grow well in the presence of CO, the final CO concentrations were confirmed. This was performed using an assay of the spectral shift of myoglobin upon exposure to CO. Myoglobin reduced with sodium dithionite has an absorbance peak at 435 nm; this peak is shifted to 423 nm with CO. Due to the low wavelength and need to record a whole spectrum from 300 nm on upwards, quartz cuvettes must be used. CO concentration is measured against a standard curve and depends upon the Henry's Law constant for CO of maximum water solubility=970 micromolar at 20° C. and 1 atm.

For the myoglobin test of CO concentration, cuvettes were washed 10× with water, 1× with acetone, and then stoppered as with the CODH assay. N$_2$ was blown into the cuvettes for ~10 min. A volume of 1 ml of anaerobic buffer (HEPES, pH 8.0, 2 mM DTT) was added to the blank (not equilibrated with CO) with a Hamilton syringe. A volume of 10 microliter myoglobin (~1 mM—can be varied, just need a fairly large amount) and 1 microliter dithionite (20 mM stock) were added. A CO standard curve was made using CO saturated buffer added at 1 microliter increments. Peak height and shift was recorded for each increment. The cultures tested were pZA33/CO, ACS90/CO, and ACS91/CO. each of these was added in 1 microliter increments to the same cuvette. Midway through the experiment a second cuvette was set up and used. The results are shown in Table 3.

TABLE 3

| Carbon Monoxide Concentrations, 36 hrs. | |
|---|---|
| Strain and Growth Conditions | Final CO concentration (micromolar) |
| pZA33-CO | 930 |
| ACS90-CO | 638 |
|  | 494 |
|  | 734 |
|  | 883 |
| ave | 687 |
| SD | 164 |
| ACS91-CO | 728 |
|  | 812 |
|  | 760 |
|  | 611 |
| ave. | 728 |
| SD | 85 |

The results shown in Table 3 indicate that the cultures grew whether or not a strain was cultured in the presence of CO or not. These results indicate that *E. coli* can tolerate exposure to CO under anaerobic conditions and that *E. coli* cells expressing the CODH-ACS operon can metabolize some of the CO.

These results demonstrate that *E. coli* cells, whether expressing CODH/ACS or not, were able to grow in the presence of saturating amounts of CO. Furthermore, these grew equally well as the controls in nitrogen in place of CO. This experiment demonstrated that laboratory strains of *E. coli* are insensitive to CO at the levels achievable in a syngas project performed at normal atmospheric pressure. In addition, preliminary experiments indicated that the recombinant *E. coli* cells expressing CODH/ACS actually consumed some CO, probably by oxidation to carbon dioxide.

Example IXX

Exemplary Pathways for Production of 4-Hydroxybutyrate and 1,4-Butanediol

This example describes exemplary pathways for the production of 4-hydroxybutyrate and 1,4-butanediol from acetyl-CoA.

As disclosed herein, the combination of (1) pathways for the conversion of synthesis gases with and without methanol to acetyl-CoA and (2) pathways for the conversion of acetyl-CoA to 4-hydroxybutyrate, or 1,4-butanediol. As such, this invention provides production organisms and conversion routes with inherent yield advantages over organisms engineered to produce 4-hydroxybutyrate, or 1,4-butanediol from carbohydrate feedstocks. For example, the maximum theoretical yields of 4-hydroxybutyrate, and 1,4-butanediol from glucose are 1 mole per mole using the metabolic pathways proceeding from acetyl-CoA as described herein. Specifically, 2 moles of acetyl-CoA are derived per mole of glucose via glycolysis and 2 moles of acetyl-CoA are required per mole of 4-hydroxybutyrate, or 1,4-butanediol. The net conversions are described by the following stoichiometric equations:

4-Hydroxybutyate: $C_6H_{12}O_6 + 1.5O_2 \rightarrow C_4H_8O_3 + 2CO_2 + 2H_2O$ 1,4-Butanediol: $C_6H_{12}O_6 \rightarrow C_4H_{10}O_2 + CH_2O_2 + CO_2$ On the other hand, gasification of glucose to its more simpler components, CO and $H_2$, followed by their conversion to 4-hydroxybutyrate, and 1,4-butanediol using the pathways described herein results in the following maximum theoretical yields:

4-Hydroxybutyate: $6CO + 6H_2 \rightarrow 1.333C_4H_8O_3 + 0.667CO_2 + 0.667H_2O$ 1,4-Butanediol: $6CO + 6H_2 \rightarrow 1.091C_4H_{10}O_2 + 1.636CO_2 + 0.545H_2O$ Note that the gasification of glucose can at best provide 6 moles of CO and 6 moles of $H_2$. The maximum theoretical yields of 4-hydroxybutyrate, and 1,4-butanediol from synthesis gases can be further enhanced by the addition of methanol as described below:

4-Hydroxybutyate: $CH_4O + 6CO + 6H_2 \rightarrow 1.667C_4H_8O_3 + 0.333CO_2 + 1.333H_2O$ 1,4-Butanediol: $CH_4O + 6CO + 6H_2 \rightarrow 1.364C_4H_{10}O_2 + 1.545CO_2 + 1.182H_2O$ 4-Hydroxybutyate: $2CH_4O + 6CO + 6H_2 \rightarrow 2C_4H_8O_3 + 2H_2O$ 1,4-Butanediol: $2CH_4O + 6CO + 6H_2 \rightarrow 1.636C_4H_{10}O_2 + 1.455CO_2 + 1.818H_2O$ Thus it is clear that the organisms and conversion routes described herein provide an efficient means of converting carbohydrates to 4-hydroxybutyrate, or 1,4-butanediol.

Acetoacetyl-CoA thiolase converts two molecules of acetyl-CoA into one molecule each of acetoacetyl-CoA and CoA. Exemplary acetoacetyl-CoA thiolase enzymes include the gene products of atoB from *E. coli* (Martin et al., *Nat. Biotechnol* 21:796-802 (2003)), thlA and thlB from *C. acetobutylicum* (Hanai et al., *Appl Environ Microbiol* 73:7814-7818 (2007); Winzer et al., *J. Mol. Microbiol Biotechnol* 2:531-541 (2000), and ERG10 from *S. cerevisiae* Hiser et al., *J. Biol. Chem.* 269:31383-31389 (1994)).

| Protein | GenBank ID | Organism |
|---|---|---|
| AtoB | NP_416728 | *Escherichia coli* |
| ThlA | NP_349476.1 | *Clostridium acetobutylicum* |
| ThlB | NP_149242.1 | *Clostridium acetobutylicum* |
| ERG10 | NP_015297 | *Saccharomyces cerevisiae* |

Exemplary 3-hydroxyacyl dehydrogenases which convert acetoacetyl-CoA to 3-hydroxybutyryl-CoA include hbd from *C. acetobutylicum* (Boynton et al., Journal of Bacteriology 178:3015-3024 (1996)), hbd from *C. beijerinckii* (Colby and Chen et al., Appl Environ. Microbiol 58:3297-3302 (1992)), and a number of similar enzymes from *Metallosphaera sedula* (Berg et al., 2007 Science 318:1782-1786 (2007)).

| Protein | GenBank ID | Organism |
|---|---|---|
| hbd | NP_349314.1 | *Clostridium acetobutylicum* |
| hbd | AAM14586.1 | *Clostridium beijerinckii* |
| Msed_1423 | YP_001191505 | *Metallosphaera sedula* |
| Msed_0399 | YP_001190500 | *Metallosphaera sedula* |
| Msed_0389 | YP_001190490 | *Metallosphaera sedula* |
| Msed_1993 | YP_001192057 | *Metallosphaera sedula* |

The gene product of crt from *C. acetobutylicum* catalyzes the dehydration of 3-hydroxybutyryl-CoA to crotonyl-CoA (Atsumi et at, *Metab Eng* (2007); Boynton et al., *Journal of Bacteriology* 178:3015-3024 (1996)). Further, enoyl-CoA hydratases are reversible enzymes and thus suitable candidates for catalyzing the dehydration of 3-hydroxybutyryl-CoA to crotonyl-CoA. The enoyl-CoA hydratases, phaA and phaB, of *P. putida* are believed to carry out the hydroxylation of double bonds during phenylacetate catabolism (Olivera et al., *Proc Nat Acad Sci U.S.A.* 95:6419-6424 (1998)). The ipaaA and paaB from *P. fluorescens* catalyze analogous transformations (Olivera et al., *Proc Nat Acad Sci U.S.A.* 95:6419-6424 (1998)). Lastly, a number of *Escherichia coli* genes have been shown to demonstrate enoyl-CoA hydratase functionality including maoC, paaF, and paaG (Ismail et al., *European Journal of Biochemistry* 270:3047-3054 (2003); Park and Lee, *J Bacteriol.* 185:5391-5397 (2003); Park and Lee, *Appl Biochem. Biotechnol* 113-116: 335-346 (2004); Park and Yup, *Biotechnol Bioeng* 86:681-686 (2004)).

| Protein | GenBank ID | Organism |
|---|---|---|
| crt | NP_349318.1 | *Clostridium acetobutylicum* |
| paaA | NP_745427.1 | *Pseudomonas putida* |
| paaB | NP_745426.1 | *Pseudomonas putida* |
| phaA | ABF82233.1 | *Pseudomonas fluorescens* |
| phaB | ABF82234.1 | *Pseudomonas fluorescens* |

| Protein | GenBank ID | Organism |
| --- | --- | --- |
| maoC | NP_415905.1 | Escherichia coli |
| paaF | NP_415911.1 | Escherichia coli |
| paaG | NP_415912.1 | Escherichia coli |

Several enzymes that naturally catalyze the reverse reaction (i.e., the dehydration of 4-hydroxybutyryl-CoA to crotonoyl-CoA) in vivo have been identified in numerous species. This transformation is used for 4-aminobutyrate fermentation by Clostridium aminobutyricum (Scherf and Buckel, Eur. J Biochem. 215:421-429 (1993)) and succinate-ethanol fermentation by Clostridium kluyveri (Scherf et al., Arch. Microbiol 161:239-245 (1994)). The transformation is also a step in Archaea, for example, Metallosphaera sedula, as part of the 3-hydroxypropionate/4-hydroxybutyrate autotrophic carbon dioxide assimilation pathway (Berg et al., Science 318:1782-1786 (2007)). This pathway uses the hydration of crotonoyl-CoA to form 4-hydroxybutyryl-CoA. The reversibility of 4-hydroxybutyryl-CoA dehydratase is well-documented (Friedrich et al., Angew. Chem. Int. Ed. Engl. 47:3254-3257 (2008); Muh et al., Eur. J. Biochem. 248:380-384 (1997); Muh et al., Biochemistry 35:11710-11718 (1996)) and the equilibrium constant has been reported to be about 4 on the side of crotonoyl-CoA (Scherf and Buckel, Eur. J Biochem. 215:421-429 (1993)). This indicates that the downstream 4-hydroxybutyryl-CoA dehydrogenase keeps the 4-hydroxybutyryl-CoA concentration low so as to not create a thermodynamic bottleneck at crotonyl-CoA.

| Protein | GenBank ID | Organism |
| --- | --- | --- |
| AbfD | CAB60035 | Clostridium aminobutyricum |
| AbfD | YP_001396399 | Clostridium kluyveri |
| Msed_1321 | YP_001191403 | Metallosphaera sedula |
| Msed_1220 | YP_001191305 | Metallosphaera sedula |

4-Hydroxybutyryl-CoA transferase transfers the CoA moiety from 4-hydroxybutyryl-CoA to acetate, in turn, forming 4-hydroxybutyrate and acetyl-CoA. One exemplary 4-hydroxybutyryl-CoA transferase is encoded by the cat2 gene of Clostridium kluyveri (Seedorf et al., Proc. Natl. Acad. Sci. U.S.A. 105:2128-2133 (2008); Sohling and Gottschalk J Bacteriol. 178:871-880 (1996)). The abfT-2 gene from Porphyromonas gingivalis was also shown to exhibit 4-hydroxybutyryl-CoA transferase activity when implemented as part of a pathway to produce 4-hydroxybutyate and 1,4-butanediol (Burk, et al., WO/2008/115840 (2008)). An additional candidate enzyme, encoded by abfT-1, from P. gingivalis can be inferred by sequence homology. Another 4-hydroxybutyryl-CoA transferase is encoded by the gene product of abfT from Clostridium aminobutyricum (Gerhardt et al., Arch. Microbiol 174:189-199 (2000)).

| Protein | GenBank ID | Organism |
| --- | --- | --- |
| cat2 | YP_001396397 | Clostridium kluyveri |
| abfT-2 | NP_906037 | Porphyromonas gingivalis |
| abfT-1 | NP_904965.1 | Porphyromonas gingivalis |
| abfT | CAB60036 | Clostridium aminobutyricum |

Exemplary phosphate transferring acyltransferases include phosphotransacetylase, encoded by pta, and phosphotransbutyrylase, encoded by ptb. The pta gene from E. coli encodes an enzyme that can convert acetyl-CoA into acetyl-phosphate, and vice versa (Suzuki, T. 1969 Biochim. Biophys. Acta 191:559-569 (1969)). This enzyme can also utilize propionyl-CoA instead of acetyl-CoA forming propionate in the process (Hesslinger et al., Mol. Microbiol 27:477-492 (1998)). Similarly, the ptb gene from C. acetobutylicum encodes an enzyme that can convert butyryl-CoA into butyryl-phosphate (Huang et al., J. Mol. Microbiol Biotechnol 2:33-38 (2000); (Walter et al., Gene 134:107-111(1993)). This same enzyme was shown to have activity on 4-hydroxybutyryl-CoA when implemented as part of a pathway to produce 1,4-butanediol WO/2008/115840 (2008). Additional ptb genes can be found in butyrate-producing bacterium L2-50 (Ljungdahl and Andreesen, Methods Enzymol. 53:360-372 (1978) and Bacillus megaterium (Vazquez et al., Curr. Microbiol 42:345-349 (2001)).

| Protein | GenBank ID | Organism |
| --- | --- | --- |
| pta | NP_416800.1 | Escherichia coli |
| ptb | NP_349676 | Clostridium acetobutylicum |
| ptb | AAR19757.1 | butyrate-producing bacterium L2-50 |
| ptb | CAC07932.1 | Bacillus megaterium |

Exemplary kinases include the E. coli acetate kinase, encoded by ackA (Skarstedt and Silverstein, J. Biol. Chem. 251:6775-6783 (1976)), the C. acetobutylicum butyrate kinases, encoded by buk1 and buk2 (Huang et al., 2000 J. Mol. Microbiol Biotechnol 2:33-38 (2000); Walter et al., Gene 134:107-111(1993)), and the E. coli gamma-glutamyl kinase, encoded by proB (Smith et al., J. Bacteriol. 157:545-551 (1984)). These enzymes phosphorylate acetate, butyrate, and glutamate, respectively. The acM gene product from E. coli also phosphorylates propionate (Hesslinger et al., Mol. Microbiol 27:477-492 (1998)). The gene product of buk1 from C. acetobutylicum was shown in Burk et al., WO/2008/115840 (2008) to have activity on 4-hydroxybutyryl-CoA when implemented as part of a pathway to produce 1,4-butanediol.

| Protein | GenBank ID | Organism |
| --- | --- | --- |
| ackA | NP_416799.1 | Escherichia coli |
| buk1 | NP_349675 | Clostridium acetobutylicum |
| buk2 | Q97II1 | Clostridium acetobutylicum |
| proB | NP_414777.1 | Escherichia coli |

Alcohol-forming 4-hydroxybutyryl-CoA reductase enzymes catalyze the 2 reduction steps required to form 1,4-butanediol from 4-hydroxybutyryl-CoA. Exemplary 2-step oxidoreductases that convert an acyl-CoA to alcohol include those that transform substrates such as acetyl-CoA to ethanol (e.g., adhE from E. coli (Kessler et al., FEBS. Lett. 281:59-63 (1991)) and butyryl-CoA to butanol (e.g. adhE2 from C. acetobutylicum (Fontaine et al., J. Bacteriol. 184:821-830 (2002)). The adhE2 enzyme from C. acetobutylicum was specifically shown in ref. Burk et al., WO/2008/115840 (2008), to produce BDO from 4-hydroxybutyryl-CoA. In addition to reducing acetyl-CoA to ethanol, the enzyme encoded by adhE in Leuconostoc mesenteroides has been shown to oxide the branched chain compound isobutyraldehyde to isobutyryl-CoA (Kazahaya et al., J. Gen. Appl. Microbiol. 18:43-55 (1972); Koo et al., Biotechnol Lett. 27:505-510 (2005)).

| Protein | GenBank ID | Organism |
| --- | --- | --- |
| adhE | NP_415757.1 | Escherichia coli |
| adhE2 | AAK09379.1 | Clostridium acetobutylicum |
| adhE | AAV66076.1 | Leuconostoc mesenteroides |

Another exemplary enzyme can convert malonyl-CoA to 3-HP. An NADPH-dependent enzyme with this activity has characterized in Chloroflexus aurantiacus where it participates in the 3-hydroxypropionate cycle (Hugler et al., J. Bacteriol. 184:2404-2410 (2000); Strauss and Fuchs, Eur. J. Biochem. 215:633-643 (1993)). This enzyme, with a mass of 300 kDa, is highly substrate-specific and shows little sequence similarity to other known oxidoreductases (Hugler et al., J. Bacteriol. 184:2404-2410 (2002)). No enzymes in other organisms have been shown to catalyze this specific reaction; however there is bioinformatic evidence that other organisms may have similar pathways (Klatt et al., Environ. Microbiol. 9:2067-2078 (2007)). Enzyme candidates in other organisms including Roseiflexus castenholzii, Erythrobacter sp. NAP1 and marine gamma proteobacterium HTCC2080 can be inferred by sequence similarity.

| Protein | GenBank ID | Organism |
| --- | --- | --- |
| mcr | AAS20429.1 | Chloroflexus aurantiacus |
| Rcas_2929 | YP_001433009.1 | Roseiflexus castenholzii |
| NAP1_02720 | ZP_01039179.1 | Erythrobacter sp. NAP1 |
| MGP2080_00535 | ZP_01626393.1 | marine gamma proteobacterium HTCC2080 |

An alternative route to BDO from 4-hydroxybutyryl-CoA involves first reducing this compound to 4-hydroxybutanal. Several acyl-CoA dehydrogenases are capable of reducing an acyl-CoA to its corresponding aldehyde. Exemplary genes that encode such enzymes include the Acinetobacter calcoaceticus acr1 encoding a fatty acyl-CoA reductase (Reiser and Somerville, Journal of Bacteriology 179:2969-2975 (1997)), the Acinetobacter sp. M-1 fatty acyl-CoA reductase (Ishige et al., Anol. Environ. Microbiol. 68:1192-1195 (2002)), and a CoA- and NADP-dependent succinate semialdehyde dehydrogenase encoded by the sucD gene in Clostridium kluyveri (Sohling and Gottschalk, J Bacteriol. 178:871-880 (1996)). SucD of P. gingivalis is another succinate semialdehyde dehydrogenase (Takahashi et al., J. Bacteriol. 182:4704-4710 (2000)). These succinate semialdehyde dehydrogenases were specifically shown in ref. Burk et al., WO/2008/115840 (2008) to convert 4-hydroxybutyryl-CoA to 4-hydroxybutanal as part of a pathway to produce 1,4-butanediol. The enzyme acylating acetaldehyde dehydrogenase in Pseudomonas sp, encoded by bphG, is yet another capable enzyme as it has been demonstrated to oxidize and acylate acetaldehyde, propionaldehyde, butyraldehyde, isobutyraldehyde and formaldehyde (Powlowski et al., J Bacteriol. 175:377-385 (1993)).

| Protein | GenBank ID | Organism |
| --- | --- | --- |
| acr1 | YP_047869.1 | Acinetobacter calcoaceticus |
| acr1 | AAC45217 | Acinetobacter baylyi |
| acr1 | BAB85476.1 | Acinetobacter sp. Strain M-1 |
| sucD | P38947.1 | Clostridium kluyveri |
| sucD | NP_904963.1 | Porphyromonas gingivalis |
| bphG | BAA03892.1 | Pseudomonas sp |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archael bacteria (Berg et al., Science 318:1782-1786 (2007); Thauer, R. K. Science 318:1732-1733 (2007)). The enzyme utilizes NADPH as a cofactor and has been characterized in Metallosphaera and Sulfolobus spp (Alber et al., J. Bacteriol. 188:8551-8559 (2006); Hugler et al., J. Bacteriol. 184:2404-2410 (2002)). The enzyme is encoded by Msed_0709 in Metallosphaera sedula (Alber et al., J. Bacteriol. 188:8551-8559 (2006); Berg et al., Science 318: 1782-1786 (2007)). A gene encoding a malonyl-CoA reductase from Sulfolobus tokodaii was cloned and heterologously expressed in E. coli (Alber et al., J. Bacteriol. 188:8551-8559 (2006)). Although the aldehyde dehydrogenase functionality of these enzymes is similar to the bifunctional dehydrogenase from Chloroflexus aurantiacus, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including Sulfolobus solfatarieus and Sulfolobus acidocaldarius.

| Protein | GenBank ID | Organism |
| --- | --- | --- |
| Msed_0709 | YP_001190808.1 | Metallosphaera sedula |
| mcr | NP_378167.1 | Sulfolobus tokodaii |
| asd-2 | NP_343563.1 | Sulfolobus solfataricus |
| Saci_2370 | YP_256941.1 | Sulfolobus acidocaldarius |

Enzymes exhibiting 1,4-butanediol dehydrogenase activity are capable of forming 1,4-butanediol from 4-hydroxybutanal. Exemplary genes encoding enzymes that catalyze the conversion of an aldehyde to alcohol (i.e., alcohol dehydrogenase or equivalently aldehyde reductase) include alrA encoding a medium-chain alcohol dehydrogenase for C2-C14 (Tani et al., Appl. Environ. Microbiol. 66:5231-5235 (2000)), ADH2 from Saccharomyces cerevisiae Atsumi et al. Nature 451:86-89 (2008)), yqhD from E. coli which has preference for molecules longer than C(3) (Sulzenbacher et al., Journal of Molecular Biology 342:489-502 (2004)), and bdh I and bdh II from C. acetobutylicum which converts butyryaldehyde into butanol (Walter et al., Journal of Bacteriology 174:7149-7158 (1992)).

| Protein | GenBank ID | Organism |
| --- | --- | --- |
| alrA | BAB12273.1 | Acinetobacter sp. Strain M-1 |
| ADH2 | NP_014032.1 | Saccharymyces cerevisiae |
| yqhD | NP_417484.1 | Escherichia coli |
| bdh I | NP_349892.1 | Clostridium acetobutylicum |
| bdh ll | NP_349891.1 | Clostridium acetobutylicum |

Enzymes exhibiting 4-hydroxybutyrate dehydrogenase activity (EC 1.1.1.61) also fall into this category. Such enzymes have been characterized in Ralstonia eutropha (Bravo et al., J. Forensic Sci. 49:379-387 (2004)), Clostridium kluyveri (Wolff and Kenealy, Protein Expr. Purif. 6:206-212 (1995)) and Arabidopsis thaliana (Breitkreuz et al., J. Biol. Chem. 278:41552-41556 (2003)).

| Protein | GenBank ID | Organism |
| --- | --- | --- |
| 4hbd | YP_726053.1 | *Ralstonia eutropha* H16 |
| 4hbd | L21902.1 | *Clostridium kluyveri* DSM 555 |
| 4hbd | Q94B07 | *Arabidopsis thaliana* |

The nonnative genes needed for 4-hydroxybutyrate synthesis are cloned on expression plasmids as described previously. The host strain also expresses methanol methyltransferase activity, CODH/ACS activity, and possibly PFOR and hydrogenase activities. At this point, these (CODH/ACS, etc.) genes are integrated into the genome and expressed from promoters that can be used constitutively or with inducers (i.e., PA1-lacO1 is inducible in cells containing lacI or is otherwise constitutive). Once expression and yields of 4-hydroxybutyrate are optimized, the base strain is further modified by integration of a single copy of these genes at a neutral locus. Given the relatively limited number of genes (at minimum, 5, and at most, 6), an artificial operon encoding the required genes can be constructed. This operon is introduced using integrative plasmids and is coupled to counter-selection methods such as that allowed by the *Bacillus* sacB gene (Link et al., *J Bacteriol.* 179:6228-6237 (1997)). In this way, markerless and scar less insertions at any location in the *E. coli* chromosome can be generated. Optimization involves altering gene order as well as ribosomal binding sites and promoters.

The nonnative genes needed for 1,4-butanediol synthesis are cloned on expression plasmids as described previously. The host strain also expresses methanol methyltransferase activity, CODH/ACS activity, and possibly PFOR and hydrogenase activities. At this point, these (CODH/ACS, etc.) genes are integrated into the genome and expressed from promoters that can be used constitutively or with inducers (i.e., PA1-lacO1 is inducible in cells containing lacI or is otherwise constitutive). Once expression and yields of 1,4-butanediol are optimized, the base strain is further modified by integration of a single copy of these genes at a neutral locus. Given the relatively limited number of genes (at minimum, 5, and at most, 6), an artificial operon encoding the required genes can be constructed. This operon is introduced using integrative plasmids and is coupled to counter-selection methods such as that allowed by the *Bacillus* sacB gene (Link et al., *J Bacteriol.* 179:6228-6237 (1997)). In this way, markerless and scar less insertions at any location in the *E. coli* chromosome can be generated. Optimization involves altering gene order as well as ribosomal binding sites and promoters.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A non-naturally occurring microbial organism, comprising a microbial organism having an acetyl-coenzyme A (acetyl-CoA) pathway able to convert $CO_2$, CO or $H_2$, or a combination thereof, and methanol to acetyl-CoA, and comprising methanol-methyltransferase that catalyzes transfer of a methyl group from methanol to form methylated corrinoid protein, and acetyl-CoA synthase/carbon monoxide dehydrogenase that catalyzes reduction of carbon dioxide to carbon monoxide, and synthesis of acetyl-CoA from carbon monoxide, Coenzyme A, and a methyl group from a methylated corrinoid-iron-sulfur protein, wherein the methanol-methyltransferase and acetyl-CoA synthase/carbon monoxide dehydrogenase are encoded by exogenous nucleic acids expressed in sufficient amounts to produce acetyl-CoA.

2. The non-naturally occurring microbial organism of claim 1, wherein the acetyl-CoA synthase/carbon monoxide dehydrogenase comprises an enzyme or protein selected from the group consisting of methyltetrahydrofolate: corrinoid protein methyltransferase, corrinoid iron-sulfur protein, nickel-protein assembly protein, ferredoxin, acetyl-CoA synthase, carbon monoxide dehydrogenase and nickel-protein assembly protein.

3. The non-naturally occurring microbial organism of claim 1, wherein said microbial organism comprises three exogenous nucleic acids encoding an acetyl-CoA pathway enzyme or protein, one exogenous nucleic acid encoding the methanol-methyltransferase and another exogenous nucleic acid encoding the acetyl-CoA synthase/carbon monoxide dehydrogenase.

4. The non-naturally occurring microbial organism of claim 1, wherein said at least one exogenous nucleic acid is a heterologous nucleic acid.

5. The non-naturally occurring microbial organism of claim 1, wherein said non-naturally occurring microbial organism further comprises pyruvate ferredoxin oxidoreductase.

6. The non-naturally occurring microbial organism of claim 1, wherein said non-naturally occurring microbial organism further comprises hydrogenase.

7. The non-naturally occurring microbial organism of claim 1, wherein the methanol-methyltransferase is selected from the group consisting of *Methanosarcina barkeri* MtaB1, *Methanosarcina barkeri* MtaB2, *Methanosarcina barkeri* MtaB3, *Methanosarcina acetivorans* MtaB1, *Methanosarcina acetivorans* MtaB1, *Methanosarcina acetivorans* MtaB2, *Methanosarcina acetivorans* MtaB3, and *Moorella thermoacetica* MtaB.

8. The non-naturally occurring microbial organism of claim 1, wherein the non-naturally occurring microbial organism is *Escherichia coli* and the methanol-methyltransferase and acetyl-CoA synthase/carbon monoxide dehydrogenase are encoded by exogenous nucleic acids heterologous to *Escherichia coli*.

9. A method for producing acetyl-CoA, comprising culturing the non-naturally occurring microbial organism of claim 1, under conditions and for a sufficient period of time to produce acetyl-CoA.

10. The method of claim 9, wherein said non-naturally occurring microbial organism is in a substantially anaerobic culture medium.

* * * * *